US008058065B2

(12) United States Patent
Yamanaka et al.

(10) Patent No.: US 8,058,065 B2
(45) Date of Patent: Nov. 15, 2011

(54) OCT3/4, KLF4, C-MYC AND SOX2 PRODUCE INDUCED PLURIPOTENT STEM CELLS

(75) Inventors: Shinya Yamanaka, Kyoto (JP); Kazutoshi Takahashi, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 12/457,356

(22) Filed: Jun. 9, 2009

(65) Prior Publication Data

US 2010/0062533 A1    Mar. 11, 2010

Related U.S. Application Data

(63) Continuation of application No. 12/213,035, filed on Jun. 13, 2008, which is a continuation-in-part of application No. PCT/JP2006/324881, filed on Dec. 6, 2006.

(60) Provisional application No. 61/001,108, filed on Oct. 31, 2007, provisional application No. 60/996,289, filed on Nov. 9, 2007.

(30) Foreign Application Priority Data

Dec. 13, 2005    (JP) .................................. 2005-359537

(51) Int. Cl.
*C12N 5/02* (2006.01)
*C12N 15/00* (2006.01)

(52) U.S. Cl. .......................... 435/377; 435/373; 435/455

(58) Field of Classification Search ........................ None
See application file for complete search history.

(56) References Cited

U.S. PATENT DOCUMENTS

| | | | |
|---|---|---|---|
| 4,650,764 A | 3/1987 | Temin et al. |
| 4,861,719 A | 8/1989 | Miller |
| 4,937,190 A | 6/1990 | Palmenberg et al. |
| 5,225,348 A | 7/1993 | Nagata et al. |
| 5,266,491 A | 11/1993 | Nagata et al. |
| 5,268,290 A | 12/1993 | Mamoru et al. |
| 5,288,514 A | 2/1994 | Ellman |
| 5,324,645 A | 6/1994 | Takahara et al. |
| 5,449,614 A | 9/1995 | Danos et al. |
| 5,519,134 A | 5/1996 | Acevedo et al. |
| 5,525,735 A | 6/1996 | Gallop et al. |
| 5,549,974 A | 8/1996 | Holmes |
| 5,591,624 A | 1/1997 | Barber et al. |
| 5,637,456 A | 6/1997 | Roth et al. |
| 5,652,122 A | 7/1997 | Frankel et al. |
| 5,674,980 A | 10/1997 | Frankel |
| 5,707,618 A | 1/1998 | Armentano et al. |
| 5,716,832 A | 2/1998 | Barber et al. |
| 5,744,320 A | 4/1998 | Sherf et al. |
| 5,817,491 A | 10/1998 | Yee et al. |
| 5,830,725 A | 11/1998 | Nolan et al. |
| 5,834,256 A | 11/1998 | Finer et al. |
| 5,858,740 A | 1/1999 | Finer et al. |
| 5,910,434 A | 6/1999 | Rigg et al. |
| 5,955,331 A | 9/1999 | Danos et al. |
| 6,013,517 A | 1/2000 | Respess et al. |
| 6,017,735 A | 1/2000 | O'hare |
| 6,017,761 A | 1/2000 | Rigg et al. |
| 6,025,192 A | 2/2000 | Beach et al. |
| 6,140,111 A | 10/2000 | Riviere et al. |
| 6,146,874 A | 11/2000 | Zolotukhin et al. |
| 6,153,432 A | 11/2000 | Halvorsen et al. |
| 6,153,745 A | 11/2000 | Williams et al. |
| 6,203,975 B1 | 3/2001 | Wilson et al. |
| 6,251,398 B1 | 6/2001 | O'Hare et al. |
| 6,255,071 B1 | 7/2001 | Beach et al. |
| 6,312,948 B1 | 11/2001 | Cohen-haguenauer |
| 6,312,949 B1 | 11/2001 | Sakurada et al. |
| 6,333,195 B1 | 12/2001 | Respess et al. |
| 6,365,352 B1 | 4/2002 | Yerramilli et al. |
| 6,395,546 B1 | 5/2002 | Zobel et al. |
| 6,451,595 B1 | 9/2002 | Kim et al. |
| 6,485,959 B1 | 11/2002 | Demetriou et al. |
| 6,521,453 B1 | 2/2003 | Crameri et al. |
| 6,521,455 B2 | 2/2003 | O'Hare et al. |
| 6,605,275 B1 | 8/2003 | Boyse et al. |
| 6,660,514 B1 | 12/2003 | Zolotukhin et al. |
| 6,773,920 B1 | 8/2004 | Dalby et al. |
| 6,833,269 B2 | 12/2004 | Carpenter |
| 6,841,535 B2 | 1/2005 | Divita et al. |

(Continued)

FOREIGN PATENT DOCUMENTS

AU    2008201280 A1    4/2008

(Continued)

OTHER PUBLICATIONS

Tada et al. Nuclear Reprogramming of Somatic Cells by In Vitro Hybridization with Es Cells. Current Biology, 2001, vol. 11, 1553-1558.*
Liu. IPS Cells; a More Critical Review. Stem Cells and Development, 2008, pp. 1-11.*
Jaenisch et al. Stem Cells, the Molecular Circuitry of Pluripotency and Nuclear Reprogramming. Cell, 2008, vol. 132, pp. 567-582.*
Yamanaka. Induction of Pluripotent Stem Cells From Mouse Fibroblasts by Four Transcription Factors. Cell Proliferation, 2008, vol. 41, Suppl. 1, pp. 51-56.*
Evans et al., "Establishment in culture of pluripotential cells from mouse embryos" *Nature* 292:154-56, 1981.
Martin, "Isolation of a pluripotent cell line from early mouse embryos cultured in medium conditioned by teratocarcinoma stem cells" *Proc. Natl. Acad. Sci. U.S.A.* 78(12):7634-38, 1981.
Thomson et al., "Embryonic Stem Cell Lines Derived from Human Blastocysts" *Science* 282:1145-47, 1998.

(Continued)

*Primary Examiner* — Deborah Crouch
(74) *Attorney, Agent, or Firm* — Knobbe Martens Olson & Bear LLP

(57) ABSTRACT

The present invention relates to a nuclear reprogramming factor having an action of reprogramming a differentiated somatic cell to derive an induced pluripotent stem (iPS) cell. The present invention also relates to the aforementioned iPS cells, methods of generating and maintaining iPS cells, and methods of using iPS cells, including screening and testing methods as well as methods of stem cell therapy. The present invention also relates to somatic cells derived by inducing differentiation of the aforementioned iPS cells.

1 Claim, 57 Drawing Sheets
(41 of 57 Drawing Sheet(s) Filed in Color)

U.S. PATENT DOCUMENTS

| | | |
|---|---|---|
| 6,872,528 B2 | 3/2005 | Klatzmann et al. |
| 6,875,578 B2 | 4/2005 | Giuliano et al. |
| 6,881,825 B1 | 4/2005 | Robbins et al. |
| 6,910,434 B2 | 6/2005 | Lundgren et al. |
| 6,995,009 B1 | 2/2006 | Kitamura et al. |
| 7,029,913 B2 | 4/2006 | Thomson |
| 7,030,292 B2 | 4/2006 | Yan et al. |
| 7,070,994 B2 | 7/2006 | Barber et al. |
| 7,250,255 B2 | 7/2007 | Yamanaka |
| 7,439,064 B2 | 10/2008 | Thomson et al. |
| 2002/0090722 A1 | 7/2002 | Dominko et al. |
| 2002/0123146 A1 | 9/2002 | Klatzmann et al. |
| 2002/0174013 A1 | 11/2002 | Freeman et al. |
| 2003/0003574 A1 | 1/2003 | Toma et al. |
| 2003/0044976 A1 | 3/2003 | Dominko et al. |
| 2003/0161817 A1 | 8/2003 | Young et al. |
| 2004/0048297 A1 | 3/2004 | Scherf |
| 2004/0137460 A1 | 7/2004 | Yamanaka et al. |
| 2005/0019801 A1 | 1/2005 | Rubin et al. |
| 2005/0026133 A1 | 2/2005 | Nakatsuji et al. |
| 2005/0079606 A1 | 4/2005 | Tamaki et al. |
| 2005/0130144 A1 | 6/2005 | Nakatsuji et al. |
| 2005/0162419 A1 | 7/2005 | Kim et al. |
| 2006/0030041 A1 | 2/2006 | Furcht et al. |
| 2006/0084172 A1 | 4/2006 | Muller et al. |
| 2006/0088599 A1 | 4/2006 | Prasad et al. |
| 2006/0095319 A1 | 5/2006 | Cardwell |
| 2006/0110830 A1 | 5/2006 | Dominko et al. |
| 2006/0292620 A1 | 12/2006 | Yamanaka et al. |
| 2007/0033061 A1 | 2/2007 | Patten et al. |
| 2007/0053884 A1 | 3/2007 | Suda et al. |
| 2007/0155013 A1 | 7/2007 | Akaike et al. |
| 2007/0202592 A1 | 8/2007 | Kitagawa et al. |
| 2007/0254884 A1 | 11/2007 | Chen et al. |
| 2007/0269790 A1 | 11/2007 | Amit et al. |
| 2008/0003560 A1 | 1/2008 | Nakatsuji et al. |
| 2008/0076176 A1 | 3/2008 | Dominko et al. |
| 2008/0085555 A1 | 4/2008 | Asahara et al. |
| 2008/0132803 A1 | 6/2008 | Friedlander |
| 2008/0171358 A1 | 7/2008 | Perrault |
| 2008/0171385 A1 | 7/2008 | Bergendahl et al. |
| 2008/0206865 A1 | 8/2008 | Zhang et al. |
| 2008/0233610 A1 | 9/2008 | Thomson et al. |
| 2008/0274914 A1 | 11/2008 | Yamanaka et al. |
| 2008/0280362 A1 | 11/2008 | Jaenisch et al. |
| 2008/0293143 A1 | 11/2008 | Lin et al. |
| 2008/0299548 A1 | 12/2008 | Yamanaka |
| 2009/0047263 A1 | 2/2009 | Yamanaka et al. |
| 2009/0068742 A1 | 3/2009 | Yamanaka |
| 2009/0191159 A1 | 7/2009 | Sakurada et al. |
| 2009/0191171 A1 | 7/2009 | Ma |
| 2009/0227032 A1 | 9/2009 | Yamanaka |
| 2009/0246875 A1 | 10/2009 | Yamanaka et al. |
| 2009/0299763 A1 | 12/2009 | Sakurada |
| 2009/0304646 A1 | 12/2009 | Sakurada et al. |
| 2009/0324559 A1 | 12/2009 | Sakurada |
| 2010/0003757 A1 | 1/2010 | Mack |
| 2010/0021437 A1 | 1/2010 | Isacson |
| 2010/0062533 A1 | 3/2010 | Yamanaka |
| 2010/0062534 A1 | 3/2010 | Hochedlinger |
| 2010/0075421 A1 | 3/2010 | Yamanaka |
| 2010/0093090 A1 | 4/2010 | Deng |
| 2010/0105100 A1 | 4/2010 | Sakurada |
| 2010/0120069 A1 | 5/2010 | Sakurada |
| 2010/0144031 A1 | 6/2010 | Jaenisch |
| 2010/0184051 A1 | 7/2010 | Hochedlinger |
| 2010/0184227 A1 | 7/2010 | Thomson |
| 2010/0210014 A1 | 8/2010 | Yamanaka |
| 2010/0216236 A1 | 8/2010 | Yamanaka |
| 2010/0221827 A1 | 9/2010 | Jaenisch |
| 2010/0233804 A1 | 9/2010 | Zhou |
| 2010/0240090 A1 | 9/2010 | Sakurada |
| 2010/0267135 A1 | 10/2010 | Sakurada |
| 2010/0279404 A1 | 11/2010 | Yamanaka |
| 2011/0039332 A1 | 2/2011 | Sakurada et al. |

FOREIGN PATENT DOCUMENTS

| | | |
|---|---|---|
| CN | 101250502 A | 8/2008 |
| CN | 101250502 A | 10/2009 |
| CN | 101550428 A | 10/2009 |
| EP | 1384775 A1 | 1/2004 |
| EP | 1403366 A1 | 3/2004 |
| EP | 1970446 A1 | 9/2008 |
| EP | 2096169 A1 | 9/2009 |
| JP | 2-227075 | 9/1990 |
| JP | 2002-065261 | 3/2002 |
| JP | 2003-009854 | 1/2003 |
| JP | 2004-161682 A | 6/2004 |
| JP | 2005-095027 | 4/2005 |
| JP | 2005-359537 | 12/2005 |
| JP | 2008-283972 | 11/2008 |
| WO | WO 95/10619 A2 | 4/1995 |
| WO | WO 95/10619 A3 | 7/1995 |
| WO | WO 97/05265 A1 | 2/1997 |
| WO | WO 98/02529 | 1/1998 |
| WO | WO 99/64568 | 12/1999 |
| WO | 00/18885 | 4/2000 |
| WO | WO 00/23567 A2 | 4/2000 |
| WO | 00/27995 A1 | 5/2000 |
| WO | WO 00/23567 A3 | 7/2000 |
| WO | WO 01/21767 A2 | 3/2001 |
| WO | 01/34776 A1 | 5/2001 |
| WO | 01/51616 A2 | 7/2001 |
| WO | WO 01/21767 A3 | 8/2001 |
| WO | 01/81549 A2 | 11/2001 |
| WO | WO 00/73423 A1 | 12/2001 |
| WO | WO 02/00871 A2 | 1/2002 |
| WO | 02/061033 A2 | 8/2002 |
| WO | WO 02/00871 A3 | 10/2002 |
| WO | WO 02/86129 A1 | 10/2002 |
| WO | WO 02/086134 A2 | 10/2002 |
| WO | 02/097090 | 12/2002 |
| WO | 03/018780 A1 | 3/2003 |
| WO | WO 02/086134 A3 | 12/2003 |
| WO | 2004/081205 A1 | 9/2004 |
| WO | 2005/035741 A1 | 4/2005 |
| WO | 2005/080598 A1 | 9/2005 |
| WO | 2005/090557 A1 | 9/2005 |
| WO | 2006/035741 A1 | 4/2006 |
| WO | WO 2006/084229 A2 | 8/2006 |
| WO | WO 2006/088867 A2 | 8/2006 |
| WO | 2007/026255 A2 | 3/2007 |
| WO | WO 2007/054720 A1 | 5/2007 |
| WO | 2007/069666 A1 | 6/2007 |
| WO | 2007/097494 A1 | 8/2007 |
| WO | 2008/030610 A2 | 3/2008 |
| WO | WO 2008/035110 A1 | 3/2008 |
| WO | 2008/038148 A2 | 4/2008 |
| WO | WO 2008/089351 A1 | 7/2008 |
| WO | 2008/105630 A1 | 9/2008 |
| WO | WO 2008/105566 A1 | 9/2008 |
| WO | WO 2008/116213 A1 | 9/2008 |
| WO | 2008/118820 A2 | 10/2008 |
| WO | 2008/124133 A1 | 10/2008 |
| WO | WO 2008/118820 A3 | 11/2008 |
| WO | 2008/151058 A2 | 12/2008 |
| WO | WO 2008/150814 A2 | 12/2008 |
| WO | 2009/006930 A1 | 1/2009 |
| WO | 2009/006997 A1 | 1/2009 |
| WO | 2009/007852 A2 | 1/2009 |
| WO | WO 2008/151058 A3 | 1/2009 |
| WO | WO 2008/150814 A3 | 2/2009 |
| WO | WO 2009/023161 A1 | 2/2009 |
| WO | 2009/032456 A2 | 3/2009 |
| WO | WO 2009/032194 A1 | 3/2009 |
| WO | WO 2009/032456 A3 | 4/2009 |
| WO | 2009/057831 A1 | 5/2009 |
| WO | WO 2009/057831 A1 | 5/2009 |
| WO | WO 2009/061442 A1 | 5/2009 |
| WO | WO 2009/067563 A1 | 5/2009 |
| WO | WO 2009/007852 A3 | 8/2009 |
| WO | WO 2009/096614 A1 | 8/2009 |
| WO | WO 2009/102983 A2 | 8/2009 |
| WO | WO2009/115295 A1 | 9/2009 |
| WO | WO 2009/133971 A1 | 11/2009 |

| | | | |
|---|---|---|---|
| WO | WO 2009/102983 A3 | 12/2009 | |
| WO | WO 2009/144008 A1 | 12/2009 | |
| WO | WO2009/149233 A1 | 12/2009 | |
| WO | WO2010/013359 A1 | 2/2010 | |
| WO | WO2010/048567 A1 | 4/2010 | |

OTHER PUBLICATIONS

Wakayama et al., "Full-term development of mice from enucleated oocytes injected with cumulus cell nuclei" *Nature* 394:369-74, 1998.
Wilmut et al., "Viable offspring derived from fetal and adult mammalian cells" *Nature* 385:810-13, 1997.
Hwang et al., "Evidence of a Pluriportent Human Embryonic Stem Cell Line Derived from a Cloned Blastocyst" *Science* 303:1669-74, 2004.
Hwang et al., "Patient-Specific Embryonic Stem Cells Derived from Human SCNT Blastocysts" *Science* 308:1777-83, 2005.
Tada et al., "Nuclear reprogramming of somatic cells by in vitro hybridization with ES cells" *Current Biology* 11(19):1553-58, 2001.
Cowan et al., "Nuclear Reprogramming of Somatic Cells After Fusion with Human Embryonic Stem Cells" *Science* 309:1369-73, 2005.
Taranger et al., "Induction of Dedifferentiation, Genomewide Transcriptional Programming, and Epigenetic Reprogramming by Extracts of Carcinoma and Embryonic Stem Cells" *Mol. Biol. Cell* 16:5719-35, 2005.
Tokuzawa et al., "Fbx15 Is a Novel Target of Oct3/4 but is Dispensable for Embryonic Stem Cell Self-Renewal and Mouse Development" *Mol. Cell Biol.* 23(8): 2699-708, 2003.
Okamoto et al., "A Novel Octamer Binding Transcription Factor is Differentially Expressed in Mouse Embryonic Cells" *Cell* 60:461-72, 1990.
Nichols et al., "Formation of Pluripotent Stem Cells in the Mammalian Embryo Depends on the POU Transcription Factor Oct4" *Cell* 95:379-91, 1998.
Ghaleb et al., "Krüppel-like factors 4 and 5: the yin and yang regulators of cellular proliferation" *Cell Res.* 15(2):92-96, 2005.
Adhikary et al., "Transcriptional regulation and transformation by Myc proteins" *Nat. Rev. Mol. Cell Biol.* 6:635-45, 2005.
Cartwright et al., "LIF/STAT3 controls ES cell self-renewal and pluripotency by a Myc-dependent mechanism" *Development* 132:885-96, 2005.
Avilion et al., "Multipotent cell lineages in early mouse development depend on SOX2 function" *Genes Dev.* 17:126-40, 2003.
Horikawa et al., "Differential cis-regulation of human versus mouse *TERT* gene expression in vivo: Identification of a human-specific repressive element" *Proc. Natl. Acad. Sci. U.S.A.* 102(51):18437-42, 2005.
Akimov et al., "Bypass of Senescence, Immortalization, and Transformation of Human Hematopoietic Progenitor Cells" *Stem Cells* 23:1423-33, 2005.
Salmon et al., "Reversible Immortalization of Human Primary Cells by Lentivector-Mediated Transfer of Specific Genes" *Mol. Ther.* 2(4):404-14, 2000.
Mitsui et al., "The Homeoprotein Nanog Is Required for Maintenance of Pluripotency in Mouse Epiblast and ES cells" *Cell* 113:631-42, 2003.
Takahashi et al., "Role of ERas in promoting tumour-like properties in mouse embryonic stem cells" *Nature* 423:541-45, 2003.
Bortvin et al., "Incomplete reactivation of *Oct4*-related genes in mouse embryos cloned from somatic nuclei" *Development* 130:1673-80, 2003.
Sato et al., "Maintenance of pluripotency in human and mouse embryonic stem cells through activation of Wnt signaling by a pharmacological GSK-3-specific inhibitor" *Nat. Med.* 10(1):55-63, 2004.
Maruyama et al., "Differential Roles for Sox15 and Sox2 in Transcriptional Control in Mouse Embryonic Stem Cells" *J. Biol. Chem.* 280(26):24371-79, 2005.
Loriot et al., "Five new human cancer-germline genes identified among 12 genes expressed in spermatogonia." *Int. J. Cancer* 105:371-76, 2003.
Kohlhase et al., "Cloning and expression analysis of *Sall4*, the murine homologue of the gene mutated in Okihiro syndrome" *Cytogenet. Genome Res.* 98:274-77, 2002.

Ben-Shushan et al., "*Rex-1*, a Gene Encoding a Transcription Factor Expressed in the Early Embryo, Is Regulated via Oct-3/4 and Oct-6 Binding to an Octomer Site and a Novel Protein, Rox-1, Binding to an Adjacent Site" *Mol. Cell Biol.* 18(4):1866-78, 1998.
Okuda et al., "UTF1, a novel transcriptional coactivator expressed in pluripotent embryonic stem cells and extra-embryonic cells" *EMBO J.* 17(7):2019-32, 1998.
Niwa et al., "Self-renewal of pluripotent embryonic stem cells is meditated via activation of STAT3" *Genes Dev.* 12:2048-60, 1998.
Cheng et al., "Mammalian Grb2 Regulates Multiple Steps in Embryonic Development and Malignant Transformation" *Cell* 95:793-803, 1998.
Maherali et al., "Directly Reprogrammed Fibroblasts Show Global Epigenetic Remodeling and Widespread Tissue Contribution" *Cell Stem Cell* 1:55-70, 2007.
Okita et al., "Generation of germline-competent induced pluripotent stem cells" *Nature* 448:313-17, 2007.
Wernig et al., "In vitro reprogramming of fibroblasts into a pluripotent ES-cell-like state" *Nature* 448:318-24, 2007.
Takahashi et al., "Induction of Pluripotent Stem Cells from Mouse Embryonic and Adult Fibroblast Cultures by Defined Factors" *Cell* 126(4):663-76, published online Aug. 10, 2006.
Morita et al., "Plat-E: an efficient and stable system for transient packaging of retroviruses" *Gene Ther.* 7:1063-66, 2000.
Verrey et al., "CATs and HATs: the SLC7 family of amino acid transporters" *Pflügers Archiv-European Journal of Physiology*, DOI 10.1007/s00424-003-1086-z, pp. 1-23, published online Jun. 11, 2003.
McMahon et al., "The *Wnt-1* (*int-1*) Proto-Oncogene Is Required for Development of a Large Region of the Mouse Brain" *Cell* 62:1073-85, 1990.
Adewumi et al., "Characterization of human embryonic stem cell lines by the International Stem Cell Initiative" *Nat. Biotechnol.* 25(7):803-16, 2007.
Cowan et al., "Derivation of Embryonic Stem-Cell Lines from Human Blastocysts" *N. Engl. J. Med.* 350:1353-56, 2004.
Itskovitz-Eldor et al., "Differentiation of Human Embryonic Stem Cells into Embryoid Bodies Comprising the Three Embryonic Germ Layers" *Mol. Med.* 6(2):88-95, 2000.
Kawasaki et al., "Induction of Midbrain Dopaminergic Neurons from ES Cells by Stromal Cell-Derived Inducing Activity" *Neuron* 28:31-40, 2000.
Laflamme et al., "Cardiomyocytes derived from human embryonic stem cells in pro-survival factors enhance function of infracted rat hearts" *Nat. Biotechnol.* 25(9):1015-24, 2007.
Rao, "Conserved and divergent paths that regulate self-renewal in mouse and human embryonic stem cells" *Dev. Biol.* 275:269-86, 2004.
Amit et al., "Clonally Derived Human Embryonic Stem Cell Lines Maintain Pluripotency and Proliferative Potential for Prolonged Periods of Culture" *Dev. Biol.* 227:271-78, 2000.
Matsuda et al., "STAT3 activation is sufficient to maintain an undifferentiated state of mouse embryonic stem cells" *EMBO J.* 18(15):4261-69, 1999.
Xu et al., "Basic FGF and suppression of BMP signaling sustain undifferentiated proliferation of human ES cells" *Nat. Methods* 2(3):185-90, 2005.
Ying et al., "BMP Induction of Id Proteins Suppresses Differentiation and Sustains Embryonic Stem Cell Self-Renewal in Collaboration with STAT3" *Cell* 115:281-92, 2003.
Boyer et al., "Core Transcriptional Regulatory Circuitry in Human Embryonic Stem Cells" *Cell* 122:947-56, 2005..
Loh et al., "The Oct4 and Nanog transcription network regulates pluripotency in mouse embryonic stem cells" *Nat. Genet.* 38(4):431-40, 2006.
Wang et al., "A protein interaction network for pluripotency of embryonic stem cells" *Nature* 444:36468, 2006.
Yamanaka, "Strategies and New Developments in the Generation of Patient-Specific Pluripotent Stem Cells" *Cell Stem Cell* 1:39-49, 2007.
Evans et al., "Krüppel-like Factor 4 Is Acetylated by p300 and Regulates Gene Transcription via Modulation of Histone Acetylation" *J. Biol. Chem.* 282(47):33994-34002, 2007.

Sumi et al., "Apoptosis and differentiation of human embryonic stem cells induced by sustained activation of c-Myc" *Oncogene* 26:5564-76, 2007.

Chambers et al., "Functional Expression Cloning of Nanog, a Pluripotency Sustaining Factor in Embryonic Stem Cells" *Cell* 113:643-55, 2003.

Ryan et al., "POU domain family values: flexibility, partnerships, and developmental codes" *Genes Dev.* 11:1207-25, 1997.

Schepers et al., "Twenty Pairs of *Sox*: Extent, Homology, and Nomenclature of the Mouse and Human *Sox* Transcription Factor Gene Families" *Dev. Cell* 3:167-70, 2002.

Dang et al., "The biology of the mammalian Krüppel-like family of transcription factors" *Int. J Biochem. Cell Biol.* 32:1103-21, 2000.

Vintersten et al., "Mouse in Red: Red Fluorescent Protein Expression in Mouse ES Cells, Embryos, and Adult Animals" *Genesis* 40:241-46, 2004.

Meiner et al., "Disruption of the acyl-CoA:cholesterol acyltransferase gene in mice: Evidence suggesting multiple cholesterol esterification enzymes in mammals" *Proc. Natl. Acad. Sci. U.S.A.* 93:14041-46, 1996.

Yu et al., "Induced Pluripotent Stem Cell Lines Derived from Human Somatic Cells" *Science* 318(5858):1917-20, published online Nov. 20, 2007.

Takahashi et al., "Induction of Pluripotent Stem Cells from Adult Human Fibroblasts by Defined Factors" *Cell* 131(5):861-72, published online Nov. 20, 2007.

Nakagawa et al., "Generation of induced pluripotent stem cells without Myc from mouse and human fibroblasts" *Nat. Biotechnol.* 26(1):101-06, published online Nov. 30, 2007.

Takahashi et al., "Induction of pluripotent stem cells from fibroblast cultures" *Nat. Protocols* 2(12):3081-89, published online Nov. 29, 2007.

Yamanaka et al., "Mouse Sen'iga Saibo Kara Yudo Tanosei Kansaibo o Tsukuru (Induction of pluripotent stem cells from mouse fibroblast cultures)" *Tanpakushitsu Kakusan Koso* (*Protein, Nucleic Acid and Enzyme*) 51(15):2346-51, 2006.

Yamanaka, "Pluripotency of differentiation and miRNA" *The Journal of Biochemistry*, vol. 79, No. 11, Abstract 3BT17 from the 80th Annual Meeting of the Japanese Biochemical Society, Nov. 25, 2007, along with an English language translation.

Koyanagi et al., "Screening and functional analysis of microRNAs which involve in reprogramming of murine somatic cells" *The Journal of Biochemistry*, vol. 79, No. 11, Abstract 1T7-7 from the 80th Annual Meeting of the Japanese Biochemical Society, Nov. 25, 2007, along with an English language translation.

Zhang et al., "MicroRNA: A New Player in Stem Cells" *Journal of Cellular Physiology* 209:266-269, 2006.

Spivakov et al. "Epigenetic signatures of stem-cell identity" *Nat. Rev. Genet.* 8(4):263-271, 2007.

Suh et al. "Human embryonic stem cells express a unique set of microRNAs" *Developmental Biology* 270:488-498, 2004.

Hatfield et al., "Stem cell division is regulated by the microRNA pathway" *Nature* 435(7044):974-978, 2005.

Kanellopoulou et al. "Dicer-deficient mouse embryonic stem cells are defective in differentiation and centromeric silencing" *Genes & Development* 19:489-501, 2005.

Bang et al. "Deconstructing Pluripotency" *Science* 320:58-59, 2008.

Viswanathan et al. "Selective Blockade of MicroRNA Processing by Lin28" *Science* 320:97-100, 2008.

Aoi et al., "Generation of pluripotent stem cells from adult mouse liver and stomach cells" *Science* 321(5889):699-702, published online Feb. 14, 2008.

Brambrink et al., "Sequential expression of pluripotency markers during direct reprogramming of mouse somatic cells" *Cell Stem Cell* 2(2):151-59, 2008.

Barrett et al. "Activation Domains of L-Myc and c-Myc Determine Their Transforming Potencies in Rat Embryo Cells" *Mol. Cell. Biol.* 12(7):3130-37, 1992.

Benetti et al., "A mammalian microRNA cluster controls DNA methylation and telomere recombination via Rbl2-dependent regulation of DNA methyltransferases" *Nat. Struct. Mol. Biol.* 15(3):268-79, published online Mar. 2, 2008.

Birrer et al., "L-*myc* Cooperates with *ras* to Transform Primary Rat Embryo Fibroblasts" *Mol. Cell. Biol.* 8(6):2668-73, 1988.

Blackwood et al., "Max: a helix-loop-helix zipper protein that forms a sequence-specific DNA-binding complex with Myc" *Science* 251(4998):1211-17, 1991.

Blelloch et al., "Generation of Induced Pluripotent Stem Cells in the Absence of Drug Selection" *Cell Stem Cell* 1(3):245-247, 2007.

Block et al., "Population Expansion, Clonal Growth, and Specific Differentiation Patterns in Primary Cultures of Hepatocytes Induced by HGF/SF, EGF and TGFα in a Chemically Defined (HGM) Medium" *J. Cell Biol.* 132(6):1133-49, 1996.

Brough et al., "An Essential Domain of the c-Myc Protein Interacts with a Nuclear Factor That Is Also Required for E1A-Mediated Transformation" *Mol. Cell. Biol.* 15(3):1536-44, 1995.

Griffiths-Jones et al., "miRBase: tools for microRNA genomics" *Nucleic Acids Research* 36:D154-D158, published online Nov. 8, 2007.

Hanna et al., "Treatment of sickle cell anemia mouse model with iPS cells generated from autologous skin" *Science* 318(5858):1920-23, published online Dec. 6, 2007.

Hasegawa et al., "Efficient Multicistronic Expression of a Transgene in Human Embryonic Stem Cells" *Stem Cells* 25:1707-12, 2007.

Herold et al. "Negative Regulation of the Mammalian UV Response by Myc through Association with Miz-1" *Mol. Cell* 10(3):509-21, 2002.

Houbaviy et al., "Embryonic Stem Cell-Specific MicroRNAs" *Developmental Cell* 5(2):351-58, 2003.

Hsiao et al., "Marking Embryonic Stem Cells with a 2A Self-Cleaving Peptide: A NKX2-5 Emerald GFP BAC Reporter" *PLoS ONE* 3(7):e2532, 2008.

Humphries, C. "Reprogrammed Stem Cells Work on Parkinson's: A study in rodents suggests that skin cells can be transformed into neurons to treat neurodegeneration" *Technology Review*, published by MIT, Apr. 8, 2008; http:///www.technologyreview.com/printer_friendly_article.aspx?id=20530.

*Jikken Igaku* (*Experimental Medicine*) 24:814-19, 2006, along with an English language translation thereof.

Li et al., "Leukaemia disease genes: large-scale cloning and pathway predictions" *Nat. Genet.* 23(3):348-353, 1999.

Lowry et al., "Generation of human induced pluripotent stem cells from dermal fibroblasts" *Proc. Natl. Acad. Sci. U.S.A.* 105(8):2883-88, 2008.

Mali et al., "Improved Efficiency and Pace of Generating Induced Pluripotent Stem Cells from Human Adult and Fetal Fibroblasts" *Stem Cells*, published online May 29, 2008, DOI:10.1634/stemcells.2008-0346.

Masaki et al., "Heterogeneity of pluripotent marker gene expression in colonies generated in human iPS cell induction culture" *Stem Cell Res.* (2008) DOI:10.1016/j.scr.2008.01.001.

*microRNA Jikken Purotokoru* (*miroRNA Experimental Protocol*), pp. 20-35, 2008, Yodosha Co., Ltd.

Ying et al., "The MicroRNA: Overview of the RNA Gene That Modulates Gene Functions," *Methods in Molecular Biology, MicroRNA Protocols*, vol. 342, pp. 1-18, Humana Press, 2006.

Meissner et al., "Direct reprogramming of genetically unmodified fibroblasts into pluripotent stem cells" *Nat. Biotechnol.* 25(10):1177-1181, published online Aug. 27, 2007.

Nienhuis et al., "Genotoxicity of retroviral integration in hematopoietic cells" *Mol. Ther.* 13(6):1031-49, 2006.

Niwa et al., "Efficient selection for high-expression transfectants with a novel eukaryotic vector" *Gene* 108(2):193-99, 1991.

Nolta et al., "Transduction of pluripotent human hematopoietic stem cells demonstrated by clonal analysis after engraftment in immune-deficient mice" *Proc. Natl. Acad. Sci. USA* 93:2414-19, 1996.

Okita et al., "Generation of mouse induced pluripotent stem cells without viral vectors" *Science* 322(5903):949-53, published online Oct. 9, 2008.

Park et al., "Reprogramming of human somatic cells to pluripotency with defined factors" *Nature* 451:141-46, published online Dec. 23, 2007.

Postic et al., "Dual Roles for Glucokinase in Glucose Homeostasis as Determined by Liver and Pancreatic β Cell-specific Gene Knockouts Using Cre Recombinase" *J. Biol. Chem.* 274(1):305-15, 1999.

Sakai et al., "A Transgenic Mouse Line That Retains Cre Recombinase Activity in Mature Oocytes Irrespective of the cre Transgene Transmission" Biochem. Biophys. Res. Commun. 237(2):318-24, 1997.
Sinkkonen et al., "MicroRNAs control de novo DNA methylation through regulation of transcriptional repressors in mouse embryonic stem cells" Nat. Struct. Mol. Biol. 15(3):259-267, published online Mar. 2, 2008.
Spencer et al., "E-Cadherin Inhibits Cell Surface Localization of the Pro-Migratory 5T4 Oncofetal Antigen in Mouse Embryonic Stem Cells" Mol. Biol. Cell 18:2838-51, 2007.
Stadtfeld et al., "Induced pluripotent stem cells generated without viral integration" Science 322(5903):945-49, published online Sep. 25, 2008.
Stadtfeld et al., "Defining Molecular Cornerstones during Fibroblast to iPS Cell Reprogramming in Mouse" Cell Stem Cell 2(3):230-40, 2008.
Takahashi et al. "Induced Pluripotent Stem Cells" Jikken Igaku (Experimental Medicine) 26(5):35-40, 2008.
Takeda et al. "Human Oct3 gene family: cDNA sequences, alternative splicing, gene organization, chromosomal location, and expression at low levels in adult tissues" Nucleic Acids Research 20(17):4613-4620, 1992.
Tateno et al., "Heterogeneity of growth potential of adult rat hepatocytes in vitro" Hepatology 31(1):65-74, 2000.
Qin et al., "Direct generation of ES-like cells from unmodified mouse embryonic fibroblasts by Oct4/Sox2/Myc/Klf4" Cell Res. 17(11):959-62, 2007.
Wernig et al., "c-Myc is dispensable for direct reprogramming of mouse fibroblasts" Cell Stem Cell 2(1):10-12, published online Dec. 13, 2007.
Wernig et al., "Neurons derived from reprogrammed fibroblasts functionally integrate into the fetal brain and improve symptoms of rats with Parkinson's disease" Proc. Natl. Acad. Sci. U.S.A. 105(15):5856-5861, 2008.
Yang et al., "Nuclear reprogramming of cloned embryos and its implications for therapeutic cloning" Nat. Genet. 39(3):295-302, 2007.
"Stem cells made to mimic disease" BBC News, http ://newsvote.bbc.co.uk/mpapps/pagetools/print/news.bbc.co.uk/2/hi/health/7334365.stm, Apr. 7, 2008.
English language Abstract of JP 2002-065261, Mar. 5, 2002.
English language Abstract of JP 2003-009854, Jan. 14, 2003.
English language Abstract of JP 2005-095027, Apr. 14, 2005.
English language Abstract of JP 2004-161682 A, Jun. 10, 2004.
English language Abstract of JP 2008-283972, Nov. 27, 2008.
Check, "Simple Recipe Gives Adult Cells Embryonic Powers" Nature 442:11, Jul. 6, 2006.
Cyranoski et al., "Simple Switch Turns Cells Embryonic" Nature 447:618-619, Jun. 7, 2007.
Correction printed in Nature 447:897, Jun. 21, 2007.
Hanna et al., "Direct Reprogramming of Terminally Differentiated Mature B Lymphocytes to Pluripotency" Cell 133:250-264, Apr. 17, 2008.
Liao et al., "Enhanced Efficiency of Generating Induced Pluripotent Stem (iPS) Cells from Human Somatic Cells by a Combination of Six Transcription Factors" Cell Research 18:600-603, doi: 10.1038/cr.2008.51, published online Apr. 15, 2008.
Surani et al., "A New Route to Rejuvenation" Nature 443:284-285, Sep. 21, 2006.
Kyoto Shimbun (Japanese Newspaper) article of Apr. 16, 2008, columns 1-3, along with a partial English language translation thereof.
Newton "Attracting world's attention. Pluripotent cells are generated from human skin. What is the 'iPS cell' that can be used not only in the regeneration therapy but also in the tailor-made therapy" pp. 70-75, Feb. 2008, along with a partial English language translation.
Asahi Shimbun Weekly AERA "The novel pluripotent cells established by Professor Yamanaka of Kyoto University may change medical care" pp. 72-73, published Dec. 24, 2007, along with a partial English language translation.
U.S. Appl. No. 12/289,873, filed Nov. 6, 2008 to Yamanaka et al., entitled "Nuclear Reprogramming Factor and Induced Pluripotent Stem Cells."
U.S. Appl. No. 12/292,717, filed Nov. 25, 2008 to Yamanaka et al., entitled "Efficient Method for Nuclear Reprogramming."
U.S. Appl. No. 12/379,564, filed Feb. 25, 2009 to Yamanaka et al., entitled "Efficient Method for Nuclear Reprogramming."
Huangfu et al., "Induction of Pluripotent Stem Cells by Defined Factors is Greatly Improved by Small-Molecule Compounds" Nature Biotechnology 26(7):795-97, 2008.
Kubicek et al., "Reversal of H3K9me2 by a Small-Molecule Inhibitor for the G9a Histone Methyltransferase" Molecular Cell 25:473-81, 2007.
Lin et al., "Mir-302 Reprograms Human Skin Cancer Cells into a Pluripotent ES-Cell-Like State" RNA 14:1-10, 2008.
Marson et al., "Wnt Signaling Promotes Reprogramming of Somatic Cells to Pluripotency" Cell Stem Cell 3:132-35, 2008.
Nolta et al., "Transduction of Pluripotent Human Hematopoietic Stem Cells Demonstrated by Clonal Analysis After Engraftment in Immune-Deficient Mice" Proc. Natl. Acad. Sci. USA 93(6):2414-19, 1996.
Shi et al., "A Combined Chemical and Genetic Approach for the Generation of Induced Pluripotent Stem Cells" Cell Stem Cell 2:525-28, 2008.
Shi et al., "Induction of Pluripotent Stem Cells from Mouse Embryonic Fibroblasts by Oct4 and Klf4 with Small-Molecule Compounds" Cell Stem Cell 3:568-74, 2008.
Silva et al., "Promotion of Reprogramming to Ground State Pluripotency by Signal Inhibition" PLoS Biology 6(10):2237-47, 2008.
Zhao et al., "Two Supporting Factors Greatly Improve the Efficiency of Human iPSC Generation" Cell Stem Cell 3:475-79, 2008.
Kim et al., "Generation of Human Induced Pluripotent Stem Cells by Direct Delivery of Reprogramming Proteins" Cell Stem Cell 4:472-476, 2009.
Ziegler et al., "The Cationic Cell-Penetrating Peptide $CPP^{TAT}$ Derived from the HIV-1 Protein TAT Is Rapidly Transported into Living Fibroblasts: Optical, Biophysical, and Metabolic Evidence" Biochemistry 44:138-148, published online Dec. 14, 2004.
Zhou et al., "Generation of Induced Pluripotent Stem Cells Using Recombinant Proteins" Cell Stem Cell 4:381-384, 2009.
Wadia et al., "Protein Transduction Technology" Curr. Opin. Biotechnol. 13:52-56, 2002.
Cosmo Bio News 49:5, 2005 (catalog of ES cell culture medium).
BioPorter™ Gene Therapy System, Inc., Wako Bio Window 40:7, 2002.
BioPorter™ Protein Delivery Reagent from www.biocarta.com.
Wakayama et al., "Differentiation of Embryonic Stem Cell Lines Generated from Adult Somatic Cells by Nuclear Transfer" Science 292:740-43, 2001.
Amsellem et al., "Ex vivo Expansion of Human Hematopoietic Stem Cells by Direct Delivery of the HOXB4 Homeoprotein" Nat. Med. 9(11):1423-27, 2003.
Krosl et al., "In vitro Expansion of Hematopoietic Stem Cells by Recombinant TAT-HOXB4 Protein" Nat. Med. 9(11):1428-32, 2003.
Kim et al., "Oct4-Induced Pluripotency in Adult Neural Stem Cells" Cell 136:411-419, 2009.
Kim et al., "Pluripotent Stem Cells Induced From Adult Neural Stem Cells by Reprogramming with Two Factors" Nature 454:646-650, 2008.
Huangfu et al., "Induction of Pluripotent Stem Cells From Primary Human Fibroblasts with Only Oct4 and Sox 2" Nature Biotechnology 26:1269-1275, 2008.
Feng et al., "Reprogramming of Fibroblasts into Induced Pluripotent Stem Cells with Orphan Nuclear Receptor Esrrb" Nature Cell Biology 11:197-203, 2009.
Mali et al. "Improved Efficiency and Pace of Generating Induced Pluripotent Stem Cells from Human Adult and Fetal Fibroblasts" Stem Cells 26:1998-2005, 2008.
Yu et al., "Human Induced Pluripotent Stem Cells Free of Vector and Transgene Sequences" Science 324:797-801, 2009.
Amit et al., Developmental Biology 227, 271-78 (2000).
Okita et al., 2008 Science 322: 949-53.
Peister et al., Gene Ther. Jan. 11, 2004(2):224-8.
Quenneville et al., Mol. Ther. Oct. 10, 2004(4): 679-87.
Stadtfeld et al., 2008 Science 322: 945-49.

Wernig et al., Nature 448, 318-324, 322 (2007).
Bibel et al., Differentiation of Mouse Embryonic Stem Cells Into a Defined Neuronal Lineage, Nature Neuroscience, 2004, vol. 7, pp. 1003-1009.
Chang et al., Embryonic Stem Cells/Induced Pluripotent Stem Cells, Stem Cells, 2009, vol. 27, pp. 1042-1049.
Cohen et al., Molecular Human Reproduction, 1998, vol. 4, pp. 269-280.
Do et al., Stem Cells, 2004, vol. 22, pp. 941-949.
Kaji et al., Virus-Free Induction of Pluripotency and Subsequent Excision of Reprogramming Factors, Nature, Mar. 1, 2009, vol. 458, Issue 7239, pp. 771-775.
Okabe et al., Green Mice as a Source of Ubiquitous Green Cells, FEBS Letters, 1997, vol. 407, pp. 313-319.
Shao et al., Generation of iPS Cells Using Defined Factors Linked Via the Self-Cleaving 2A Sequences in a Single Open Reading Frame, Cell Res., Mar. 2009, vol. 19, Issue 3, pp. 296-312.
Soldner et al., Parkinson's Disease Patient-Derived Induced Pluripotent Stem Cells Free of Viral Reprogramming Factors, Cell, Mar. 6, 2009, vol. 136, Issue 5, pp. 964-977.
Takeda et al., Characterization of Dental Pulp Stem Cells of Human Tooth Germs, Journal of Dental Research, 2008, vol. 87, pp. 676-681.
Tsunoda, The Recent Progress on Nuclear Transfer in Mammals, Zoological Science, 2000, vol. 17, pp. 1177-1184.
Woltjen et al., PiggyBac Transposition Reprograms Fibroblasts to Induced Pluripotent Stem Cells, Nature, Mar. 1, 2009, vol. 458, Issue 7239, pp. 766-770.
Wu, et al., Sall4 Interacts With Nanog and Co-Occupies Nanog Genomic Sites in Embryonic Stem Cells, J. Biol. Chem., 2000, vol. 281, Issue 34, pp. 24090-24094.
Crouch, D.H., et al., Multiple Phenotypes Associated With Myc-Induced Transformation of Chick Embryo Fibroblasts Can Be Dissociated by a Basic Region Mutation, Nucleic Acids Research 24(16):3216-3221, 1996.
International Search Report and Written Opinion issued in PCT/JP2011/051685.
Nakagawa, M., et al., Promotion of Direct Reprogramming by Transformation-Deficient Myc., Proc. Natl. Acad. Sci. USA 107(32):14152-14157, Aug. 2010.
Sarid, J., et al., Evolutionarily Conserved Regions of the Human c-Myc Protein Can Be Uncoupled From Transforming Activity, Proc. Natl. Acad. Sci. USA 84(1):170-173, 1987.
Bigdeli et al., Adaptation of Human Embryonic Stem Cells to Feeder-Free and Matrix-Free Culture Conditions Directly on Plastic Surfaces. J. Biotec., 2008, vol. 133, pp. 146-153.
Essentials of Stem Cell Biology, R. Lanza et al., Ed., 2006, Elsevier Academic Press, pp. 266-267.
Official Action issued in connection with Canadian Patent Application No. 2,632,142., 2010.
Official Action issued in connection with New Zealand Patent Application No. 569530., 2010.
Rodriquez, R.T., et al., Manipulation of OCT4 Levels in Human Embryonic Stem Cells Results in Induction of Differential Cell Types, Experimental Biology and Medicine, 2007, vol. 232, pp. 1368-1380.
Strelchenko et al. Embryonic Stem Cells from Morula, Methods in Enzymology, 2006, vol. 418, pp. 93-108.
Australian Examination Report on Patent Application No. 2006325975 to Kyoto University, issued Apr. 18, 2011.
Nagano et al., "Large-scale identification of proteins expressed in mouse embryonic stem cells," Proteomics 2005, 5, pp. 1346-1361., 2005.
Okumura-Nakanishi et al., "Oct-3/4 and Sox2 Regulate Oct-3/4 Gene in Embryonic Stem Cells," The Journal of Biological Chemistry, vols. 280, No. 7, Issue of Feb. 18, pp. 5307-5317 (2006).
Wakao et al., "Multilineage-differentiating stress-enduring (Muse) cells are a primary source of induced pluripotent stem cells in human fibroblasts," available at www.pnas.org/cgi/content/short/1100816108.
Bongso, A., et al., Isolation and Culture of Inner Cell Mass Cells From Human Blastocysts, Human Reproduction 9(11):2110-2117, 1994.

A reprogramming rush. Editorial. Nature. Mar. 27, 2008. 452:388. Published online Mar. 26, 2008.
Adachi et al. Role of SOX2 in maintaining pluripotency of human embryonic stem cells. Genes Cells. May 2010; 15(5):455-70.
Allergucci et al. Differences between human embryonic stem cell lines. Hum Reprod Update. Mar.-Apr. 2007;13(2):103-20.
Altschul et al. Gapped BLAST and PSI-BLAST: a new generation of protein database search programs. Nucleic Acids Research. 1997;25(17): 3389-3402.
Anderson et al. Transgenic enrichment of cardiomyocytes from human embryonic stem cells. Mol Ther. Nov. 2007; 15(11):2027-36.
Assady et al. Insulin production by human embryonic stem cells. Diabetes. Aug. 2001;50(8): 1691-7.
Assou et al. A meta-analysis of human embryonic stem cells transcriptome integrated into a web-based expression atlas. Stem Cells. Apr. 2007;25(4):961-73.
Bader et al. Leukemia inhibitory factor modulates cardiogenesis in embryoid bodies in opposite fashions. Circ Res. Apr. 14, 2000;86(7):787-94.
Bagutti et al. Differentiation of embryonal stem cells into keratinocytes: comparison of wild-type and beta 1 integrin-deficient cells. Dev Biol. Oct. 10, 1996; 179(1): 184-96.
Barrett et al. NCBI GEO: mining tens of millions of expression profiles—database and tools update. Nucleic Acids Res. Jan. 2007;35(Database issue):D760-S.
Berg et al. An argument against a role for Oct4 in somatic stem cells. Cell Stem Cell. Oct. 11, 2007;1(4):359-60.
Birnbaum et al. Slicing across Kingdoms: Regeneration in Plants and Animals. Cell. Feb. 22, 2008; 132(4):697-710.
Blow, N. Stem cells: in search of common ground. Nature. Feb. 14, 2008;451 (7180):855-8.
Bonetta, L. European Stem Cell Patents: Taking the moral High Road? Cell. Feb. 22,2008; 132(4):S14-S16.
Brüstle et al. Embryonic stem cell-derived glial precursors: a source of myelinating transplants. Science. Jul. 30, 1999;285(5428):754-6.
Cai et al. Directed differentiation of human embryonic stem cells into functional hepatic cells. Hepatology. May 2007;45(5): 1229-39.
Chadwick et al. Cytokines and BMP-4 promote hematopoietic differentiation of human embryonic stem cells. Blood. Aug. 1, 2003; 102(3):906-15.
Chang et al. The c-Myc transactivation domain is a direct modulator of apoptotic versus proliferative signals. Mol Cell Biol. Jun. 2000;20(12):4309-19.
Childs et al. Regression of metastatic renal-cell carcinoma after nonmyeloablative allogeneic peripheral-blood stem-cell transplantation. N Engl J Med. Sep. 14, 2000;343(11):750-8.
Chin et al. Induced pluripotent stem cells and embryonic stem cells are distinguished by gene expression signatures. Cell Stem Cell. Jul. 2, 2009;5(1): 111-23.
Cinalli et al. Germ Cells are Forever. Cell. Feb. 22, 2008; 132(4):559-562.
Cirm Public Release. $24 Million in New Stem Cell Research Funding Awarded to 25 California Institutions. California Institute for Regenerative Medicine (4 pages). Jun. 27, 2008.
Cline et al. Randomize Gene Sequences with New PCR Mutagenesis Kit. Strategies Newsletter. 2000; 13: 157-161.
Cyranoski, D. Stem cells: 5 things to know before jumping on the iPS bandwagon. Nature. 2008;452(7186)406-408.
Cyranoski. Japan ramps up patent effort to keep iPS lead. Nature. 2008; 453(7198):962-3.
Daley et al. Prospects for Stem Cell Based Therapy. Cell. Feb. 22, 2008; 132(4):544-548.
Dani, et at Differentiation of embryonic stem cells into adipocytes in vitro. J Cell Sci. Jun. 1997;110 (Pt 11):1279-85.
Dewitt et al. "Diversomers": an approach to nonpeptide, nonoligomeric chemical diversity. Proc Natl Acad Sci USA. Aug. 1, 1993;90(15):6909-13.
Dimos et al. Induced pluripotent stem cells generated from patients with ALS can be differentiated into motor neurons. Science. Aug. 29, 2008;321(5893):1218-21.

D'Ippolito et al. Marrow-isolated adult multilineage inducible (MIAMI) cells, a unique population of postnatal young and old human cells with extensive expansion and differentiation potential. J Cell Sci. Jun. 15, 2004; 117(Pt 14):2971-81.

Ehrich et al. Quantitative high-throughput analysis of DNA methylation patterns by base-specific cleavage and mass spectrometry. Proc Natl Acad Sci USA. Nov. 1, 2005; 102(44): 15785-90.

Eisen et al. Cluster analysis and display of genome-wide expression patterns. Dec. 8, 1998;95(25): 14863-14868.

Evans et al. Krüppel-like factor 4 is acetylated by p300 and regulates gene transcription via modulation of histone acetylation. J Biol Chem. Nov. 23, 2007.;282(47): 33994-4002.

Felgner et al. Lipofection: a highly efficient, lipid-mediated DNA-transfection procedure. Proc Natl Acad Sci USA. Nov. 1987;84(21):7413-7.

Ferrer-Costa et al. PMUT: a web-based tool for the annotation of pathological mutations on proteins. Bioinformatics. Jul. 15, 2005;21(14):3176-8.

Gu et al. Opposite regulation of gene transcription and cell proliferation by c-Myc and Max. Proc Natl Acad Sci USA. Apr. 1, 1993;90(7):2935-9.

Ha et al. Cryopreservation of human embryonic stem cells without the use of a programmable freezer. Hum Reprod. Jul. 2005;20(7): 1779-85.

Hanna et al. Direct Reprogramming of Terminally Differentiated Mature B Lymphocytes to Pluripotency. Cell. Apr. 18, 2008;133: 250-264. Erratum in: Cell. 2008; 134(2):365.

Hermann et al. Efficient generation of neural stem cell-like cells from adult human bone marrow stromal cells. J Cell Sci. Sep. 1, 2004; 117(Pt 19):4411-22.

Hockemeyer et al. A drug-inducible system for direct reprogramming of human somatic cells to pluripotency. Cell Stem Cell. Sep. 11, 2008;3(3):346-53.

Jaenisch et al. Stem Cells, the Molecular Circuitry of Pluripotency and Nuclear Reprogramming. Cell. Feb. 22, 2008; 132(4):567-582.

Nagy et al. Embryonic stem cells alone are able to support fetal development in the mouse. Development. Nov. 1990:110(3):815-21.

Nakatake et al. Klf4 cooperates with Oct3/4 and Sox2 to activate the Lefty1 core promoter in embryonic stem cells. Mol Cell Biol. Oct. 26, 2006(20):7772-82.

Needleman et al. A general method applicable to the search for similarities in the amino acid sequence of two proteins. J Mol Biol. Mar. 1970;48(3):443-53.

Ng et al. Predicting the effects of amino acid substitutions on protein function. Annu Rev Genomics Hum Genet. 2006;7:61-80.

Okita et al. Intracellular Signaling Pathways Regulating Pluripotency of Embryonic Stem Cells. Current Stem Cell Research & Therapy. 2006;1:103-111.

Orkin et al. Hematopoiesis: An Evolving Paradigm for Stem Cell Biology. Cell. Feb. 22, 2008; 132(4):631-644.

Osuna et al. Protein evolution by codon-based random deletions. Nucleic Acids Res. Sep. 30, 2004; 32(17): e136.

Padmanabhan et al. Visualization of telomerase reverse transcriptase (hTERT) promoter activity using a trimodality fusion reporter construct. J Nucl Med. Feb. 2006;47(2):270-7.

Park et al. Disease-specific induced pluripotent stem cells. Cell. Sep. 5, 2008; 134(5):877-86.

Park, A. Stem-cell research: The quest resumes. Time Magazine. Feb. 9, 2009. Available at http://www.time.com/time/health/article/ 0,8599,1874717,00.html. Accessed Jun. 3, 2009.

Parson, A.B. Stem Cell Biotech: Seeking a Piece of the Action. Cell. Feb. 22, 2008; 132(4):511-513.

Pear et al. Production of high-titer helper-free retroviruses by transient transfection. Proc. Natl. Acad. Sci. USA, vol. 90, pp. 8392-8396, 1993.

Pearson et al. Improved tools for biological sequence comparison. Proc Natl Acad Sci USA. Apr. 1988:85(8):2444-8.

Pearson, W.R. Rapid and sensitive sequence comparison with FASTP and FASTA. Methods Enzymol. 1990;183:63-98.

Pomp et al. Generation of peripheral sensory and sympathetic neurons and neural crest cells from human embryonic stem cells. Stem Cells. Aug. 2005;23(7):923-30.

Ratajczak et al. Bone-marrow-derived stem cells—our key to longevity? J. Appl. Genet. 2007;48(4): 307-319.

Reubinoff et al. Neural progenitors from human embryonic stem cells. Nat Biotechnol. Dec. 2001;19(12):1134-40.

Riviére et al. Effects of retroviral vector design on expression of human adenosine deaminase in murine bone marrow transplant recipients engrafted with genetically modified cells. Proc Natl Acad Sci USA. Jul. 18, 1995;92(15):6733-7.

Rodda et al. Transcriptional regulation of nanog by OCT4 and SOX2. J Biol Chem. Jul. 1, 2005;280(26):24731-7.

Rodriguez et al., Manipulation of OCT4 Levels in Human Embryonic Stem Cells Results in Induction of Differential Cell Types. Experimental Biology and Medicine, 2007, vol. 232, pp. 1368-1380.

Root et al. Genome-scale loss-of-function screening with a lentiviral RNAi library. Nat Methods. Sep. 2006;3(9):715-9.

Rossant, J. Stem Cell and Early Lineage Development. Cell. Feb. 22, 2008; 132(4):527-531.

Saldanha et al. Assessment of telomere length and factors that contribute to its stability. Eur J Biochem. Feb. 2003;270(3):389-403.

Scherr et al. Gene silencing by small regulatory RNAs in mammalian cells. Cell Cycle. Feb. 1, 2006;6(4):444-9.

Schuldiner et al. Induced neuronal differentiation of human embryonic stem cells. Brain Res. Sep. 21, 2001;913(2):201-5.

Schwenk et al. Hybrid embryonic stem cell-derived tetraploid mice show apparently normal morphological, physiological, and neurological characteristics. Mol Cell Biol. Jun. 2003;23(11):3982-9.

Science magazine names top 10 breakthroughs of 2008. Available at http://arstechnica.com/old/content/2008/12/isciencei-names-top-10-scientific-breakthroughs-of-2008.ars. Accessed May 19, 2009.

Shah, R. Pharmacogenetics in drug regulation: promise, potential and pitfalls. Philos Trans R Soc Lond B Biol Sci. Aug. 29, 2005; 360(1460):1617-1638.

Silva et al. Capturing Pluripotericy. Cell. Feb. 22, 2008; 132(4):532-536.

Silva et al. Profiling essential genes in human mammary cells by multiplex RNAi screening. Science. Feb. 1, 2008;319(5863):617-20.

Skottman et al. Culture conditions for human embryonic stem cells. Reproduction. Nov. 2006;132(5):691-8.

Stadler et al. Small RNAs: Keeping Stem Cells in Line. Cell. Feb. 22, 2008; 132(4):563-566.

Stojkovic et al. Derivation, growth and applications of human embryonic stem cells. Reproduction. Sep. 2004;128(3):259-67.

Swift et al. Rapid production of retroviruses for efficient gene delivery to mammalian cells using 293T cell-based systems. Current Protocols in Immunology, Supp. 31, 1999, pp. 10.17.14-10.17.29.

Tan et al. Changing viral tropism using immunoliposomes alters the stability of gene expression: implications for viral vector design. Mol Med. Mar.-Apr. 2007; 13(3-4):216-26.

Tantin et al. High-throughput biochemical analysis of in vivo location data reveals novel distinct classes of POU5FI(Oct4)/DNA complexes. Genome Res. Apr. 2008;18(4):631-9.

The Japan Times. Bayer team makes stem cells from skin. Apr. 12, 2008. Available at http://search.japantimes.co.jp/cgi-bin/ nn20080412a5.html. Accessed May 19, 2009.

Time. The Top 10 Everything of 2008—1. First Neurons Created from ALS Patients. Available at http://www.time.com/time/specials/ 2008/top10/article/0,30583,1855948_1863993,00.html. Accessed Dec. 15, 2008.

Troyanskaya et al. Nonparametric methods for identifying differentially expressed genes in microarray data. Bioinformatics. 2002;18(11): 1454-1461.

Tsai et al. In vivo immunological function of mast cells derived from embryonic stem cells: an approach for the rapid analysis of even embryonic lethal mutations in adult mice in vivo. Proc Natl Acad Sci USA. Aug. 1, 2000;97(16):9186-90.

Tzukerman et al. Identification of a novel transcription factor binding element involved in the regulation by differentiation of the human telomerase (hTERT) promoter. Mol Biol Cell. Dec. 2000;11(12):4381-91.

Ulloa-Montoya et al. Comparative transcriptome analysis of embryonic and adult stem cells with extended and limited differentiation capacity. Genome Biol. 2007;8(8):R163.

Vallier et al. Activin/Nodal and FGF pathways cooperate to maintain pluripotency of human embryonic stem cells. J Cell Sci. Oct. 1, 2005;118(Pt 19):4495-509.

Vermeesch et al. Guidelines for molecular karyotyping in constitutional genetic diagnosis. Eur J Hum Genet. Nov. 2007;15(11):1105-14.

Vogel, G. Breakthrough of the year. Reprogramming Cells. Science. Dec. 19, 2008;322(5909): 1766-7.

Wang et al. Inhibition of caspase-mediated anoikis is critical for bFGF-sustained culture of human pluripotent stem cells. J Biol Chern. Oct. 16, 2009. [Epub ahead of print].

Watson et al. Identifying Genes Regulated in a Myc-dependent Manner. J Biol Chem. Oct. 4, 2002;277(40):36921-30.

Werbowetski-Ogilvie et al. Characterization of human embryonic stem cells with features of neoplastic progression. Nat Biotechnol. Jan. 2009;27(1):91-7.

Wernig et al. c-Myc is dispensable for direct reprogramming of mouse fibroblast. Cell Stem Cell. 2008; 2, 10-12.

Wernig et al. In vitro reprogramming of fibroblasts into a pluripotent ES-cell-like state. Nature. Jul. 19, 2007;448:318-324.

Wernig et al. Neurons derived from reprogrammed fibroblasts functionally integrate into the fetal brain and improve symptoms of rats with Parkinson's disease. Proc Natl Acad Sci USA. Apr. 15, 2008;105(15):5856-61.

What are adult stem Cells? Stem Cell Information. The National Institutes of Health resource for stem cell research. 2007. Available at: http://stemcells.nih.gov/info/basics/basics4.asp. Accessed Jun. 4, 2007.

Wu et al. Origins and Fates of Cardiovascular Progenitor Cells. Cell. Feb. 22, 2008; 132(4):537-543.

Yamane et al. Derivation of melanocytes from embryonic stem cells in culture. Dev. Dyn. 1999;216:450-458.

Yamashita et al. Flk1-positive cells derived from embryonic stem cells serve as vascular progenitors. Nature. Nov. 2, 2000;408(6808):92-6.

Yu et al. Induced pluripotent stem cell lines derived from human somatic cells. Science. Dec. 21, 2007;318(5858):1917-20.

Yuasa et al. Transient inhibition of BMP signaling by Noggin induces cardiomyocyte differentiation of mouse embryonic stem cells. Nat Biotechnol. May 2005;23(5):607-11.

Zhang et al. In vitro differentiation of transplantable neural precursors from human embryonic stem cells. Nat Biotechnol. Dec. 2001;19(12):1129-33.

Zhao et al. Mechanisms and Functional Implications of Adult Neurogenesis. Cell. Feb. 22, 2008; 132(4):645-660.

Bayani et al. Multi-color FISH techniques. Curr. Protoc. Cell Biol. 2004; Chapter 22:Unit 22.5.

Becker-Hapak et al. Protein transduction: generation of full-length transducible proteins using the TAT system. Curr Protoc Cell Biol. May 2003;Chapter 20: Unit 20.2.

Bendall et al. IGF and FGF cooperatively establish the regulatory stem cell niche of pluripotent human cells in vitro. Nature. Aug. 30, 2007;448(7157): 1015-21.

Bigdeli et al., Adaptation of Human Embryonic Stem Cells to Feeder-Free and Matrix-Free Culture Conditions Directly on Plastic Surfaces. J. Biotec., 2008, vol. 133, pp. 146-153.

Boquest et al. Epigenetic programming of mesenchymal stem cells from human adipose tissue. Stem Cell Rev. 2006;2(4):319-29.

Brena et al. Quantitative assessment of DNA methylation: Potential applications for disease diagnosis, classification, and prognosis in clinical settings. J Mol Med. May 2006;84(5):365-77.

Burns et al. Diabetes mellitus: a potential target for stem cell therapy. Curr Stem Cell Res Ther. May 2006; 1 (2):255-66.

Buttery et al. Differentiation of osteoblasts and in vitro bone formation from murine embryonic stem cells. Tissue Eng. Feb. 2001;7(1):89-99.

Campbell et al. Phosphonate Ester Synthesis Using a Modified Mitsunobu Condensation. J. Org. Chem.1994;59: 658-660.

Chen et al. Analogous Organic-Synthesis of Small-Compound Libraries—Validation of Combinatorial Chemistry in Small-Molecule Synthesis. Journal of the American Chemical Society. 1994;116(6): 2661-2662.

Chen et al. From stem cells to oligodendrocytes: prospects for brain therapy. Stem Cell Rev. Dec. 2007;3(4):280-8.

Cho et al. An unnatural biopolymer. Science. Sep. 3, 1993;261 (5126): 1303-5.

Cirm: Summaries of Review for Applications to RFA 07-05. California Institute for Regenerative Medicine Web site. 2007. Available at: http://www.cirm.ca.gov/RFAlrfa_07-05/. Accessed Jul. 1, 2008.

Coutts et al. Stem cells for the treatment of spinal cord injury. Exp Neurol. Feb. 2008;209(2):368-77.

Cowling et al. Mechanism of transcriptional activation by the Myc oncoproteins. Semin Cancer Biol. Aug. 2006; 16(4):242-52.

D'Amour et al. Efficient differentiation of human embryonic stem cells to definitive endoderm. Nat Biotechnol. Dec. 2005;23(12):1534-41.

D'Amour et al. Production of pancreatic hormone-expressing endocrine cells from human embryonic stem cells. Nat Biotechnol. Nov. 2006;24(11): 1392-401.

Deb, et al. Embryonic Stem Cells: From Markers to Market. Feb. 2008; 11(1): 19-37.

Denker, H. W. Human embryonic stem cells: the real challenge for research as well as for bioethics is still ahead of us. Cells Tissues Organs. 2008;187(4):250-6.

Durcova-Hills et al. Induced reprogramming of human somatic cells into pluripotency: a new way how to generate pluripotent stem cells. Differentiation. Apr. 2008;76(4):323-5.

Ebert, L. Yamanaka scooped on iPS (stem cell) patent?!. TMCNews reports on Jan. 4, 2009. Available at http://ipbiz.blogspot.com/2009/01/yamanaka-scooped-on-ips-stemcell.html. Accessed May 19, 2009.

Elefanty, A. Ed. In this Issue . . . Stem Cell Research. 2008; 1:87.

Essentials of Stem Cell Biology, R. Lanza et al. Ed., 2006, Elsevier Academic Press, pp. 266-267.

Forsyth et al. Human Embryonic Stem Cell Telomere Length Impacts Directly on Clonal Progenitor Isolation Frequency. Rejuvenation Research. Feb. 2008;11(1):5-17.

Gallop et al. Applications of combinatorial technologies to drug discovery. 1. Background and peptide combinatorial libraries. J Med Chem. Apr. 29, 1994;37(9): 1233-51.

Goswami et al. Embryonic stem cell therapy. IDrugs. Oct. 2007;10(10):713-9.

Heng et al. Incorporating protein transduction domains (PTD) within intracellular proteins associated with the 'stemness' phenotype. Novel use of such recombinant 'fusion' proteins to overcome current limitations of applying autologous adult stem cells in regenerative medicine? Med Hypotheses. 2005;64(5):992-6.

Highfield, R. Dolly creator Proflan Wilmut shuns cloning. Available at http://www.telegraph.co.uk/earth/main.jhtml?xml= /earth/2007/11/16/scidolly116.xml. Accessed Nov. 12, 2008.

Huangfu et al. Efficient Induction of Pluripotent Stem Cells Using Small Molecule Compounds. Companion manuscript to U.S. Appl. No. 61/029,287, 2010.

International search report dated Jul. 10, 2009 for PCT Application No. IB2008/002540.

Itsykson et al. Derivation of neural precursors from human embryonic stem cells in the presence of noggin. Mol Cell Neurosci. Sep. 2005;30(1):24-36.

Jahagirdar et al. Multipotent adult progenitor cell and stem cell plasticity. Stem Cell Rev. 2005;1(1):53-9.

Janssens et al. Autologous bone marrow-derived stem-cell transfer in patients with ST-segment elevation myocardial infarction: double-blind, randomised controlled trial. Lancet. Jan. 14, 2006;367(9505):113-21.

Jiang et al. A core Klf circuitry regulates self-renewal of embryonic stem cells. Nat Cell Biol. Mar. 2008; 10(3):353-60.

Jiang et al. Pluripotency of mesenchymal stem cells derived from adult marrow. Nature. Jul. 4, 2002;418(6893):41-9.

Kim et al. Ex vivo characteristics of human amniotic membrane-derived stem cells. Cloning Stem Cells. 2007 Winter; 9(4):581-94.

Kitamura et al. Retrovirus-mediated gene transfer and expression cloning: powerful tools in functional genomics. Exp Hematol. Nov. 2003;31(11):1007-14.

Kitamura, T. New experimental approaches in retrovirus-mediated expression screening. Int J Hematol. Jun. 1998;67(4):351-9.

Klingemann, H. Discarded stem cells with a future? Expert Opin Biol Ther. Dec. 2006;6(12): 1251-4.

Knoblich, J.A. Mechanisms of Asymmetric Stem Cell Division. Cell. Feb. 22, 2008; 132(4):583-597.

Koch et al. Transduction of human embryonic stem cells by ecotropic retroviral vectors. Nucl Acids Res. 2006; 34, e120.

Kohge et al. Promotion of antigen-specific antibody production in murine B cells by a moderate increase in histone acetylation. Biochem Pharmacol. Nov. 15, 1998;56(10): 1359-64.

Kopsidas et al. RNA mutagenesis yields highly diverse mRNA libraries for in vitro protein evolution. BMC Biotechnol. Apr. 11, 2007;7:18.

Kramer et al. Embryonic stem cell-derived chondrogenic differentiation in vitro: activation by BMP-2 and BMP-4. Mech Dev. Apr. 2000;92(2):193-205.

Krausz, E. High-content siRNA screening. Mol Biosyst. Apr. 2007;3(4):232-40.

Kunath et al. FGF stimulation of the Erk1/2 signalling cascade triggers transition of pluripotent embryonic stem cells from self-renewal to lineage commitment. Development. Aug. 2007;134(16):2895-902.

Kuroda et al. Octamer and Sox Elements Are Required for Transcriptional cis Regulation of Nanog Gene Expression. Mol Cell Biol. Mar. 2005; 25(6):2475-2485.

Laird et al. Stem Cell Trafficking in Tissue Development, Growth, and Disease. Cell. Feb. 22, 2008; 132(4):612-630.

Lee et al. Efficient generation of midbrain and hindbrain neurons from mouse embryonic stem cells. Nat Biotechnol. Jun. 2000;18(6):675-9.

Lemken et al. Evidence for intercellular trafficking of VP22 in living cells. Mol Ther. Feb. 2007;15(2):310-9.

Lengner et al. The pluripotency regulator Oct4: a role in somatic stem cells? Cell Cycle. Mar. 2008;7(6):725-8.

Li et al. Small dsRNAs induce transcriptional activation in human cells. Proc Natl Acad Sci. 2006; 103, 17337-17342.

Lieschke et al. Development of functional macrophages from embryonal stem cells in vitro. Exp Hematol. Apr. 1995;23(4):328-34.

Lin-Goerke et al. PCR-based random mutagenesis using manganese and reduced dNTP concentration. Biotechniques. Sep. 1997;23(3):409-12.

Link et al. Therapeutic protein transduction of mammalian cells and mice by nucleic acid-free lentiviral nanoparticles. Nucleic Acids Res. Jan. 30, 2006;34(2):e16.

Littlewood et al. A modified oestrogen receptor ligand-binding domain as an improved switch for the regulation of heterologous proteins. Nucleic Acids Res. May 25, 1995;23(10):1686-90.

Loudig et al. Transcriptional co-operativity between distant retinoic acid response elements in regulation of Cyp26A1 inducibility. Biochem J. Nov. 15, 2005;392(Pt 1):241-8.

Ludwig et al. Derivation of human embryonic stem cells in defined conditions. Nat Biotechnol. Feb. 2006;24(2):185-7.

Lumelsky et al. Differentiation of embryonic stem cells to insulin-secreting structures similar to pancreatic islets. Science. May 18, 2001;292(5520):1389-94.

Lunde et al. Zebrafish pou5f1/pou2, homolog of mammalian Oct4, functions in the endoderm specification cascade. Curr Biol. Jan. 6, 2004;14(1):48-55.

Lungwitz et al. Polyethylenimine-based non-viral gene delivery systems. Eur J Pharm Biopharm. Jul. 2005;60(2):247-66.

Maherali et al. A high-efficiency system for the generation and study of human induced pluripotent stem cells. Cell Stem Cell. Sep. 11, 2008;3(3):340-5.

Masaki et al. Tendency of Pluripotential marker gene expression in colonies derived from human neonatal fibroblasts induced by the human iPS cell method. Stem Cell Researchr. 2008. doi: 10.1016/j.scr.2008.01.001 (Accepted Manuscript).

Mathe et al. Computational approaches for predicting the biological effect of p53 missense mutations: a comparison of three sequence analysis based methods. Nucleic Acids Res. Mar. 6, 2006;34(5):1317-25.

Mikkelsen et al. Dissecting direct reprogramming through integrative genomic analysis. Nature. Jul. 3, 2008;454(7200):49-55. Erratum in: Nature. 2008;454(7205):794.

Miyagishi et al. Strategies for generation of an siRNA expression library directed against the human genome. Oligonucleotides. 2003;13(5):325-33.

Miyoshi et al. Development of a self-inactivating lentivirus vector. J Virol. Oct. 1998;72(10):8150-7.

More California Dough—$23 Million—Rolls Out the Door for Stem Cell Research. California Stem Cell Report Web Site. 2005. Available at: http://californiastemcellreport.blogspot.com/2008/06/more-dough-25-million-rolls-out-door-in.html. Accessed Jul. 1, 2008.

Morgenstern et al. Advanced mammalian gene transfer: high titre retroviral vectors with multiple drug selection markers and a complementary helper-free packaging cell line. Nucleic Acids Res. Jun. 25, 1990; 18(12):3587-3596.

Morizane et al. From bench to bed: the potential of stem cells for the treatment of Parkinson's disease. Cell Tissue Res. Jan. 2008;331(1):323-36.

Morling et al. Enhanced transduction efficiency of retroviral vectors coprecipitated with calcium phosphate. Gene Ther. Sep. 1995;2(7):504-8.

Morrison, S.J. Stem Cells and Niches: Mechanisms that Promote Stem Cell Maintenance throughout Life. Cell. Feb. 22, 2008; 132(4):598-611.

Mummery et al. Differentiation of human embryonic stem cells to cardiomyocytes: role of coculture with visceral endoderm-like cells. Circulation. Jun. 3, 2003; 107(21):2733-40.

Murry et al. Differentiation of Embryonic Stem Cells to Clinically Relevant Populations: Lessons from Embryonic Development. Cell. Feb. 22, 2008; 132(4):661-680.

Naldini et al. In vivo gene delivery and stable transduction of nondividing cells by a lentiviral vector. Science. Apr. 12, 1996;272(5259):263-7.

Négre et al. Lentiviral vectors derived from simian immunodeficiency virus. Curr Top Microbiol lmmunol. 2002;261:53-74.

Onishi et al. Applications of retrovirus-mediated expression cloning. Exp Hematol. Feb. 1996;24(2):324-9.

Pera, M.F. On the Road to Reprogramming. Stem Cell Research. 2008; 1:103-104.

Pralong et al. Cell fusion for reprogramming pluripotency: toward elimination of the pluripotent genome. Stem Cell Rev. 2006;2(4):331-40.

Prelle et al. Overexpression of insulin-like growth factor-II in mouse embryonic stem cells promotes myogenic differentiation. Biochem Biophys Res Commun. Nov. 2, 2000;277(3):631-8.

Rambhatla et al. Generation of hepatocyte-like cells from human embryonic stem cells. Cell Transplant. 2003;12(1):1-11.

Rosenfeld et al. Adenovirus-mediated transfer of a recombinant alpha 1-antitrypsin gene to the lung epithelium in vivo. Science. Apr. 19, 1991;252(5004):431-4.

Rossant, J. Stem Cells: The Magic Brew. Nature. Jul. 19, 2007;448, 260-262.

Rossi et al. Stem Cells and the Pathways to Aging and Cancer. Cell. Feb. 22, 2008; 132(4):681-696.

Rubin, L. Stem Cell and Drug Discovery: The Beginning of a New Era? Cell. Feb. 22, 2008; 132(4):549-552.

Sadowski et al. GAL4-VP16 is an unusually potent transcriptional activator. Nature. Oct. 6, 1988;335(6190):563-;4.

Sottile et al. In vitro osteogenic differentiation of human ES cells. Cloning Stem Cells. 2003;5(2):149-55.

Stewart et al. Mechanisms of self-renewal in human embryonic stem cells. Eur J Cancer. Jun. 2006;42(9):1257-72.

Strelchenko et al., Embryonic Stem Cells from Morula, Methods in Enzymology, 2006, vol. 418, pp. 93-108.

Sumi et al. Apoptosis and differentiation of human embryonic stem cells induced by sustained activation of c-Myc. Oncogene. Aug. 16, 2007;26(38):5564-76.

Tokuzawa et al. Utilization of Digital Differential Display to Identify Novel Targets of Oct3/4. In: Turksen, K., ed. Embryonic Stem Cell Protocols: vol. I: Isolation and Characterization. Humana Press; 2nd ed. Edition. Feb. 15, 2006: 223-231.

Trompeter, et. al. Rapid and highly efficient gene transfer into natural killer cells by nucleofection. J Immunol Methods. Mar. 1, 2003 ;274(1-2):245-56.

Wagner et al. Mesenchymal stem cell preparations—comparing apples and oranges. Stem Cell Rev. Dec. 2007;3(4):239-48.

Watanabe et al. A Rock inhibitor permits survival of dissociated human embryonic stem cells. Nat Biotechnol. 2007; 25, 681-686.

Xu et al. Random mutagenesis libraries: optimization and simplification by PCR. Biotechniques. Dec. 1999;27(6):1102, 1104, 1106, 1108.

Yee et al. Generation of high-titer pseudotyped retroviral vectors with very broad host range. Methods Cell Biol. 1994;43 Pt A:99-112.

Zhan et al. Conservation and variation of gene regulation in embryonic stem cells assessed by comparative genomics. Cell Biochem Biophys. 2005;43(3):379-405.

Belmonte et al. "Induced pluripotent stem cells and reprogramming: seeing the science through the hype." Nat Rev Genet. Dec. 2009;10(12):878-83. Epub Oct. 27, 2009.

Carey et al., "Reprogramming of murine and human somatic cells using a single polycistronic vector," Proc. Natl. Acad. Sci. USA, Jan. 6, 2009, vol. 106(1), pp. 157-62, Epub. Dec. 24, 2008. Erratum in: Proc. Natl. Acad. Sci. USA, Mar. 31, 2009, vol. 106(13), p. 5449.

Daley, et al., "Broader implications of defining standards for the pluripotency of iPSCs." Cell Stem Cell. Mar. 6, 2009;4(3):200-1; author reply 202.

Hakelien et al., Reprogramming Fibroblasts to Express T-cell Functions Using Cell Extracts, Nature Biotechnology, May 2002, vol. 20, pp. 460-466.

Hong et al., "Suppression of induced pluripotent stem cell generation by the p53-p21 pathway." Nature. Aug. 27, 2009;460(7259):1132-5. Epub Aug. 9, 2009.

Hyun et al., "New advances in iPS cell research do not obviate the need for human embryonic stem cells." Cell Stem Cell. Oct. 11, 2007;1(4):367-8.

Lewitzky et al., "Reprogramming somatic cells towards pluripotency by defined factors." Curr Opin Biotechnol. Oct. 2007;18(5):467-73.

Miura et al. "Variation in the safety of induced pluripotent stem cell lines." Nat Biotechnol. Aug. 2009;27(8):743-5. Epub Jul. 9, 2009.

Nakagawa et al., "Promotion of direct reprogramming by transformation-deficient Myc." Proc Natl Acad Sci U S A. Aug. 10, 2010;107(32):14152-7. Epub Jul. 26, 2010.

Office Action issued in connection with Chinese Patent Application No. 200680048227.7, Sep. 14, 2010.

Office Action issued in connection with European Patent Application No. EP 06834636.0, Apr. 30, 2010.

Office Action issued in connection with European Patent Application No. EP 06834636.0, Oct. 25, 2010.

Office Action issued in connection with Israeli Patent Application No. 191903, Aug. 19, 2010.

Office Action issued in connection with Japanese Patent Application No. JP 2009-056747, mailed Jun. 2, 2009.

Office Action issued in connection with Japanese Patent Application No. JP 2009-056748, mailed Jun. 2, 2009.

Official Action issued in connection with Japanese Patent Application No. JP 2009-056748, mailed Nov. 4, 2009.

Official Rejection issued in connection with Japanese Patent Application No. JP 2009-056748, mailed Feb. 23, 2010.

Office Action issued in connection with Japanese Patent Application No. JP 2009-056749, mailed Jun. 4, 2009.

Official Rejection issued in connection with Japanese Patent Application No. JP 2009-056749, mailed Nov. 4, 2009.

Office Action issued in connection with Japanese Patent Application No. JP 2009-056750, mailed Jun. 2, 2009.

Office Action issued in connection with New Zealand Patent Application No. 569530, Apr. 20, 2010.

Office Action issued in connection with Singapore Patent Application No. 200804231-9, Apr. 13, 2010.

Office Action issued in connection with Singapore Patent Application No. 200901803-7, Jan. 22, 2010.

Official Action issued in connection with Eurasian Patent Application No. 200870046, Nov. 9, 2009.

Official Action issued in connection with Eurasian Patent Application No. 201000858, Jul. 14, 2010.

Ohnuki et al., "Generation and characterization of human induced pluripotent stem cells." Curr Protoc Stem Cell Biol. Jun. 2009;Chapter 4:Unit 4A.2.

Okita et al., "Generation of mouse-induced pluripotent stem cells with plasmid vectors." Nat Protoc. 2010;5(3):418-28. Epub Feb. 11, 2010.

Okita et al., "Induction of pluripotency by defined factors." Exp Cell Res. Oct. 1, 2010;316(16):2565-70. Epub Apr. 24, 2010.

Takahashi, K. et al, "Human induced pluripotent stem cells on autologous feeders." PLoS One. Dec. 2, 2009;4(12):e8067.

Tsubooka et al. "Roles of Sall4 in the generation of pluripotent stem cells from blastocysts and fibroblasts." Genes Cells. Jun. 2009;14(6):683-94. Epub May 19, 2009.

Xu et al., "BMP4 initiates human embryonic stem cell differentiation to trophoblast." Nature Biotechnology, Dec. 2002, vol. 20, pp. 1261-1264.

Yamanaka et al., "Nuclear reprogramming to a pluripotent state by three approaches." Nature. Jun. 10, 2010;465(7299):704-12.

Yamanaka S., "An interview with . . . Shinya Yamanaka. Interview by Mary Muers." Nat Rev Genet. Jun. 2010;11(6):390. Epub May 5, 2010.

Yamanaka S., "Patient-specific pluripotent stem cells become even more accessible" Cell Stem Cell. Jul. 2, 2010;7(1):1-2.

Yamanaka S., "Pluripotency and nuclear reprogramming." Philos Trans R Soc Lond B Biol Sci. Jun. 27, 2008;363(1500):2079-87.

Yamanaka S., "Symposium: Nuclear reprogramming and the control of differentiation in mammalian embryos. Introduction." Reprod Biomed Online. Jan. 2008;16(1):11-2.

Yamanaka, S., "A fresh look at iPS cells." Cell. Apr. 3, 2009;137(1):13-7.

Yamanaka, S., "Ekiden to iPS Cells." Nat Med. Oct. 2009;15(10):1145-8.

Yamanaka, S., "Elite and stochastic models for induced pluripotent stem cell generation." Nature. Jul. 2, 2009;460(7251):49-52.

Yamanaka, S., "Induction of Pluripotency by Defined Factors—The History of iPS Cells", Gairdner Award acceptance speech, presented on or about Oct. 29, 2009.

Yamanaka, S., "Induction of Pluripotency by Defined Factors", lecture presented on or about Oct. 29, 2009.

Yoshida et al. "Hypoxia enhances the generation of induced pluripotent stem cells." Cell Stem Cell. Sep. 4, 2009;5(3):237-41. Epub Aug. 27, 2009.

Yoshida et al., "Recent stem cell advances: induced pluripotent stem cells for disease modeling and stem cell-based regeneration." Circulation. Jul. 6, 2010;122(1):80-7.

* cited by examiner

Figure 17
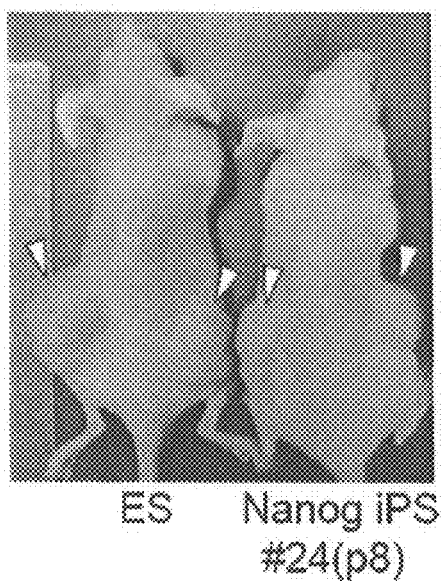
ES    Nanog iPS
      #24(p8)
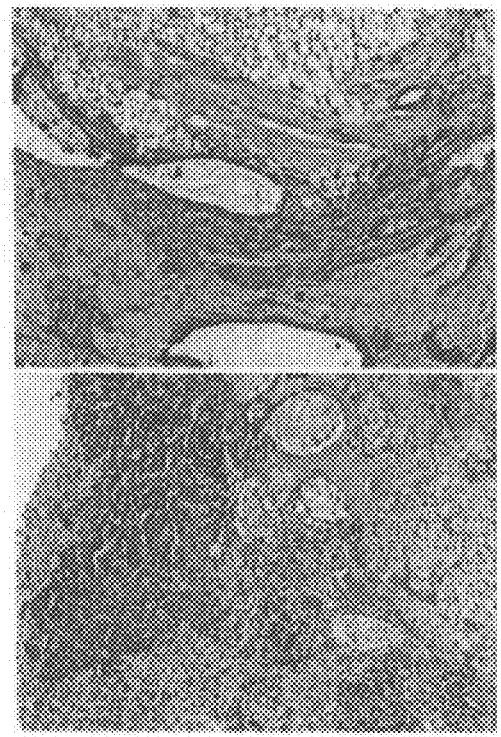

4 male chimera
/ 90 transplantation

NPMF4EK-24 (p6)

Figures 29(A)-(D)

Figures 32(A)-(N)
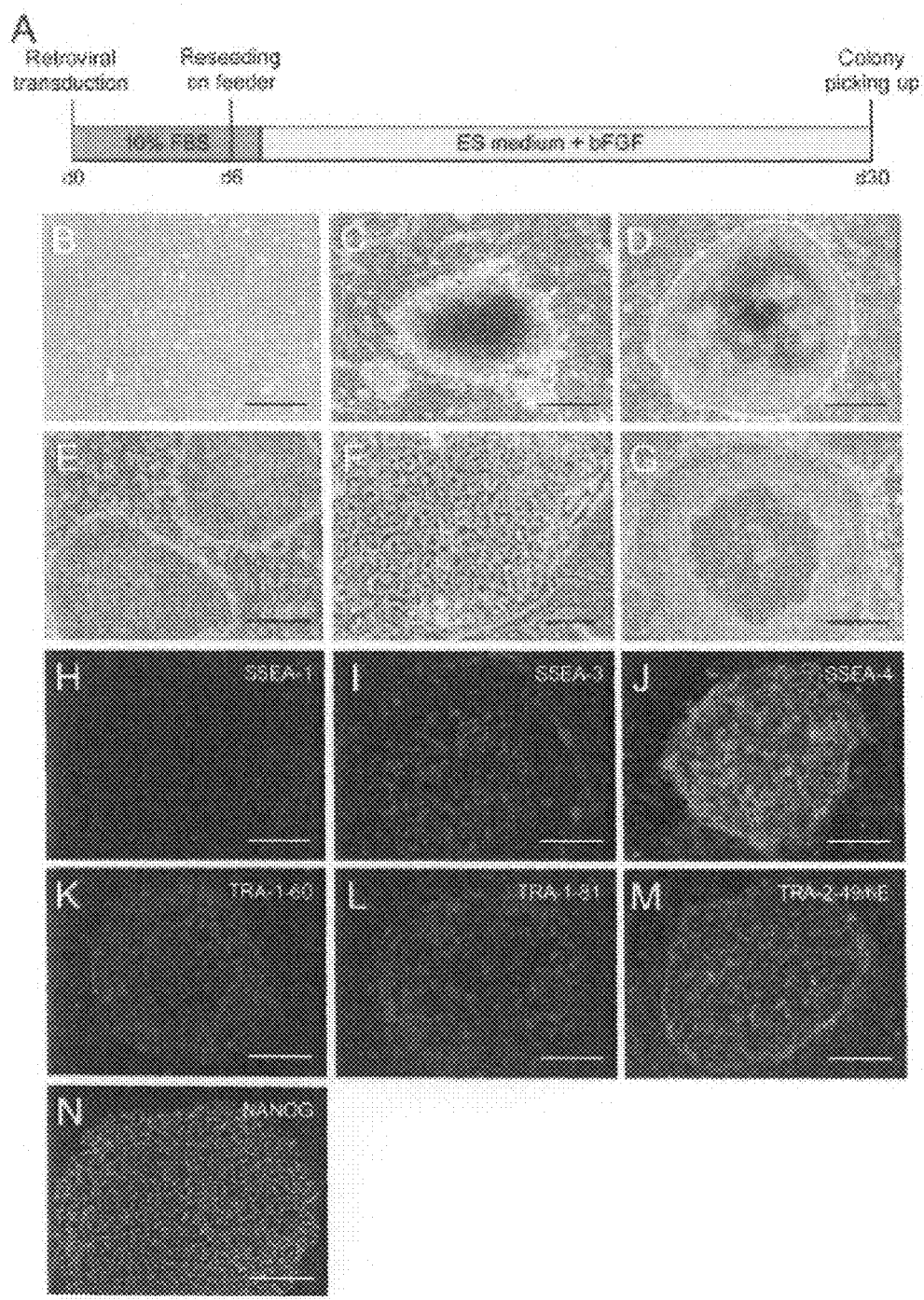

Figures 33(A)-(C)
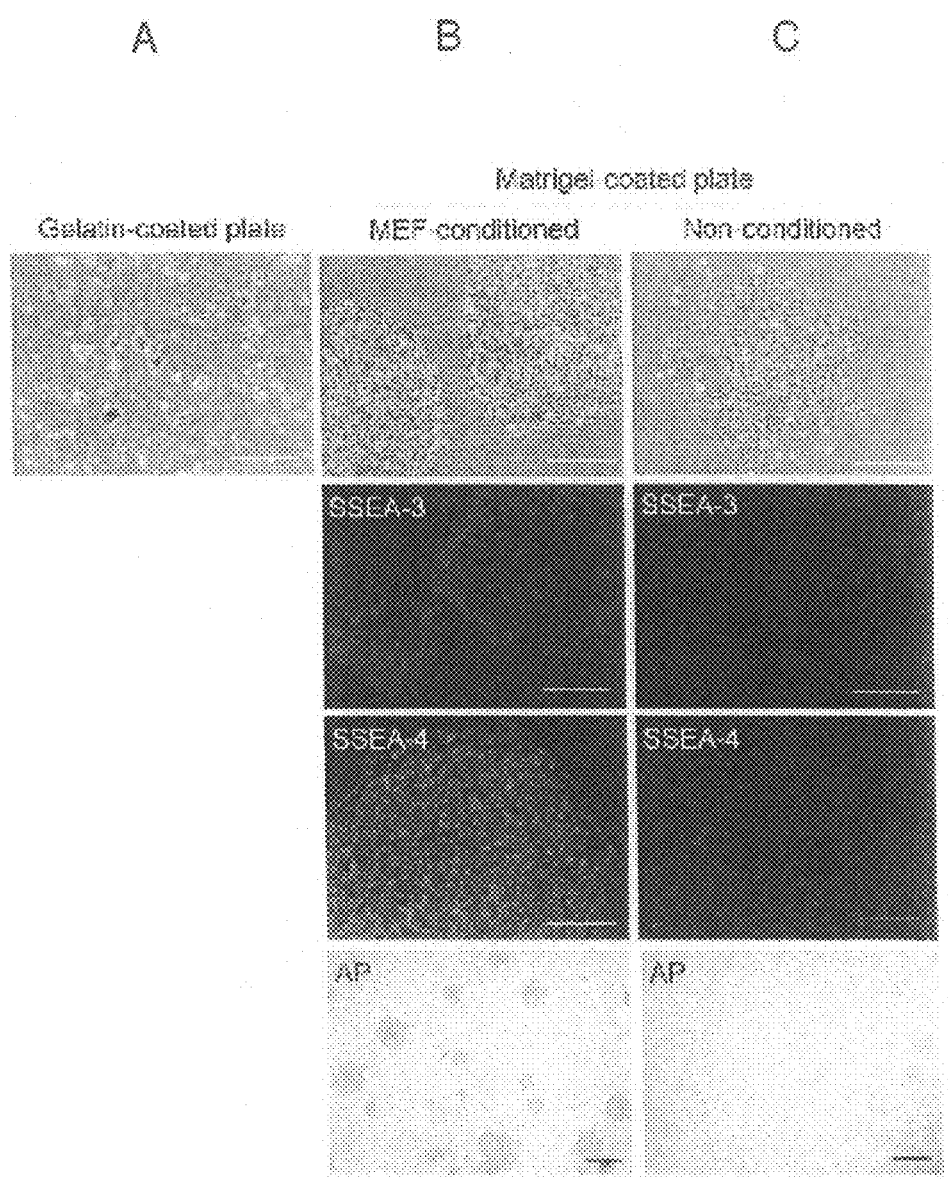

Figures 34(B)-(C)
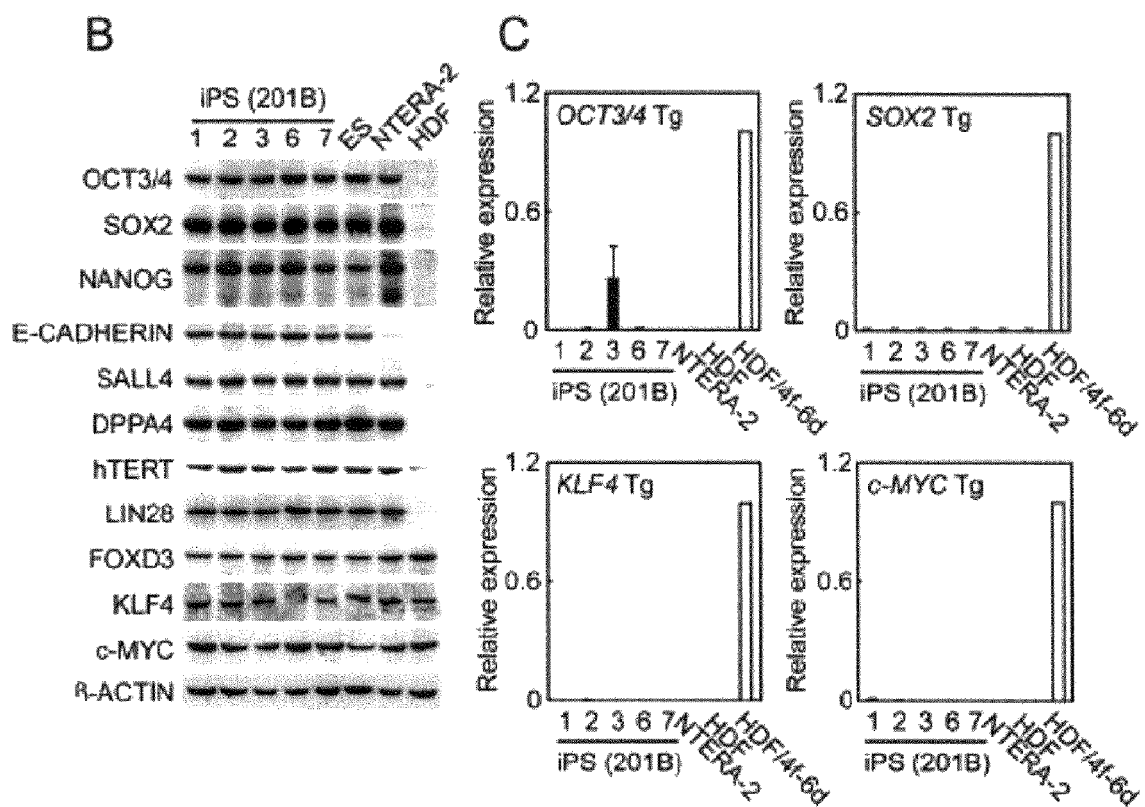

Figures 34(D)-(E)
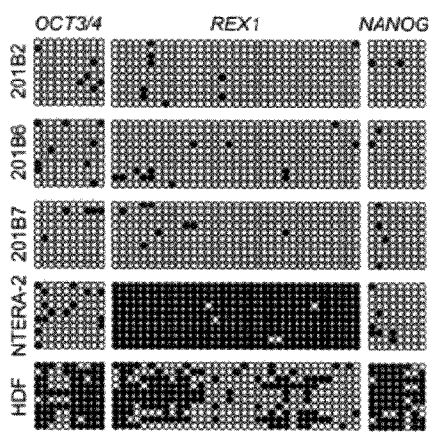
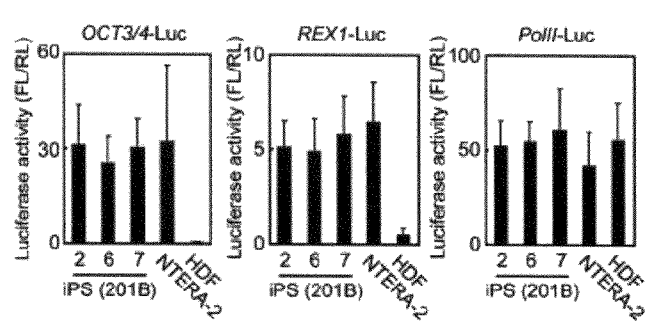

Figures 35(A)-(B)
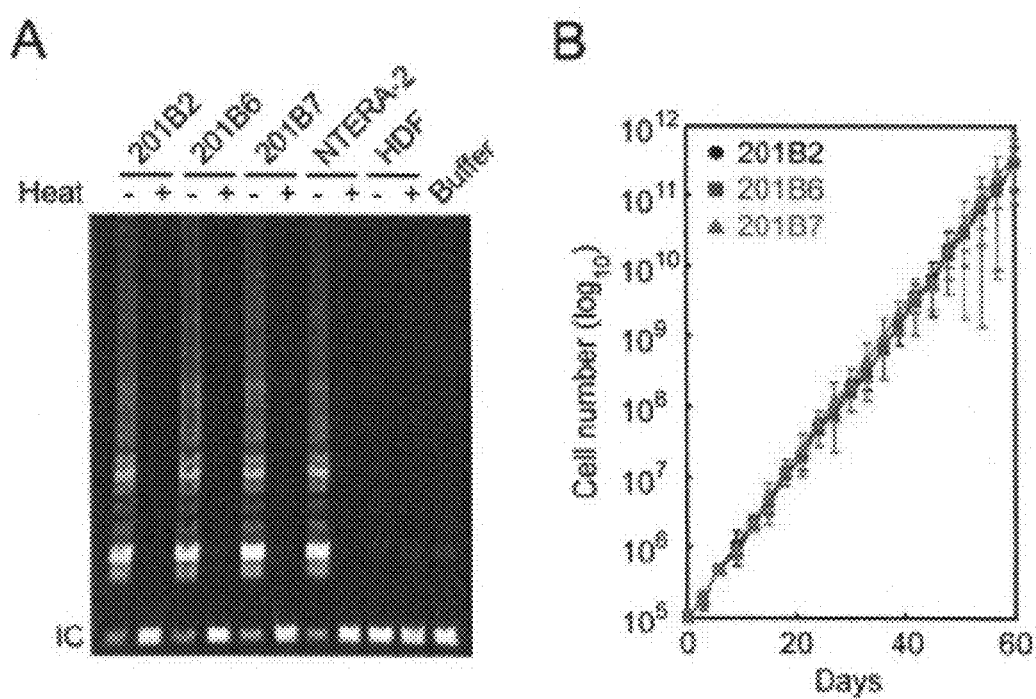

Figures 36(A)-(B)
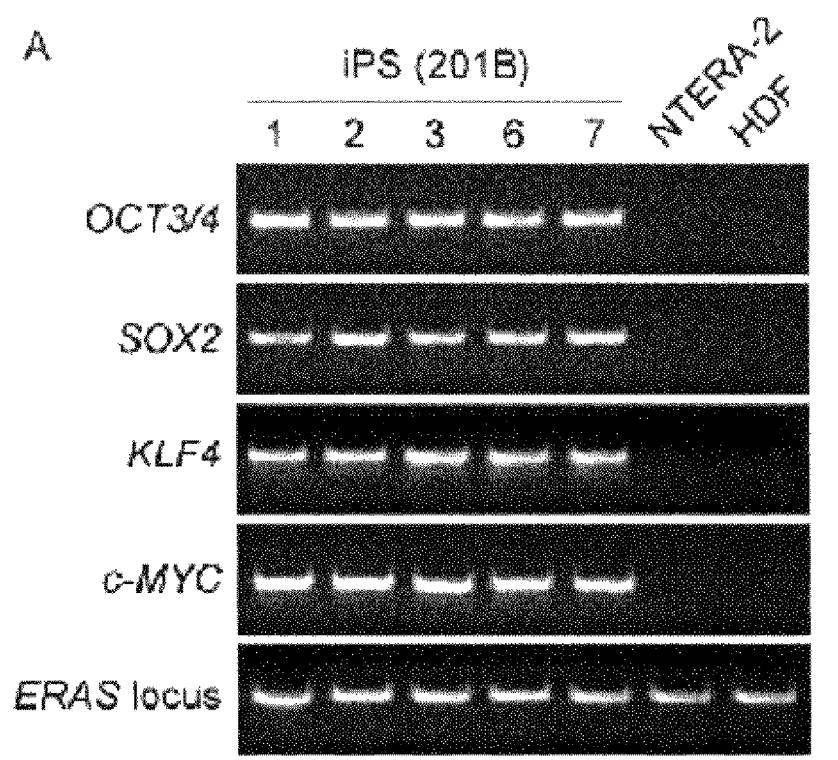
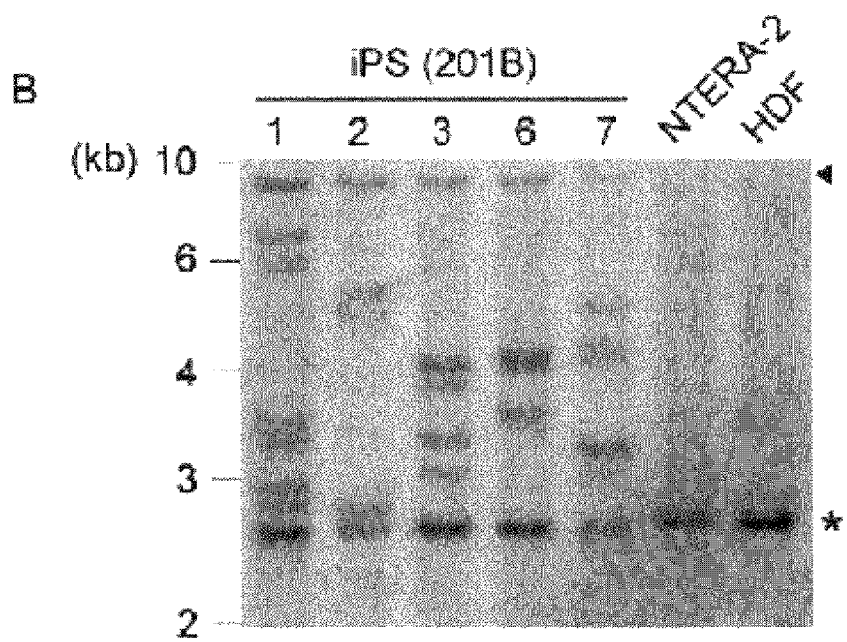

Figures 37(A)-(L)
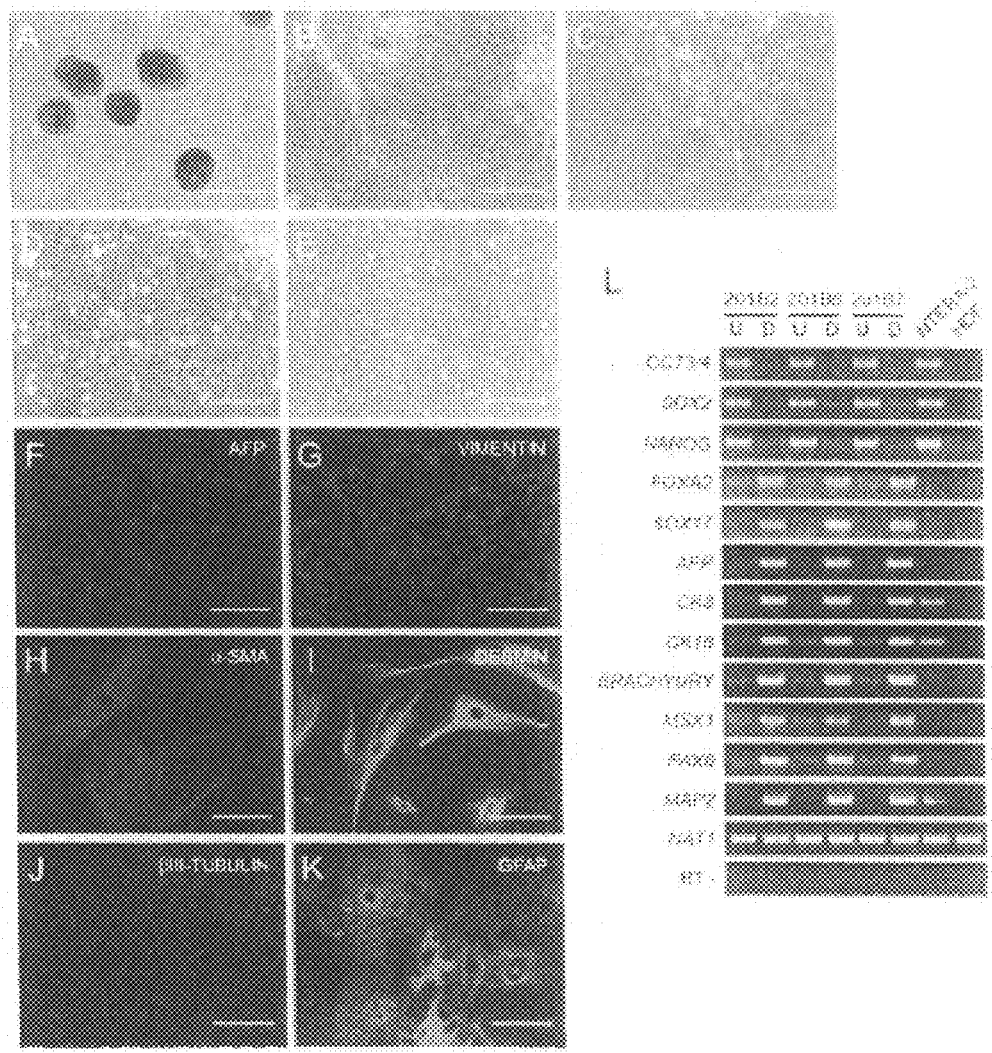

Figures 38(A)-(E)
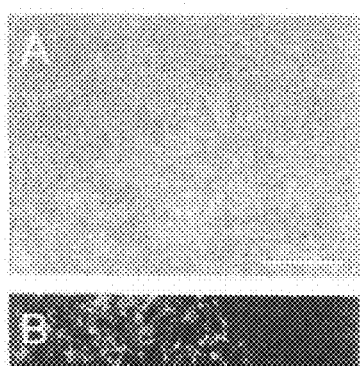
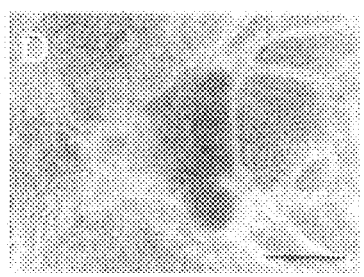
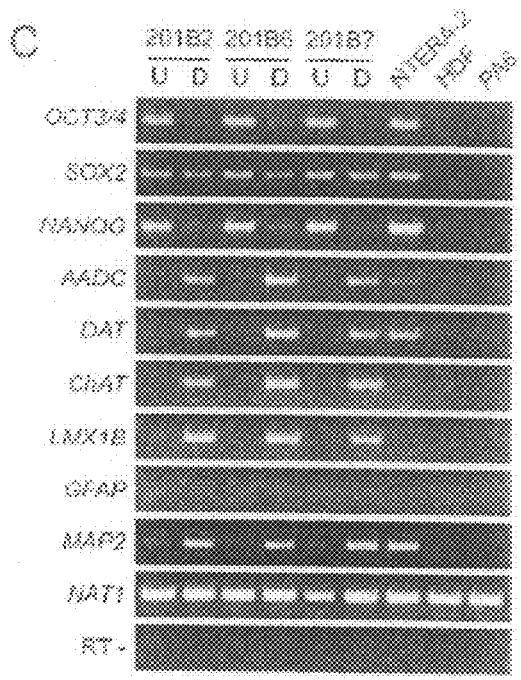
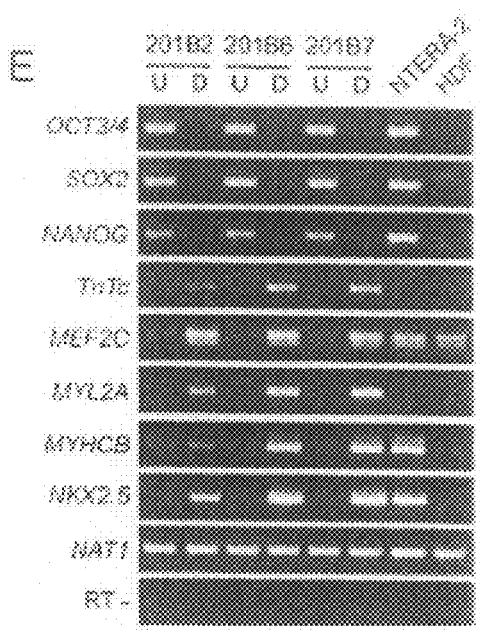

Figures 43(A)-(C)
A
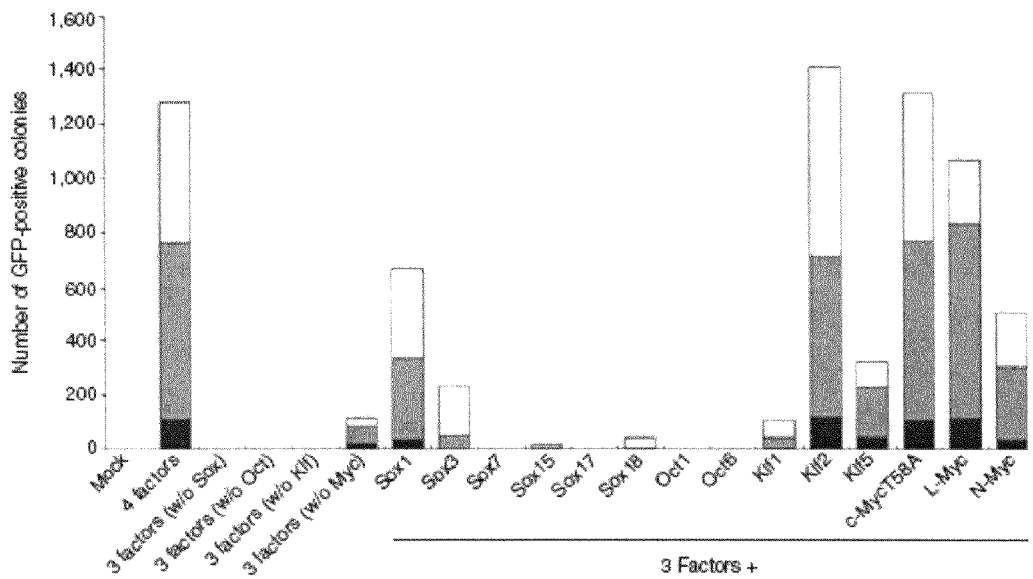
B
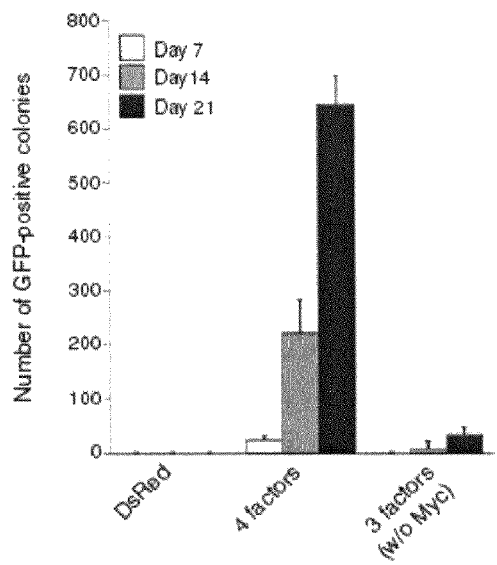
C
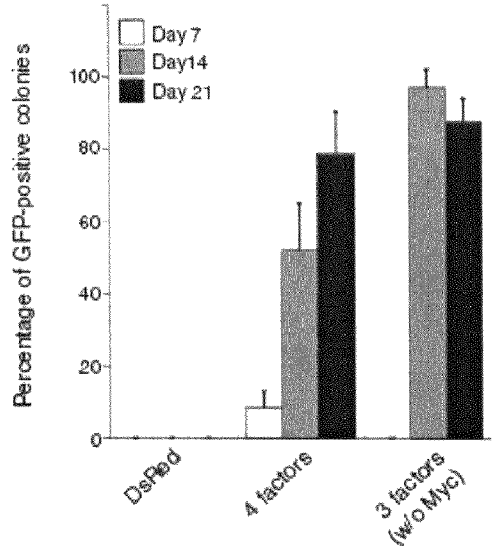

Figures 46(A)-(B)
A
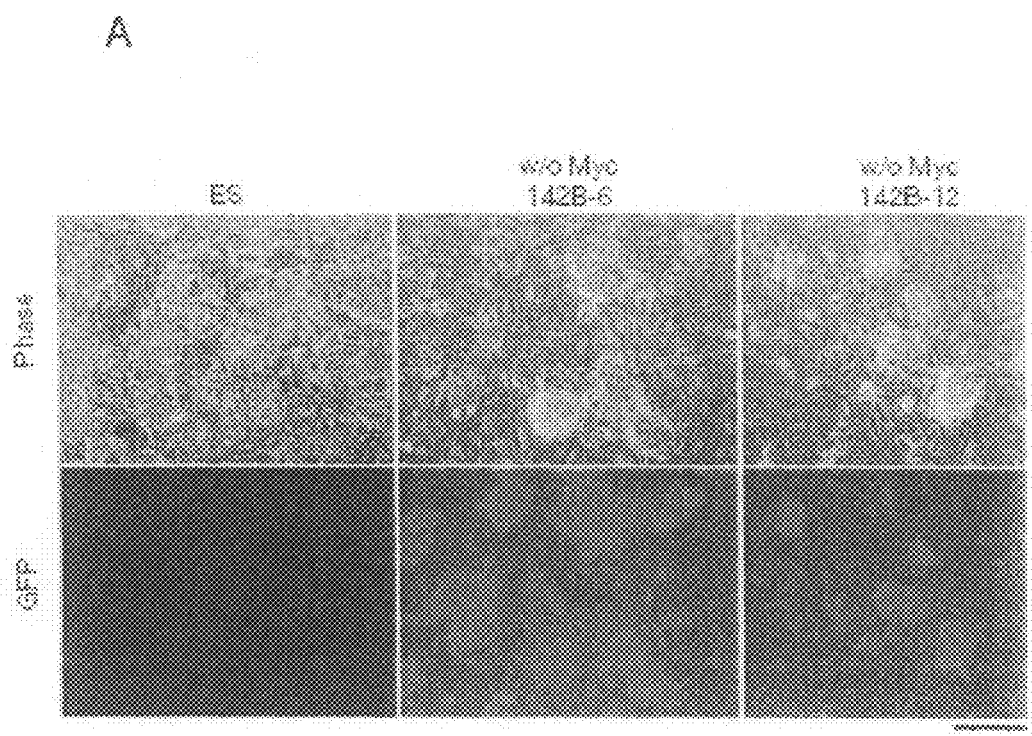
B
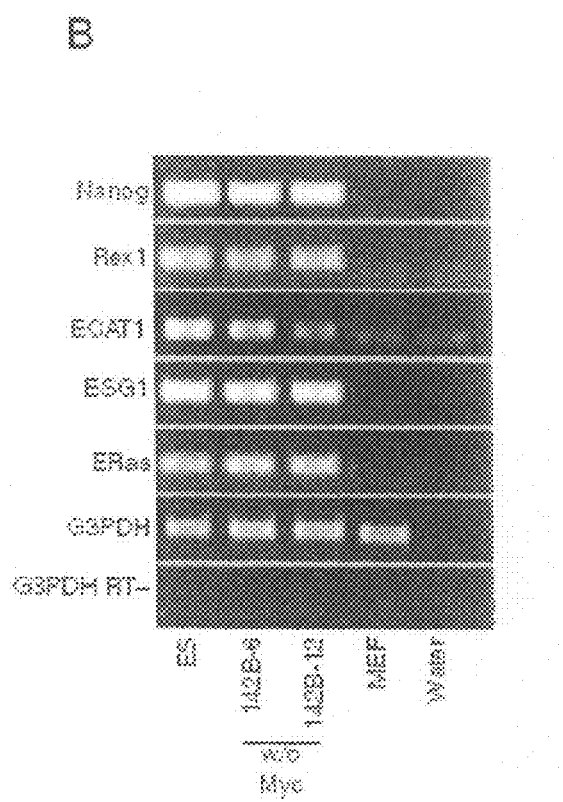

Figures 47(A)-(D)
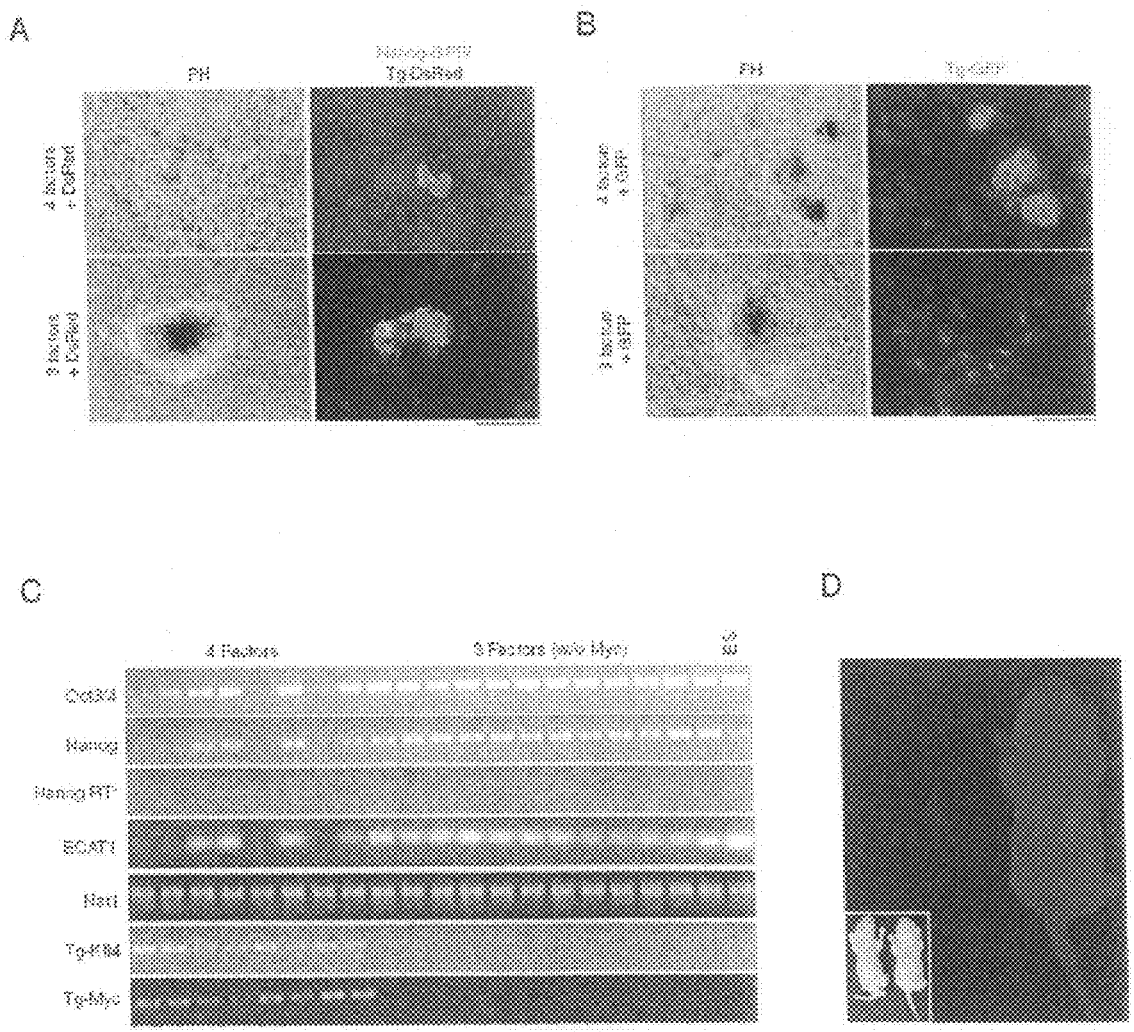

Figures 48(A)-(B)
A
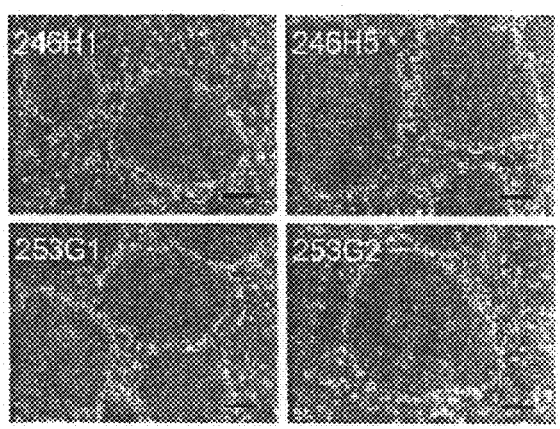
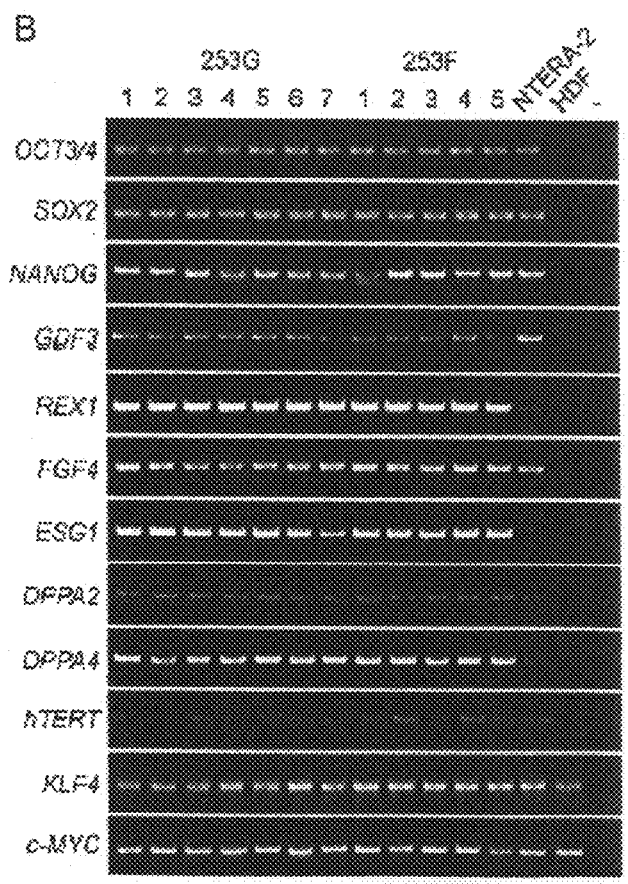

Figures 50(A)-(C)
A
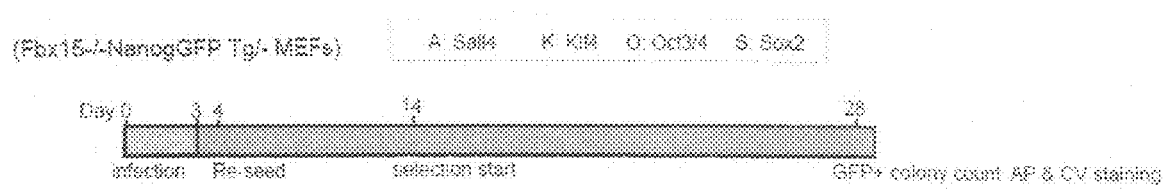
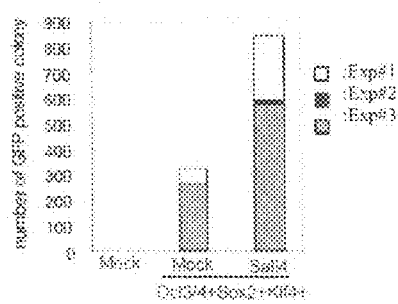
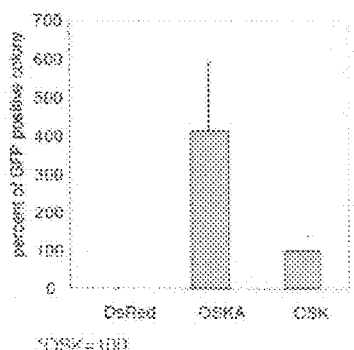
B  C

Figure 51

SEQUENCE LISTING

<160> NUMBER OF SEQ ID NOS: 133

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgtggggccc tgaaaggcga gctgagat                                              28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgggccgcc atacgacgac gctcaact                                              28

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaagtctggt tccttggcag gatg                                                  24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actcgataca ctggcctagc                                                       20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caggtgtttg agggtagctc                                                       20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
cggttcatca tggtacagtc                                               20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
actgcccctc atcagactgc tact                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cactgccttg tactcgggta gctg                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gttccaacct gtgcctcgcg tctt                                          24

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agcgaggcat ggagagagcg gagcag                                        26

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtggtgagc atcttcggag tgg                                           23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccttcttggt ccgcccgttc tta                                           23
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggacgcaa ctgtgaacat gatgttcgca                                    30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctttgaggtc ctggtccatc acgtgaccat                                    30

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccattagggg ccatcatcgc tttc                                          24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cactgctcac tggaggggc ttgc                                           24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgctgcggtc caggccatca agag                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggcactgtt cagttcagcg gatc                                          24

<210> SEQ ID NO 19

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctttccacc aggcccccgg ctc                                              23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgcgggcgga catggggaga tcc                                              23

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
attcttcgtt gtcaagccgc caaagtggag                                       30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agttgtttgc tgcggagttg tcatctcgtc                                       30

<210> SEQ ID NO 23
<211> LENGTH: 2127
<212> TYPE: DNA
<213> ORGANISM: Simian virus 40

<400> SEQUENCE: 23
atggataaag ttttaaacag agaggaatct ttgcagctaa tggaccttct aggtcttgaa       60
aggagtgcct gggggaatat tcctctgatg agaaaggcat atttaaaaaa atgcaaggag      120
tttcatcctg ataaaggagg agatgaagaa aaaatgaaga aaatgaatac tctgtacaag      180
aaaatggaag atggagtaaa atatgctcat caacctgact tggaggctt ctgggatgca       240 actgagattc aacctatgg aactgatgaa tgggagcagt ggtggaatgc ctttaatgag       300
gaaaacctgt tttgctcaga agaaatgcca tctagtgatg atgaggctac tgctgactct      360
caacattcta ctcctccaaa aaagaagaga aaggtagaag accccaagga ctttccttca      420
gaattgctaa gttttttgag tcatgctgtg tttagtaata aactcttgc ttgctttgct       480 atttacacca caaaggaaaa agctgcactg ctatacaaga aaattatgga aaatattct       540 gtaaccttta taagtaggca taacagttat aatcataaca tactgttttt tcttactcca      600
cacaggcata gagtgtctgc tattaataac tatgctcaaa aattgtgtac ctttagcttt      660
```

-continued

| | |
|---|---|
| ttaatttgta aaggggttaa taaggaatat ttgatgtata gtgccttgac tagagatcca | 720 |
| ttttctgtta ttgaggaaag tttgccaggt gggttaaagg agcatgattt taatccagaa | 780 |
| gaagcagagg aaactaaaca agtgtcctgg aagcttgtaa cagagtatgc aatggaaaca | 840 |
| aaatgtgatg atgtgttgtt attgcttggg atgtacttgg aatttcagta cagttttgaa | 900 |
| atgtgtttaa aatgtattaa aaaagaacag cccagccact ataagtacca tgaaaagcat | 960 |
| tatgcaaatg ctgctatatt tgctgacagc aaaaaccaaa aaccatatg ccaacaggct | 1020 |
| gttgatactg ttttagctaa aaagcgggtt gatagcctac aattaactag agaacaaatg | 1080 |
| ttaacaaaca gatttaatga tcttttggat aggatggata taatgtttgg ttctacaggc | 1140 |
| tctgctgaca tagaagaatg gatggctgga gttgcttggc tacactgttt gttgcccaaa | 1200 |
| atggattcag tggtgtatga cttttttaaaa tgcatggtgt acaacattcc taaaaaaaga | 1260 |
| tactggctgt ttaaaggacc aattgatagt ggtaaaacta cattagcagc tgctttgctt | 1320 |
| gaattatgtg gggggaaagc tttaaatgtt aatttgccct tggacaggct gaactttgag | 1380 |
| ctaggagtag ctattgacca gttttttagta gttttttgagg atgtaaaggg cactggaggg | 1440 |
| gagtccagag atttgccttc aggtcaggga attaataacc tggacaattt aagggattat | 1500 |
| ttggatggca gtgttaaggt aaacttagaa aagaaacacc taaataaaag aactcaaata | 1560 |
| tttccccctg aatagtcac catgaatgag tacagtgtgc ctaaaacact gcaggccaga | 1620 |
| tttgtaaaac aaatagattt taggcccaaa gattatttaa agcattgcct ggaacgcagt | 1680 |
| gagttttgt tagaaaagag aataattcaa agtggcattg ctttgcttct tatgttaatt | 1740 |
| tggtacagac ctgtggctga gtttgctcaa agtattcaga gcagaattgt ggagtggaaa | 1800 |
| gagagattgg acaaagagtt tagtttgtca gtgtatcaaa aaatgaagtt taatgtggct | 1860 |
| atgggaattg gagtttttaga ttggctaaga acagtgatg atgatgatga agacagccag | 1920 |
| gaaaatgctg ataaaaatga agatggtggg gagaagaaca tggaagactc agggcatgaa | 1980 |
| acaggcattg attcacagtc ccaaggctca tttcaggccc ctcagtcctc acagtctgtt | 2040 |
| catgatcata tcagccata ccacatttgt agaggtttta cttgctttaa aaaacctccc | 2100 |
| acacctcccc ctgaacctga aacataa | 2127 |

<210> SEQ ID NO 24
<211> LENGTH: 456
<212> TYPE: DNA
<213> ORGANISM: Human papilloma virus type 16

<400> SEQUENCE: 24

| | |
|---|---|
| atgtttcagg acccacagga gcgacccaga agttaccac agttatgcac agagctgcaa | 60 |
| acaactatac atgatataat attagaatgt gtgtactgca agcaacagtt actgcgacgt | 120 |
| gaggtatatg actttgcttt tcgggattta tgcatagtat atagagatgg gaatccatat | 180 |
| gctgtatgtg ataaatgttt aaagttttat tctaaaatta gtgagtatag acattattgt | 240 |
| tatagtttgt atggaacaac attagaacag caatacaaca accgttgtg tgatttgtta | 300 |
| attaggtgta ttaactgtca aaagccactg tgtcctgaag aaaagcaaag acatctggac | 360 |
| aaaaagcaaa gattccataa tataagggt cggtggaccg tcgatgtat gtcttgttgc | 420 |
| agatcatcaa gaacacgtag agaaacccag ctgtaa | 456 |

<210> SEQ ID NO 25
<211> LENGTH: 297
<212> TYPE: DNA
<213> ORGANISM: Human papilloma virus type 16

<400> SEQUENCE: 25

```
atgcatggag atacacctac attgcatgaa tatatgttag atttgcaacc agagacaact    60
gatctctact gttatgagca attaaatgac agctcagagg aggaggatga aatagatggt   120
ccagctggac aagcagaacc ggacagagcc cattacaata ttgtaacctt ttgttgcaag   180
tgtgactcta cgcttcggtt gtgcgtacaa agcacacacg tagacattcg tactttggaa   240
gacctgttaa tgggcacact aggaattgtg tgccccatct gttctcagaa accataa     297
```

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
ccccagggcc ccattttggt acc                                            23
```

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
ggcacccctg gcatggctct tggctc                                         26
```

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
acgatcgtgg ccccggaaaa ggacc                                          25
```

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
caacaaccga aaatgcacca gccccag                                        27
```

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
ttatcgtcga ccactgtgct gctg                                           24
```

<210> SEQ ID NO 31
<211> LENGTH: 24

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31 cccttttct ggagactaaa taaa                                            24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gacaggggga ggggaggagc tagg                                           24

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cttccctcca accagttgcc ccaaac                                         26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gggaaatggg aggggtgcaa aagagg                                         26

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttgcgtgagt gtggatggga ttggtg                                         26

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cagccccgat tcttccacca gtccc                                          25

<210> SEQ ID NO 37
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 37
cggaagattc ccagtcgggt tcacc                                            25

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cttatgctac gtaaaggagc tggg                                             24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtgccaaccc aggtcccgga agtt                                             24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cagatcctaa acagctcgca gaat                                             24

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcgtacgcaa attaaagtcc aga                                              23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctacaacgcc tacgagtcct aca                                              23

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued

```
                         primer

<400> SEQUENCE: 43
gttgcaccag aaaagtcaga gttg                                           24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atatcccgcc gtgggtgaaa gttc                                           24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
actcagccat ggactggagc atcc                                           24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggagccgcct gccctggaaa attc                                           24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tttttcctga tattctattc ccat                                           24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccgtccccgc aatctccttc catc                                           24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 49
atgatgccaa catggctccc ggtg                                            24

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 50
cctgctcaag ctgactcgac accgtg                                          26

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 51
ggaaaagctg gccctggggt ggagc                                           25

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 52
tgattgtagt gctttctggc tgggctcc                                        28

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 53
gcgtcctggg aagggagatc cggagc                                          26

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 54
ttgaggggca tcgtcgcggg aggctg                                          26

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 55

-continued cgagaggacc ccgtggatgc agag                                              24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggcggccatc ttcagcttct ccag                                              24

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gccctctccc tccctccac gcacag                                             26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cggcgccgtt gctcacagac cacagg                                            26

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggcccgccac ttgcaggagt accagg                                            26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cttctgctcg ggcccctcat gagacg                                            26

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acccattatc cagatgtgtt tgcccgag                                          28

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atggtgaagc tgggcatagg cggcag                                          26

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgggagcggt gaagatggaa gggcac                                          26

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tcatgccagc gcccacgtac gacgac                                          26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cgctttcatg gtgtgggcta aggacg                                          26

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tagttggggt ggtcctgcat gtgctg                                          26

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cgccaggatc cccgctttga aatctg                                          26

<210> SEQ ID NO 68

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tcggccgcca gctctttgat gtgttc                                            26

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggaggcgtgg agctcagcga cacc                                              24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cggggagctc gctgacggag tctg                                              24

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
caggtggcgg acgtgtgaaa attgagagtg                                        30

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cacgctggat ctgcctgggg actgtg                                            26

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acagagggga ggtgcgccag ttcacg                                            26

<210> SEQ ID NO 74
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 74
acggggtgga cctcgctgca cagatc                                              26

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggcaccagca gcagcaggag cagcag                                              26

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccacgtctga ggagccgagg aagcag                                              26

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gggccccatc aacttcaccg tcttcc                                              26

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgtagtcgat gttccccgcc aggtcc                                              26

<210> SEQ ID NO 79
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
atgagcggga gaaggagcgg cagaac                                              26

<210> SEQ ID NO 80
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 80
tcaatggcca gcaccttcct cctctc                                          26

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tttaacaccg ccagcgctct tcaccttg                                        28

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tcgtggcgcg tgtgttgtgg gtatctcg                                        28

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctggaggccg agcagaagcg caacg                                           25

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gtccgcccgc tcctctgcct catcc                                           25

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tttttttttt tttttttttt                                                 20

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 86
gccacagcaa acctcctcac agcccac                                            27

<210> SEQ ID NO 87
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ctcgtcgttt ccgcaacaag tcctcttc                                           28

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
caccatggcg ggacacctgg cttcag                                             26

<210> SEQ ID NO 89
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acctcagttt gaatgcatgg gagagc                                             26

<210> SEQ ID NO 90
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
caccatgtac aacatgatgg agacggagct g                                       31

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tcacatgtgt gagaggggca gtgtgc                                             26

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
```

-continued

```
caccatggct gtcagtgacg cgctgctccc                                30
```

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

```
ttaaaaatgt ctcttcatgt gtaaggcgag                                30
```

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

```
caccatgccc ctcaacgtta gcttcaccaa                                30
```

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95

```
tcacgcacaa gagttccgta gctgttcaag                                30
```

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

```
caccatgggc tgcaaaaacc tgctcgg                                   27
```

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

```
tcatttgcac tggtccaagt tgctgtc                                   27
```

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

```
attgtcgacg gggatttggc agggtcacag gac                            33
```

<210> SEQ ID NO 99
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cccagatctc caatgccacc tcctcccaaa cg                                    32

<210> SEQ ID NO 100
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cactcgaggt ggaggagctg agggcactgt gg                                    32

<210> SEQ ID NO 101
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cacagatctg aaatgagggc ttgcgaaggg ac                                    32

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ggtttaaaag ggtaaatgtg attatattta                                       30

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
caaactacaa ccacccatca ac                                               22

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gaggttggag tagaaggatt gttttggttt                                       30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cccccctaac ccatcacctc caccacctaa                                   30

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tggttaggtt ggttttaaat ttttg                                        25

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
aacccaccct tataaattct caatta                                       26

<210> SEQ ID NO 108
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
caccatgtac agcatgatga tggagaccga cct                               33

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ctagatatgc gtcaggggca ccgtgc                                       26

<210> SEQ ID NO 110
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
caccatgtac agcctgctgg agactgaact caag                              34

<210> SEQ ID NO 111
<211> LENGTH: 30

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tcagatgtgg gtcagcggca ccgttccatt                                       30

<210> SEQ ID NO 112
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cacctcggcc atggcctcgc tgctggg                                          27

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ctccattcct ccagctctat gacacac                                          27

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
caccatggcg ctgaccagct cctcacaa                                         28

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ttaaaggtgg gttactggca tggg                                             24

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
caccagagcc atgagcagcc cggatg                                           26

<210> SEQ ID NO 117
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 117
cgtcaaatgt cggggtagtt gcaata                                          26

<210> SEQ ID NO 118
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
caccatgcag agatcgccgc ccggctacg                                       29

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ctagcctgag atgcaagcac tgtaatagac                                      30

<210> SEQ ID NO 120
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
caccatgaat aatccatcag aaaccaat                                        28

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gctctgcact cagctcactg tgcc                                            24

<210> SEQ ID NO 122
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
caccatggcc accaccgcgc agtatctg                                        28

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 123
ggaacccagt ccgcagggtc actg                                          24

<210> SEQ ID NO 124
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
caccatgagg cagaagagag agaggaggc                                     29

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tcagaggtga cgcttcatgt gcagagctaa                                    30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
caccatggcg ctcagcgagc ctatcttgcc                                    30

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ctacatatgt cgcttcatgt gcaaggccag                                    30

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
caccatgccc acgcgggtgc tgaccatg                                      28

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 129
tcgctcagtt ctggtggcgc ttca                                         24

<210> SEQ ID NO 130
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
caccatggac ttcgactcgt atcagcacta tttc                              34

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ttagtagcca ctgaggtacg cgattctctt                                   30

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
caccatgccc agctgcaccg cgtccaccat                                   30

<210> SEQ ID NO 133
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ttagcaagtc cgagcgtgtt cgatct                                       26
```

OCT3/4, KLF4, C-MYC AND SOX2 PRODUCE INDUCED PLURIPOTENT STEM CELLS

PRIOR RELATED APPLICATIONS

This application is a continuation of U.S. patent application Ser. No. 12/213,035, filed Jun. 13, 2008, which is a continuation-in-part of PCT/JP2006/324881, filed Dec. 6, 2006, which claims priority to Japanese Application No. 2005-359537, filed Dec. 13, 2005, and this application is a continuation of U.S. patent application Ser. No. 12/213,035, filed Jun. 13, 2008, which claims priority to U.S. Provisional Application No. 61/001,108, filed Oct. 31, 2007, and U.S. Provisional Application No. 60/996,289, filed Nov. 9, 2007. The entire disclosures of each of the above-cited applications are considered as being part of this application and are expressly incorporated by reference herein in their entireties.

FIELD OF THE INVENTION

The present invention relates to a nuclear reprogramming factor having an action of reprogramming a somatic cell to derive an induced pluripotent stem (iPS) cell. The present invention also relates to the aforementioned iPS cells, methods of generating and maintaining iPS cells, and methods of using iPS cells, including screening and testing methods as well as methods of stem cell therapy. The present invention also relates to somatic cells derived by inducing differentiation of the aforementioned iPS cells.

BACKGROUND OF THE INVENTION

Embryonic stem cells (ES cells) are stem cells established from human or mouse early embryos which have a characteristic feature that they can be cultured over a long period of time while maintaining pluripotent ability to differentiate into all kinds of cells existing in living bodies. Human embryonic stem cells are expected for use as resources for cell transplantation therapies for various diseases such as Parkinson's disease, juvenile diabetes, and leukemia, taking advantage of the aforementioned properties. However, transplantation of ES cells has a problem of causing rejection in the same manner as organ transplantation. Moreover, from an ethical viewpoint, there are many dissenting opinions against the use of ES cells which are established by destroying human embryos.

Embryonic stem (ES) cells, derived from the inner cell mass of mammalian blastocysts, have the ability to grow indefinitely while maintaining pluripotency (Evans et al., *Nature* 292:154-156, 1981; Martin, *P.N.A.S. USA* 78:7634-7638, 1981). These properties have led to expectations that human ES cells might be useful to understand disease mechanisms, to screen effective and safe drugs, and to treat patients of various diseases and injuries, such as juvenile diabetes and spinal cord injury (Thomson et al., *Science* 282:1145-1147, 1998). Use of human embryos, however, faces ethical controversies that hinder the applications of human ES cells. In addition, it is difficult to generate patient- or disease-specific ES cells, which are required for their effective application. Therefore, if dedifferentiation of a patient's own somatic cells could be induced to establish cells having pluripotency and growth ability similar to those of ES cells (in this specification, these cells are referred to as "induced pluripotent stem cells (iPS cells)", though they are sometimes called "embryonic stem cell-like cells" or "ES-like cells"), it is anticipated that such cells could be used as ideal pluripotent cells, free from rejection or ethical difficulties.

Methods for nuclear reprogramming of a somatic cell nucleus have been reported. One technique for nuclear reprogramming which has been reported involves nuclear transfer into oocytes (Wakayama et al., *Nature* 394:369-374, 1998; Wilmut et al., *Nature* 385:810-813, 1997). Another method, for example, a technique of establishing an embryonic stem cell from a cloned embryo, prepared by transplanting a nucleus of a somatic cell into an egg, was reported (Hwang et al., *Science* 303:1669-74, 2004; Hwang et al., *Science* 308:1777-83, 2005): these articles were, however, proved to be fabrications and later withdrawn. Others have reported techniques for nuclear reprogramming of a somatic cell nucleus by fusing a somatic cell and an ES cell (Tada et al., *Curr. Biol.* 11:1553-1558, 2001; Cowan et al., *Science* 309:1369-73, 2005). Another reported technique for reprogramming a cell nucleus involves treatment of a differentiated cell with an undifferentiated human carcinoma cell extract (Taranger et al., *Mol. Biol. Cell* 16:5719-35, 2005). However, these methods all have serious drawbacks. Methods of nuclear transfer into oocytes and techniques which involve the fusion of ES and differentiated cells both comprise the use of ES cells, which present ethical problems. In addition, cells generated by such methods often lead to problems with rejection upon transplantation into an unmatched host. Furthermore, the use of cell extracts to treat differentiated cells is technically unreliable and unsafe, in part because the cell extract components responsible for the nuclear programming are mixed in solution with other unknown factors.

A method for screening a nuclear reprogramming factor having an action of reprogramming differentiated somatic cells to derive induced pluripotent stems cell was proposed in International Publication WO2005/80598, which is incorporated by reference in its entirety. This method comprises the steps of: contacting somatic cells containing a marker gene under expression regulatory control of an ECAT (ES cell associated transcript) gene expression control region with a test substance; examining presence or absence of the appearance of a cell that expresses the marker gene; and choosing a test substance inducing the appearance of said cell as a candidate nuclear reprogramming factor for somatic cells. A method for reprogramming a somatic cell is disclosed in Example 6 and the like of the above publication. However, this publication fails to report an actual identification of a nuclear reprogramming factor.

In view of these problems, there remains a need in the art for nuclear reprogramming factors capable of generating pluripotent stem cells from somatic cells. There also remains a need for pluripotent stem cells, which can be derived from a patient's own somatic cells, so as to render ethical issues and avoid problems with rejection. Such cells would have enormous potential for both research and clinical applications.

SUMMARY OF THE INVENTION

The present invention provides induced pluripotent stem (iPS) cells derived by nuclear reprogramming of a somatic cell. The present invention also provides methods for reprogramming of a differentiated cell without using eggs, embryos, or embryonic stem (ES) cells. The present invention also provides nuclear reprogramming factors for induction of pluripotent stem cells. The disclosed methods and nuclear reprogramming factors may be used to conveniently and highly reproducibly establish iPS cells having pluripotency and growth ability similar to that of ES cells. More specifically, the present invention provides for inducing reprogramming of a differentiated cell without using eggs, embryos, or ES cells to conveniently and highly reproducibly establish the iPS cells having pluripotency and growth ability similar to that of ES cells.

The invention provides a pluripotent stem cell induced by reprogramming a somatic cell in the absence of eggs, embryos, or embryonic stem (ES) cells. The somatic cell can be a mammalian cell, for example a mouse cell or a human cell. The present invention also provides such a pluripotent stem cell, wherein the reprogramming comprises contacting the somatic cell with a nuclear reprogramming factor.

The nuclear reprogramming factor can comprise at least one gene product, for example a protein. The nuclear reprogramming factor can comprise a gene product of an Oct family gene, a Klf family gene, a Myc family gene, or a Sox family gene. The nuclear reprogramming factor can comprise one or more gene products of each of: an Oct family gene, a Klf family gene, and a Sox family gene. The nuclear reprogramming factor can comprise one or more gene products of each of: an Oct family gene, a Klf family gene, a Myc family gene, and a Sox family gene. Furthermore, the nuclear reprogramming factor can comprise one or more gene products of each of: an Oct family gene, a Klf family gene, together with a cytokine. The cytokine can be at least one of basic fibroblast growth factor (bFGF) and stem cell factor (SCF).

The invention also provides a method for preparing an induced pluripotent stem cell by nuclear reprogramming of a somatic cell, which comprises contacting a nuclear reprogramming factor with the somatic cell to obtain an induced pluripotent stem cell. The invention also provides such a method which is performed in the absence of eggs, embryos, or embryonic stem (ES) cells. The present invention also provides an induced pluripotent stem cell obtained by such a method. The present invention also provides a pluripotent stem cell induced by reprogramming a somatic cell, wherein the reprogramming comprises contacting the somatic cell with a nuclear reprogramming factor.

The present invention also provides such a method wherein the nuclear reprogramming factor comprises one or more gene products of each of: an Oct family gene, a Klf family gene, and a Sox family gene. The present invention also provides such a method wherein the nuclear reprogramming factor comprises one or more gene products of each of: Oct3/4, Klf4, and Sox2. The present invention also provides such a method wherein the nuclear reprogramming factor further comprises one or more gene products of a Sall4 gene. The present invention also provides pluripotent stem cells prepared by such methods.

The present invention also provides such a method wherein the nuclear reprogramming factor comprises one or more gene products of each of: wherein the nuclear reprogramming factor comprises one or more gene products of each of: an Oct family gene, a Klf family gene, a Myc family gene, and a Sox family gene. The present invention also provides such a method wherein the nuclear reprogramming factor comprises one or more gene products of each of: Oct3/4, Klf4, c-Myc, and Sox2. The present invention also provides such a method wherein the nuclear reprogramming factor further comprises one or more gene products of a Sall4 gene. The present invention also provides pluripotent stem cells prepared by such methods.

The present invention also provides such a method wherein the nuclear reprogramming factor comprises one or more gene products of each of: Klf4, c-Myc, Oct3/4, Sox2, Nanog, and Lin28. The present invention also provides pluripotent stem cells prepared by a method.

The present invention also provides a method of inducing a somatic cell to become a pluripotent stem cell comprising contacting the somatic cell with a nuclear reprogramming factor under conditions to obtain a pluripotent stem cell free of rejection.

The present invention also provides a somatic cell derived by inducing differentiation of an induced pluripotent stem cell as disclosed herein.

The present invention also provides a method for stem cell therapy comprising: (1) isolating and collecting a somatic cell from a patient; (2) inducing said somatic cell from the patient into an iPS cell (3) inducing differentiation of said iPS cell, and (4) transplanting the differentiated cell from (3) into the patient.

The present invention also provides a method for evaluating a physiological function of a compound comprising treating cells obtained by inducing differentiation of an induced pluripotent stem cell as disclosed herein with the compound.

The present invention also provides a method for evaluating the toxicity of a compound comprising treating cells obtained by inducing differentiation of an induced pluripotent stem cell as disclosed herein with the compound.

Other features and advantages of the present invention will be set forth in the description of the invention that follows, and will be apparent, in part, from the description or may be learned by practice of the invention. The invention will be realized and attained by the compositions, products, and methods particularly pointed out in the written description and claims hereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

However, the cells gave differentiated morphology which was apparently different from that of iPS cells.

Figure 7:
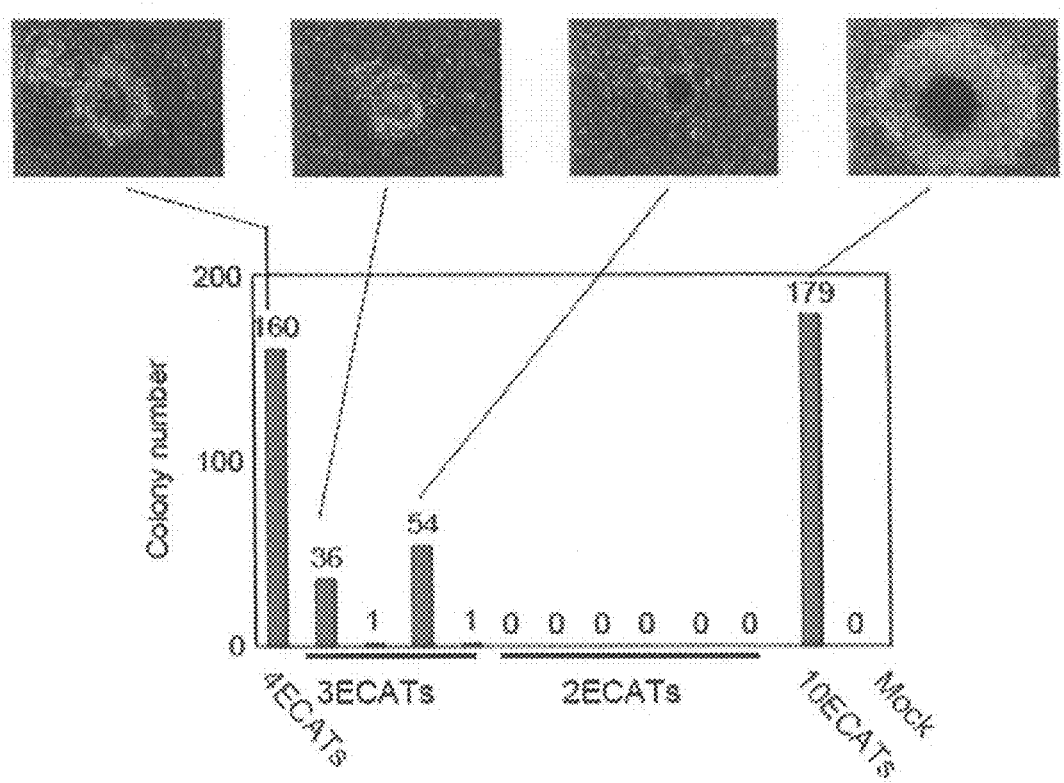

FIG. 7 shows numbers of G418-resistant emerged colonies (reprogrammed colony) with 10-gene group, 4-gene group, 3-gene groups, or 2-gene groups. Typical morphology and sizes of the colonies are shown.

Figure 8:
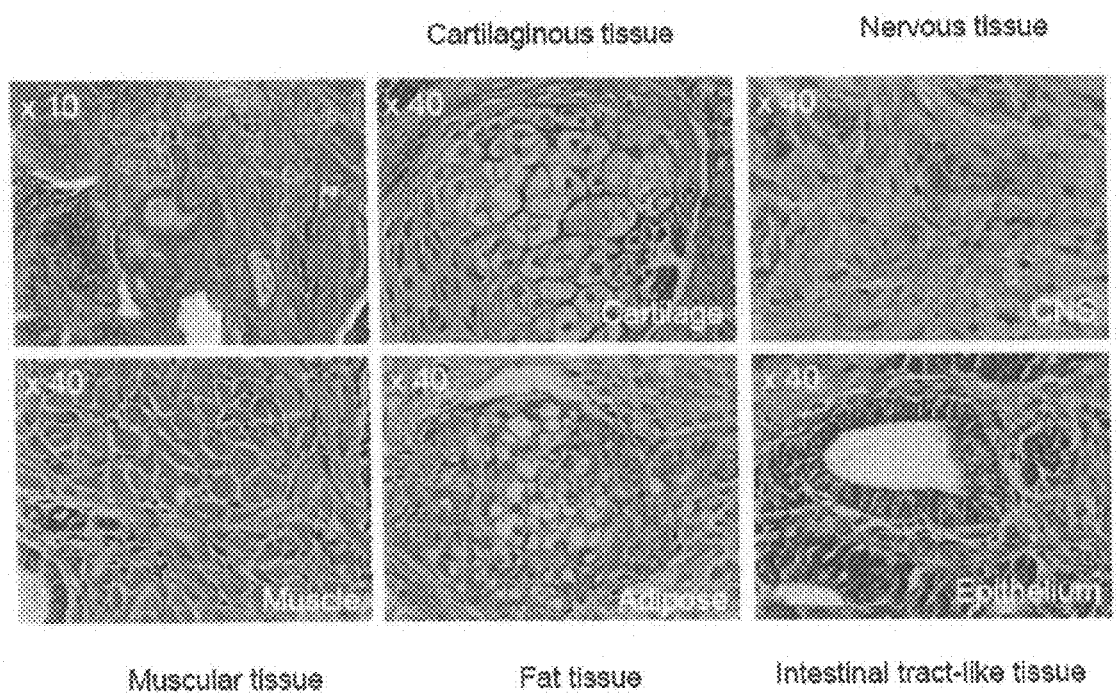

FIG. 8 depicts photographs showing results of hematoxylin-eosin (H & E) staining of tumors formed after subcutaneous transplantation of iPS cells derived from MEFs into nude mice. Differentiation into a variety of tissues in a triploblastic system was observed.

Figure 9:
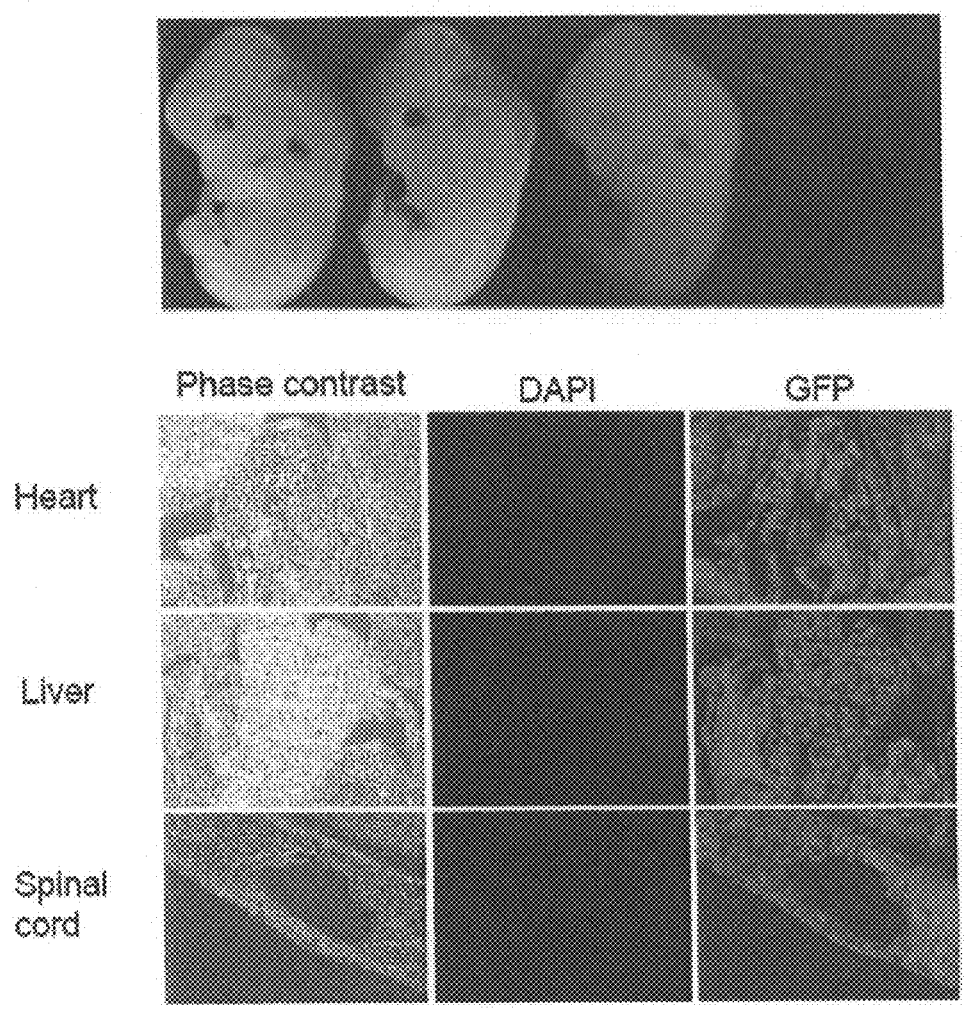

FIG. 9 depicts photographs of embryos prepared by transplanting iPS cells derived from adult dermal fibroblasts into mouse blastocysts and transplanting the cells into the uteri of pseudopregnant mice. It can be observed that, in the upper left embryo, cells derived from the iPS cells (emitting green fluorescence) were systemically distributed. In the lower photographs, it can be observed that almost all cells of the heart, liver, and spinal cord of the embryo were GFP-positive and were derived from the iPS cells.

Figure 10:
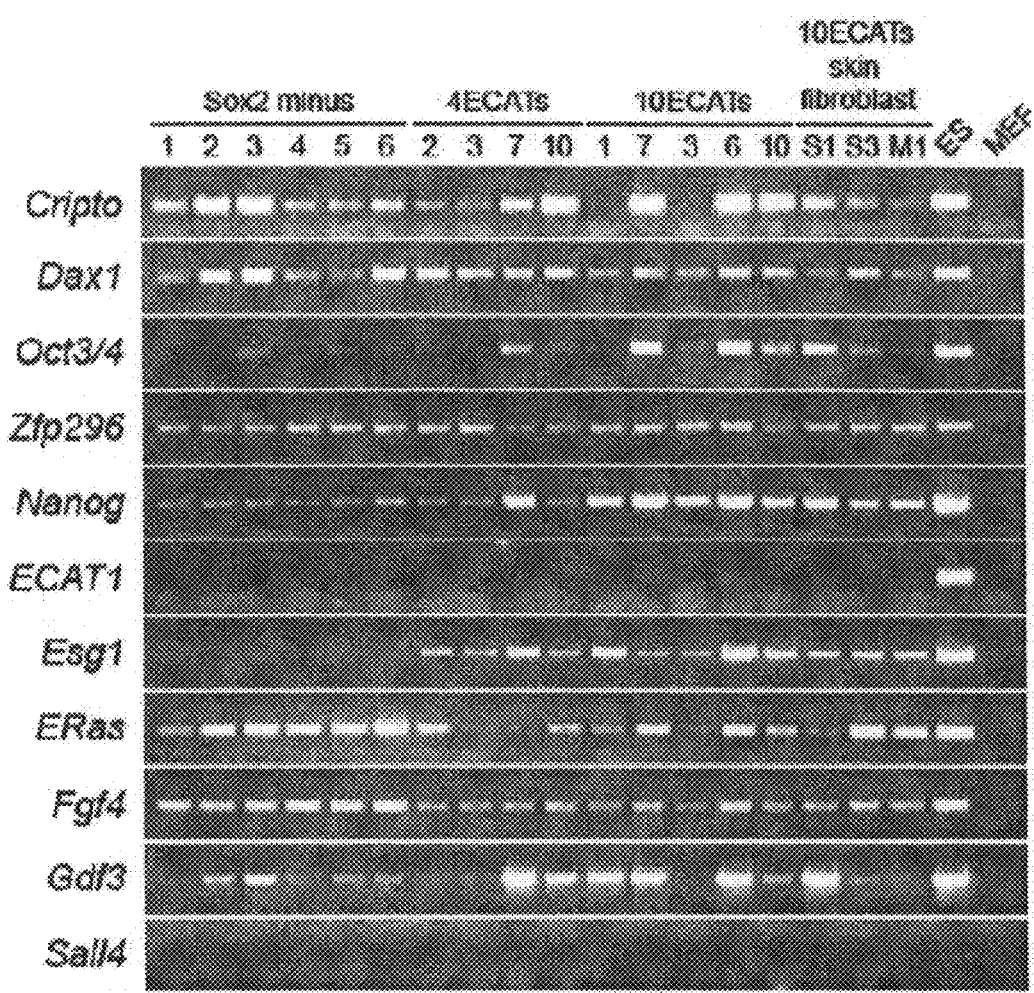

FIG. 10 depicts photographs showing results of RT-PCR confirming the expression of the ES cell marker genes. In the photographs, Sox2 minus indicates iPS cells established by the transduction of 3 genes into MEFs, 4ECATs indicates iPS cells established by the transduction of 4 genes into MEFs, 10ECATs indicates iPS cells established by the transduction of 10 genes into MEFs, 10ECATs Skin fibroblast indicates iPS cells established by the transduction of 10 genes into dermal fibroblasts, ES indicates mouse ES cells, and MEF indicates MEF cells without gene transduction. The numerical values under the symbols indicate clones numbers.

Figure 11:
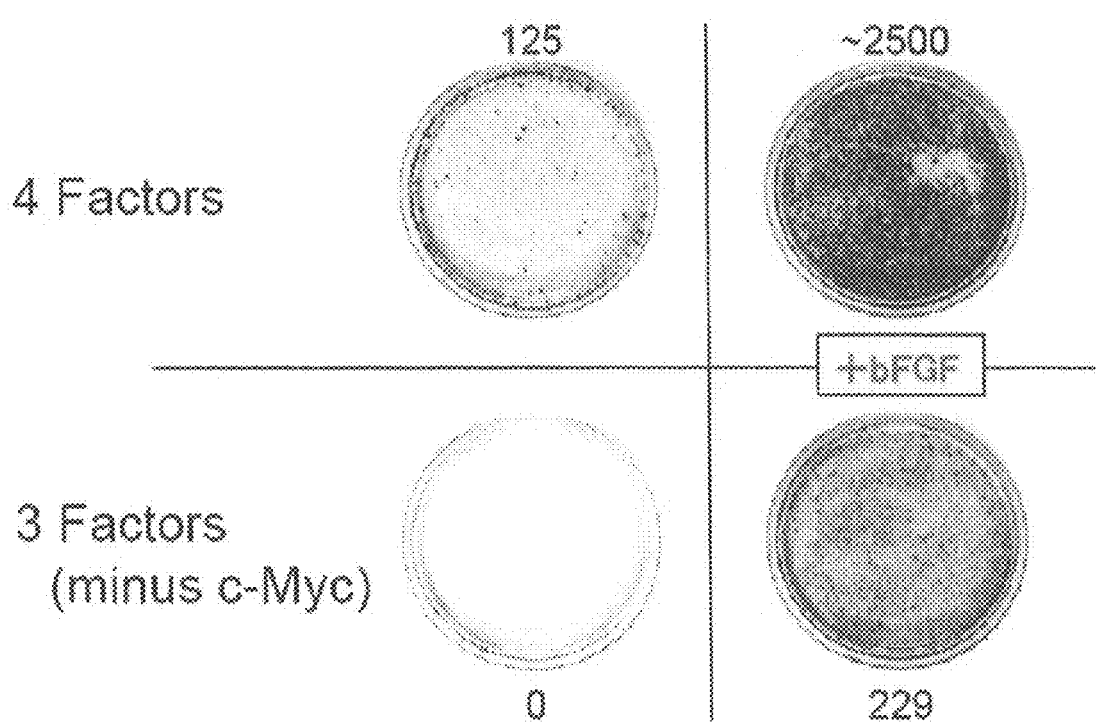

FIG. 11 shows an effect of bFGF on the establishment of iPS cells from MEFs. Four factors (upper row) or three factors except for c-Myc (lower row) were retrovirally transduced into MEFs derived from Fbx15$^{62\ geo/\beta geo}$ mice, and cultured on ordinary feeder cells (STO cells) (left) and bFGF expression vector-introduced STO cells (right). G418 selection was performed for 2 weeks, and cells were stained with crystal blue and photographed. The numerical values indicate the number of colonies.

Figure 12:
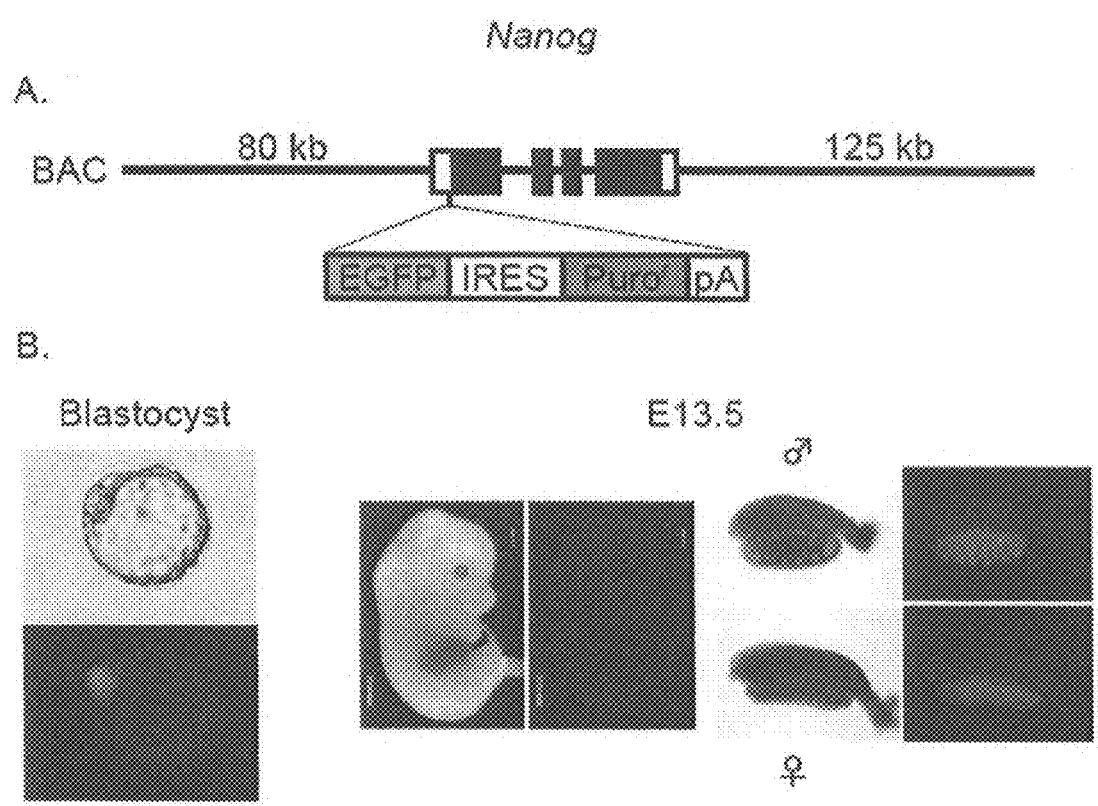

FIGS. 12(A)-(B) depict explanations of the experiments using Nanog-EGFP-IRES-Puro$^r$ mice. (A) *E. coli* artificial chromosome (BAC) containing the mouse Nanog gene in the center was isolated, and the EGFP-IRES-Puro$^r$ cassette was inserted upstream from the coding region of Nanog by recombineering. (B) Transgenic mice were prepared with the modified BAC. GFP expression was observed limitedly in inner cell masses of blastocysts and gonads.

Figure 13:
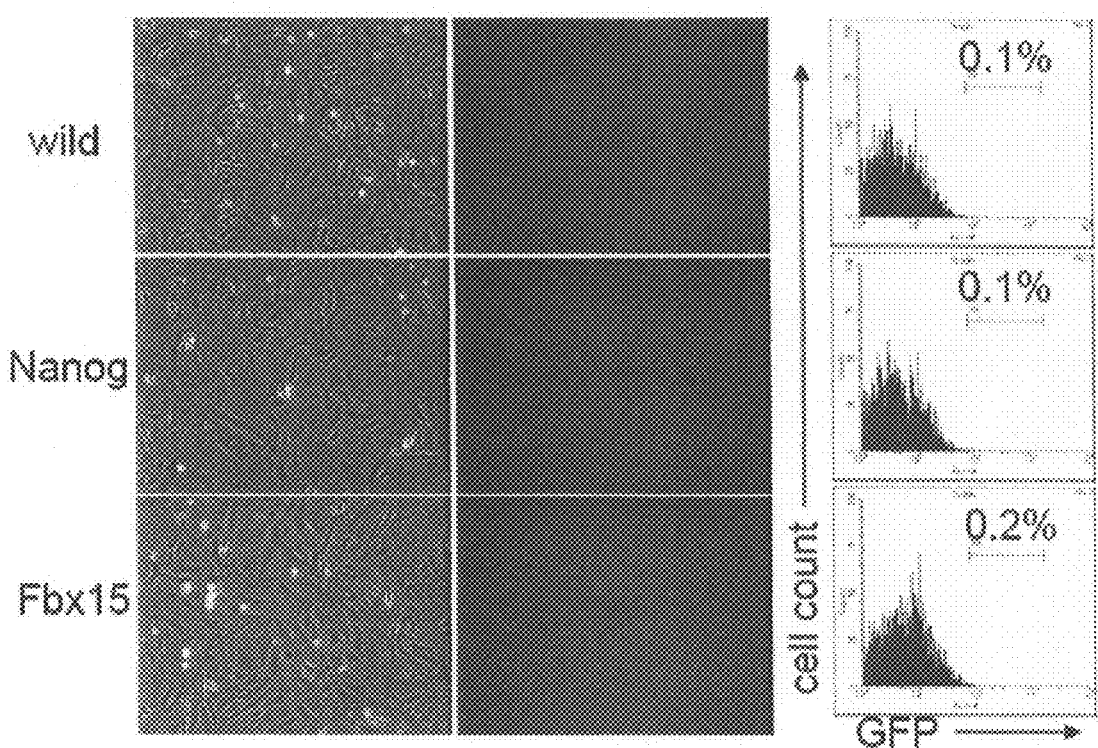

FIG. 13 depicts explanations of the experiments using Nanog-EGFP-IRES-Puro$^r$ mice. From embryos of Nanog-EGFP-IRES-Puro$^r$ mice (13.5 days after fertilization), heads, viscera and gonads were removed to establish MEFs. As a result of analysis with a cell sorter, almost no GFP-positive cells existed in MEFs derived from the Nanog-EGFP-IRES-Puro mice (Nanog) in the same manner as the Fbx15$^{\beta geo/\beta geo}$ mouse-derived MEFs (Fbx15) or wild-type mouse-derived MEFs (Wild).

Figure 14:
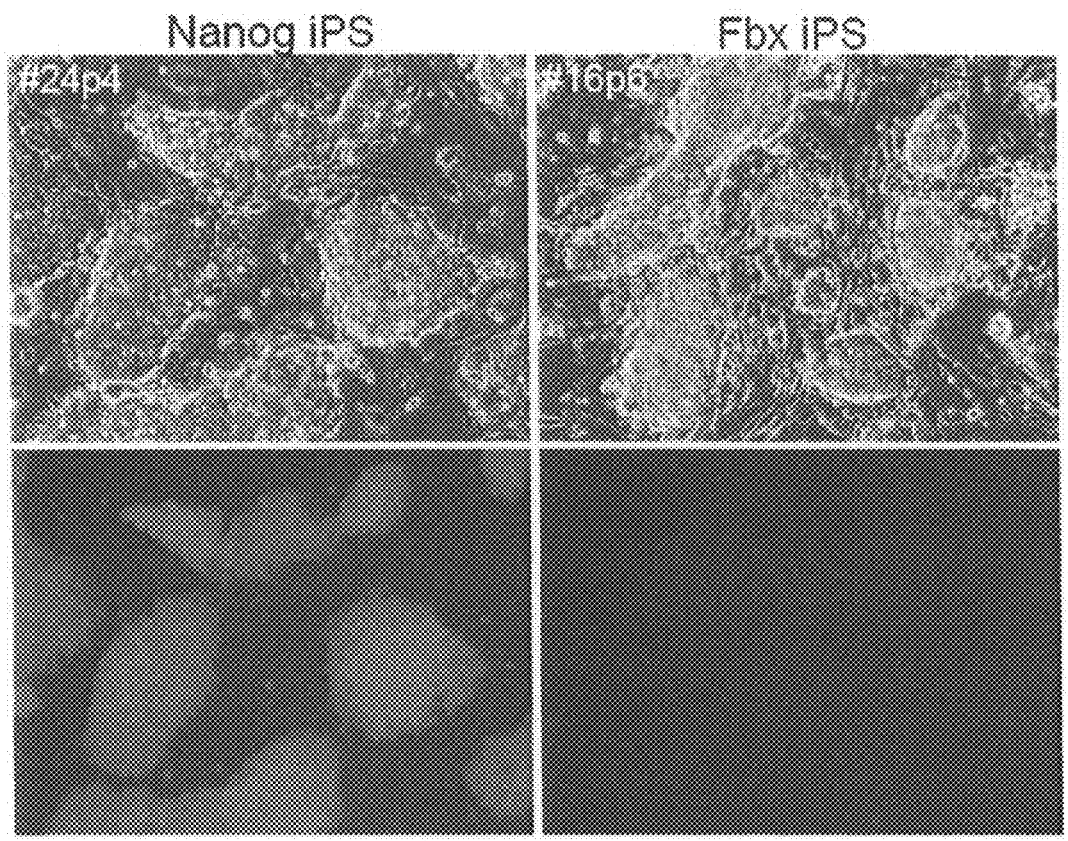

FIG. 14 depicts photographs of iPS cells established from the Nanog-EGFP-IRES-Puro mouse MEFs (left) and the Fbx15$^{\beta geo/\beta geo}$ mouse MEFs (right). The cells were selected with puromycin and G418, respectively.

Figure 15:
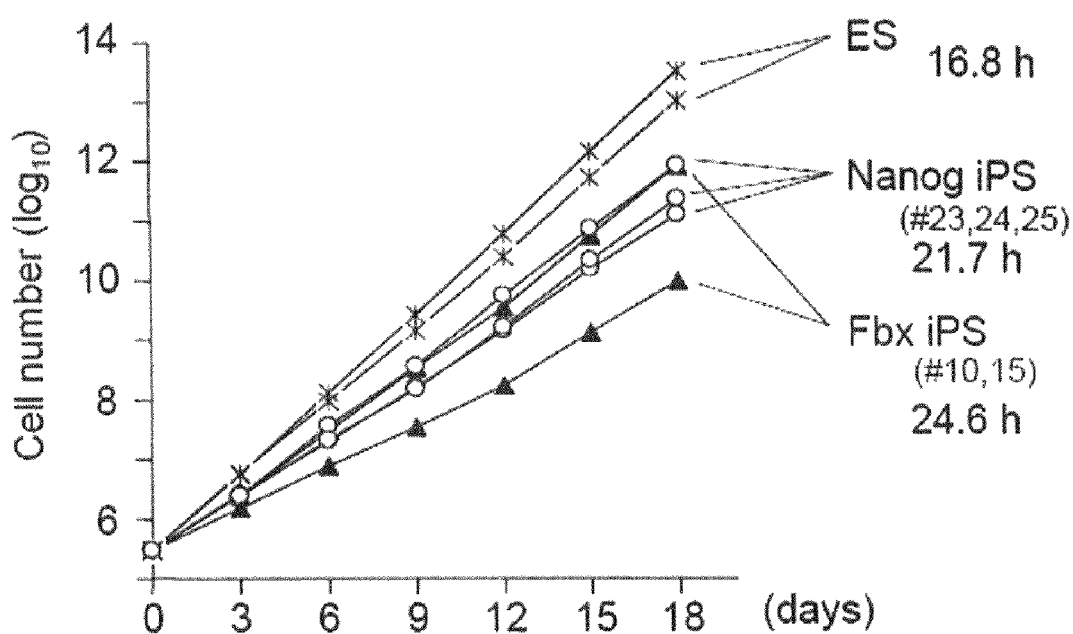

FIG. 15 shows results of growth of iPS cells. 100,000 cells of each of ES cells, iPS cells derived from the Nanog-EGFP-IRES-Puro mouse MEFs (Nanog iPS, left), and iPS cells derived from the Fbx15$^{\beta geo/\beta geo}$ mouse MEFs (Fbx iPS) were seeded on 24-well plates, and passaged every 3 days. Cell count results are shown. The numerical values represent average doubling times.

Figure 16:
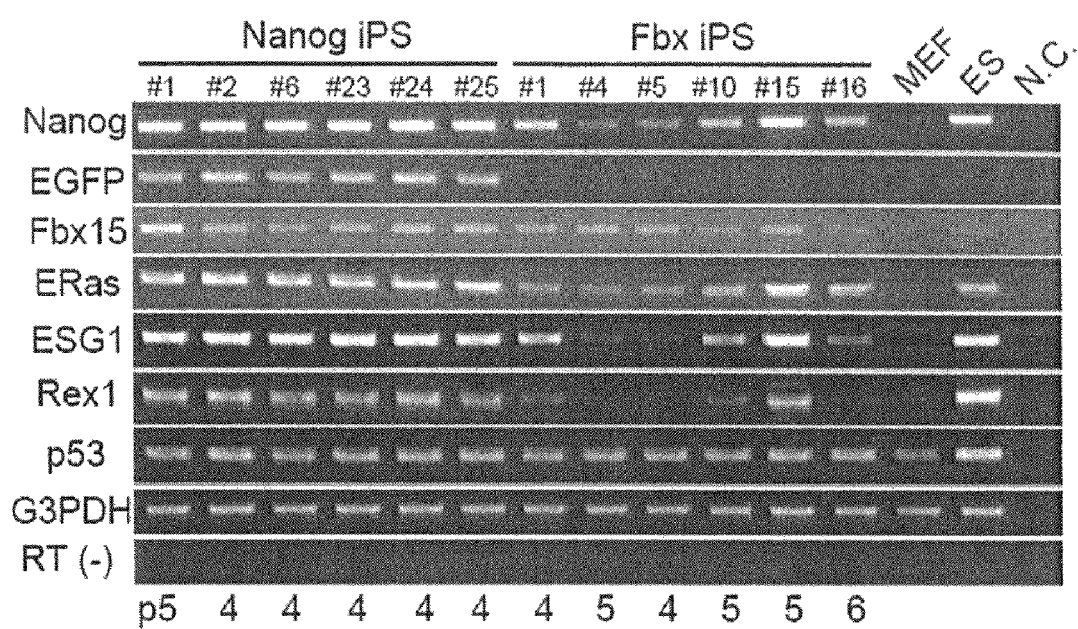

FIG. 16 shows gene expression profiles of iPS cells. Expression of the marker genes in MEFs, ES cells, iPS cells derived from Nanog-EGFP-IRES-Puro mouse MEFs (Nanog iPS, left), and iPS cells derived from Fbx15$^{\beta geo/\beta geo}$ mouse MEFs (Fbx iPS) were analyzed by RT-PCR. The numerical values at the bottom indicate the numbers of passages.

FIG. 17 shows teratoma formation from the Nanog iPS cells. 1,000,000 cells of each of ES cells or Nanog iPS cells #24 (passage 8 times) were subcutaneously injected into the backs of nude mice, and the appearance of tumors formed after 3 weeks (left) and tissue images (right, H & E stained) are shown.

Figure 18:
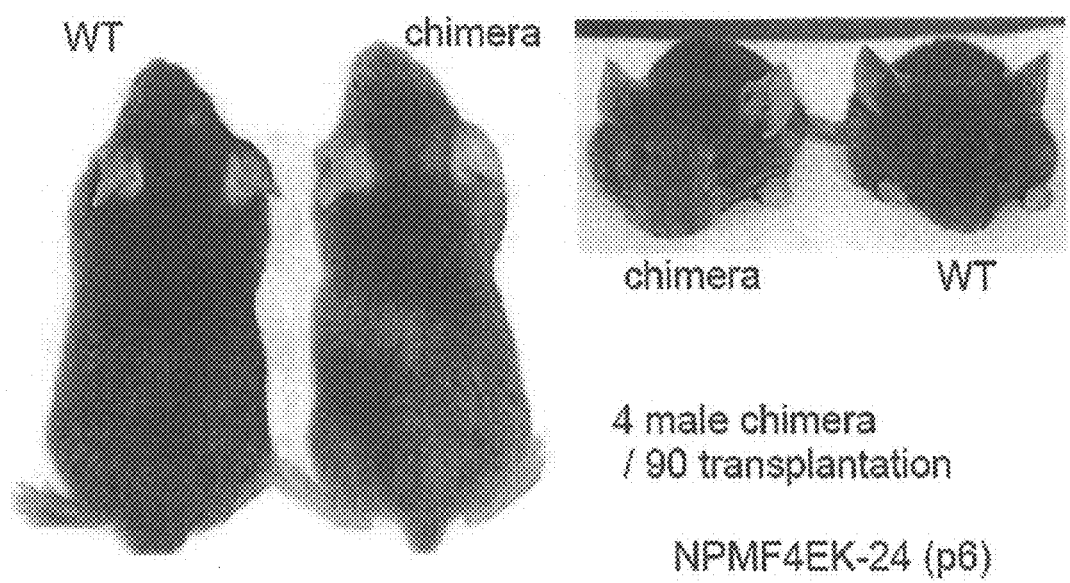

FIG. 18 shows preparation of chimeric mice with the Nanog iPS cells. The chimeric mice that were born after transplantation of the Nanog iPS cells (clone NPMF4EK-24, passaged 6 times) into the blastocysts. Four chimeric mice were born from 90 transplanted embryos.

Figure 19:
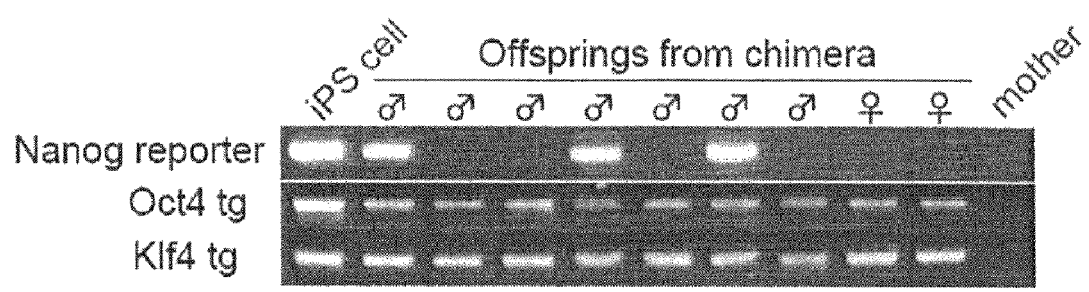

FIG. 19 shows germ-line transmission from the Nanog iPS cells. PCR analysis of genomic DNA of mice, born by mating of the chimeric mice shown in FIG. 18 and C57BL/6 mice, revealed the existence of transgenes of Oct3/4 and Klf4 in all of the mice, thereby confirming germ-line transmission.

Figure 20:
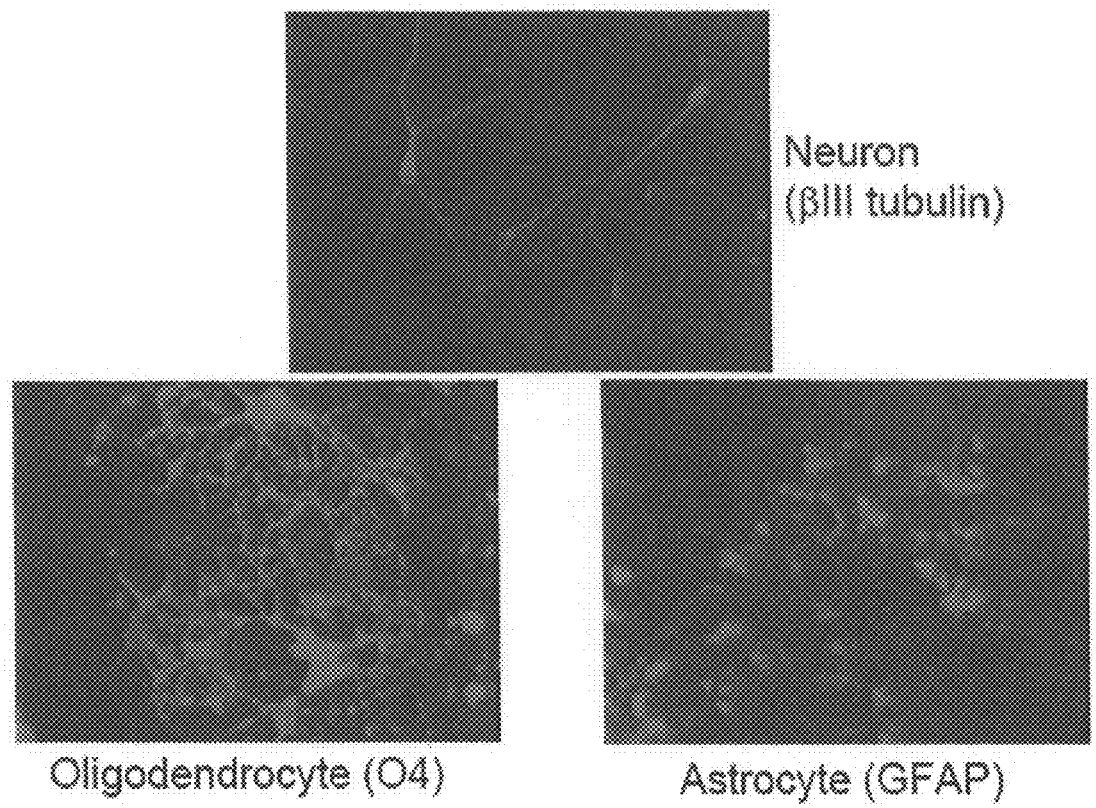

FIG. 20 shows induction of differentiation into nerve cells from iPS cells. Nerve cells (top, βIII tubulin-positive), oligodendrocytes (left, O4-positive), and astrocytes (right, GFAP-positive) differentiated in vitro from dermal fibroblasts-derived iPS cells are shown.

Figure 21:
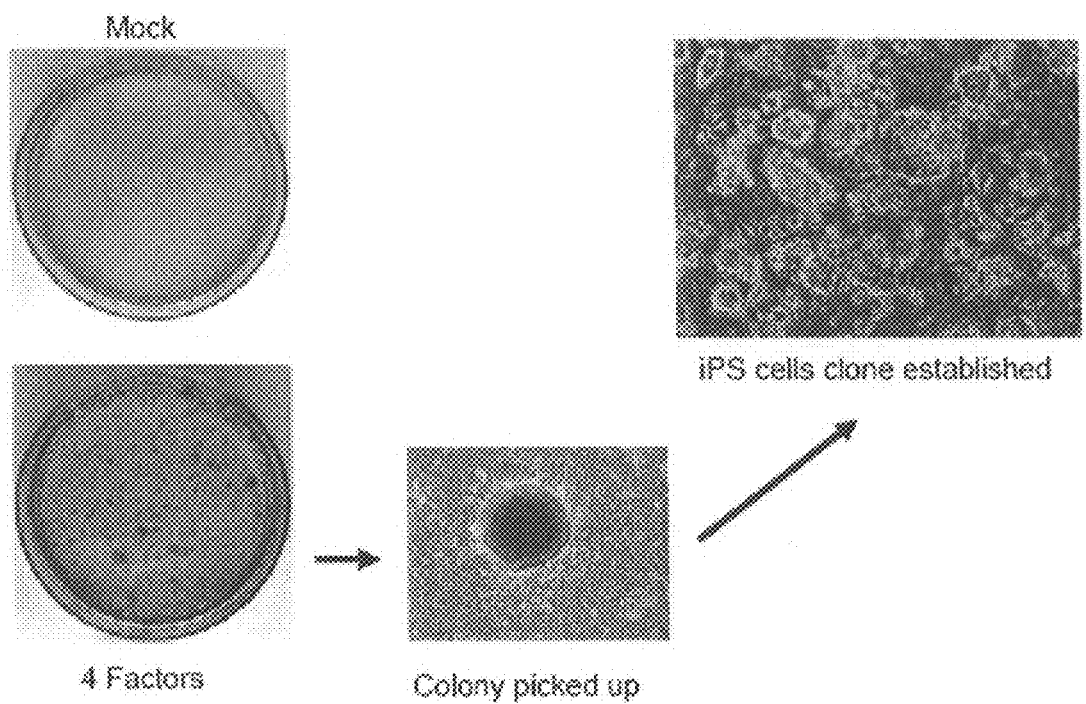

FIG. 21 depicts explanations of establishment of the iPS cells without using drug selection. MEFs at 10,000 to 100,000 cells per 10 cm dish were seeded, and the 4 factors were retrovirally transduced. No colony appeared in the control (Mock, top left), whilst in the dish with the transduction by the 4 factors, swelling colonies similar to those of the iPS cells were obtained (bottom left and center), as well as flat transformant colonies. When the cells were passaged, cells similar to the iPS cells were obtained (right).

Figure 22:
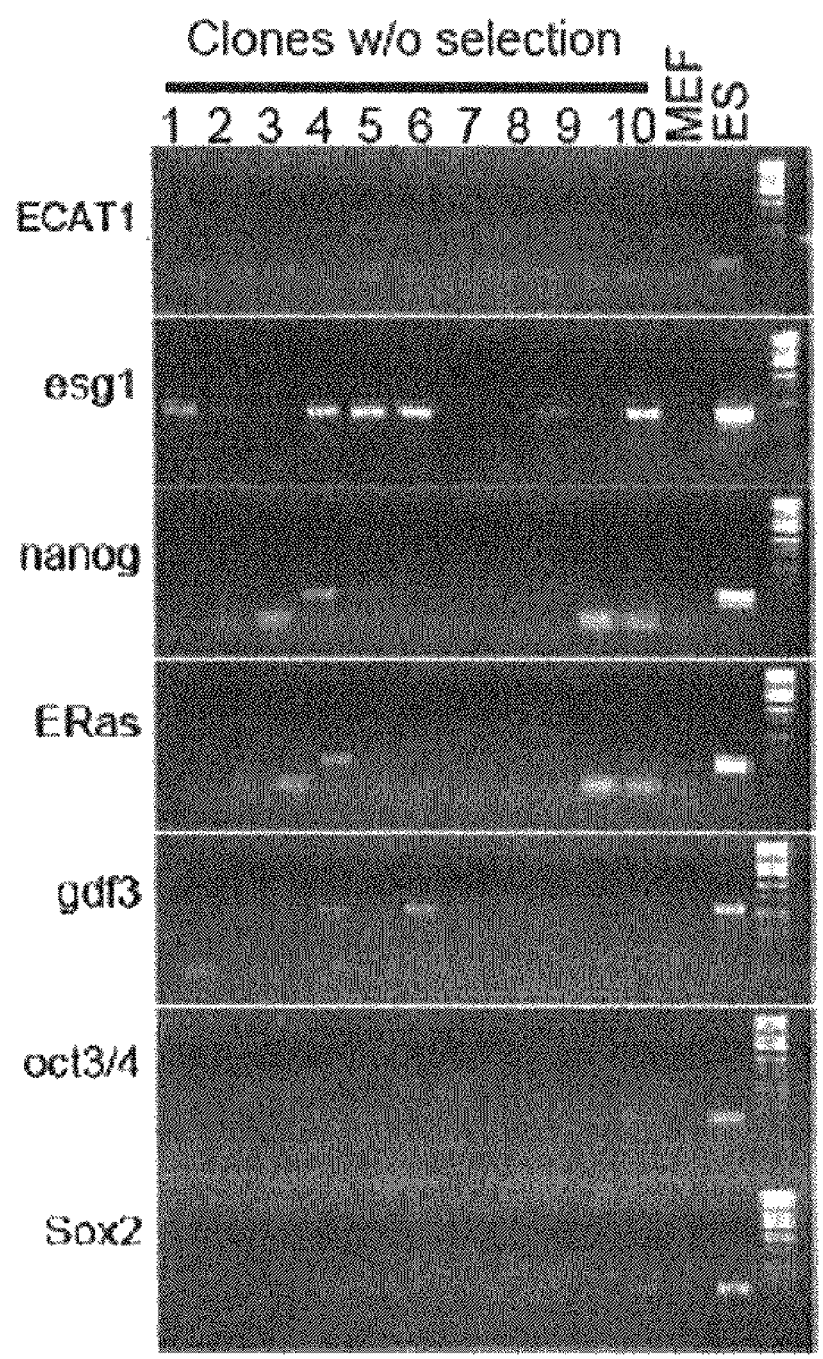

FIG. 22 shows gene expression profiles of cells established without using drug selection. RNA was extracted from the established cells shown in FIG. 21, and expression of the ES cell marker genes was analyzed by RT-PCR.

Figure 23:
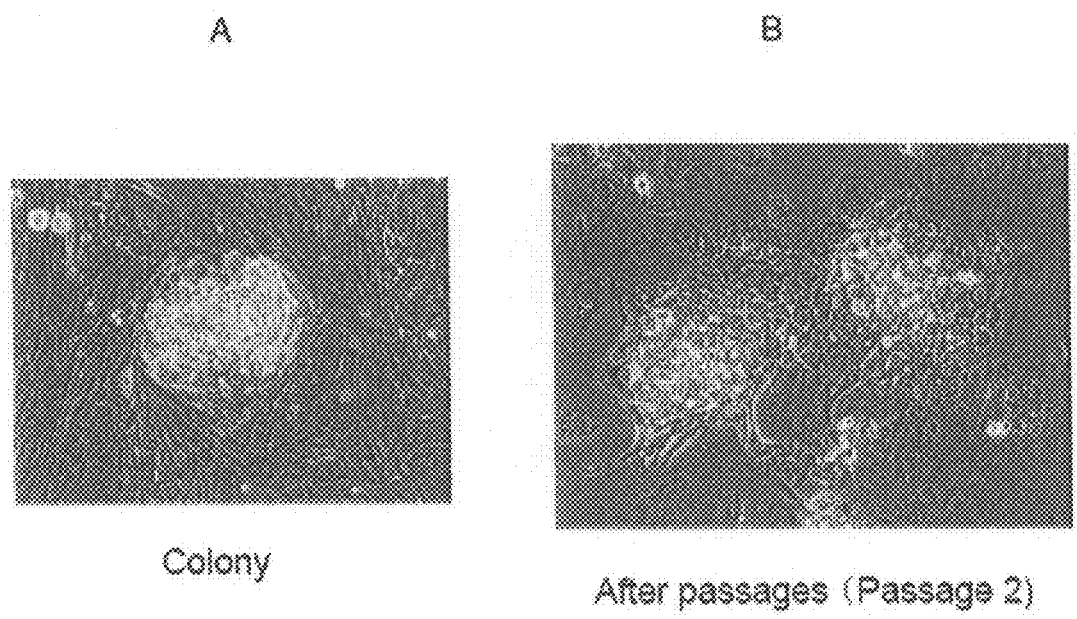

FIG. 23(A)-(B) show iPS cell-like cells derived from human fibroblasts. The colonies obtained by retroviral transduction with human homologous genes of the 4 factors into fibroblasts derived from human embryos (FIG. 23(A)), and the cells after two passages (FIG. 23(B)) are shown.

Figure 24:
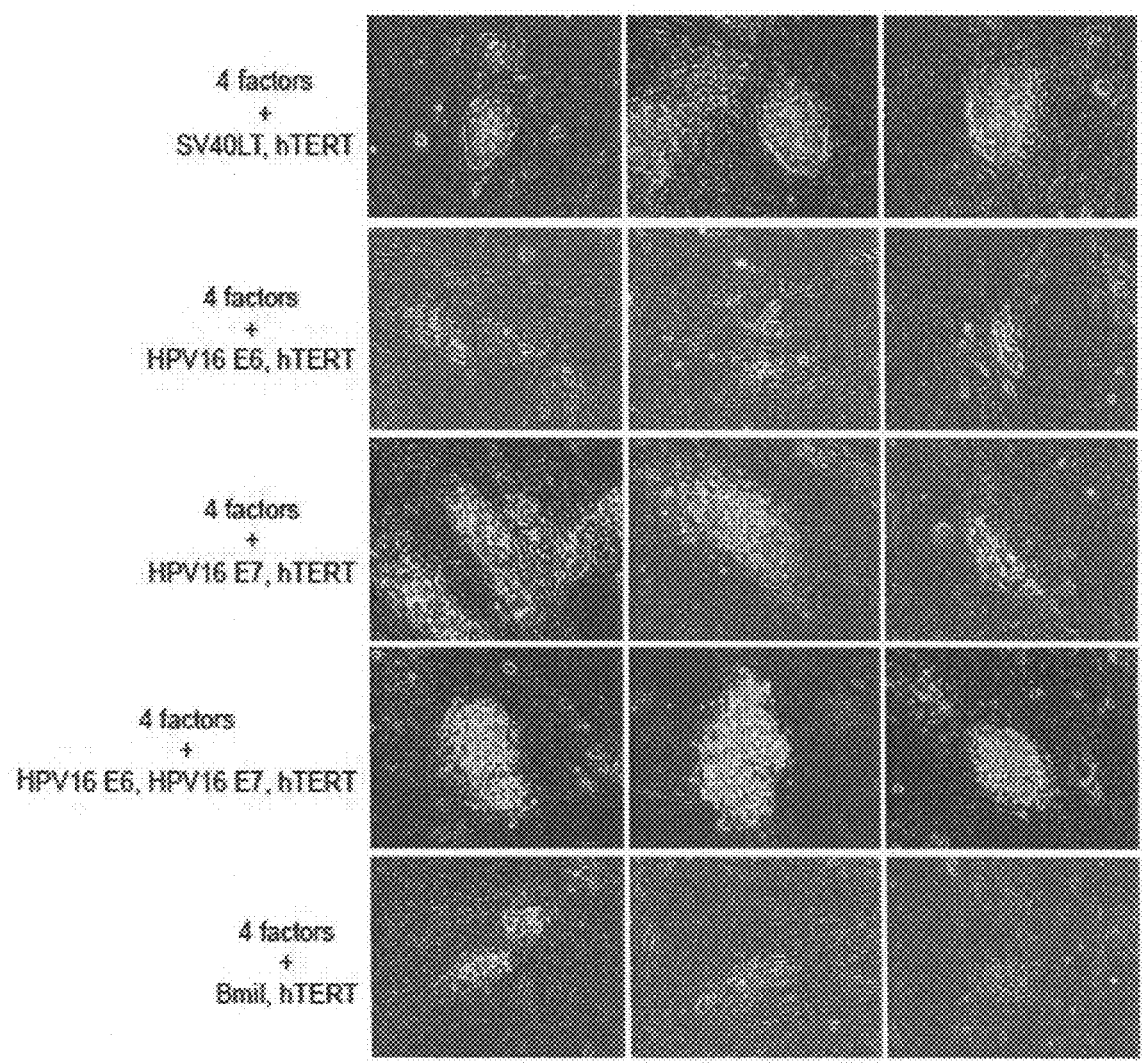

FIG. 24 shows establishment of the iPS cells from human adult dermal fibroblasts. The factors mentioned in the left column were transduced retrovirally into human adult dermal fibroblasts infected with the mouse retroviral receptor with lentivirus. The photographs shows phase contrast images (object×10) on day 8 after the viral infection.

Figure 25A:
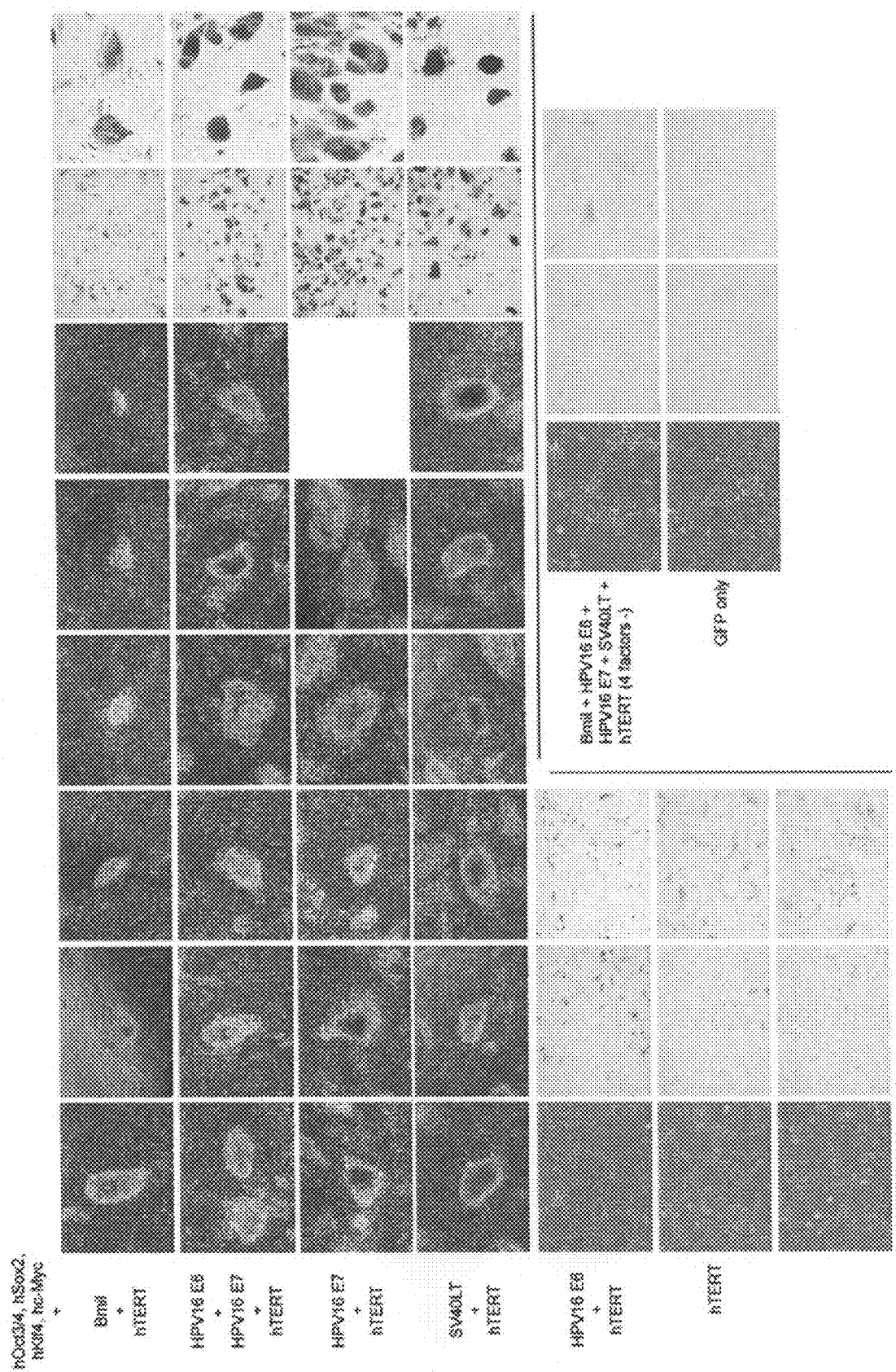
Figure 25B:
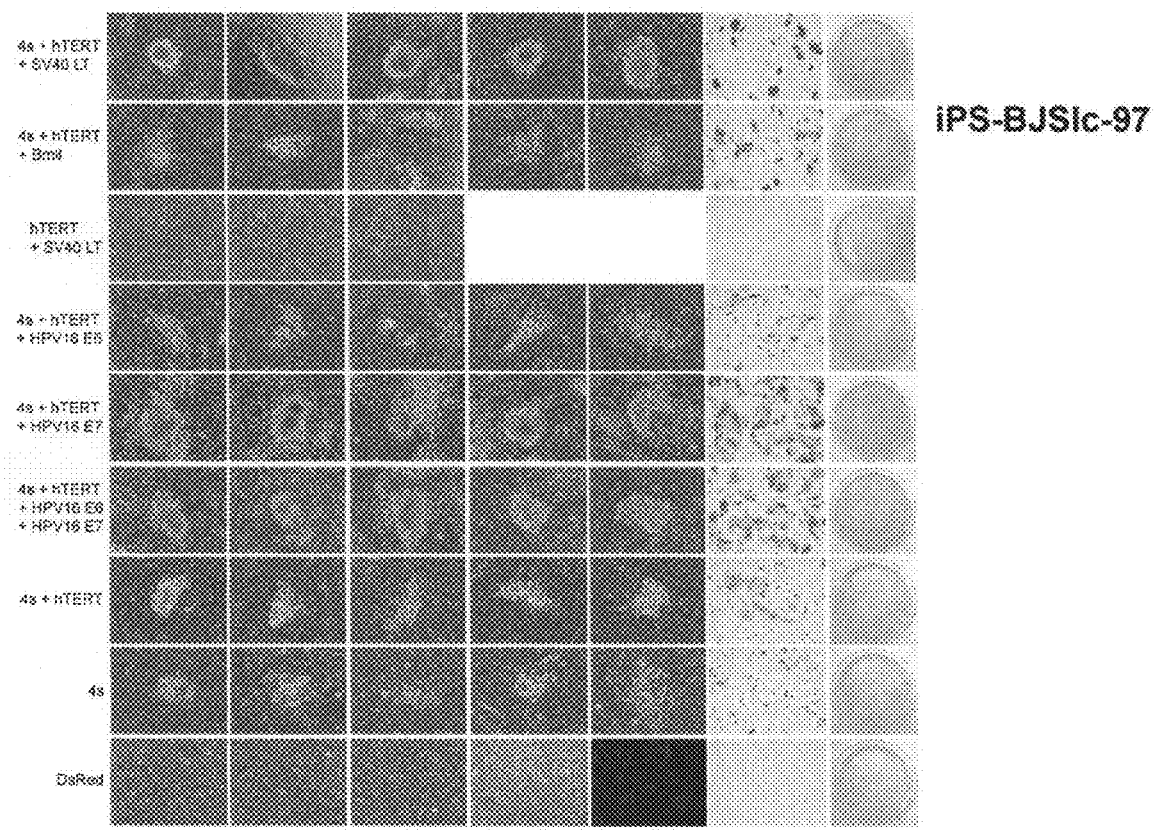

FIGS. 25(A)-(B) show the results of alkaline phosphatase staining of iPS cells from two different experiments. (A) 8×10$^5$ HDFs derived from adult skin expressing mouse Slc7a1 gene and introduced with pMXs encoding the genes indicated were plated on mitomycin C-treated STO cells. The infected cells were cultured in ES medium for 12 days. The cells were stained with alkaline phosphatase. (B) BJ fibroblasts expressing mouse Slc7a1 gene were plated at 8×10$^5$ cells per 100 mm dish on mitomycin C treated STO cells. Next day, the cells were transduced with the genes indicated (left) by retroviral infection. After transduction, the cells were maintained in ES medium for 2 weeks. After picking up the colonies, the cells were stained with alkaline phosphatase.

Figure 26A:
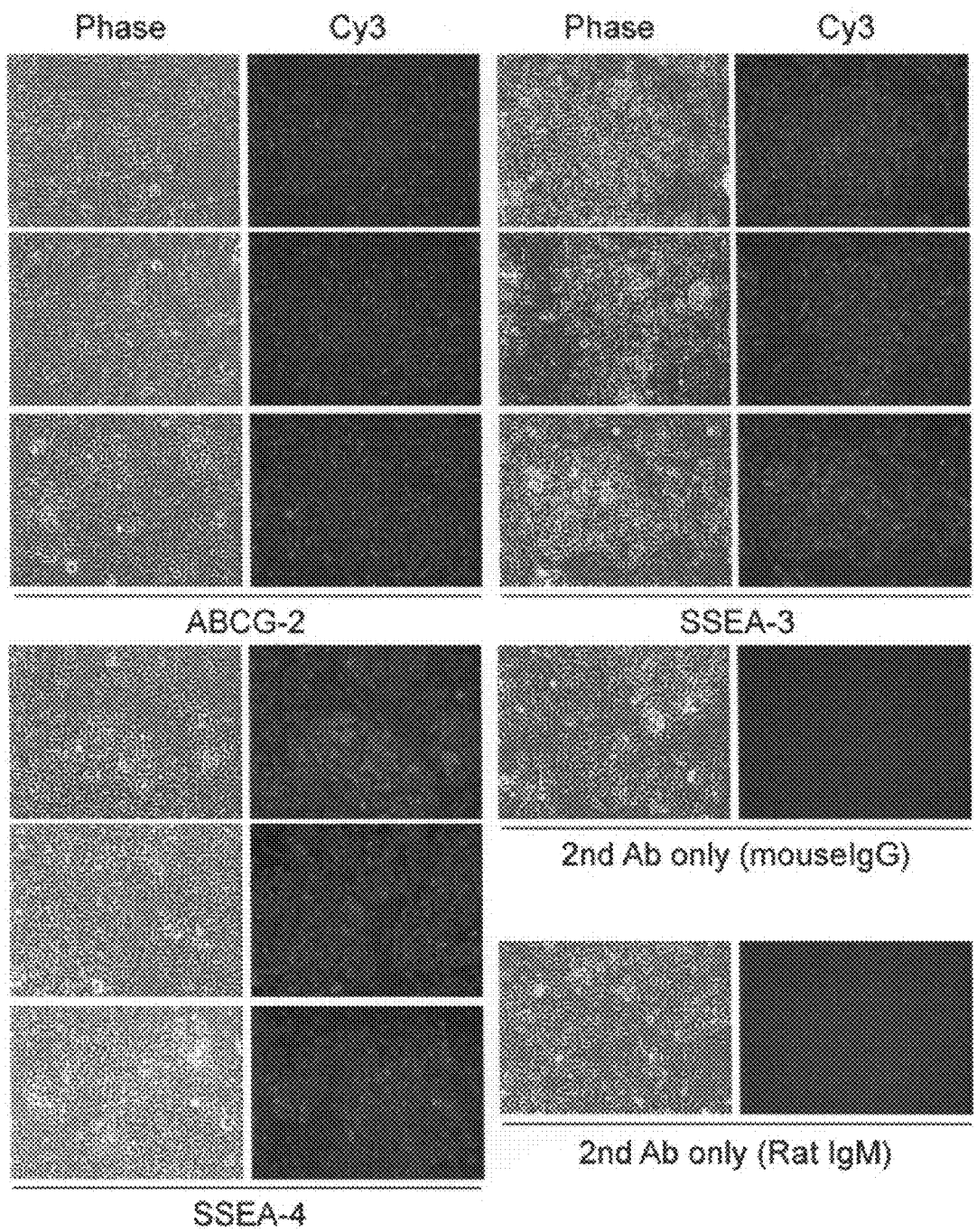
Figure 26B:
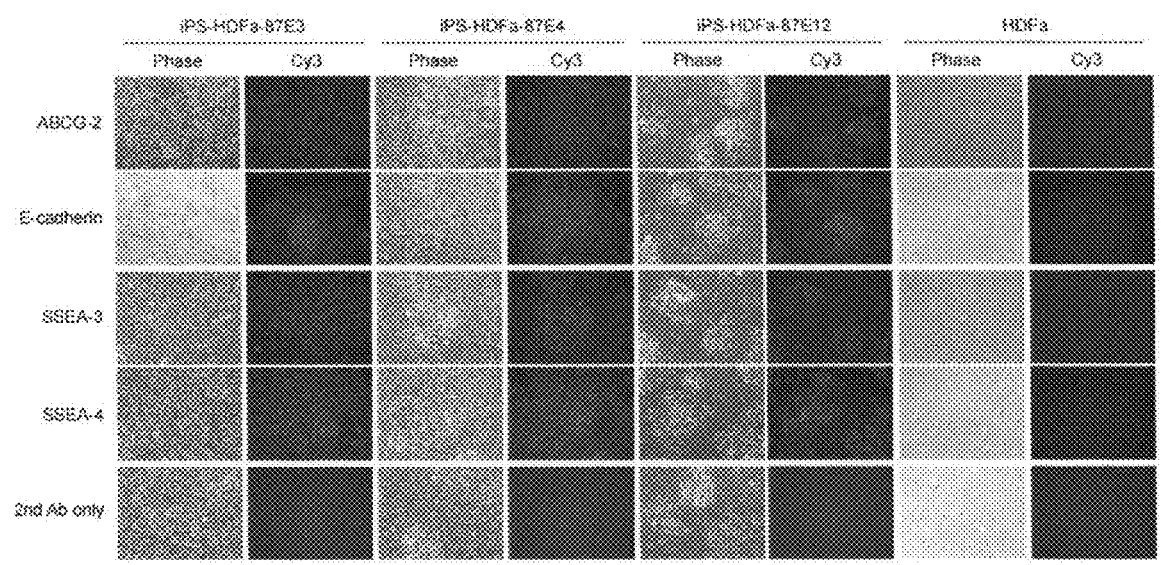

FIG. 26(A)-(B) show Cyanine 3 (Cy-3) staining of iPS (-like) cells with ES cell markers. (A) iPS (-like) cells derived from adult human dermal fibroblasts (HDFs) were plated at $5\times10^4$ cells per well of 6 well plates on mitomycin C-treated STO cells, and grown for 4 days. The cells were fixed with PBS containing 10% formalin, and blocked with blocking buffer (0.1% bovine serum albumin and 10 mg/ml normal donkey serum in PBS) for 45 minutes at room temperature. Primary antibodies indicated above were diluted 1:100 in blocking buffer. Overnight incubation with primary antibody, the cells were washed with PBS, and then incubated with secondary antibody. Cy-3-conjugated anti-mouse IgG (for ABCG-2 and SSEA-4) and anti-rat IgM (for SSEA-3) antibodies were used. (B) iPS (-like) cells derived from adult HDFs (clone 87E3, 87E4 and 87E12) were plated at $5\times10^4$ cells per well of a 6 well plate on mitomycin C-treated STO cells, and grown for 5 days. Parental HDFs also plated on 6 well plate and maintained for 2 days. The cells were fixed with PBS containing 10% formalin, and blocked with blocking buffer (3% BSA in PBS) for 45 minutes at room temperature. Primary antibodies indicated above were diluted 1:100 in blocking buffer. Overnight incubation with primary antibody, the cells were washed with PBS, and then incubated with secondary antibody. Cy-3-conjugated anti-mouse IgG (for ABCG-2, E-cadherin, and SSEA-4) and anti-rat IgM (for SSEA-3) antibodies were used as secondary antibodies.

Figure 27:
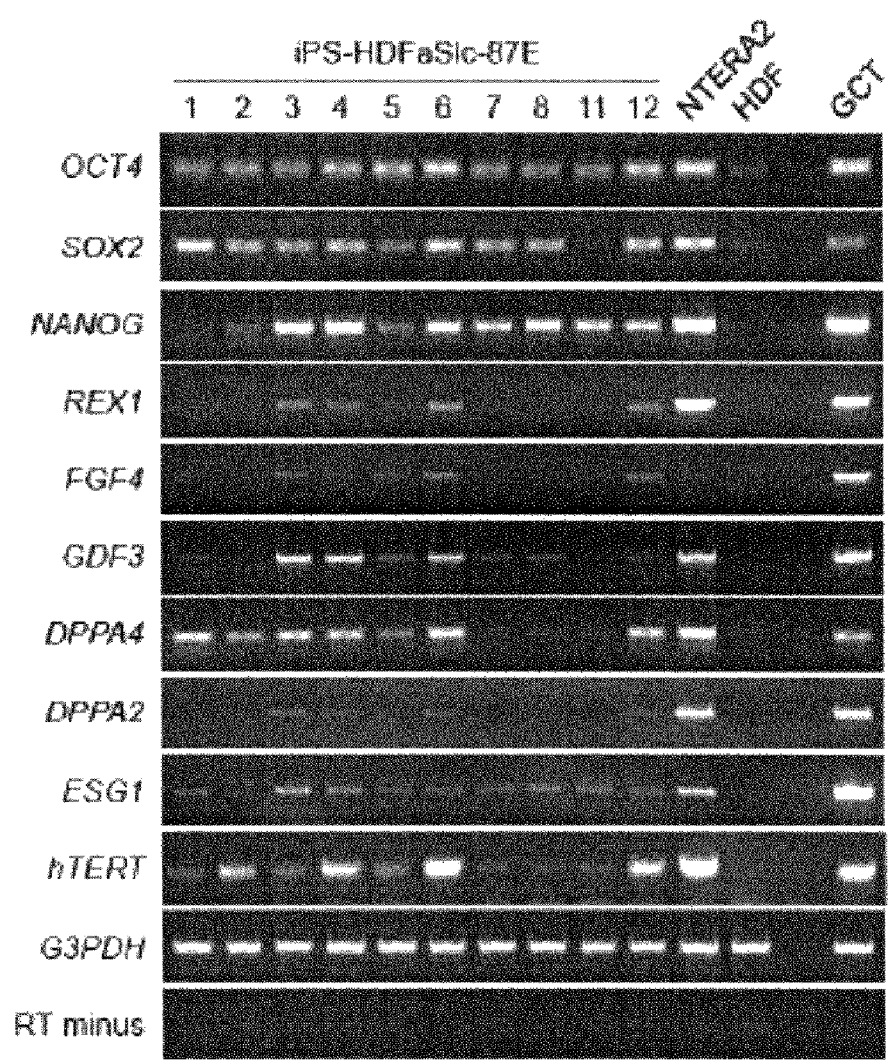

FIG. 27 shows human iPS (-like) cells express ECATs. Total RNA was isolated from human iPS (-like) cells (iPS-HDFaSlc-87E-1~8, 11 and 12), NTERA2 cloneD1 human embryonic carcinoma cells (passage 35) and adult HDFs expressing mouse Slc7a1 gene (passage 6). First-strand cDNA was synthesized by using oligo-dT20 primer and Rever Tra Ace-α-kit (Toyobo) according to manufacturer's protocol. PCR was performed with the primers as follows: hOct4 S1165 and hOct4-AS1283 for endogenous OCT4, hSox2-S1430 and hSox2-AS1555 for endogenous SOX2, ECAT4-macaca-968S and ECAT4-macaca-1334AS for NANOG, hRex1-RT-U and hRex1-RT-L for REX1, hFGF4-RT-U and hFGF4-RT-L for FGF4, hGDF3-S243 and hGDF3-AS850 for GDF3, hECAT15-S532 and hECAT15-AS916 for ECAT15-1, hECAT15-2-S85 and hECAT15-2-AS667 for ECAT15-2, hpH34-S40 and hpH34-AS259 for ESG1, hTERT-S3556 and hTERT-AS3713 for hTERT, and G3PDH-F and G3PDH-R for G3PDH.

Figure 28:
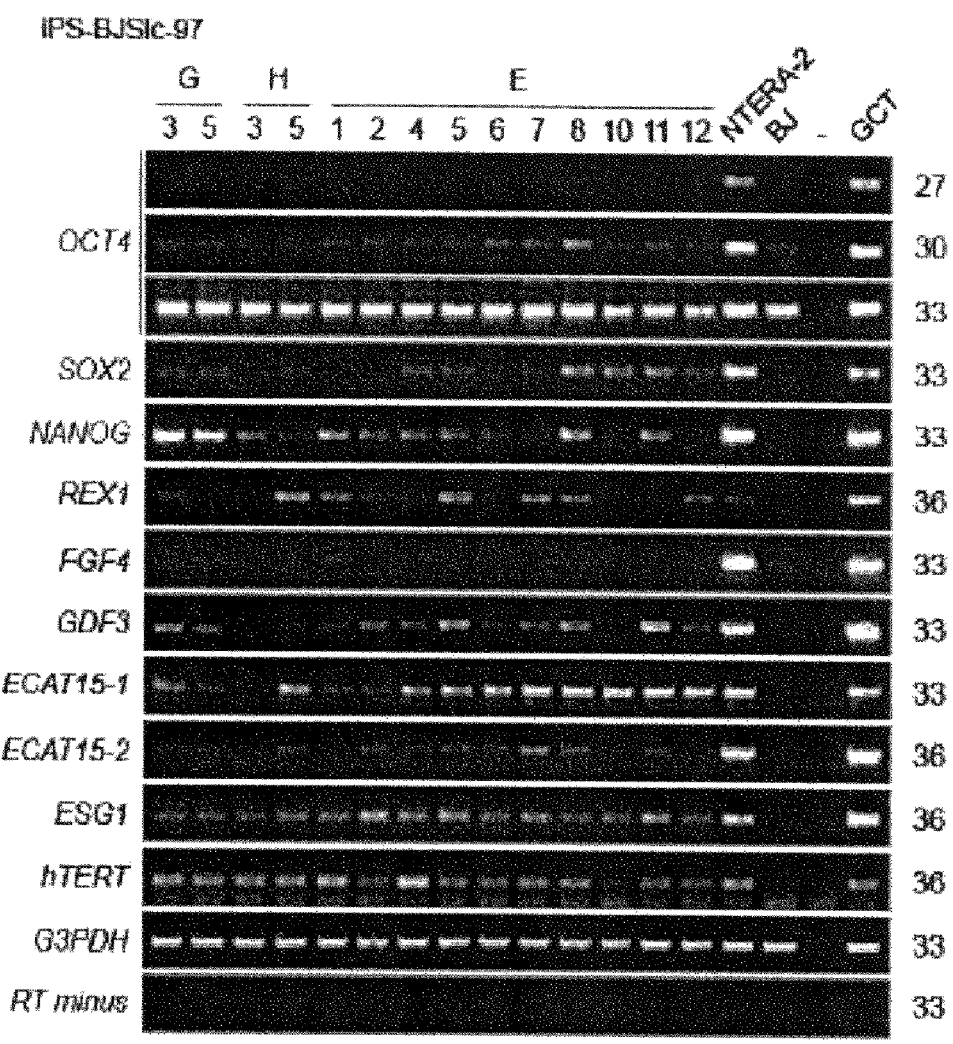
Figure 29:
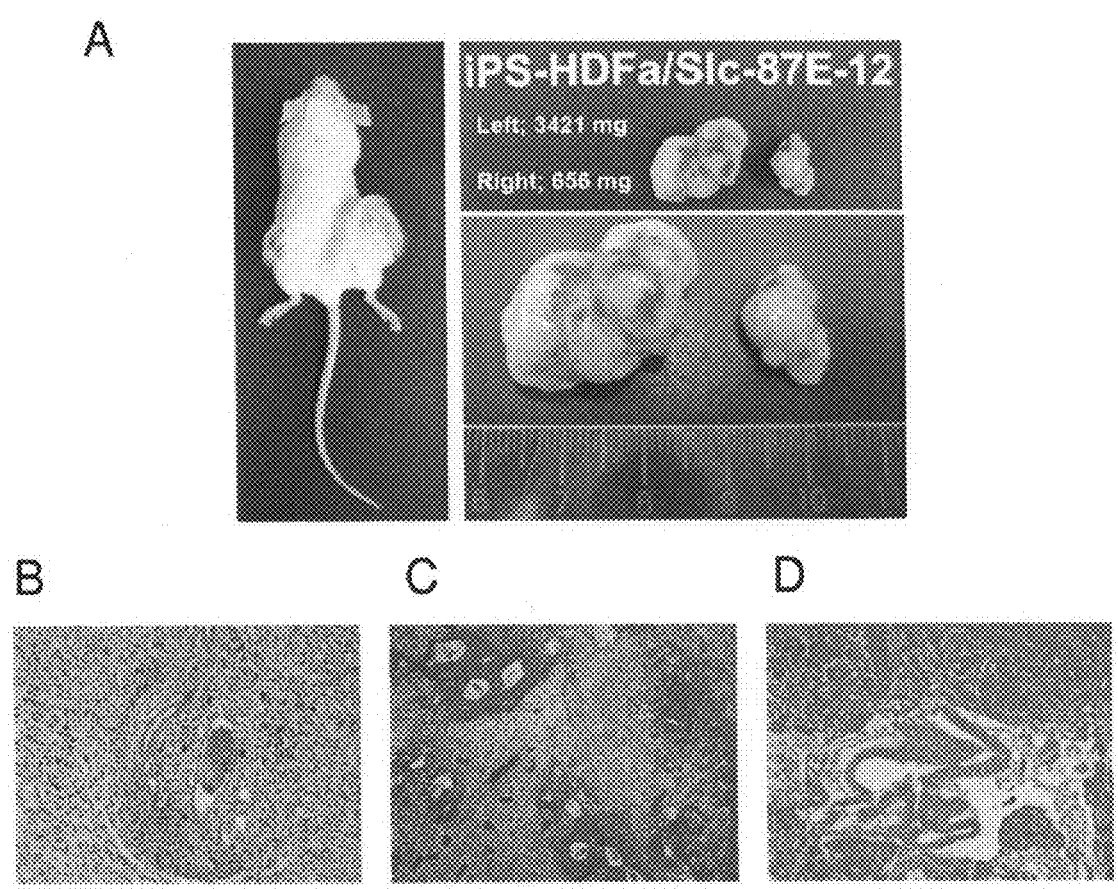

FIG. 28 shows human iPS (-like) cells express ECATs. Total RNA was isolated from human iPS (-like) cells (iPS-BJSlc-97E-1, 2, 4, 5, 6, 7, 8, 10, 11, 12, -97G-3, 5, -97H-3, 5), NTERA2 clone D1 human embryonic carcinoma cells (passage 35) and BJ fibroblasts expressing mouse Slc7a1 gene (passage 6). First-strand cDNA was synthesized by using oligo-dT20 primer and Rever Tra Ace-α-kit (Toyobo) according to manufacturer's protocol. PCR was performed with the primers as follows: hOct4 S1165 and hOct4-AS1283 for endogenous OCT4, hSox2-S1430 and hSox2-AS1555 for endogenous SOX2, ECAT4-macaca-968S and ECAT4-macaca-1334AS for NANOG, hRex1-RT-U and hRex1-RT-L for REX1, hFGF4-RT-U and hFGF4-RT-L for FGF4, hGDF3-S243 and hGDF3-AS850 for GDF3, hECAT15-S532 and hECAT15-AS916 for ECAT15-1, hECAT15-2-S85 and hECAT15-2-AS667 for ECAT15-2, hpH34-S40 and hpH34-AS259 for ESG1, hTERT-S3556 and hTERT-AS3713 for hTERT, and G3PDH-F and G3PDH-R for G3PDH.

FIGS. 29(A)-(D) show teratoma formation. Five million of hiPS (-like) cells were subcutaneously injected into dorsal flanks of SCID mouse (female, 5 weeks old). Two months after injection, large tumors were observed. Tumors were dissected, weighed and photographed. Then these tumors were fixed with PBS containing 10% formalin. Paraffin-embedded tumor was sliced and then stained with hematoxylin and eosin. (A) Mouse from clone iPS-HDFa/Slc-87E-12. (B)-(D) indicate mouse teratomas from clones iPS-HDFa/Slc-97E-3 (B); iPS-HDFa/Slc-87E-6(C); and iPS-HDFa/Slc-87E-12 (D).

Figure 30:
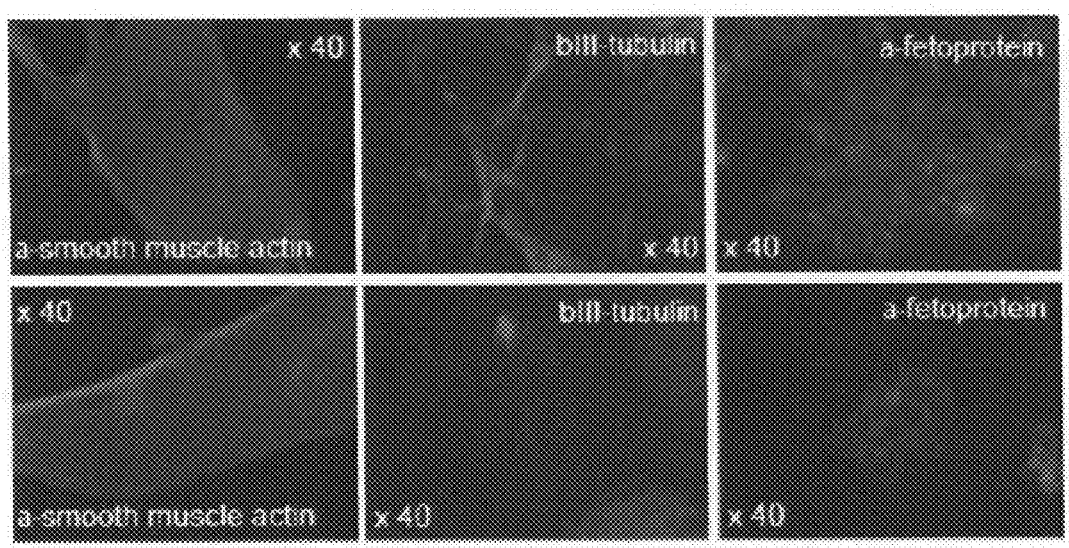

FIG. 30 shows in vitro differentiation of human iPS-like cells. The cells (iPS-HDFaSlc-127F2, E3) were suspended in hES medium (w/o bFGF). $2\times10^6$ cells were transferred to HEMA (2-hydroxyethyl methacrylate)-coated 100 mm tissue culture dish. The medium was changed every other day. After seven days floating culture, the cells were collected, plated to six gelatinized 35 mm dishes and incubated another 7 days. The cells were fixed with PBS containing 10% formalin for 10 min at room temperature, permeabilized with PBS containing 0.5% TritonX-100 for 5 min at room temperature, and blocked with PBS containing 3% BSA for 30 min at room temperature. Primary antibodies used in this experiment were as follows; anti-α-smooth muscle actin (Ms mono, pre-diluted, DAKO), anti-βIII-tubulin (Ms mono, 1:100 in blocking buffer, Chemicon), anti-α-fetoprotein (Rb poly, pre-diluted, DAKO), normal mouse IgG (2 mg/ml, Chemicon), and normal rabbit IgG (2 mg/ml, Chemicon). After incubation with primary antibody (1 hour at room temperature), the cells were washed with PBS, and incubated with secondary antibody (1:300 in blocking buffer).

Figure 31:
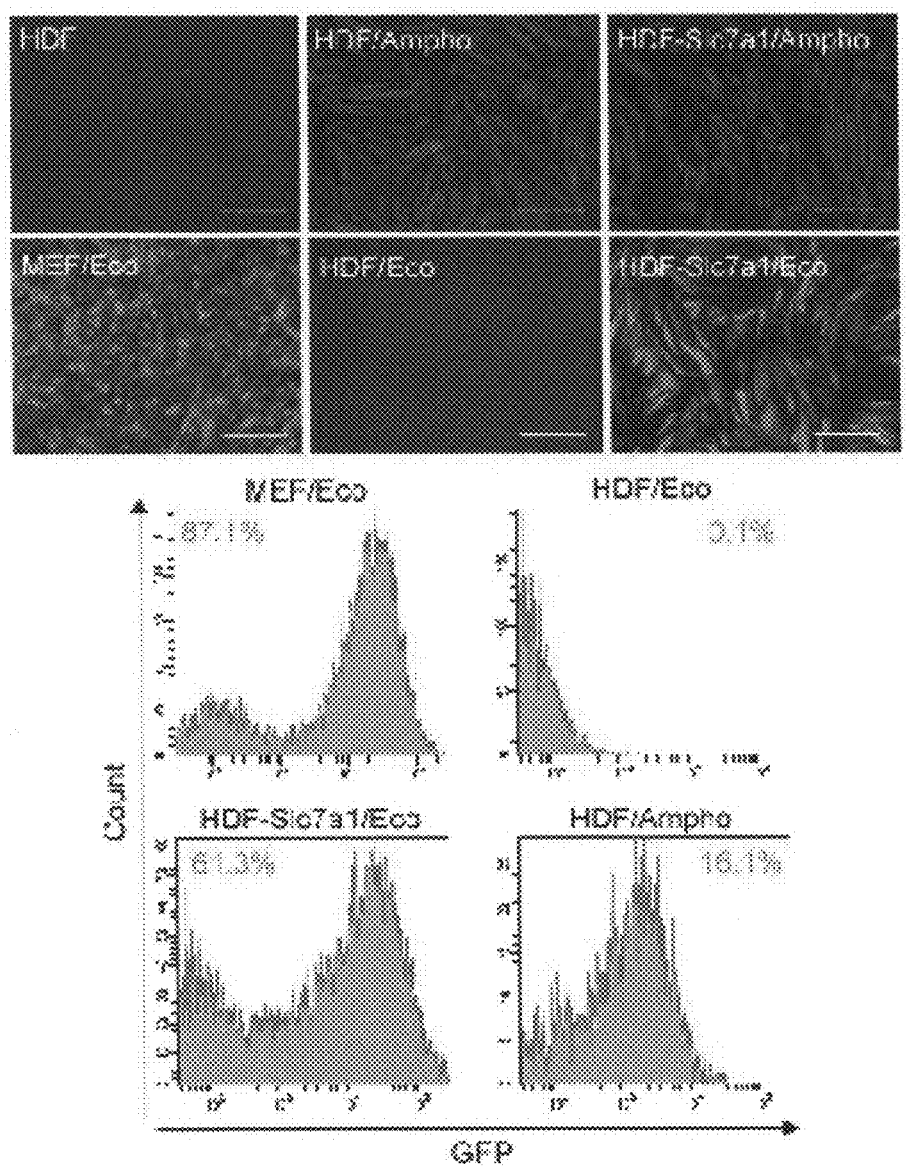

FIG. 31 shows improved transduction efficiency of retroviruses in human HDFs. HDFs or HDFs expressing mouse Slc7a1 gene (HDF-Slc7a1) were introduced with ecotropic (Eco) or amphotropic (Ampho) pMX retroviruses containing the GFP cDNA. Shown are results of fluorescent microscope (upper) and flow cytometry (lower). Bars=100 μm.

FIGS. 32(A)-(N) show induction of iPS cells from adult HDFs in primate ES cell media. (A) Time schedule of iPS cell generation. (B) Morphology of HDFs. (C) Typical image of non-ES cell-like colony. (D) Typical image of hES cell-like colony. (E) Morphology of established iPS cell line at passage number 6 (clone 201B7). (F) Image of iPS cells with high magnification. (G) Spontaneously differentiated cells in the center part of human iPS cell colonies. (H—N) Immunocytochemistry for SSEA-1 (H), SSEA-3 (I), SSEA-4 (J), TRA-1-60 (K), TRA-1-81 (L), TRA-2-4916E (M), and Nanog (N). Nuclei were stained with Hoechst 33342 (blue). Bars=200 μm (B-E, G), 20 μm (F), and 100 μm (H—N).

FIGS. 33(A)-(C) show feeder dependency of human iPS cells. (A) Image of iPS cells plated on gelatin-coated plate. (B) Images of iPS cells cultured on Matrigel-coated plates in MEF-conditioned medium (MEF-CCM). (C) Images of iPS cells cultured in ES medium on Matrigel-coated plates with non-conditioned hES medium.

FIGS. 34(A)-(E) show expression of hES cell marker genes in human iPS cells. (A) RT-PCR analysis of ES cell marker genes. (B) Western blot analysis of ES cell marker genes. (C) Quantitative PCR for expression of retroviral transgenes. The graph shows the average of three assays. Bars indicate standard deviation. (D) Bisulfite genomic sequencing of the promoter regions of OCT3/4, REXJ and NANOG. Open and closed circles indicate unmethylated and methylated CpGs. (E) Luciferase assays. The graphs show the average of the results from four assays. Bars indicate standard deviation.

FIGS. 35(A)-(B) show high levels of telomerase activity and exponential proliferation of human iPS cells. (A) Detection of telomerase activities by the TRAP method. Heat-inactivated (+) samples were used as negative controls. IC=internal control. (B) Growth curve of iPS cells. Shown are averages and standard deviations in quadruplicate.

FIGS. 36(A)-(B) show genetic analyses of human iPS cells. (A) Genomic PCR revealed integration of all the four retroviruses in all clones. (B) Southern blot analyses with a c-MYC cDNA probe. Asterisk indicates the endogenous c-MYC alleles (2.7 kb). Arrowhead indicates mouse c-Myc alleles derived from SNL feeder cells (9.8 kb).

FIGS. 37(A)-(L) show embryoid body-mediated differentiation of human iPS cells. (A) Floating culture of iPS cells at day 8. (B-E) Images of differentiated cells at day 16 (B), neuron-like cells (C), epithelial cells (D), and cobblestone-like cells (E). (F-K) Immunocytochemistry of alpha-fetoprotein (F), vimentin (G), α-smooth muscle actin (H), desmin (I), βIII-tubulin (J), and GFAP (K). Bars=200 μm (A, B) and 100 μm (C-K). Nuclei were stained with Hoechst 33342 (blue). (L) RT-PCR analyses of various differentiation markers for the three germ layers.

FIGS. 38(A)-(E) show directed differentiations of human iPS cells. (A) Phase contrast image of differentiated iPS cells after 18 days cultivation on PA6. (B) Immunocytochemistry of the cells shown in A with III-tubulin (red) and tyrosine hydroxylase (green) antibodies. Nuclei were stained with Hoechst 33342 (blue). (C) RT-PCR analyses of dopaminergic neuron markers. (D) Phase contrast image of iPS cells differentiated into cardiomyocytes. (E) RT-PCR analyses of cardiomyocyte markers. Bars=200 μm (A, D) and 100 μm (B).

Figure 39:
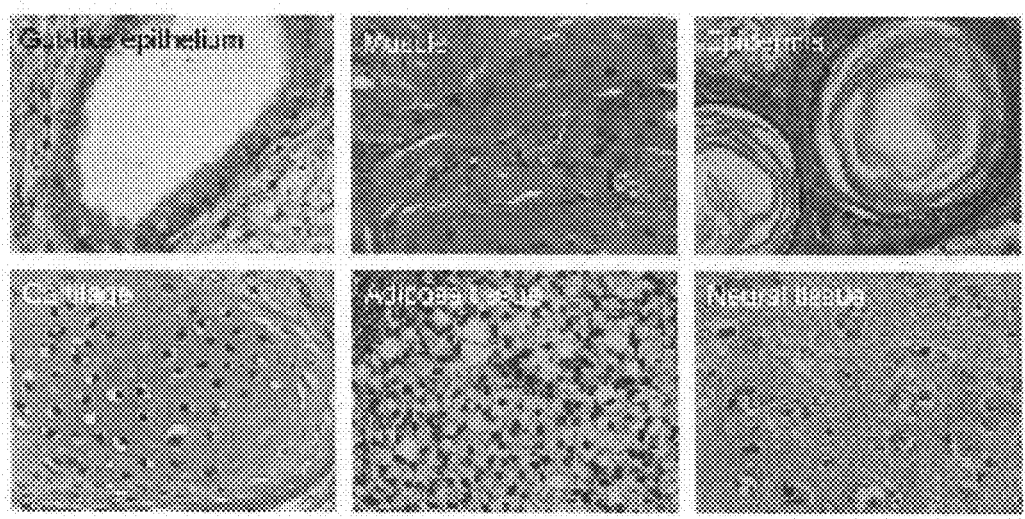

FIG. 39 shows hematoxylin and eosin staining of teratoma derived from human iPS cells (clone 201B7).

Figure 40:
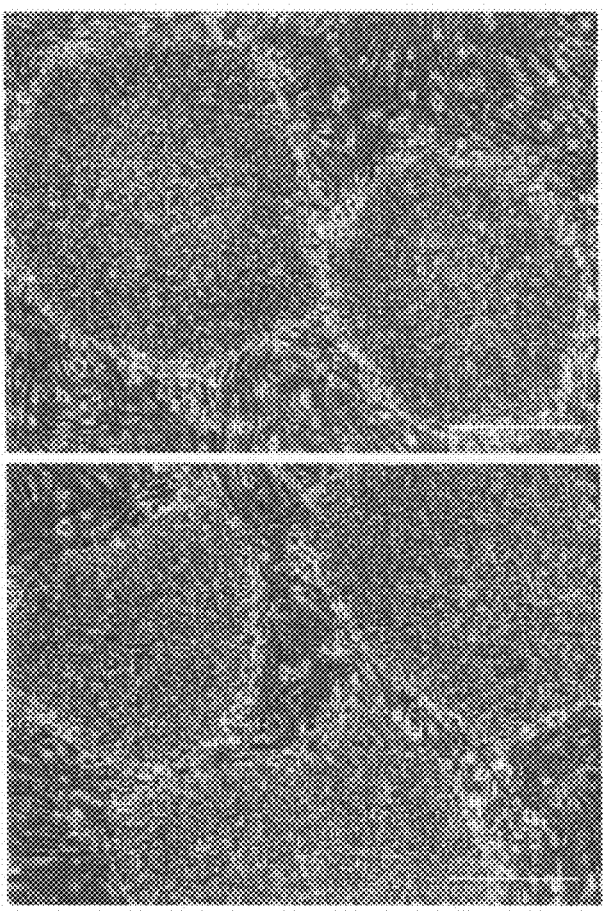

FIG. 40 shows human iPS cells (phase contrast images) derived from fibroblast-like synoviocytes (HFLS, clone 243H1) and BJ fibroblasts (clone 246G1). Bars=200 μm.

Figure 41:
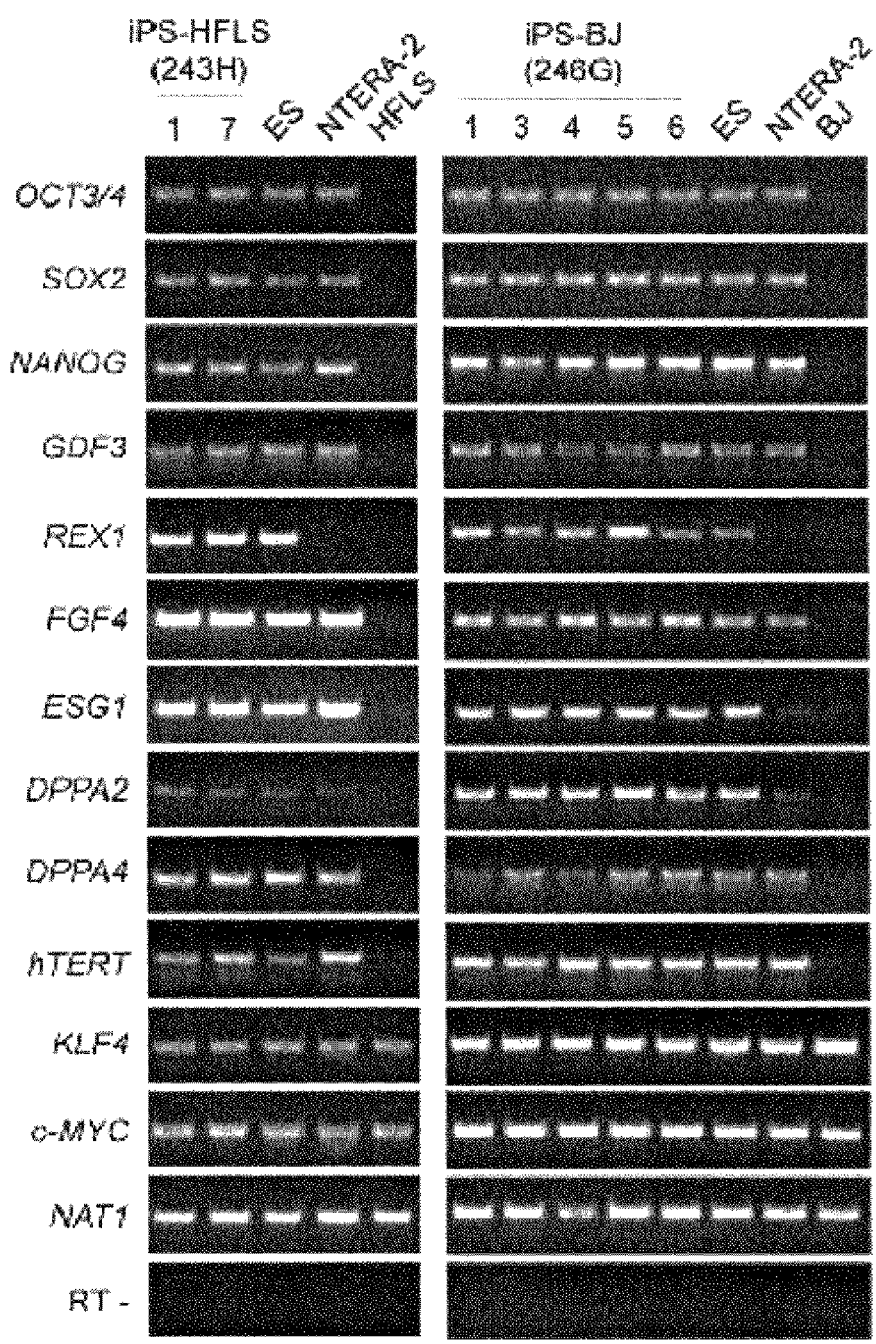

FIG. 41 shows expression of ES cell marker genes in iPS cells derived from HFLS and BJ fibroblasts.

Figure 42:
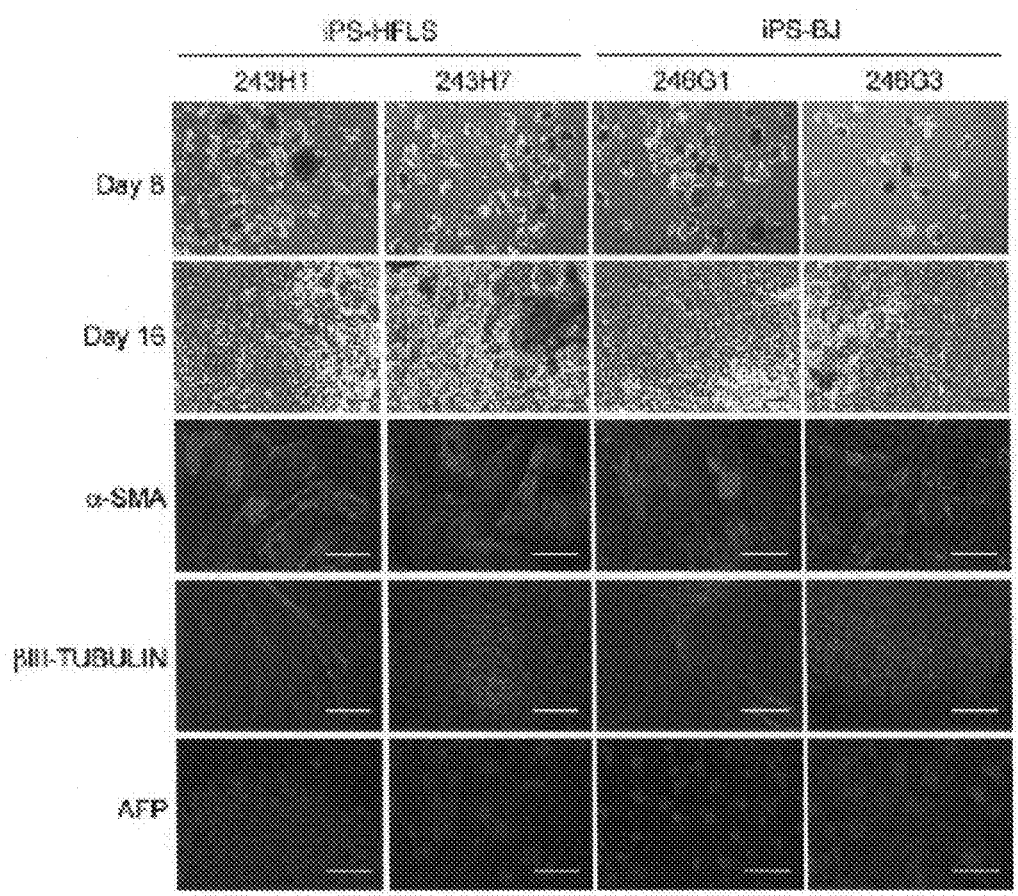

FIG. 42 shows embryoid body-mediated differentiation of iPS cells derived from HFLS and BJ fibroblasts.

FIGS. 43(A)-(C) show the effect of family factors and the omission of Myc on generation of iPS cells from Nanog-reporter MEFs. (A) Generation of iPS cells with family genes from MEF by Nanog selection. The number of GFP-positive colonies is shown. The results of three independent experiments were shown with different colors (white, gray, and black). The "4 factors" indicate the combination of Oct3/4, Sox2, Klf4, and c-Myc. (B) The effect of puromycin selection timing on iPS cell generation. Shown are GFP-positive colonies observed 28 days after the transduction of the four factors or the three factors devoid of Myc. (C) The effect of puromycin selection timing on the percentage of GFP-positive colonies per all colonies.

Figure 44:
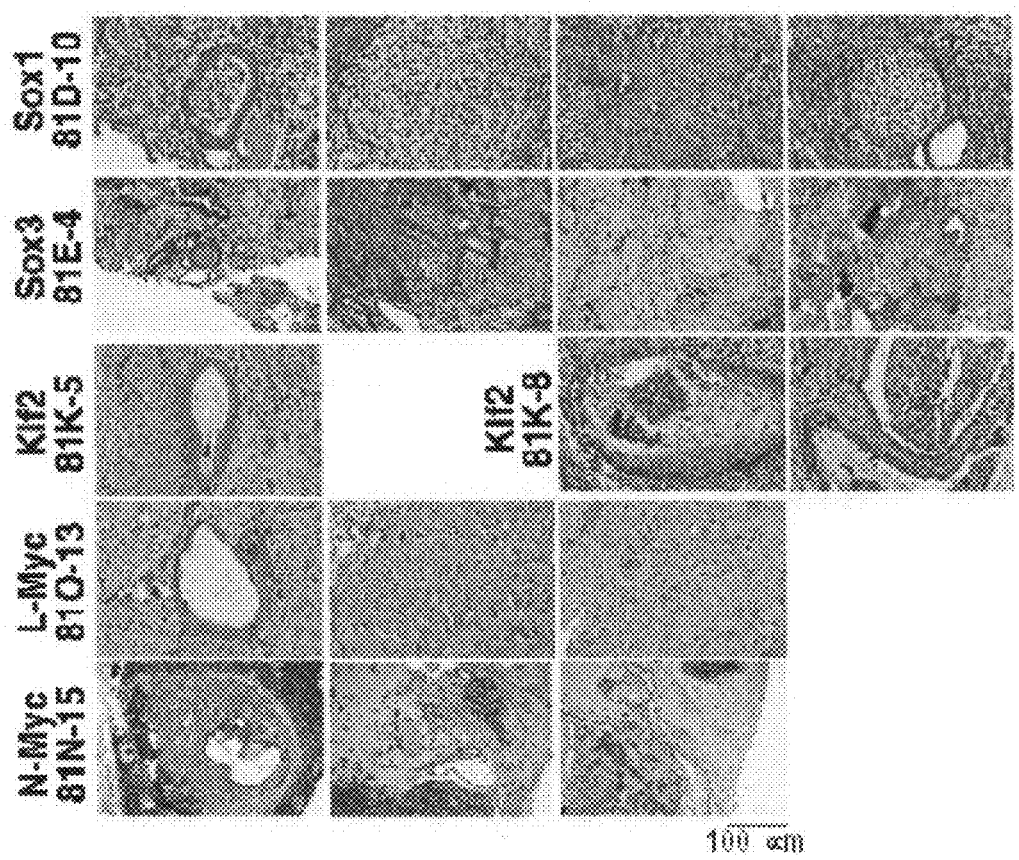

FIG. 44 shows teratomas derived from iPS cells, which were induced from Fbx15-reporter MEFs with family proteins.

Figure 45:
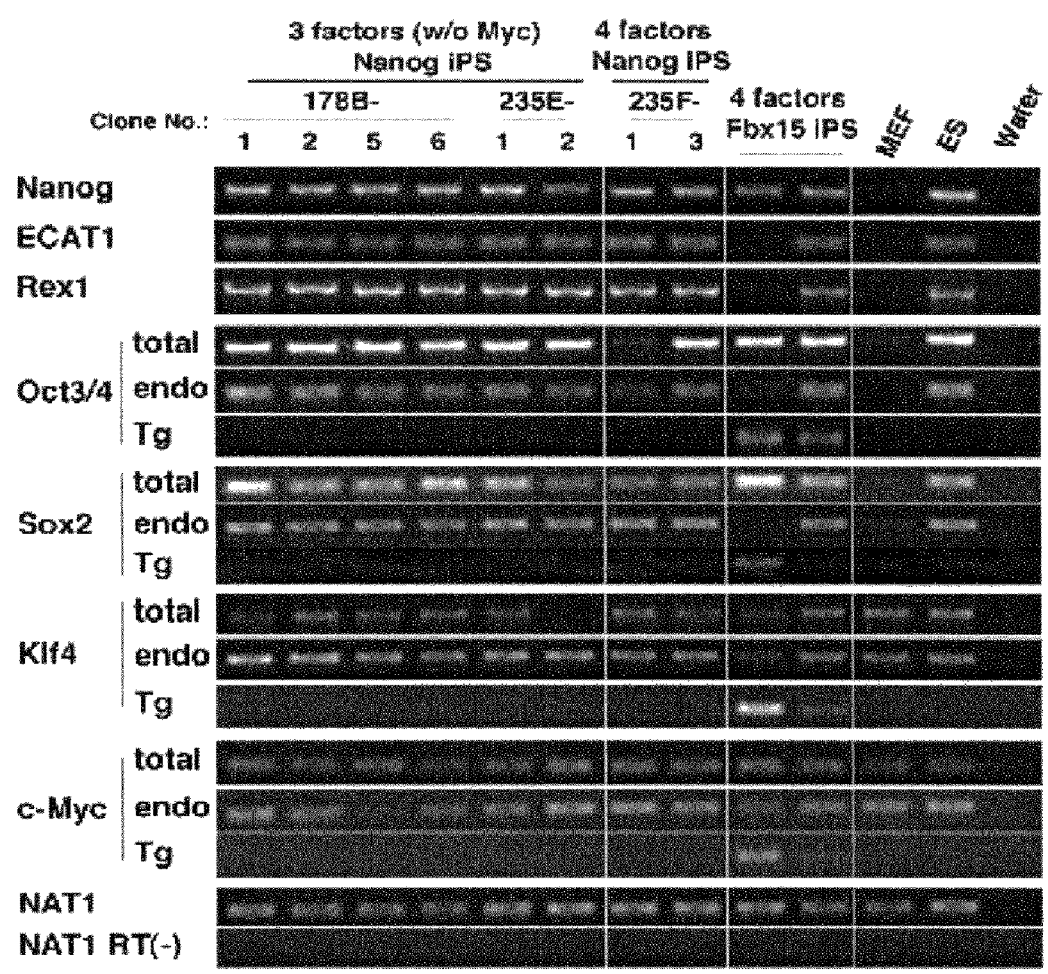

FIG. 45 shows characterization of iPS cells induced from Nanog-reporter MEFs without Myc retroviruses. RT-PCR showing expression levels of ES cell marker genes and the four factors. By using specific primer sets, total transcripts, transcripts from the endogenous genes (endo), and the transcripts from the retroviruses (Tg) were distinguished for the four factors.

Figure 46C:
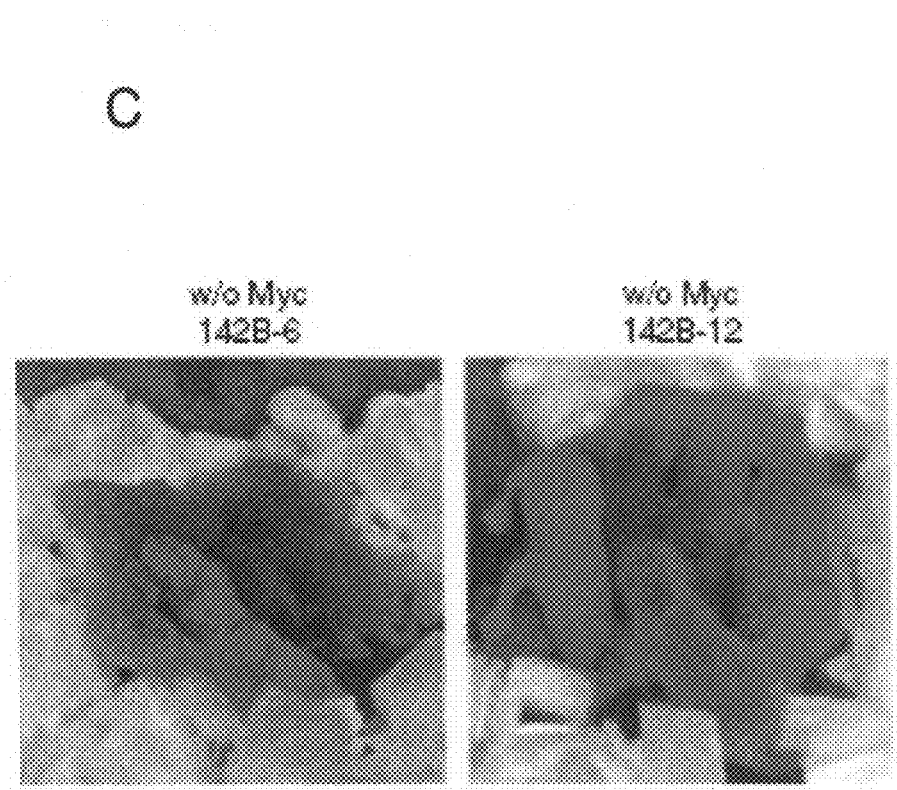

FIGS. 46(A)-(C) show generation of iPS cells without Myc retroviruses from MEFs containing the Fbx15-reporter and the constitutively active GFP-transgene. (A) Morphology of iPS cells generated without Myc retroviruses. The bar indicates 500 μm. (B) RT-PCR analyses of ES marker genes in ES, MEF, and iPS cells induced without Myc. (C) Chimeras derived from iPS cells induced without Myc (clones 142B-6 and -12).

FIGS. 47(A)-(D) show the efficient isolation of iPS cells without drug selection. (A) Morphology of iPS cells induced from adult TTF containing the Nanog-GFP-IRES-Puro$^r$ reporter. Cells were transduced with either the four factors or the three factors devoid of Myc, together with DsRed, and then were cultured for 30 days without drug selection. The expression of the Nanog reporter (Nanog-GFP) and the DsRed retrovirus (Tg-DsRed) was examined by fluorescent microscopy. The bar indicates 500 μm. (B) Morphology of iPS cells induced from adult TTF, which contained a DsRed transgene driven by a constitutively active promoter (ACTB, β-actin gene), but lacking the Nanog- or Fbx15-selection cassettes. The cells were transduced with either the four factors or the three factors devoid of Myc, together with GFP, and then cultured for 30 days without drug selection. The expression of the GFP retrovirus (Tg-GFP) was examined by fluorescent microscopy. The bar indicates 500 μm. (C) RT-PCR analyses of ES maker genes in iPS cells generated from TTF without drug selection and ES cells. (D) Chimeras derived from iPS cells, which were generated from adult TTF without drug selection or the Myc retroviruses.

Figure 48C:
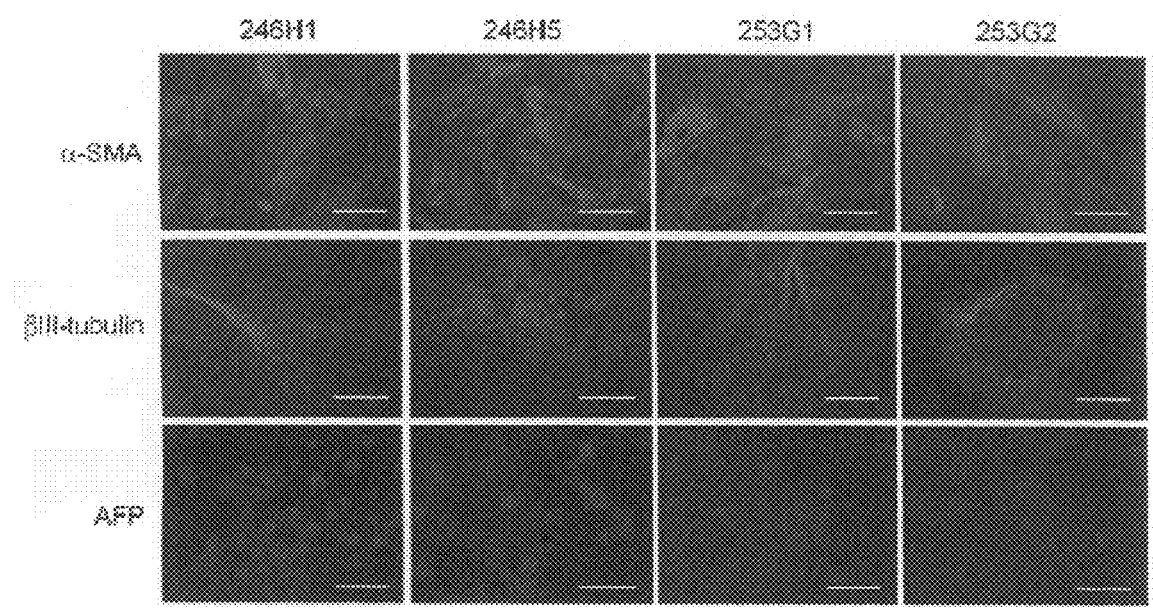

FIGS. 48(A)-(C) show induction of human iPS cells without Myc retroviruses. (A) The retroviruses for Oct3/4, Sox2 and Klf4 were introduced into BJ fibroblasts (246G) or HDF (253G). After 30 days, a few hES cell-like colonies emerged. These cells were expandable and showed hES cell-like morphology. (B) The expression of ES cell marker genes in human iPS cells derived from HDF without Myc retroviruses (253G) or with Myc (253F). (C) Embryoid body-mediated differentiation of human iPS cells generated without Myc retroviruses.

Figure 49:
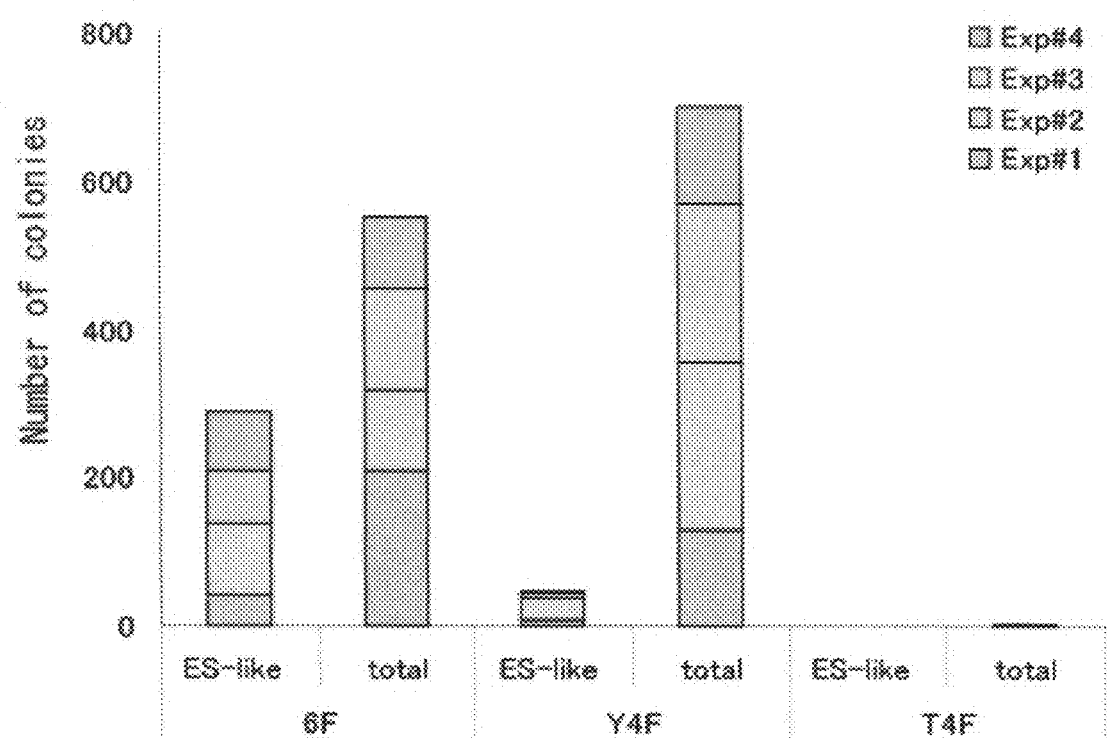

FIG. 49 shows results from experiments using six factors and two different combinations of four factors. The vertical axis shows the number of colonies. The term "6F" refers to the six factors (klf4, c-myc, oct3/4, sox2, nanog and Lin-28), the term "Y4F" refers to the first combination of four factors (klf4, c-myc, oct3/4 and sox2), and the term "T4F" refers to the second combination of four factors (oct3/4, sox2, nanog and Lin-28), respectively. The term "ES like" refers to ES-like cell colony morphologically, and the term "total" shows total number of ES-like cell colonies and non-ES like cell colonies. Exp#1, Exp#2, Exp#3, and Exp#4 show individual experimental results, respectively.

FIGS. 50(A)-(C) show a summary of data from experiments performed with mouse embryonic fibroblasts (MEFs). (A) $1.0 \times 10^5$ MEF cells obtained from Nanog GFP$^{tg/-}$ Fbx15$^{-/-}$ mouse were seeded on gelatin coated 6 well plates. Next day, four factors (Oct3/4, Klf4, Sox2, c-Myc) or three factors (Oct3/4, Klf4, Sox2) were retrovirally transduced into the cells. After 4 days of the infection, cells were re-seeded 1 to 2 or 1 to 6-ratio on 6 well plates covered with mitomycin C-treated STO cells. Drug selection was started at 14 days or 21 days. At day 28, GFP positive cells were counted and cells were stained for alkaline phosphatase (AP) and crystal violet (CV). (B) Summary of the number of the GFP positive colonies from three independent experiments, Exp. #1, 2, and 3. (C) Percentage of GFP positive colonies from three independent iPS experiments, Exp. #1, 2, and 3.

Figure 51:
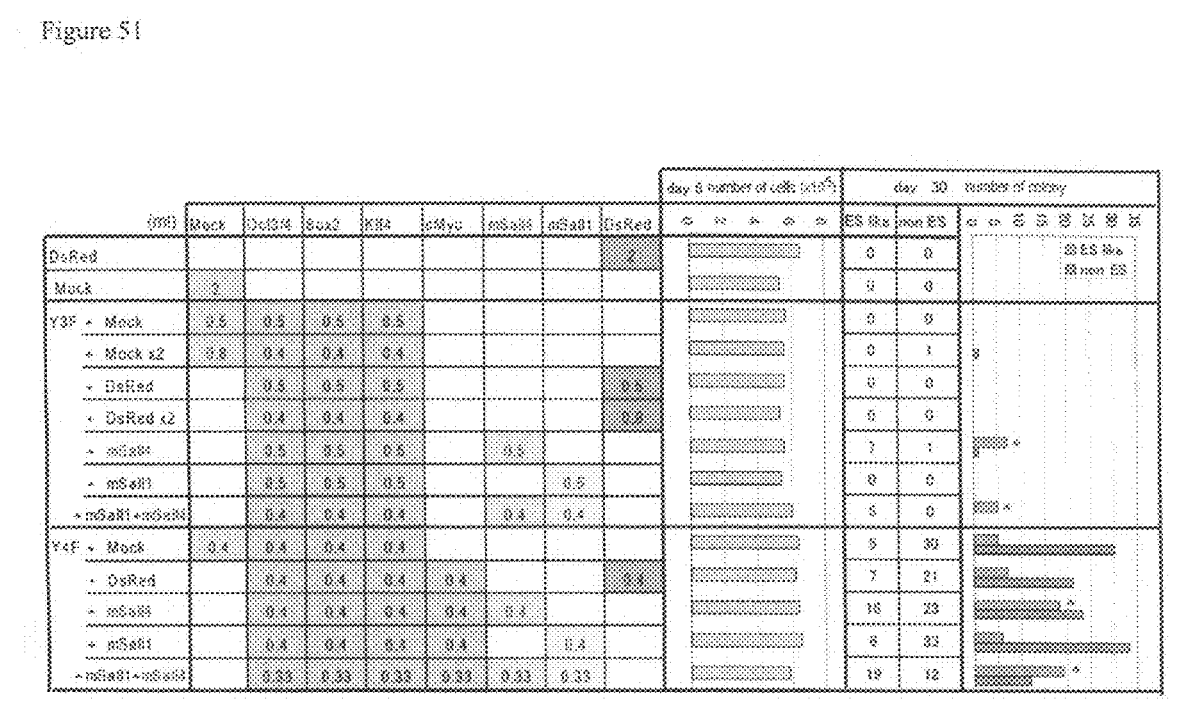

FIG. 51 shows a summary of data from experiments performed with adult human dermal fibroblasts. $1.0 \times 10^5$ adult HDF cells expressing slc7a were seeded on 6 well plates. Next day, four factors (Oct3/4, Klf4, Sox2, c-Myc) or three factors (Oct3/4, Klf4, Sox2) were retrovirally transduced into the cells. After 6 days of the infection, $5.0 \times 10^5$ cells were re-seeded on 100 mm plates covered with $1.5 \times 10^6$ of mitomycin C-treated STO cells. At day 7 the medium was replaced with Primate ES cell medium supplemented with 4 ng/ml bFGF. This figure shows colony numbers at 30 days after infections.

DETAILED DESCRIPTION OF THE INVENTION

Various investigations were conducted to address the aforementioned need for pluripotent stem cells which can be derived from a patient's own somatic cells, and for nuclear reprogramming factors capable of generating pluripotent stem cells from somatic cells. Investigations were also conducted to identify nuclear reprogramming factors by using the screening method for a nuclear reprogramming factor disclosed in International Publication WO2005/80598. While International Publication WO 2005/80598 discloses a screening method, this document fails to disclose any nuclear reprogramming factor. Furthermore, this document fails to specify any nuclear reprogramming factor or candidate nuclear reprogramming factor which would be capable of generating an induced pluripotent stem cell.

Ultimately, 24 kinds of candidate genes were found as genes relating to nuclear reprogramming, and among them, three kinds of the genes were found as particularly preferred for nuclear reprogramming: sometimes these genes are referred to as essential in certain embodiments. As further discussed throughout the specification, the nuclear reprogramming factor of the present invention may contain one or more factors relating to differentiation, development, proliferation or the like and factors having other physiological activities, as well as other gene products which can function as a nuclear reprogramming factor. The present invention was achieved on the basis of these findings.

The present invention provides at least the following advantages and features: induced pluripotent stem (iPS) cells derived by nuclear reprogramming of a somatic cell, including methods for reprogramming of a differentiated cell without using eggs, embryos, or embryonic stem (ES) cells.

As further discussed herein with respect to the general guidance for the reprogramming of differentiated cells and the examples, the present invention also provides various nuclear reprogramming factors capable of generating pluripotent stem cells from somatic cells. The nuclear reprogramming factor may comprise one or more gene products. The nuclear reprogramming factor may also comprise a combination of gene products. Each nuclear reprogramming factor may be used alone or in combination with other nuclear reprogramming factors as disclosed herein. In addition, nuclear reprogramming may be performed with small molecules, compounds, or other agents such that iPS cells are obtained.

In a preferred embodiment, the nuclear reprogramming factor comprises a gene product of each of the following three kinds of genes: an Oct family gene, a Klf family gene, and a Sox family gene. According to a more preferred embodiment of the invention, there is provided the aforementioned factor comprising a gene product of each of the following three kinds of genes: Oct3/4, Klf4, and Sox2.

In another embodiment of the invention, there is provided a nuclear reprogramming factor comprising a gene product of each of the following three kinds of genes: an Oct family gene, a Klf family gene, and a Myc family gene. According to a preferred embodiment of the invention, there is provided the aforementioned factor comprising a gene product of each of the following three kinds of genes: Oct3/4, Klf4 and c-Myc.

According to another preferred embodiment, there is provided the aforementioned factor, which further comprises a gene product of the following gene: a Sox family gene, and as a more preferred embodiment, there is provided the aforementioned factor, which comprises a gene product of Sox2.

According to still another preferred embodiment, there is provided the aforementioned factor, which comprises a cytokine together with the gene product of the Myc family gene, or alternatively, instead of the gene product of the Myc family gene. As a more preferred embodiment, there is provided the aforementioned factor, wherein the cytokine is basic fibroblast growth factor (bFGF) and/or stem cell factor (SCF). Accordingly, it is understood that the nuclear reprogramming factor can be with or without the Myc family gene.

According to particularly preferred embodiments, there is provided a nuclear reprogramming factor for a somatic cell, which comprises a gene product of the TERT gene in addition to a gene product of each of an Oct family gene, a Klf family gene, a Myc family gene, and a Sox family gene; and the aforementioned factor, which comprises a gene product or gene products of one or more kinds of genes selected from the group consisting of the following genes: SV40 Large T antigen (SEQ ID NO: 23), HPV16 E6 (SEQ ID NO: 24), HPV16 E7 (SEQ ID NO: 25), and Bmi1, in addition to a gene product of each of the Oct family gene, the Klf family gene, the Myc family gene, the Sox family gene, and the TERT gene.

In addition to these factors, there is provided the aforementioned factor, which further comprises a gene product or gene products of one or more kinds of genes selected from the group consisting of the following: Fbx15, Nanog, ERas, ECAT15-2, Tcl1, and β-catenin.

There is also provided the aforementioned factor, which comprises a gene product or gene products of one or more kinds of genes selected from the group consisting of the following: ECAT1, Esg1, Dnmt3L, ECAT8, Gdf3, Sox15, ECAT15-1, Fthl17, Sall4, Rex1, UTF1, Stella, Stat3, and Grb2.

The present invention also provides a nuclear reprogramming factor comprising a gene product or gene products of one or more kinds of the following genes: Oct3/4, Sox2, Klf4, Nanog, Lin-28, and c-Myc.

The present invention also provides a nuclear reprogramming factor comprising any combination of gene products, small molecules and/or substances as described herein, further comprising one or more factors improving the efficiency of iPS cell induction, such as one or more gene products of a Sall1 or Sall4 gene.

In another aspect, the present invention provides a method for preparing an induced pluripotent stem cell by nuclear reprogramming of a somatic cell, which comprises the step of contacting the aforementioned nuclear reprogramming factor with the somatic cell.

There is also provided the aforementioned method, which comprises the step of adding the aforementioned nuclear reprogramming factor to a culture of the somatic cell; the aforementioned method, which comprises the step of introducing a gene encoding the aforementioned nuclear reprogramming factor into the somatic cell; the aforementioned method, which comprises the step of introducing said gene into the somatic cell by using a recombinant vector containing at least one kind of gene encoding the aforementioned nuclear reprogramming factor; and the aforementioned method, wherein a somatic cell isolated from a patient is used as the somatic cell.

In another aspect, the present invention provides an induced pluripotent stem cell obtained by the aforementioned method. The present invention also provides a somatic cell derived by inducing differentiation of the aforementioned induced pluripotent stem cell.

The present invention further provides a method for stem cell therapy, which comprises the step of transplanting a somatic cell, wherein said cell is obtained by inducing differentiation of an induced pluripotent stem cell obtained by the aforementioned method using a somatic cell isolated and collected from a patient, into said patient. Several kinds of, preferably approximately 200 kinds of iPS cells prepared from somatic cells derived from healthy humans can be stored in an iPS cell bank as a library of iPS cells, and one kind or more kinds of the iPS cells in the library can be used for preparation of somatic cells, tissues, or organs that are free of rejection by a patient to be subjected to stem cell therapy.

The present invention further provides a method for evaluating a physiological function or toxicity of a compound, a medicament, a poison or the like by using various cells obtained by inducing differentiation of an induced pluripotent stem cell obtained by the aforementioned method.

The present invention also provides a method for improving ability of differentiation and/or growth of a cell, which comprises the step of contacting the aforementioned nuclear reprogramming factor with the cell, and further provides a cell obtained by the aforementioned method, and a somatic cell derived by inducing differentiation of a cell obtained by the aforementioned method.

By using the nuclear reprogramming factor provided by the present invention, reprogramming of a differentiated cell nucleus can be conveniently and highly reproducibly induced without using embryos or ES cells, and an induced pluripotent stem cell, as an undifferentiated cell having differentiation ability, pluripotency, and growth ability similar to those of ES cells, can be established. For example, an induced pluripotent stem cell having high growth ability and differentiation pluripotency can be prepared from a patient's own somatic cell by using the nuclear reprogramming factor of the present invention. Cells obtainable by differentiating said cell (for example, cardiac muscle cells, insulin producing cells, nerve cells and the like) are extremely useful, because they can be utilized for stem cell transplantation therapies for a variety of diseases such as cardiac insufficiency, insulin dependent diabetes mellitus, Parkinson's disease and spinal cord injury, thereby the ethical problem concerning the use of human embryo and rejection after transplantation can be avoided. Further, various cells obtainable by differentiating the induced pluripotent stem cell (for example, cardiac muscle cells, hepatic cells and the like) are highly useful as systems for evaluating efficacy or toxicity of compounds, medicaments, poisons and the like.

As noted above, transplantation of ES cells has a problem of causing rejection in the same manner as organ transplantation. Moreover, from an ethical viewpoint, there are many dissenting opinions against the use of ES cells, which are established by destroying human embryos.

The present invention provides at least the following advantages and features:

Identification of Nuclear Reprogramming Factors

As will be further disclosed below, the nuclear reprogramming factor of the present invention may contain one or more factors relating to differentiation, development, proliferation or the like and factors having other physiological activities, as well as other gene products which can function as a nuclear reprogramming factor. It is understood that such embodiments fall within the scope of the present invention, and the present invention is, in other words, directed to factors inducing pluripotent stem cells and various methods of obtaining induced pluripotent stem cells, including various manners of reprogramming differentiated cells as well as various manners of culturing, maintaining, and differentiating the induced pluripotent stem cells.

Furthermore, by using somatic cells in which only one or two genes among the three kinds of genes Oct3/4, Klf4, and c-Myc are expressed, other gene products which can function as a nuclear reprogramming factor can be identified by, for example, performing screening for a gene product which can induce nuclear reprogramming of said cells. For example, depending on the kinds of genes expressed in a differentiated cell, one or more genes useful as a reprogramming factor can be determined using the guidance herein provided. According to the present invention, the aforementioned screening method is also provided as a novel method for screening for a nuclear reprogramming factor. In other words, the present invention is not limited to any particular combination of nuclear reprogramming factors and the nuclear reprogramming factors of the present invention can be identified by screening methods, for example, the aforementioned screening method.

In one embodiment, the nuclear reprogramming factor of the present invention is characterized in that it comprises one or more gene products. As a means for confirming the nuclear reprogramming factor of the present invention, for example, the screening method for nuclear reprogramming factors disclosed in International Publication WO 2005/80598 can be used. The entire disclosure of the aforementioned publication is incorporated into the disclosure of the specification by reference. By referring to the aforementioned publication, those skilled in the art can perform screening of nuclear reprogramming factors to confirm the existence and the action of the reprogramming factor of the present invention.

For example, as an experimental system allowing for observation of the reprogramming phenomenon, a mouse can be used in which the βgeo (a fusion gene of the β galactosidase gene and the neomycin resistance gene) is knocked into the Fbx15 locus (Tokuzawa et al., *Mol. Cell. Biol.* 23:2699-708, 2003). The details are described in the examples of the specification. The mouse Fbx15 gene is a gene specifically expressed in differentiation pluripotent cells such as ES cells and early embryos. In a homomutant mouse in which βgeo is knocked into the mouse Fbx15 gene so as to be deficient in the Fbx15 function, abnormal phenotypes including those relating to differentiation pluripotency or generation are not generally observed. In this mouse, the expression of the βgeo is controlled by the enhancer and promoter of the Fbx15 gene, and differentiated somatic cells in which βgeo is not expressed have sensitivity to G418. In contrast, βgeo knockin homomutant ES cells have resistance against G418 at an extremely high concentration (higher than 12 mg/ml). By utilizing this phenomenon, an experimental system can be constructed to visualize reprogramming of somatic cells.

By applying the aforementioned experimental system, fibroblasts (Fbx $15^{\beta geo/\beta geo}$ MEFs) can be first isolated from an embryo of the βgeo knockin homomutant mouse (13.5 days after fertilization). The MEFs do not express the Fbx15 gene, and accordingly also do not express βgeo to give sensitivity to G418. However, when the MEFs are fused with genetic manipulation-free ES cells (also have sensitivity to G418), βgeo is expressed and the cells become G418-resistant as a result of reprogramming of nuclei of MEFs. Therefore, by utilizing this experimental system, the reprogramming phenomenon can be visualized as G418 resistance.

Nuclear reprogramming factors can be selected by using the aforementioned experimental system. As candidates of genes relevant to nuclear reprogramming factors, a plurality of genes can be selected which show specific expression in ES cells or of which important roles in the maintenance of pluripotency of ES cells are suggested, and it can be confirmed whether or not each candidate gene can induce nuclear reprogramming alone or in an appropriate combination thereof. For example, a combination of all of the selected primary candidate genes is confirmed to be capable of inducing the reprogramming of differentiated cells into a state close to that of ES cells. Combinations are then prepared by withdrawing each individual gene from the aforementioned combination, and the same actions of the combinations are confirmed in order to select each secondary candidate gene whose absence causes a reduction of the reprogramming induction ability or loss of the reprogramming induction ability. By repeating similar steps for the secondary candidate genes selected as described above, an essential combination of nuclear reprogramming genes can be selected, and it can be confirmed that a combination of gene products of each of the three kinds of genes, e.g., an Oct family gene, a Klf family gene, and a Myc family gene, acts as a nuclear reprogramming factor. It can be further confirmed that a combination of a gene product of a Sox family gene additionally with the gene products of the aforementioned three kinds of genes has extremely superior characteristics as a nuclear reprogramming factor. Specific examples of the selection method for the nuclear reprogramming factors are demonstrated in the examples of the specification.

Therefore, by referring to the above general explanations and specific explanations of the examples, those skilled in the art can readily confirm that the combination of these three kinds of genes induces the reprogramming of somatic cells, and that the combination of these three kinds of gene products is essential for nuclear reprogramming in certain embodiments. Thus, the embodiments herein illustrate various combinations of gene products and/or nuclear reprogramming factors which can provide iPS cells. In other words, based on the disclosure provided herein, one of ordinary skill in the art would know from the disclosed examples and/or readily determine which combination and/or combinations of nuclear reprogramming factors, including gene products, can generate pluripotent stem cells.

Nuclear Reprogramming Factor (NRF)

In a preferred embodiment, the NRF comprises a gene product. The nuclear reprogramming factor can be used to induce reprogramming of a differentiated cell without using eggs, embryos, or ES cells, to conveniently and highly reproducibly establish an induced pluripotent stem cell having pluripotency and growth ability similar to those of ES cells. For example, the nuclear reprogramming factor can be introduced into a cell by transducing the cell with a recombinant vector comprising a gene encoding the nuclear reprogramming factor. Accordingly, the cell can express the nuclear reprogramming factor expressed as a product of a gene contained in the recombinant vector, thereby inducing reprogramming of a differentiated cell.

The nuclear reprogramming factor may comprise a protein or peptide. The protein may be produced from the aforementioned gene, or alternatively, in the form of a fusion gene product of said protein with another protein, peptide or the like. The protein or peptide may be a fluorescent protein and/or a fusion protein. For example, a fusion protein with green fluorescence protein (GFP) or a fusion gene product with a peptide such as a histidine tag can also be used. Further, by preparing and using a fusion protein with the TAT peptide derived form the virus HIV, intracellular uptake of the nuclear reprogramming factor through cell membranes can be promoted, thereby enabling induction of reprogramming only by adding the fusion protein to a medium thus avoiding complicated operations such as gene transduction. Since preparation methods of such fusion gene products are well known to those skilled in the art, skilled artisans can easily design and prepare an appropriate fusion gene product depending on the purpose.

Nuclear reprogramming may also be accomplished with one or more small molecules, compounds, including inorganic and organic compounds, or mixtures thereof, extracts, epigenetic factors, and/or other components of the cytoplasm of a pluripotent cell.

In a particularly preferred embodiment, the nuclear reprogramming factor may comprise one or more gene products of each of the following three kinds of genes: an Oct family gene, a Klf family gene, and a Sox family gene.

In another preferred embodiment, the nuclear reprogramming factor may comprise one or more gene products of each of: an Oct family gene, a Klf family gene, and a Myc family gene.

The nuclear reprogramming factor may also comprise one or more gene products of each of: an Oct family gene, a Klf family gene, a Myc family gene, and a Sox family gene.

The nuclear reprogramming factor may also comprise one or more gene products of each of: an Oct family gene, a Klf family gene, and a cytokine. In one exemplary embodiment, the above-referenced nuclear reprogramming factor may further comprise one or more gene products of a Myc family gene. In another exemplary embodiment, the above referenced nuclear reprogramming factor may further comprise one or more gene products of a Sox family gene.

The cytokines of the present invention are not particularly limited. For example, the cytokine may comprise basic fibroblast growth factor (bFGF/FGF2) or stem cell factor (SCF).

With regard to gene family members, the nuclear reprogramming factor may comprise any combination of members from one or more gene families. For example, a combination of one or more gene products of Oct3/4, Klf4, and c-Myc. Examples of the Oct family gene include, for example, Oct3/4, Oct1A, Oct6, and the like. Oct3/4 is a transcription factor belonging to the POU family, and is reported as a marker of undifferentiated cells (Okamoto et al., *Cell* 60:461-72, 1990). Oct3/4 is also reported to participate in the maintenance of pluripotency (Nichols et al., *Cell* 95:379-91, 1998). Examples of the Klf family gene include Klf1, Klf2, Klf4, Klf5 and the like. Klf4 (Kruppel like factor-4) is reported as a tumor repressing factor (Ghaleb et al., *Cell Res.* 15:92-96, 2005). Examples of the Myc family gene include c-Myc, N-Myc, L-Myc and the like. c-Myc is a transcription control factor involved in differentiation and proliferation of cells (Adhikary & Eilers, *Nat. Rev. Mol. Cell. Biol.* 6:635-45, 2005), and is also reported to be involved in the maintenance of pluripotency (Cartwright et al., *Development* 132:885-96, 2005). The NCBI accession numbers of the genes of the families other than Oct3/4, Klf4 and c-Myc are set in TABLE 1 as follows:

TABLE 1

|  |  | Mouse | Human |
|---|---|---|---|
| Klf1 | Kruppel-like factor 1 (erythroid) | NM_010635 | NM_006563 |
| Klf2 | Kruppel-like factor 2 (lung) | NM_008452 | NM_016270 |
| Klf5 | Kruppel-like factor 5 | NM_009769 | NM_001730 |
| c-Myc | myelocytomatosis oncogene | NM_010849 | NM_002467 |
| N-Myc | v-Myc myelocytomatosis viral related oncogene, neuroblastoma derived (avian) | NM_008709 | NM_005378 |
| L-Myc | v-Myc myelocytomatosis viral oncogene homolog 1, lung carcinoma derived (avian) | NM_008506 | NM_005376 |
| Oct1A | POU domain, class 2, transcription factor 1 | NM_198934 | NM_002697 |
| Oct6 | POU domain, class 3, transcription factor 1 | NM_011141 | NM_002699 |

All of these genes are those commonly existing in mammals including human, and for use of the aforementioned gene products in the present invention, genes derived from arbitrary mammals (those derived from mammals such as mouse, rat, bovine, ovine, horse, and ape) can be used. In addition to wild-type gene products, mutant gene products including substitution, insertion, and/or deletion of several (for example, 1 to 10, preferably 1 to 6, more preferably 1 to 4, still more preferably 1 to 3, and most preferably 1 or 2) amino acids and having similar function to that of the wild-type gene products can also be used. For example, as a gene product of c-Myc, a stable type product (T58A) may be used as well as the wild-type product. The above explanation may be applied similarly to the other gene products.

The nuclear reprogramming factor of the present invention may comprise a gene product other than the aforementioned three kinds of gene products. An example of such gene product includes a gene product of a Sox family gene. Examples of the Sox family genes include, for example, Sox1, Sox3, Sox7, Sox15, Sox17 and Sox18, and a preferred example includes Sox2. A nuclear reprogramming factor comprising at least a combination of the gene products of four kinds of genes, an Oct family gene (for example, Oct3/4), a Klf family gene (for example, Klf4), a Myc family gene (for example, c-Myc), and a Sox family gene (for example, Sox2) is a preferred embodiment of the present invention from a viewpoint of reprogramming efficiency, and in particular, a combination of a gene product of a Sox family gene is sometimes preferred to obtain pluripotency. Sox2, expressed in an early development process, is a gene encoding a transcription factor (Avilion et al., *Genes Dev.* 17:126-40, 2003). The NCBI accession numbers of Sox family genes other than Sox2 are in TABLE 2 as follows.

TABLE 2

|  |  | Mouse | Human |
|---|---|---|---|
| Sox1 | SRY-box containing gene 1 | NM_009233 | NM_005986 |
| Sox3 | SRY-box containing gene 3 | NM_009237 | NM_005634 |
| Sox7 | SRY-box containing gene 7 | NM_011446 | NM_031439 |
| Sox15 | SRY-box containing gene 15 | NM_009235 | NM_006942 |
| Sox17 | SRY-box containing gene 17 | NM_011441 | NM_022454 |
| Sox18 | SRY-box containing gene 18 | NM_009236 | NM_018419 |

Further, a gene product of a Myc family gene may be replaced with a cytokine. As the cytokine, for example, SCF, bFGF or the like is preferred. However, cytokines are not limited to these examples.

As a more preferred embodiment, an example includes a factor which induces immortalization of cells, in addition to the aforementioned three kinds of gene products, preferably, the four kinds of gene products. For example, an example includes a combination of a factor comprising a gene product of the TERT gene. In another exemplary embodiment, the nuclear reprogramming factor comprises any of the aforementioned gene products in combination with a factor comprising a gene product or gene products of one or more kinds of the following genes: SV40 Large T antigen, HPV16 E6, HPV16 E7, and Bmi1. TERT is essential for the maintenance of the telomere structure at the end of chromosome at the time of DNA replication, and the gene is expressed in stem cells or tumor cells in humans, whilst it is not expressed in many somatic cells (Horikawa et al., *P.N.A.S. USA* 102:18437-442, 2005). SV40 Large T antigen, HPV16 E6, HPV16 E7, or Bmi1 was reported to induce immortalization of human somatic cells in combination with Large T antigen (Akimov et al., *Stem Cells* 23:1423-33, 2005; Salmon et al., *Mol. Ther.* 2:404-14, 2000). These factors are extremely useful particularly when iPS cells are induced from human cells. The NCBI accession numbers of TERT and Bmi1 genes are listed in TABLE 3 as follows.

TABLE 3

|  |  | Mouse | Human |
|---|---|---|---|
| TERT | telomerase reverse transcriptase | NM_009354 | NM_198253 |
| Bmi1 | B lymphoma Mo-MLV insertion region 1 | NM_007552 | NM_005180 |

Furthermore, a gene product or gene products of one or more kinds of genes selected from the group consisting of the following: Fbx15, Nanog, ERas, ECAT15-2, Tcl1, and β-catenin may be combined. As a particularly preferred embodiment from a viewpoint of reprogramming efficiency, an example includes a nuclear reprogramming factor comprising a total of ten kinds of gene products, wherein gene products of Fbx15, Nanog, ERas, ECAT15-2, Tcl1, and β-catenin are combined with the aforementioned four kinds of gene products. Fbx15 (Tokuzawa et al., *Mol. Cell. Biol.* 23:2699-708, 2003), Nanog (Mitsui et al., *Cell* 113:631-42, 2003), ERas (Takahashi et al. *Nature* 423:541-45, 2003), and ECAT15-2 (Bortvin et al., *Development* 130:1673-80, 2003) are genes specifically expressed in ES cells. Tcl1 is involved in the activation of Akt (Bortvin et al., *Development* 130: 1673-80, 2003), and β-catenin is an important factor constituting the Wnt signal transmission pathway, and also reported to be involved in the maintenance of pluripotency (Sato et al, *Nat. Med.* 10:55-63, 2004).

Further, the nuclear reprogramming factor of the present invention may comprise, for example, a gene product or gene products of one or more kinds of genes selected from the group consisting of the following: ECAT1, Esg1, Dnmt3L, ECAT8, Gdf3, Sox15, ECAT15-1, Fthl17, Sall4, Rex1, UTF1, Stella, Stat3, and Grb2. ECAT1, Esg1, ECAT8, Gdf3, and ECAT15-1 are genes specifically expressed in ES cells (Mitsui et al., *Cell* 113:631-42, 2003). Dnmt3L is a DNA methylating enzyme-related factor, and Sox 15 is a class of genes expressed in an early development process and encoding transcription factors (Maruyama et al., *J. Biol. Chem.* 280:24371-79, 2005). Fthl17 encodes ferritin heavy polypeptide-like 17 (colLoriot et al., *Int. J. Cancer* 105:371-76, 2003), Sall4 encodes a Zn finger protein abundantly expressed in embryonic stem cells (Kohlhase et al., *Cytogenet. Genome Res.* 98:274-77, 2002), and Rex1 encodes a transcription factor locating downstream from Oct3/4 (Ben-Shushan et al., *Mol. Cell. Biol.* 18:1866-78, 1998). UTF1 is a transcription cofactor locating downstream from Oct3/4, and it is reported that the suppression of the proliferation of ES cells is induced when this factor is suppressed (Okuda et al., *EMBO J.* 17:2019-32, 1998). Stat3 is a signal factor for proliferation and differentiation of cells. The activation of Stat3 triggers the operation of LIF, and thereby the factor plays an important role for the maintenance of pluripotency (Niwa et al., *Genes Dev.* 12:2048-60, 1998). Grb2 encodes a protein mediating between various growth factor receptors existing in cell membranes and the Ras/MAPK cascade (Cheng et al. *Cell* 95:793-803, 1998).

However, as noted above, the gene products which may be included in the nuclear reprogramming factor of the present invention are not limited to the gene products of the genes specifically explained above. The nuclear reprogramming factor of the present invention may contain one or more factors relating to differentiation, development, proliferation or the like and factors having other physiological activities, as well as other gene products which can function as a nuclear reprogramming factor. It is understood that such embodiments fall within the scope of the present invention. By using somatic cells in which only one or two genes among the three kinds of the gene Oct3/4, Klf4, and c-Myc are expressed, the other gene products which can function as a nuclear reprogramming factor can be identified by, for example, performing screening for a gene product which can induce nuclear reprogramming of said cells. According to the present invention, the aforementioned screening method is also provided as a novel method for screening for a nuclear reprogramming factor.

Cells of the Invention and Methods of Generating the Same

By using the nuclear reprogramming factor of the present invention, the nucleus of a somatic cell can be reprogrammed to obtain an induced pluripotent stem cell. In the specification, the term "induced pluripotent stem cells" means cells having properties similar to those of ES cells, and more specifically, the term encompasses undifferentiated cells having pluripotency and growth ability. However, the term should not be construed narrowly in any sense, and should be construed in the broadest sense. The method for preparing induced pluripotent stem cells by using a nuclear reprogramming factor is explained in International Publication WO2005/80598 (the term "ES-like cells" is used in the publication), and a means for isolating induced pluripotent stem cells is also specifically explained. Therefore, by referring to the aforementioned publication, those skilled in the art can easily prepare induced pluripotent stem cells by using the nuclear reprogramming factor of the present invention. Methods for preparing induced pluripotent stem cells from somatic cells by using the nuclear reprogramming factor of the present invention are not particularly limited. Any method may be employed as long as the nuclear reprogramming factor can contact with somatic cells under an environment in which the somatic cells and induced pluripotent stem cells can proliferate. An advantage of the present invention is that an induced pluripotent stem cell can be prepared by contacting a nuclear reprogramming factor with a somatic cell in the absence of eggs, embryos, or embryonic stem (ES) cells.

For example, a gene product contained in the nuclear reprogramming factor of the present invention may be added to a medium. Alternatively, by using a vector containing a gene that is capable of expressing the nuclear reprogramming factor of the present invention, a means of transducing said gene into a somatic cell may be employed. When such vector is used, two or more kinds of genes may be incorporated into the vector, and each of the gene products may be simultaneously expressed in a somatic cell. When one or more of the gene products contained in the nuclear reprogramming factor of the present invention are already expressed in a somatic cell to be reprogrammed, said gene products may be excluded from the nuclear reprogramming factor of the present invention. It is understood that such embodiments fall within the scope of the present invention.

As indicated above, the nuclear reprogramming factor of the present invention can be used to generate iPS cells from differentiated adult somatic cells. In the preparation of induced pluripotent stem cells by using the nuclear reprogramming factor of the present invention, types of somatic cells to be reprogrammed are not particularly limited, and any kind of somatic cells may be used. For example, matured somatic cells may be used, as well as somatic cells of an embryonic period. Other examples of cells capable of being generated into iPS cells and/or encompassed by the present invention include mammalian cells such as fibroblasts, B cells, T cells, dendritic cells, ketatinocytes, adipose cells, epithelial cells, epidermal cells, chondrocytes, cumulus cells, neural cells, glial cells, astrocytes, cardiac cells, esophageal cells, muscle cells, melanocytes, hematopoietic cells, pancreatic cells, hepatocytes, macrophages, monocytes, mononuclear cells, and gastric cells, including gastric epithelial cells. The cells can be embryonic, or adult somatic cells, differentiated cells, cells with an intact nuclear membrane, non-dividing cells, quiescent cells, terminally differentiated primary cells, and the like.

Induced pluripotent stem cells may express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; βIII-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sall4; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; SV40 Large T Antigen; HPV16 E6; HPV16 E7, β-catenin, and Bmi1. Such cells can also be characterized by the down-regulation of markers characteristic of the differentiated cell from which the iPS cell is induced. For example, iPS cells derived from fibroblasts may be characterized by down-regulation of the fibroblast cell marker Thy1 and/or up-regulation of SSEA-1. It is understood that the present invention is not limited to those markers listed herein, and encompasses markers such as cell surface markers, antigens, and other gene products including ESTs, RNA (including microRNAs and antisense RNA), DNA (including genes and cDNAs), and portions thereof.

When induced pluripotent stem cells are used for therapeutic treatment of diseases, it is desirable to use somatic cells isolated from patients. For example, somatic cells involved in diseases, somatic cells participating in therapeutic treatment of diseases and the like can be used. A method for selecting induced pluripotent stem cells that appear in a medium according to the method of the present invention is not particularly limited, and a well-known means may be suitably employed, for example, a drug resistance gene or the like can be used as a marker gene to isolate induced pluripotent stem cells using drug resistance as an index. Various media that can maintain undifferentiated state and pluripotency of ES cells and various media which cannot maintain such properties are known in this field, and induced pluripotent stem cells can be efficiently isolated by using a combination of appropriate media. Differentiation and proliferation abilities of isolated induced pluripotent stem cells can be easily confirmed by those skilled in the art by using confirmation means widely applied to ES cells.

Thus, another preferred embodiment of the invention comprises a pluripotent stem cell induced by reprogramming a somatic cell in the absence of eggs, embryos, or embryonic stem (ES) cells. The pluripotent stem cell can be a mammalian cell, for example a mouse, human, rat, bovine, ovine, horse, hamster, dog, guinea pig, or ape cell. For example, direct reprogramming of somatic cells provides an opportunity to generate patient- or disease-specific pluripotent stem cells. Mouse iPS cells are indistinguishable from ES cells in morphology, proliferation, gene expression, and teratoma formation. Furthermore, when transplanted into blastocysts, mouse iPS cells can give rise to adult chimeras, which are competent for germline transmission (Maherali et al., *Cell Stem Cell* 1:55-70, 2007; Okita et al., *Nature* 448:313-17, 2007; Wernig et al., *Nature* 448:318-324, 2007). Human iPS cells are also expandable and indistinguishable from human embryonic stem (ES) cells in morphology and proliferation. Furthermore, these cells can differentiate into cell types of the three germ layers in vitro and in teratomas.

The present invention also provides for the generation of somatic cells derived by inducing differentiation of the aforementioned pluripotent stem cells. The present invention thus provides a somatic cell derived by inducing differentiation of the aforementioned induced pluripotent stem cell.

In another embodiment, there is disclosed a method for improving differentiation ability and/or growth ability of a cell, which comprises contacting a nuclear reprogramming factor with a cell.

In a particularly preferred embodiment, the present invention comprises a method for stem cell therapy comprising: (1) isolating and collecting a somatic cell from a patient; (2) inducing said somatic cell from the patient into an iPS cell; (3) inducing differentiation of said iPS cell, and (4) transplanting the differentiated cell from step (3) into the patient.

In another preferred embodiment, the present invention includes a method for evaluating a physiological function of a compound comprising treating cells obtained by inducing differentiation of an induced pluripotent stem cell with the compound.

A method for evaluating the toxicity of a compound comprising treating cells obtained by inducing differentiation of an induced pluripotent stem cell in the presence of the compound.

EXAMPLES

Various terms, abbreviations and designations for the raw materials and tests used in the following Examples are explained as follows:

Abbreviations
 iPS cell (induced pluripotent stem cell)
 NRF (nuclear reprogramming factor)
 ES cell (embryonic stem cell)
 TTF (tail tip fibroblast)
 MEF (mouse embryonic fibroblast)
 HDF (human dermal fibroblast)
 bFGF (basic fibroblast growth factor)
 SCF (stem cell factor)
 GFP (green fluorescent protein)

The present invention will be more specifically explained with reference to examples. However, the scope of the present invention is not limited to the following examples.

Example 1

Selection of A Nuclear Reprogramming Factor

In order to identify reprogramming factors, an experimental system for easy observation of the reprogramming phenomenon is required. As an experimental system, a mouse in which βgeo (a fusion gene of β-galactosidase gene and neomycin resistance gene) was knocked into the Fbx15 locus (Tokuzawa et al., *Mol. Cell. Biol.* 23:2699-708, 2003) was used. The mouse Fbx15 gene is a gene specifically expressed in differentiation pluripotent cells such as ES cells and early embryos. However, in a homomutant mouse in which βgeo was knocked into the mouse Fbx15 gene so as to delete the function of Fbx15, no abnormal phenotypes including those concerning differentiation pluripotency or development were observed. In this mouse, expression control of βgeo is attained by the enhancer and promoter of the Fbx15 gene. Specifically, βgeo is not expressed in differentiated somatic cells, and they have sensitivity to G418. In contrast, the βgeo knockin homomutant ES cells have resistance against G418 at an extremely high concentration (higher than 12 mg/ml). By utilizing the above phenomenon, an experimental system for visualizing the reprogramming of somatic cells was constructed.

Figure 1:
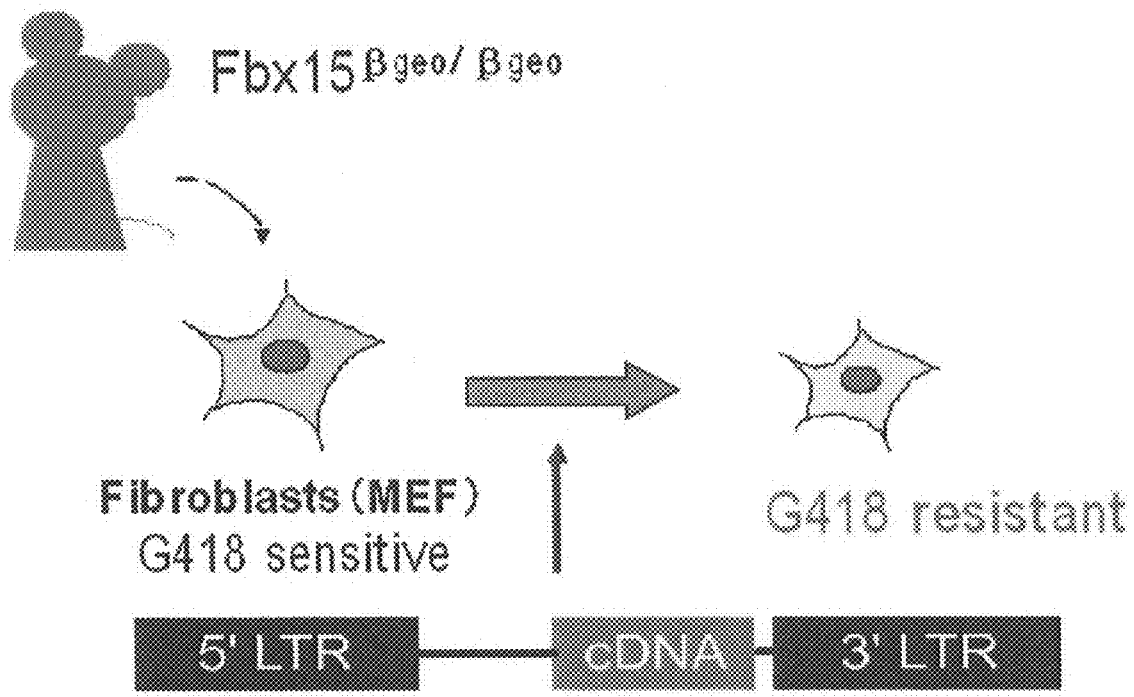
FIG. 1 shows a screening method for reprogramming factors using embryonic fibroblasts (MEFs) of a mouse having βgeo knock-in Fbx15 gene.

In the aforementioned experimental system, fibroblasts (Fbx15$^{\beta geo/\beta geo}$, MEFs) were first isolated from an embryo of the βgeo knockin homomutant mouse (13.5 days after fertilization). Since MEFs do not express the Fbx15 gene, the cells also do not express βgeo and thus have sensitivity to G418. Whilst when the MEFs are fused with ES cells that have not been gene-manipulated (also having sensitivity to G418), the nuclei of MEFs are reprogrammed, and as a result, βgeo is expressed to give G418-resistance. The reprogramming phenomenon can thus be visualized as G418 resistance by using this experimental system (International Publication WO2005/80598). Searches for reprogramming factors were performed by using the aforementioned experimental system (FIG. 1), and total 24 kinds of genes were selected as candidate reprogramming factors, including genes showing specific expression in ES cells and genes suggested to have important roles in the maintenance of differentiation pluripotency of ES cells. These genes are shown in TABLES 4 and 5 below. For β-catenin (#21) and c-Myc (#22), active type mutants (catenin: S33Y, c-Myc: T58A) were used.

TABLE 4

| Number | Name of Gene | Explanation of Gene |
|---|---|---|
| 1 | ECAT1 | ES cell associated transcript 1 (ECAT1) |
| 2 | ECAT2 | developmental pluripotency associated 5 (DPPA5), ES cell specific gene 1 (ESG1) |
| 3 | ECAT3 | F-box protein 15 (Fbx15), |
| 4 | ECAT4 | homeobox transcription factor Nanog |
| 5 | ECAT5 | ES cell expressed Ras (ERas) |
| 6 | ECAT7 | DNA (cytosine-5-)-methyltransferase 3-like (Dnmt31), valiant 1 |
| 7 | ECAT8 | ES cell associated transcript 8 (ECAT8) |
| 8 | ECAT9 | growth differentiation factor 3 (Gdf3) |
| 9 | ECAT10 | SRY-box containing gene 15 (Sox15) |
| 10 | ECAT15-1 | developmental pluripotency associated 4 (Dppa4), variant 1 |
| 11 | ECAT15-2 | developmental pluripotency associated 2 (Dppa2) |
| 12 | Fthl17 | ferritin, heavy polypeptide-like 17 (Fthl17) |
| 13 | Sall4 | sal-like 4 (*Drosophila*) (Sall4), transcript variant a |

TABLE 4-continued

| Number | Name of Gene | Explanation of Gene |
| --- | --- | --- |
| 14 | Oct3/4 | POU domain, class 5, transcription factor 1 (Pou5f1) |
| 15 | Sox2 | SRY-box containing gene 2 (Sox2) |
| 16 | Rex1 | zinc finger protein 42 (Zfp42) |
| 17 | Utf1 | undifferentiated embryonic cell transcription factor 1 (Utf1) |
| 18 | Tcl1 | T-cell lymphoma breakpoint 1 (Tcl1) |
| 19 | Stella | developmental pluripotency-associated 3 (Dppa3) |
| 20 | Klf4 | Kruppel-like factor 4 (gut) (Klf4) |
| 21 | β-catenin | catenin (cadherin associated protein), beta 1, 88 kDa (Ctnnb1) |
| 22 | c-Myc | myelocytomatosis oncogene (Myc) |
| 23 | Stat3 | signal transducer and activator of transcription 3 (Stat3), transcript variant 1 |
| 24 | Grb2 | growth factor receptor bound protein 2 (Grb2) |

TABLE 5

| Number | Name of Gene | Characteristic Feature | NCBI accession number Mouse | NCBI accession number Human |
| --- | --- | --- | --- | --- |
| 1 | ECAT1 | Gene specifically expressed in ES cell | AB211060 | AB211062 |
| 2 | ECAT2 | Gene specifically expressed in ES cell | NM_025274 | NM_001025290 |
| 3 | ECAT3 | Gene specifically expressed in ES cell | NM_015798 | NM_152676 |
| 4 | ECAT4 | Transcription factor having homeodomain, essential factor for differentiation pluripotency maintenance | AB093574 | NM_024865 |
| 5 | ECAT5 | Ras family protein, ES cell growth promoting factor | NM_181548 | NM_181532 |
| 6 | ECAT7 | DNA methylation enzyme-related factor, essential for imprinting | NM_019448 | NM_013369 |
| 7 | ECAT8 | Gene specifically expressed in ES cell, having Tudor domain | AB211061 | AB211063 |
| 8 | ECAT9 | Gene specifically expressed in ES cell, belonging to TGFβ family | NM_008108 | NM_020634 |
| 9 | ECAT10 | Gene specifically expressed in ES cell, SRY family transcription factor | NM_009235 | NM_006942 |
| 10 | ECAT15-1 | Gene specifically expressed in ES cell | NM_028610 | NM_018189 |
| 11 | ECAT15-2 | Gene specifically expressed in ES cell | NM_028615 | NM_138815 |
| 12 | Fthl17 | Gene specifically expressed in ES cell, similar to ferritin heavy chain | NM_031261 | NM_031894 |
| 13 | Sall4 | Gene specifically expressed in ES cell, Zn finger protein | NM_175303 | NM_020436 |
| 14 | Oct3/4 | POU family transcription factor, essential for pluripotency maintenance | NM_013633 | NM_002701 |
| 15 | Sox2 | SRY family transcription factor, essential for pluripotency maintenance | NM_011443 | NM_003106 |
| 16 | Rex1 | Gene specifically expressed in ES cell, Zn finger protein | NM_009556 | NM_174900 |
| 17 | Utf1 | Transcription regulation factor highly expressed in ES cell, promoting growth of ES | NM_009482 | NM_003577 |
| 18 | Tcl1 | Oncogene activating AKT, abundantly expressed in ES cell | NM_009337 | NM_021966 |
| 19 | Stella | Gene specifically expressed in ES cell | NM_139218 | NM_199286 |
| 20 | Klf4 | Abundantly expressed in ES cell, both actions as antioncogene and oncogene are reported | NM_010637 | NM_004235 |
| 21 | β-catenin | Transcription factor activated by Wnt signal, involvement in pluripotency maintenance is reported | NM_007614 | NM_001904 |
| 22 | c-Myc | Transcription control factor participating in cell proliferation and differentiation and oncogene, involvement in pluripotency maintenance is reported | NM_010849 | NM_002467 |

TABLE 5-continued

Figure 2:
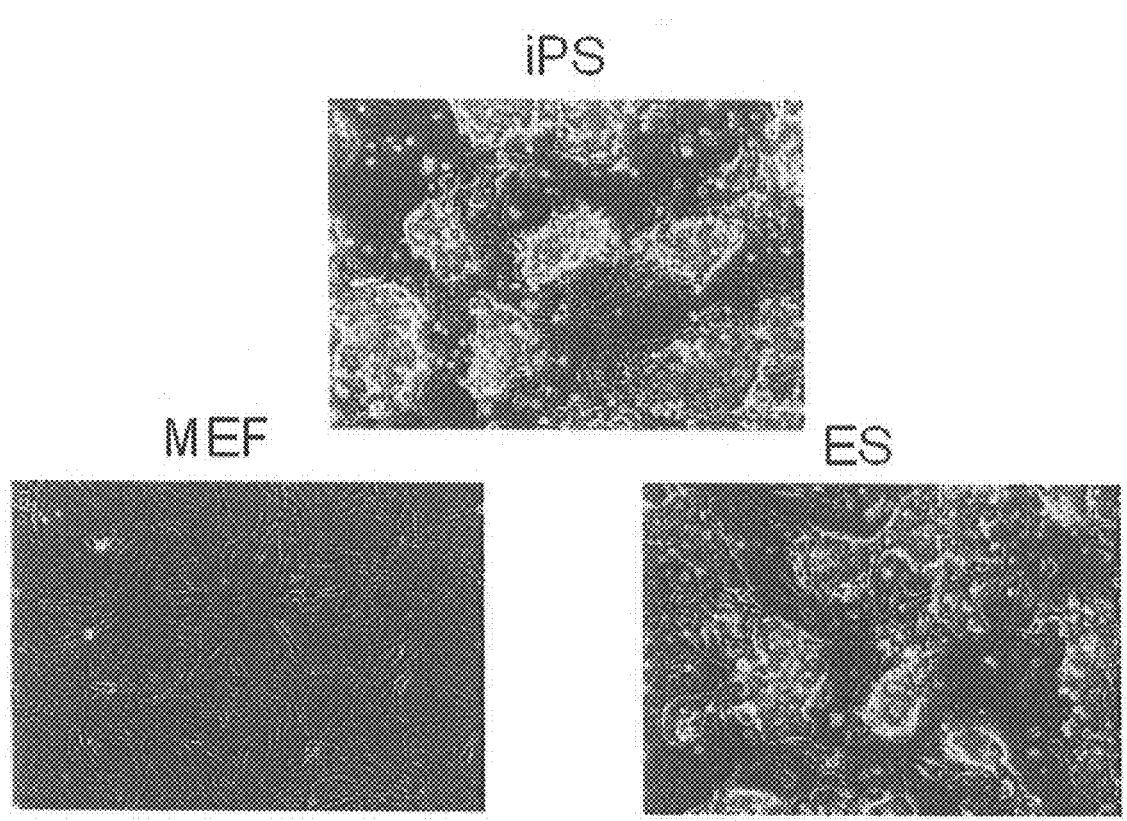
FIG. 2 depicts photographs showing morphology of iPS cells obtained by introducing the 24 genes shown in TABLE 4. Morphologies of differentiated cells (MEF) and of normal embryonic stem cells (ES) are also shown as a reference.

| Number | Name of Gene | Characteristic Feature | NCBI accession number | |
|---|---|---|---|---|
| | | | Mouse | Human |
| 23 | Stat3 | Transcription factor activated by LIF signal, considered essential for pluripotency maintenance of mouse ES cells | NM_213659 | NM_139276 |
| 24 | Grb2 | Adapter protein mediating growth factor receptors and Ras/MAPK cascade | NM_008163 | NM_002086 | cDNAs of these genes were inserted into the retroviral vector pMX-gw by the Gateway technology. First, each of the 24 genes was infected into Fbx15$^{\beta geo/\beta geo}$ MEFs, and then G418 selection was performed under ES cell culture conditions. However, no G418-resistant colony was obtained. Next, the retroviral vectors of all of the 24 genes were simultaneously infected into Fbx15$^{\beta geo/\beta geo}$ MEFs. When G418 selection was performed under ES cell culture conditions, a plurality of drug resistant colonies were obtained. These colonies were isolated, and cultivation was continued. It was found that cultivation of these cells over a long period of time could be performed, and that these cells had morphology similar to that of ES cells (FIG. 2). In the figure, iPS cells represent induced pluripotent stem cells (also called "ES like cells", "ES-like cells", or "ESL cells"), ES represents embryonic stem cells, and MEF represents differentiated cells (embryonic fibroblasts).

Figure 3:
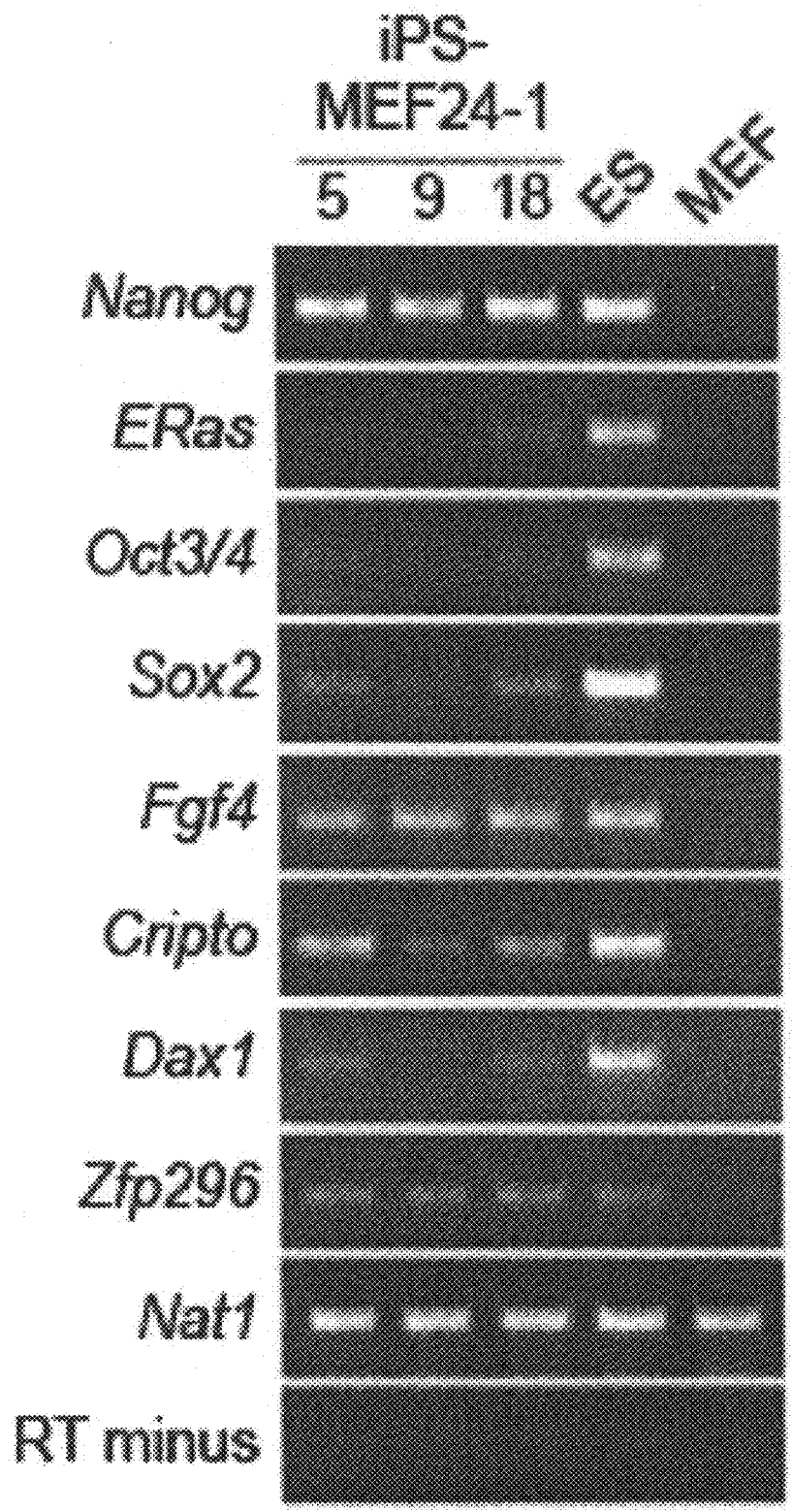
FIG. 3 shows expression profiles of marker genes in iPS cells. The results of RT-PCR using total RNAs extracted from iPS cells, ES cells and MEF cells as templates are shown.
Figure 4:
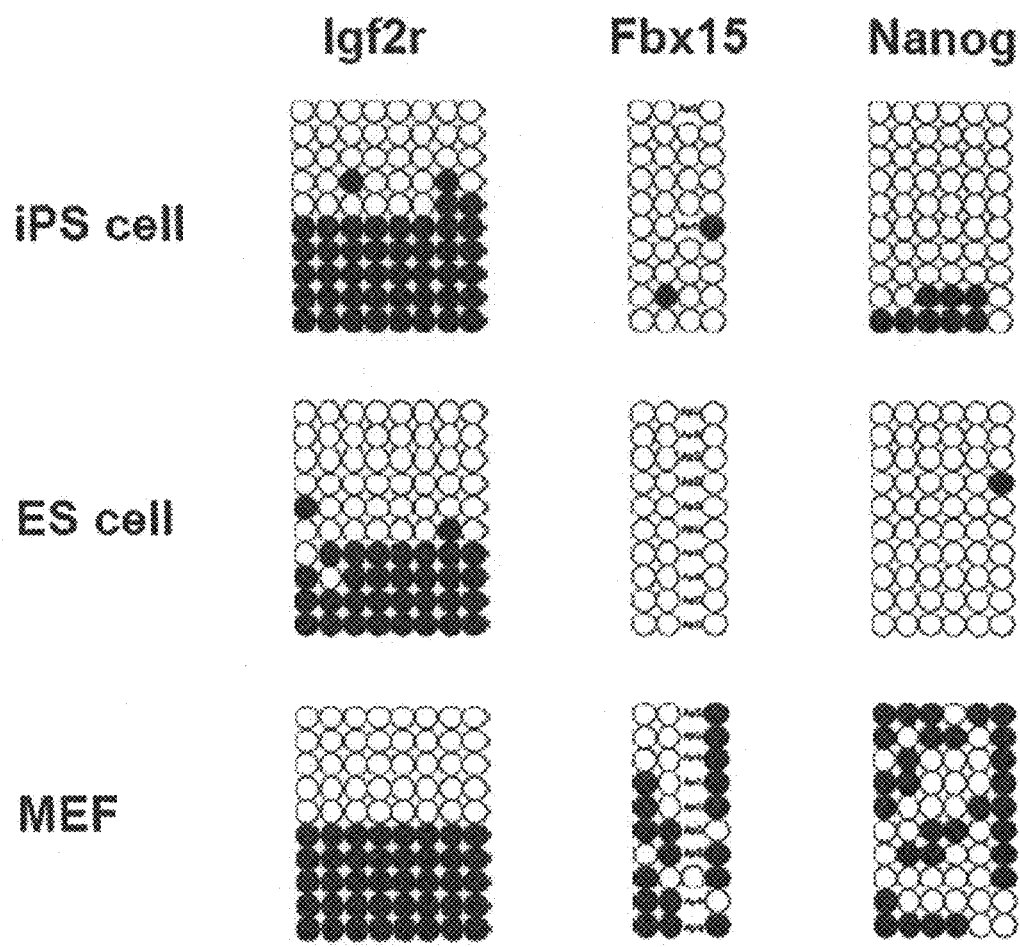
FIG. 4 shows methylation status of DNA in iPS cells. Genomic DNAs extracted from iPS cells, ES cells, and MEF cells were treated with bisulfite. The target DNAs were amplified by PCR and then inserted into plasmid. Ten clones of plasmid were isolated for each of the genes, and sequenced. Methylated CpGs are indicated with closed circles, and unmethylated CpGs with open circles.

When expression profiles of the marker genes were examined by RT-PCR, undifferentiation markers such as Nanog and Oct3/4 were found to be expressed (FIG. 3). It was found that the expression of Nanog was close to that of ES cells, whereas the expression of Oct3/4 was lower than that of ES cells. When DNA methylation status was examined by the bisulfite genomic sequencing, it was found that the Nanog gene and Fbx15 gene were highly methylated in MEFs, whereas they were demethylated in the iPS cells (FIG. 4). About 50% of IGF2 gene, an imprinting gene, was methylated both in the MEF and iPS cells. Since it was known that the imprinting memory was deleted and the IGF2 gene was almost completely demethylated in the primordial germ cells at 13.5 days after fertilization, from which the Fbx15$^{\beta geo/\beta geo}$ MEFs were isolated, it was concluded that iPS cells were not derived from primordial germ cells contaminated in the Fbx15$^{\beta geo/\beta geo}$ MEFs. The above results demonstrated that reprogramming of the differentiated cells (MEFs) into a state close to that of ES cells was able to be induced with the combination of the 24 kinds of factors.

Figure 5:
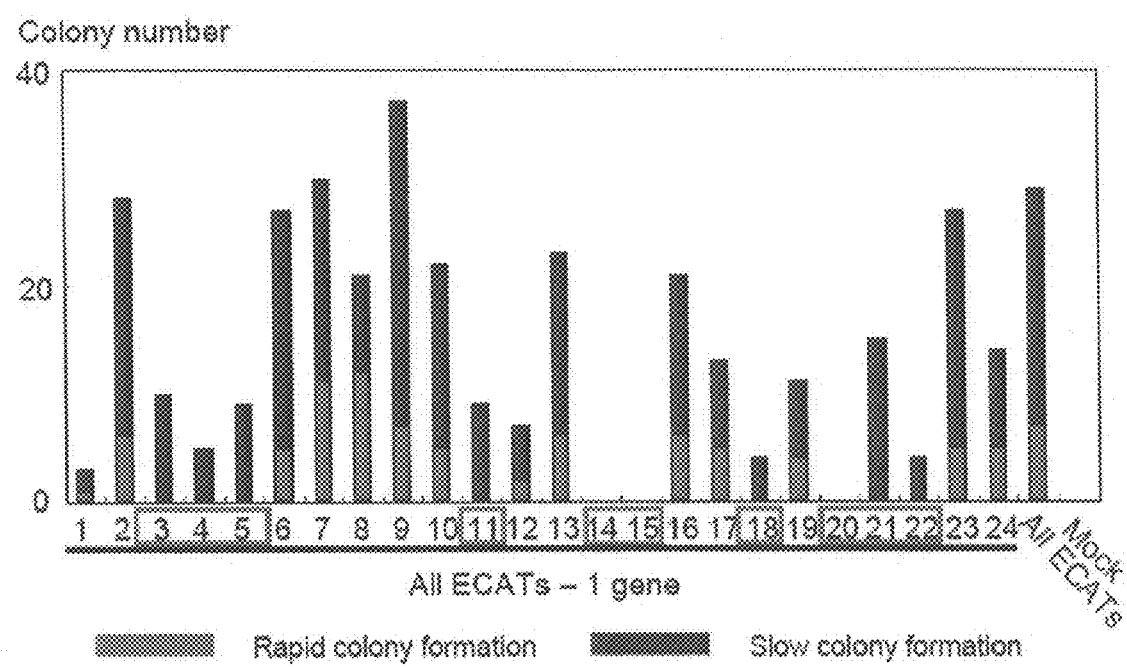
FIG. 5 shows colony numbers of G418-resistant cells obtained by transduction of 24-gene group and 23-gene groups wherein each individual gene was withdrawn from the 24-gene group. The lower parts of the graph show colony numbers obtained in one week after the G418 selection, and the upper parts of the graph show numbers of clones obtained in three weeks. When each boxed gene (the reference number for each gene is the same as that indicated in TABLE 4) was withdrawn, no colonies were obtained at all, or only a few colonies were observed after 3 weeks.

Then, studies were made as to whether or not all of the 24 kinds of genes were required for the reprogramming. With withdrawal of each individual gene, 23 genes were transfected into the Fbx15$^{\beta geo/\beta geo}$ MEFs. As a result, for 10 genes, colony formation was found to be inhibited with each withdrawal thereof (FIG. 5, the gene numbers correspond to the gene numbers shown in TABLE 4, and the genes are the following 10 kinds of genes: #3, #4, #5, #11, #14, #15, #18, #20, #21, and #22). When these ten genes were simultaneously transfected into the Fbx15$^{\beta geo/\beta geo}$ MEFs, G418-resistant colonies were significantly more efficiently obtained as compared to simultaneous transfection with the 24 genes.

Figure 6:
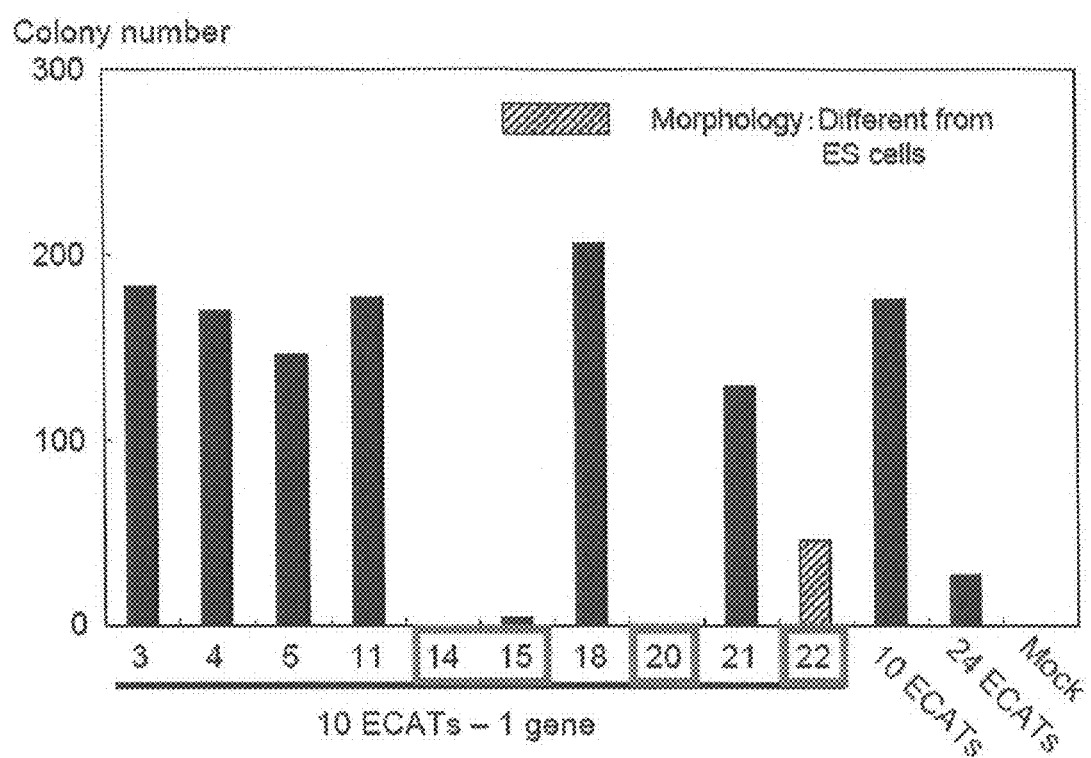
FIG. 6 shows colony numbers of G418-resistant cells obtained by transduction of 10-gene group and 9-gene groups wherein each individual gene was withdrawn from the 10-gene group. When each of genes #14, #15 or #20 was withdrawn, no colony was obtained. When gene #22 was withdrawn, a few G418-resistant colonies were obtained.

Furthermore, 9 genes, with drawal of each individual gene from the 10 genes, were transfected into Fbx15$^{\beta geo/\beta geo}$ MEFs. As a result, it was found that G418-resistant iPS cell colonies were not formed when each of 4 kinds of genes (#14, #15, #20, or #22) was withdrawn (FIG. 6). Therefore, it was suggested that these four kinds of genes, among the ten genes, had particularly important roles in the induction of reprogramming.

Example 2

Induction of Reprogramming with a Combination of 4 Kinds of Genes

It was examined whether or not induction of reprogramming of somatic cells was achievable with the four kinds of genes of which particular importance was suggested among the 10 genes. By using the combination of the aforementioned 10 kinds of genes, the combination of the aforementioned 4 kinds of genes, combinations of only 3 kinds of genes among the 4 kinds of genes, and combinations of only 2 kinds of genes among the 4 kinds of genes, these sets of genes were retrovirally transduced into the MEF cells as somatic cells in which βgeo was knocked into the Fbx15 gene. As a result, when the 4 kinds of genes were transduced, 160 G418-resistant colonies were obtained. Although this result was almost the same as that obtained by the transduction with the 10 kinds of genes (179 colonies), the colonies obtained by the 4-gene transduction were smaller than those by the 10-gene transduction. When these colonies were passaged, the numbers of colonies having iPS cell morphology was 9 clones among 12 clones in the case of the 10-gene transduction, whereas there was a somewhat lower tendency of 7 clones among 12 clones in the case of the 4-gene transduction. As for the 4 genes, almost the same numbers of iPS cells were obtained with either of those derived from mouse or those derived from human.

When 3 genes selected from the aforementioned 4 genes were transduced, 36 flat colonies were obtained with one combination (#14 (Oct3/4), #15 (Sox2), and #20 (Klf4)). However, iPS cells were not observed when they were passaged. With another combination (#14 (Oct3/4), #20 (Klf4), and #22 (c-Myc)), 54 small colonies were obtained. When 6 of the relatively large colonies from among those colonies were passaged, cells similar to ES cells were obtained for all these 6 clones. However, it seemed that adhesion of the cells between themselves and to the culture dish was weaker than that of ES cells. The proliferation rate of the cells was also slower than that observed in the case of the transduction with the 4 genes. Further, one colony each was formed with each of the other two kinds of combinations of 3 genes among the 4 genes. However, proliferation of the cells was not observed when the cells were passaged. With any of combinations of 2 genes selected from the 4 genes (6 combinations), no G418-resistant colonies were formed. The above results are shown in FIG. 7.

Further, the results of observation of expression profiles of the ES cell marker genes by RT-PCR are shown in FIG. 10. The details of the method are as follows. From iPS cells established by transducing 3 genes (Oct3/4, Klf4, and c-Myc: represented as "Sox2 minus"), 4 genes (Sox2 was added to the three genes: represented as "4ECAT"), and 10 genes (#3, #4, #5, #11, #18, and #21 in TABLE 4 were added to the four genes: represented as "10ECAT") into Fbx15$^{βgeo/βgeo}$ MEFs; iPS cells established by transducing 10 genes into fibroblasts established from tail tip of an adult mouse in which βgeo was knocked into the Fbx15 gene (represented as "10ECAT Skin fibroblast"), mouse ES cells, and MEF cells with no gene transduction, total RNAs were purified, and treated with DNaseI to remove contamination of genomic DNA. First strand cDNAs were prepared by a reverse transcription reaction, and expression profiles of the ES cell marker genes were examined by PCR. For Oct3/4, Nanog, and ERas, PCR was performed by using primers which only amplified a transcript product from an endogenous gene, not from the transduced retrovirus. The primer sequences are shown in TABLE 6.

iPS cell induction under a given set of experimental conditions could be further optimized as evidenced below.

Example 3

Analysis of Pluripotency of Reprogrammed Cells

In order to evaluate the differentiation pluripotency of the established iPS cells, the iPS cells established with 24 factors, 10 factors, and 4 factors were subcutaneously transplanted into nude mice. As a result, tumors having a size similar to that observed with ES cells were formed in all animals. Histologically, the tumors consisted of a plurality of kinds of cells, and cartilaginous tissues, nervous tissues, muscular tissues, fat tissues, and intestinal tract-like tissues were observed (FIG. 8), which verified pluripotency of the iPS cells. In contrast, although tumors were formed when the cells established with

TABLE 6

| | | |
|---|---|---|
| ECAT1 | ECAT1-RT-S | TGT GGG GCC CTG AAA GGC GAG CTG AGA T (SEQ ID NO: 1) |
| | ECAT1-RT-AS | ATG GGC CGC CAT ACG ACG ACG CTC AAC T (SEQ ID NO: 2) |
| Esg1 | pH34-U38 | GAA GTC TGG TTC CTT GGC AGG ATG (SEQ ID NO: 3) |
| | pH34-L394 | ACT CGA TAC ACT GGC CTA GC (SEQ ID NO: 4) |
| Nanog | 6047-S1 | CAG GTG TTT GAG GGT AGC TC (SEQ ID NO: 5) |
| | 6047-AS1 | CGG TTC ATC ATG GTA CAG TC (SEQ ID NO: 6) |
| ERas | 45328-S118 | ACT GCC CCT CAT CAG ACT GCT ACT (SEQ ID NO: 7) |
| | ERas-AS304 | CAC TGC CTT GTA CTC GGG TAG CTG (SEQ ID NO: 8) |
| Gdf3 | Gdf3-U253 | GTT CCA ACC TGT GCC TCG CGT CTT (SEQ ID NO: 9) |
| | GDF3 L16914 | AGC GAG GCA TGG AGA GAG CGG AGC AG (SEQ ID NO: 10) |
| Fgf4 | Fgf4-RT-S | CGT GGT GAG CAT CTT CGG AGT GG (SEQ ID NO: 11) |
| | Fgf4-RT-AS | CCT TCT TGG TCC GCC CGT TCT TA (SEQ ID NO: 12) |
| Cripto | Cripto-S | ATG GAC GCA ACT GTG AAC ATG ATG TTC GCA (SEQ ID NO: 13) |
| | Cripto-AS | CTT TGA GGT CCT GGT CCA TCA CGT GAC CAT (SEQ ID NO: 14) |
| Zfp296 | Zfp296-S67 | CCA TTA GGG GCC ATC ATC GCT TTC (SEQ ID NO: 15) |
| | Zfp296-AS350 | CAC TGC TCA CTG GAG GGG GCT TGC (SEQ ID NO: 16) |
| Dax1 | Dax1-S1096 | TGC TGC GGT CCA GGC CAT CAA GAG (SEQ ID NO: 17) |
| | Dax1-AS1305 | GGG CAC TGT TCA GTT CAG CGG ATC (SEQ ID NO: 18) |
| Oct3/4 | Oct3/4-S9 | TCT TTC CAC CAG GCC CCC GGC TC (SEQ ID NO: 19) |
| | Oct3/4-AS210 | TGC GGG CGG ACA TGG GGA GAT CC (SEQ ID NO: 20) |
| NAT1 | NAT1 U283 | ATT CTT CGT TGT CAA GCC GCC AAA GTG GAG (SEQ ID NO: 21) |
| | NAT1 L476 | AGT TGT TTG CTG CGG AGT TGT CAT CTC GTC (SEQ ID NO: 22) |

The results shown in this figure revealed that, by transduction of the 3 genes, expression of each of ERas and Fgf4 was efficiently induced, but expression of each of Oct3/4 and Nanog, essential factors for the maintenance of pluripotency, was not induced, or was very weak even when induced. However, when the 4 genes were transduced, there was one clone (#7) in which Oct3/4 and Nanog were relatively strongly induced among 4 clones examined. Further, when the 10 genes were transduced, strong induction of each of Oct3/4 and Nanog was observed in 3 clones among 5 clones examined.

These results revealed that a combination of at least 3 genes (#14 (Oct3/4), #20 (Klf4), and #22 (c-Myc)) was essential for reprogramming under these conditions, and in the cases of the 4-gene group and 10-gene group including the 3 kinds of genes, the reprogramming efficiency was increased in proportion to the increasing number of genes. In other words, in accordance with the guidance disclosed herein, the minimum combination of nuclear reprogramming factors required for the 3 factors were transplanted into nude mice, they were formed histologically only from undifferentiated cells. These results suggested that a Sox family gene was essential for the induction of differentiation pluripotency.

Example 4

Reprogramming of Fibroblasts Derived from Tails of Adult Mice

The 4 factors identified in the mouse embryonic fibroblasts (MEFs) were transduced into fibroblasts derived from tails of βgeo knockin Fbx15 adult mice systemically expressing green fluorescence protein (GFP). Then, the cells were cultured on feeder cells under the same conditions as ES cell culture conditions, and G418 selection was performed. In about two weeks after the start of the drug selection, a plurality of colonies of iPS cells were obtained. When these cells were subcutaneously transplanted to nude mice, teratomas consisting of a variety of all three germ layer tissues were formed. Further, when the iPS cells derived from adult dermal fibroblasts were transplanted to the blastocysts, and then transplanted into the uteri of pseudopregnant mice, embryos in which the GFP-positive cells were systemically distributed were observed among those at 13.5 days after fertilization (FIG. 9), demonstrating that the iPS cells had pluripotency and were able to contribute to mouse embryogenesis. These results indicate that the identified class of factors had an ability to induce reprogramming of not only somatic cells in an embryonic period, but also somatic cells of mature mice. Practically, it is extremely important that the reprogramming can be induced in cells derived from adult skin.

Example 5

Effect of Cytokine on iPS Cell Establishment

An effect of cytokine on iPS cell establishment was investigated. Expression vector (pMX retroviral vector) for basic fibroblast growth factor (bFGF) or stem cell factor (SCF) was transduced into feeder cells (STO cells) to establish cells permanently expressing the cytokines. MEFs derived from the Fbx15$^{\beta geo/\beta geo}$ mouse (500,000 cells/100 mm dish) were cultured on these STO cells and transduced with the 4 factors, and then subjected to G418 selection. As a result, the number of formed colonies increased 20 times or higher on the STO cells producing bFGF (FIG. 11) or SCF (data not shown), as compared with the culture on normal STO cells. Further, although no iPS cell colony was formed on the normal STO cells when the 3 factors other than c-Myc were transduced, colony formation was observed on the STO cells producing bFGF (FIG. 11) or SCF (data not shown). These results revealed that stimulation with the cytokine increased the efficiency of the establishment of iPS cells from MEFs, and the nuclear reprogramming was achievable by using a cytokine instead of c-Myc.

Example 6 iPS Cell Generation with Other Oct, Klf, Myc, and Sox Family Members

Family genes exist for all of the Oct3/4, Klf4, c-Myc, and Sox2 genes (TABLES 1 and 2). Accordingly, studies were made as to whether iPS cells could be established with the family genes instead of the 4 genes. In TABLE 7, combined experimental results in duplicate are shown. With regard to the Sox family, Sox1 gave almost the same number of G418-resistant colonies formed and iPS cell establishment efficiency as those with Sox2. As for Sox3, the number of G418-resistant colonies formed was about 1/10 of that with Sox2, however, iPS cell establishment efficiency of the colonies picked up was in fact higher than that with Sox2. As for Sox 15, both the number of G418-resistant colonies formed and iPS cell establishment efficiency were lower than those with Sox2. As for Sox 17, the number of G418-resistant colonies formed was almost the same as that with Sox2, however, iPS cell establishment efficiency was low. With regard to the Klf family, Klf2 gave a smaller number of G418-resistant colonies than Klf4, however, they gave almost the same iPS cell establishment efficiency. With regard to the Myc family, it was found that wild-type c-Myc was almost the same as a T58A mutant both in the number of G418-resistant colonies formed and iPS cell establishment efficiency. Further, each of N-Myc and L-Myc (each wild type) was almost the same as c-Myc in both of the number of G418-resistant colonies formed and iPS cell establishment efficiency.

TABLE 7

| Transduced gene | Number of formed colonies | Number of picked colonies | Number of established iPS cell strain | iPS cell establishment efficiency (%) |
|---|---|---|---|---|
| 4 Factors (cMycT58A) | 85 | 12 | 5 | 42 |
| Sox1 | 84 | 12 | 7 | 58 |
| Sox3 | 8 | 8 | 7 | 92 |
| Sox15 | 11 | 11 | 1 | 8 |
| Sox17 | 78 | 12 | 2 | 17 |
| Klf2 | 11 | 10 | 5 | 50 |
| c-MycWT | 53 | 11 | 8 | 72 |
| N-MycWT | 40 | 12 | 7 | 58 |
| L-MycWT | 50 | 12 | 11 | 92 |
| 3 Factors (-Sox2) | 6 | 6 | 2 | 17 |

Example 7

Use of a Nanog-GFP-Puro$^r$ Reporter to Establish iPS Cells

Studies were made as to whether iPS cells could be established with a reporter other than Fbx15-βgeo. *Escherichia coli* artificial chromosome (BAC) containing the Nanog gene in the center was isolated, and then the GFP gene and the puromycin resistance gene were knocked in by recombination in *E. coli* (FIG. 12A). Subsequently, the above modified BAC was introduced into ES cells to confirm that the cells became GFP-positive in an undifferentiated state specific manner (data not shown). Then, these ES cells were transplanted in mouse blastocysts to create transgenic mice via chimeric mice. In these mice, GFP-positive cells were specifically observed in inner cell masses of the blastocysts or gonads of embryos at 13.5 days after fertilization (FIG. 12B). The gonads were removed from the embryos at 13.5 days after fertilization (hybrid of DBA, 129, and C57BL/6 mice), and MEFs were isolated. The isolated MEFs were confirmed to be GFP-negative (FIG. 13) by flow cytometry. These MEFs were retrovirally transduced with the 4 factors and subjected to puromycin selection, and as a result, a plural number of resistant colonies were obtained. Only about 10 to 20% of the colonies were GFP-positive. When the GFP-positive colonies were passaged, they gave morphology (FIG. 14) and proliferation (FIG. 15) similar to those of ES cells. Examination of the gene expression pattern revealed that the expression pattern was closer to that of ES cells as compared to the iPS cells isolated from Fbx15$^{geo/\beta geo}$ MEFs by G418 selection (FIG. 16). When these cells were transplanted to nude mice, teratoma formation was induced, thereby the cells were confirmed to be iPS cells (FIG. 17). Further, chimeric mice were born by transplanting the iPS cells obtained by Nanog-GFP selection to the blastocysts of C57BL/6 mice (FIG. 18). When these chimeric mice were mated, germ-line transmission was observed (FIG. 19). In these iPS cells established by Nanog-GFP selection, which were closer to ES cells, the expressions of the 4 factors from the retroviruses were almost completely silenced, suggesting that self-replication was maintained by endogenous Oct3/4 and Sox2.

Example 8

In Vitro Differentiation Induction

Confluent iPS cells in 10 cm dishes were trypsinized and suspended in ES cell medium (the STO cells were removed by adhesion to a gelatin-coated dish for 10 to 20 minutes after the suspension). 2×10⁶ cells were cultured for four days in a HEMA (2-hydroxyethyl methacrylate) coated E. coli culture dish as a suspension culture to form embryoid bodies (EBs) (day 1 to 4). On the 4th day of EB formation (day 4), all of the EBs were transferred to a 10-cm tissue culture dish, and cultured in ES cell medium for 24 hours to allow adhesion. After 24 hours (day 5), the medium was changed to an ITS/fibronectin-containing medium. The culture was performed for 7 days (medium was exchanged every 2 days), and nestin-positive cells were selected (cells of other pedigrees were dying to some extent in a culture under serum-free condition) (day 5 to 12). A2B5-positive cells were then induced. After 7 days (day 12), the cells were separated by trypsinization, and the remaining EBs were removed. 1×10⁵ cells were seeded on a poly-L-ornithine/fibronectin-coated 24-well plate, and cultured for 4 days in an N2/bFGF-containing medium (medium was exchanged every 2 days)(day 12 to 16). After 4 days (day 16), the medium was changed to an N2/bFGF/EGF-containing medium, and the culture was continued for 4 days (medium was exchanged every 2 days)(day 16 to 20). After 4 days (day 20), the medium was changed to an N2/bFGF/PDGF-containing medium, and the culture was continued for 4 days (medium was exchanged every 2 days)(day 20 to 24). During this period (day 12 to 24), when the cells had increased excessively and reached confluent, they were passaged at appropriate times, and 1 to 2×10⁵ cells were seeded (the number of the cells varied depending on the timing of the passage). After 4 days (day 24), the medium was changed to an N2/T3 medium, and the culture was continued for 7 days (day 24 to 31) with medium exchange every 2 days. On day 31, the cells were fixed and subjected to immunostaining. As a result, differentiation of the iPS cells into βIII tubulin-positive nerve cells, O4-positive oligodendrocytes, and GFAP-positive astrocytes was observed (FIG. 20).

Example 9

Establishment of iPS Cells Without Drug Selection

In order to establish iPS cells from arbitrary mouse somatic cells other than those derived from the Fbx15-βgeo knockin mouse, a method for the establishment without using drug selection was developed. 10,000, 50,000, or 100,000 cells mouse embryo fibroblasts (MEFs) were cultured on a 10 cm dish (on STO feeder cells). This is less than the number of cells used above, Control DNA or the 4 factors were retrovirally transduced. When culture was performed for 2 weeks in the ES cell medium (without G418 selection), no colony formation was observed in the dish in which the control DNA was transduced, whilst in the dish in which the 4 factors were transduced, a plurality of compact colonies were formed as well as flat colonies considered to be transformed (FIG. 21). When 24 colonies were picked up from these colonies and culture was continued, ES cell-like morphology was observed. Gene expression profiles thereof were examined by RT-PCR, and as a result, the expression of Esg1, an ES cell marker, was observed in 7 clones. Induction of many ES cell markers such as Nanog, ERas, GDF3, Oct3/4, and Sox2 was observed in clone 4, and therefore the cells were considered to be iPS cells (FIG. 22). The above results demonstrated that drug selection using Fbx15-βgeo knockin or the like was not indispensable for iPS cell establishment, and iPS cells could be established from arbitrary mouse-derived somatic cells. This also suggested the possibility that iPS cells could be established from somatic cells of a disease model mouse by the aforementioned technique.

Example 10 iPS Cell Generation from Hepatocytes and Gastric Mucous Cells

As cells from which iPS cells were induced, hepatocytes and gastric mucous cells being cells other than fibroblasts were examined. Hepatocytes were isolated from the liver of the Fbx15$^{\beta geo/\beta geo}$ mice by perfusion. These hepatocytes were retrovirally introduced with the 4 factors, and then subjected to G418 selection to obtain plural iPS cell colonies. As a result of gene expression pattern analysis using a DNA microarray, the iPS cells derived from the liver were found to be more similar to ES cells than the iPS cells derived from dermal fibroblasts or embryonic fibroblasts. iPS cells were obtained also from gastric mucous cells in the same manner as those from hepatocytes.

Example 11

Effect of MAP Kinase Inhibitor on iPS Cell Establishment

PD98059 is an inhibitor of MAP kinase which suppresses proliferation of various differentiated cells. However, it is known to promote maintenance of undifferentiated status and proliferation of ES cells. Effects of PD98059 on iPS cell establishment were thus examined. MEFs established from a mouse having the selective markers of Nanog-EGFP-IRES-Puro were retrovirally introduced with the 4 factors and subjected to puromycin selection. When PD98059 was not added, the percentage of GFP-positive colonies was 8% of the iPS cell colonies obtained. However, in the group to which PD98059 (final concentration: 25 µM) was continuously added from the next day of the retroviral transfection, 45% of the colonies obtained were GFP-positive. The results were interpreted to be due to PD98059 promoting the proliferation of the GFP-positive iPS cells, which are closer to ES cells, whilst PD98059 suppressing the proliferation of the GFP-negative iPS cells or differentiated cells. From these results, PD98059 was demonstrated to be able to be used for establishment of the iPS cells closer to ES cells or establishment of iPS cells without using drug selection.

Example 12

Establishment of iPS Cells from Embryonic HDFs in Mouse ES Cell Medium

A plasmid, containing the red fluorescence protein gene downstream from the mouse Oct3/4 gene promoter and the hygromycin resistance gene downstream from the PGK promoter, was introduced by nucleofection into embryonic human dermal fibroblasts (HDFs) in which solute carrier family 7 (Slc7a1, NCBI accession number NM_007513) as a mouse ecotropic virus receptor was expressed by lentiviral transduction. Hygromycin selection was performed to establish strains with stable expression. 800,000 cells were seeded on the STO cells treated with mitomycin, and on the next day, Oct3/4, Sox2, Klf4, and c-Myc (each derived from human) were retrovirally transduced into the cells. 24 colonies were picked up from those obtained after 3 weeks (FIG. 23, left), and transferred on a 24-well plate on which the STO cells were seeded and then cultured. After 2 weeks, one grown clone was passaged on a 6-well plate on which the STO cells were seeded and cultured. As a result, cells morphologically similar to ES cells were obtained (FIG. 23, right), suggesting that the cells were iPS cells. The mouse ES cell medium was used as every medium.

Example 13

Establishment of iPS Cells from Adult HDFs in Mouse ES Cell Medium

Human adult dermal fibroblasts (adult HDFs) or human neonatal foreskin cells (BJ) were transduced with Slc7a1 (mouse retroviral receptor) by using lentivirus, and the resulting cells were seeded on 800,000 feeder cells (mitomycin-treated STO cells). The genes were retrovirally transduced as the following combinations.
1. Oct3/4, Sox2, Klf4, c-Myc, TERT, and SV40 Large T antigen
2. Oct3/4, Sox2, Klf4, c-Myc, TERT, HPV16 E6
3. Oct3/4, Sox2, Klf4, c-Myc, TERT, HPV16 E7
4. Oct3/4, Sox2, Klf4, c-Myc, TERT, HPV16 E6, HPV16 E7
5. Oct3/4, Sox2, Klf4, c-Myc, TERT, Bmi1
(Oct3/4, Sox2, Klf4, c-Myc and TERT were derived from human, and Bmi1 was derived from mouse)

The culture was continued under the culture conditions for mouse ES cells without drug selection. As a result, colonies considered to be those of iPS cells emerged on the 8th day after the virus transfection on the dish in which the factors were introduced according to Combination 1 (FIG. 24). iPS cell-like colonies also emerged with the other combinations (2 to 5), although they were not as apparent when compared to Combination 1. When only the 4 factors were transduced, no colonies emerged. Cells transduced with only the four factors under the experimental conditions used in this Example showed only faint staining for alkaline phosphatase (FIG. 25(A)-(B)).

However, optimization of the methods heretofore described revealed successful induction of iPS cells through staining of any number of pluripotent markers, including alkaline phosphatase, ABCG-2, E-cadherin, SSEA-3, and SSEA-4 when adult human dermal fibroblasts expressing mouse Slc7a1 gene were generated into iPS cells by reprogramming with the four factors plus TERT and SV40 Large T antigen (i.e. six factors total: c-Myc, Klf4, Sox2, Oct3/4, TERT, and SV40 Large T antigen) (FIG. 26(A)-(B)). These cells were assessed for pluripotent cell markers (FIG. 27). These cells were found to express ECATS, including Nanog and ESG1. Similarly, BJ fibroblasts expressing mouse Slc7a1 gene were generated into iPS cells by reprogramming with the following same factors. These cells were also tested for pluripotent cell markers (FIG. 28). In addition, iPS cells generated from adult HDFs were selected for subcutaneous injection into the dorsal flanks of SCID mice. Teratoma formation was observed (FIGS. 29(A)-(D)). Human dermal fibroblasts were also shown to differentiate in vitro upon culturing in HEMA-coated plates (7 days) and gelatinized dishes (7 days) (FIG. 30).

Example 14

Optimization of Retroviral Transduction for Generating Human iPS Cells

Next, iPS cell generation from adult human somatic cells was further evaluated by optimizing retroviral transduction in human fibroblasts and subsequent culture conditions. Induction of iPS cells from mouse fibroblasts requires retroviruses with high transduction efficiencies (Takahashi et al., Cell 126: 663-676, 2006). Therefore, transduction methods in adult human dermal fibroblasts (HDFs) were optimized. First, green fluorescent protein (GFP) was introduced into adult HDF with amphotropic retrovirus produced in PLAT-A packaging cells. As a control, GFP was introduced into mouse embryonic fibroblasts (MEF) with ecotropic retrovirus produced in PLAT-E packaging cells (Morita et al., Gene Ther. 7:1063-66, 2000). In MEF, more than 80% of cells expressed GFP (FIG. 31). In contrast, less than 20% of HDF expressed GFP with significantly lower intensity than in MEF. To improve the transduction efficiency, the mouse receptor for retroviruses, Slc7a1 (Verrey et al., Pflugers Arch. 447:532-542, 2004) (also known as mCAT1), was introduced into HDF with lentivirus. Then GFP was introduced into HDF-Slc7a1 with ecotropic retrovirus. This strategy yielded a transduction efficiency of 60%, with a similar intensity to that in MEF.

Example 15

Generation of iPS Cells from Adult HDFs in Primate ES Cell Culture Medium

The protocol for human iPS cell induction is summarized in FIG. 32A. pMXs encoding human Oct3/4, Sox2, Klf4, and c-Myc were introduced into HDF-Slc7a1 cells (FIG. 32B; $8 \times 10^5$ cells per 100 mm dish). The HDFs were derived from facial dermis of 36-year-old Caucasian female.

Six days after transduction, the cells were harvested by trypsinization and plated onto mitomycin C-treated SNL feeder cells (McMahon et al., Cell 62:1073-85, 1990) at $5 \times 10^4$ or $5 \times 10^5$ cells per 100 mm dish. The next day, the medium (DMEM containing 10% FBS) was replaced with a medium for primate ES cell culture supplemented with 4 ng/ml basic fibroblast growth factor (bFGF). Approximately two weeks later, some granulated colonies appeared that were not similar to hES cells in morphology (FIG. 32C). Around day 25, distinct types of colonies that were flat and resembled hES cell colonies were observed (FIG. 32D). From $5 \times 10^4$ fibroblasts, ~10 hES cell-like colonies and ~100 granulated colonies (7/122, 8/84, 8/171, 5/73, 6/122, and 11/213 in six independent experiments, summarized in TABLE 8) were observed.

TABLE 8

Summary of the iPS cell induction experiments

| Exp. ID | Parental cells | Cell No. seeded at d6 | No. of ES-like colony | No. of total colony | No. of picked up colony | No. of established clone |
|---|---|---|---|---|---|---|
| 201B | HDF | 50000 | 7 | 129 | 7 | 5 |
| 243H | HFLS | 500000 | 0 | >1000 | | |
| | | 50000 | 17 | 679 | 6 | 2 |
| 246B | HDF | 500000 | 0 | 420 | | |
| | | 500000 | 2 | 508 | | |
| | | 50000 | 8 | 92 | 6 | 6 |
| 246G | BJ | 50000 | 7 | 10 | 6 | 5 |
| | | 500000 | 86 | 98 | | |
| | | 500000 | 106 | 108 | | |
| 249D | HDF | 500000 | 0 | 320 | | |
| | | 500000 | 0 | 467 | | |
| | | 50000 | 8 | 179 | 6 | 4 |

TABLE 8-continued

Summary of the iPS cell induction experiments

| Exp. ID | Parental cells | Cell No. seeded at d6 | No. of ES-like colony | No. of total colony | No. of picked up colony | No. of established clone |
|---|---|---|---|---|---|---|
| 253F | HDF | 50000 | 5 | 78 | 3 | 2 |
|  |  | 50000 | 6 | 128 | 3 | 3 |
|  |  | 500000 | 10 | 531 |  |  |
|  |  | 500000 | 3 | 738 |  |  |
| 282C | HDF | 50000 | 11 | 224 | 3 | 1 |
| 282H | BJ | 50000 | 13 | 15 | 3 | 2 |
| 282R | HFLS | 5000 | 31 | 98 | 6 | 2 |

At day 30, hES cell-like colonies were picked up and mechanically disaggregated into small clumps without enzymatic digestion. When starting with 5×10⁵ fibroblasts, the dish was nearly covered with more than 300 granulated colonies. Occasionally some hES cell-like colonies in between the granulated cells were observed, but it was difficult to isolate hES cell-like colonies because of the high density of granulated cells.

The hES-like cells expanded on SNL feeder cells under the human ES cell culture condition. They formed tightly packed and flat colonies (FIG. 32E). Each cell exhibited morphology similar to that of human ES cells, characterized by large nucleoli and scant cytoplasm (FIG. 32F). As is the case with hES cells, occasionally spontaneous differentiation was observed in the center of the colony (FIG. 32G).

These cells also showed similarity to hES cells in feeder dependency. They did not attach to gelatin-coated tissue-culture plates. By contrast, they maintained an undifferentiated state on Matrigel-coated plates in MEF-conditioned medium (MEF-CM), but not in ES medium (FIG. 33).

Since these cells were indistinguishable from hES cells in morphology and other aspects noted above, the selected cells after transduction of HDFs are referred to as human iPS cells. The molecular and functional evidence for this claim is further described below. Human iPS cells clones established in this study are summarized in TABLE 9.

TABLE 9

Characterization of established clones

| Clone | Source | Marker expression | | Pluripotency | | | |
|---|---|---|---|---|---|---|---|
|  |  | RT-PCR | IC | EB | PA6 | Cardio-myocyte | Teratoma |
| 201B1 | HDF | ✓ |  |  |  |  |  |
| 201B2 |  | ✓ | ✓ | ✓ | ✓ | ✓ |  |
| 201B3 |  | ✓ |  |  |  |  |  |
| 201B6 |  | ✓ | ✓ | ✓ | ✓ | ✓ |  |
| 201B7 |  | ✓ | ✓ | ✓ | ✓ | ✓ | ✓ |
| 243H1 | HFLS | ✓ |  | ✓ |  |  |  |
| 243H7 |  | ✓ |  | ✓ |  |  |  |
| 246B1 | HDF | ✓ |  |  |  |  |  |
| 246B2 |  | ✓ |  |  |  |  |  |
| 246B3 |  | ✓ |  |  |  |  |  |
| 246B4 |  | ✓ |  |  |  |  |  |
| 246B5 |  | ✓ |  |  |  |  |  |
| 246B6 |  | ✓ |  |  |  |  |  |
| 246G1 | BJ | ✓ |  | ✓ |  |  |  |
| 246G3 |  | ✓ |  | ✓ |  |  |  |
| 246G4 |  | ✓ |  |  |  |  |  |
| 246G5 |  | ✓ |  |  |  |  |  |
| 246G6 |  | ✓ |  |  |  |  |  |
| 253F1 | HDF | ✓ |  |  |  |  |  |

TABLE 9-continued

Characterization of established clones

| Clone | Source | Marker expression | | Pluripotency | | | |
|---|---|---|---|---|---|---|---|
|  |  | RT-PCR | IC | EB | PA6 | Cardio-myocyte | Teratoma |
| 253F2 |  | ✓ |  |  |  |  |  |
| 253F3 |  | ✓ |  |  |  |  |  |
| 253F4 |  | ✓ |  |  |  |  |  |
| 253F5 |  | ✓ |  |  |  |  |  |

IC; immunocytochemistry,
EB; embryoid body

Human iPS Cells Express hES Markers

In general, except for a few cells at the edge of the colonies, human iPS cells did not express stage-specific embryonic antigen (SSEA)-1 (FIG. 32H). In contrast, they expressed hES cell-specific surface antigens (Adewumi et al., *Nat. Biotechnol.* 25:803-816, 2007), including SSEA-3, SSEA-4, tumor-related antigen (TRA)-1-60, TRA-1-81, and TRA-2-49/6E (alkaline phosphatase), and NANOG protein (FIG. 32I-N).

Figure 34A:
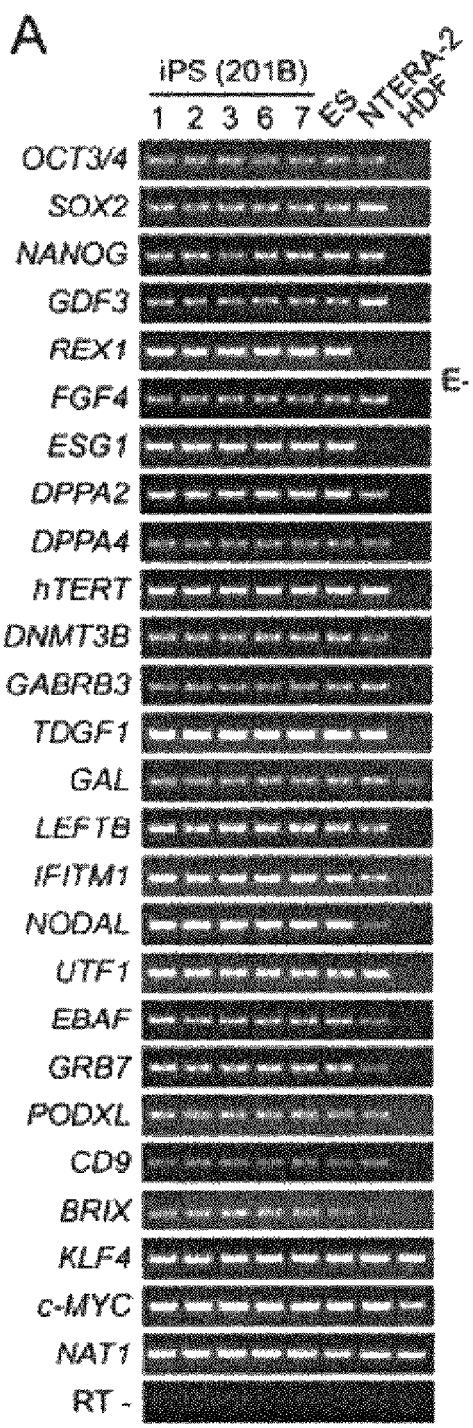

RT-PCR showed human iPS cells expressed many undifferentiated ES cell gene markers (Adewumi et al., *Nat. Biotechnol.* 25:803-816, 2007), such as OCT3/4, SOX2, NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (hTER7) at levels equivalent to or higher than those in the human embryonic carcinoma cell line, NTERA-2 (FIG. 34A). By western blotting, proteins levels of OCT3/4, SOX2, NANOG, SALL4, E-CADHERIN, and hTERT were similar in human iPS cells and hES cells (FIG. 34B). In human iPS cells, the expression of transgenes from integrated retroviruses was efficiently silenced, indicating that they depend on the endogenous expression of these genes (FIG. 34C).

Promoters of ES Cell-Specific Genes are Active in Human iPS Cells

Bisulfite genomic sequencing analyses evaluating the methylation statuses of cytosine guanine dinucleotides (CpG) in the promoter regions of pluripotent-associated genes, such as OCT3/4, REX1, and NANOG, revealed that they were highly unmethylated, whereas the CpG dinucleotides of the regions were highly methylated in parental HDFs (FIG. 34D). These findings indicate that these promoters are active in human iPS cells.

Luciferase reporter assays also showed that human OCT3/4 and REX1 promoters had high levels of transcriptional activity in human iPS cells, but not in HDF. The promoter activities of ubiquitously expressed genes, such as human RNA polymerase II (PolII), showed similar activities in both human iPS cells and HDF (FIG. 34E).

High Telomerase Activity and Exponential Growth of Human iPS Cells

As predicted from the high expression levels of hTERT, human iPS cells showed high telomerase activity (FIG. 35A). They proliferated exponentially for at least 4 months (FIG. 35B). The calculated doubling time of human iPS cells were 46.9±12.4 (clone 201B2), 47.8±6.6 (201B6) and 43.2±11.5 (201B7) hours (FIG. 35B). These times are equivalent to the reported doubling time of hES cells (Cowan et al., *N. Engl. J. Med.* 350:1353-56, 2004).

Human iPS Cells Are Derived from HDF, not Cross-Contamination

PCR of genomic DNA of human iPS cells showed that all clones have integration of all the four retroviruses (FIG. 36A). Southern blot analysis with a c-Myc cDNA probe revealed that each clone had a unique pattern of retroviral integration sites (FIG. 36B). In addition, the patterns of 16 short tandem repeats were completely matched between human iPS clones and parental HDF (TABLE 10).

TABLE 10

STR analyses of HDF-derived iPS cells

| Locus | 201B1 | | 201B2 | | 201B3 | | 201B6 | | 201B7 | | NTERA-2 | | HDF | |
|---|---|---|---|---|---|---|---|---|---|---|---|---|---|---|
| D3S1358 | 15 | 17 | 15 | 17 | 15 | 17 | 15 | 17 | 15 | 17 | 15 | | 15 | 17 |
| TH01 | 5 | | 5 | | 5 | | 5 | | 5 | | 9 | | 5 | |
| D21S11 | 28 | | 28 | | 28 | | 28 | | 28 | | 29 | 30 | 28 | |
| D18S51 | 14 | | 14 | | 14 | | 14 | | 14 | | 13 | | 14 | |
| Penta_E | 7 | 19 | 7 | 19 | 7 | 19 | 7 | 19 | 7 | 19 | 5 | 14 | 7 | 19 |
| D5S818 | 11 | | 11 | | 11 | | 11 | | 11 | | 8 | 11 | 11 | |
| D13S317 | 10 | 14 | 10 | 14 | 10 | 14 | 10 | 14 | 10 | 14 | 14 | | 10 | 14 |
| D7S820 | 9 | 10 | 9 | 10 | 9 | 10 | 9 | 10 | 9 | 10 | 12 | | 9 | 10 |
| D16S539 | 11 | 13 | 11 | 13 | 11 | 13 | 11 | 13 | 11 | 13 | 11 | 16 | 11 | 13 |
| CSF1PO | 10 | | 10 | | 10 | | 10 | | 10 | | 9 | 11 | 10 | |
| Penta_D | 8 | 10 | 8 | 10 | 8 | 10 | 8 | 10 | 8 | 10 | 11 | 12 | 8 | 10 |
| AMEL | X | | X | | X | | X | | X | | X | Y | X | |
| vWA | 15 | 18 | 15 | 18 | 15 | 18 | 15 | 18 | 15 | 18 | 19 | | 15 | 18 |
| D8S1179 | 8 | 10 | 8 | 10 | 8 | 10 | 8 | 10 | 8 | 10 | 13 | 15 | 8 | 10 |
| TPOX | 8 | 9 | 8 | 9 | 8 | 9 | 8 | 9 | 8 | 9 | 8 | 9 | 8 | 9 |
| FGA | 20 | 22 | 20 | 22 | 20 | 22 | 20 | 22 | 20 | 22 | 23 | | 20 | 22 |

These patterns differed from any established hES cell lines reported on National Institutes of Health website (http://stemcells.nih.gov/research/nihresearch/scunit/genotyping.htm). In addition, chromosomal G-band analyses showed that human iPS cells had a normal karyotype of 46XX (not shown). Thus, human iPS clones were derived from HDF and were not a result of cross-contamination.

Example 16

Embryoid Body-Mediated Differentiation of Human iPS Cells

To determine the differentiation ability of human iPS cells in vitro, floating cultivation was used to form embryoid bodies (EBs) (Itskovitz-Eldor et al., Mol. Med. 6:88-95, 2000). After 8 days in suspension culture, iPS cells formed ball-shaped structures (FIG. 37A). These embryoid body-like structures were transferred to gelatin-coated plates and continued cultivation for another 8 days. Attached cells showed various types of morphologies, such as those resembling neuronal cells, cobblestone-like cells, and epithelial cells (FIG. 37B-E). Immunocytochemistry detected cells positive for βIII-tubulin (a marker of ectoderm), glial fibrillary acidic protein (GFAP, ectoderm), α-smooth muscle actin (α-SMA, mesoderm), desmin (mesoderm), α-fetoprotein (AFP, endoderm), and vimentin (mesoderm and parietal endoderm) (FIG. 37F-K). RT-PCR confirmed that these differentiated cells expressed forkhead box A2 (FOXA2, a marker of endoderm), AFP (endoderm), cytokeratin 8 and 18 (endoderm), SRY-box containing gene 17 (SOX17, endoderm), BRACHYURY (mesoderm), Msh homeobox 1 (MSX1, mesoderm), microtubule-associated protein 2 (MAP2, ectoderm), and paired box 6 (PAX6, ectoderm) (FIG. 37L). In contrast, expression of OCT3/4, SOX2, and NANOG was significantly decreased. These data demonstrated that iPS cells could differentiate into three germ layers in vitro.

Example 17

Directed Differentiation of Human iPS Cells into Neural Cells

Next, it was examined whether lineage-directed differentiation of human iPS cells could be induced by reported methods for hES cells. Human iPS cells were seeded on PA6 feeder layer and maintained under differentiation conditions for 2 weeks (Kawasaki et al., Nueron 28:31-40, 2000). Cells spread drastically, and some neuronal structures were observed (FIG. 38A). Immunocytochemistry detected cells positive for tyrosine hydroxylase and βIII tubulin in the culture (FIG. 38B). PCR analysis revealed expression of dopaminergic neuron markers, such as aromatic-L-amino acid decarboxylase (AADC), choline acetyltransferase (ChAT), solute carrier family 6 (neurotransmitter transporter, dopamine), member 3 (DAT), and LIM homeobox transcription factor 1 beta (LMX1B), as well as another neuron marker, MAP2 (FIG. 38C). In contrast, GFAP expression was not induced with this system. On the other hand, expression of OCT3/4, SOX2, and NANOG decreased (FIG. 38C). These data demonstrated that iPS cells could differentiate into neuronal cells, including dopaminergic neurons, by co-culture with PA6 cells.

Example 18

Directed Differentiation of Human iPS Cells into Cardiac Cells

Next directed cardiac differentiation of human iPS cells was examined with the recently reported protocol, which utilizes activin A and bone morphogenetic protein (BMP) 4 (Laflamme et al., Nat. Biotechnol. 25:1015-24, 2007). Twelve days after the induction of differentiation, clumps of cells started beating (FIG. 38D). RT-PCR showed that these cells expressed cardiomyocyte markers, such as troponin T type 2 cardiac (TnTc); myocyte enhancer factor 2C (MEF2C); NK2 transcription factor related, locus 5 (NKX2.5) myosin, light polypeptide 7, regulatory (MYL2A), and myosin, heavy polypeptide 7, cardiac muscle, beta (MYHCB) (FIG. 38E). In contrast, the expression of Oct3/4, Sox2, and Nanog markedly decreased. Thus, human iPS cells can differentiate into cardiac myocytes in vitro.

Example 19

Teratoma Formation from Human iPS Cells

To test pluripotency in vivo, human iPS cells (clone 201B7) were transplanted subcutaneously into dorsal flanks of immunodeficient (SCID) mice. Nine weeks after injection, tumor formation was observed. Histological examination showed that the tumor contained various tissues (FIG. 39), including gut-like epithelial tissues (endoderm), striated muscle (mesoderm), cartilage (muscle), neural tissues (ectoderm), and keratin-containing squamous tissues (ectoderm).

Example 20

Generation of iPS Cells from Other Human Somatic Cells

In addition to HDF, primary human fibroblast-like synoviocytes (HFLS) from synovial tissue of 69-year-old Caucasian male and BJ cells, a cell line established from neonate fibroblasts, were used (TABLE 8). From $5\times10^4$ HFLS cells per 100 mm dish, more than 600 hundred granulated colonies and 17 hES cell-like colonies were obtained. Six colonies were picked, of which only two were expandable as iPS cells (FIG. 40). Dishes seeded with $5\times10^5$ HFLS were covered with granulated cells, and no hES cell-like colonies were distinguishable. In contrast, 7 to 8 and ~100 hES cell-like colonies were obtained from $5\times10^4$ and $5\times10^5$ BJ cells, respectively, with only a few granulated colonies (TABLE 8). Six hES cell-like colonies were picked and iPS cells were generated from five colonies (FIG. 40). Human iPS cells derived from HFLS and BJ expressed hES cell-marker genes at levels similar to or higher than those in hES cells (FIG. 41). They differentiated into all three germ layers through EBs (FIG. 42). STR analyses confirmed that iPS-HFLS cells and iPS-BJ cells were derived from HFLS and BJ fibroblasts, respectively (TABLE 11 and TABLE 12).

TABLE 11

STR analyses of HFLS-derived IPS cells

| Locus | 243H1 | | 243H7 | | HFLS | |
|---|---|---|---|---|---|---|
| D3S1358 | 16 | 17 | 16 | 17 | 16 | 17 |
| TH01 | 5 | 9 | 5 | 9 | 5 | 9 |
| D21S11 | 28 | 30 | 28 | 30 | 28 | 30 |
| D18S51 | 14 | 17 | 14 | 17 | 14 | 17 |
| Penta_E | 5 | 12 | 5 | 12 | 5 | 12 |
| D5S818 | 10 | 12 | 10 | 12 | 10 | 12 |
| D13S317 | 13 | | 13 | | 13 | |
| D7S820 | 9 | 12 | 9 | 12 | 8 | 12 |
| D16S539 | 11 | 13 | 11 | 13 | 11 | 13 |
| CSF1PO | 10 | 11 | 10 | 11 | 10 | 11 |
| Penta_D | 9 | 11 | 9 | 11 | 9 | 11 |
| AMEL | X | | X | Y | X | Y |
| vWA | 17 | 19 | 17 | 19 | 17 | 19 |
| D8S1179 | 13 | | 13 | | 13 | |
| TPOX | 8 | 11 | 8 | 11 | 8 | 11 |
| FGA | 21 | 22 | 21 | 22 | 21 | 22 |

TABLE 12

STR analyses of BJ-derived iPS cells

| Locus | 246G1 | | 246G3 | | 246G4 | | 246G5 | | 246G6 | | BJ | |
|---|---|---|---|---|---|---|---|---|---|---|---|---|
| D3S1358 | 13 | 15 | 13 | 15 | 13 | 15 | 13 | 15 | 13 | 15 | 13 | 15 |
| TH01 | 6 | 7 | 6 | 7 | 6 | 7 | 6 | 7 | 6 | 7 | 6 | 7 |
| D21S11 | 28 | | 28 | | 28 | | 28 | | 28 | | 28 | |
| D18S51 | 16 | 18 | 16 | 18 | 16 | 18 | 16 | 18 | 16 | 18 | 16 | 18 |
| Penta_E | 7 | 17 | 7 | 17 | 7 | 17 | 7 | 17 | 7 | 17 | 7 | 17 |
| D5S818 | 11 | | 11 | | 11 | | 11 | | 11 | | 11 | |
| D13S317 | 9 | 10 | 9 | 10 | 9 | 10 | 9 | 10 | 9 | 10 | 9 | 10 |
| D7S820 | 11 | 12 | 11 | 12 | 11 | 12 | 11 | 12 | 11 | 12 | 11 | 12 |
| D16S539 | 9 | 13 | 9 | 13 | 9 | 13 | 9 | 13 | 9 | 13 | 9 | 13 |
| CSF1PO | 9 | 11 | 9 | 11 | 9 | 11 | 9 | 11 | 9 | 11 | 9 | 11 |
| Penta_D | 11 | 12 | 11 | 12 | 11 | 12 | 11 | 12 | 11 | 12 | 11 | 12 |
| AMEL | X | Y | X | Y | X | Y | X | Y | X | Y | X | Y |
| vWA | 16 | 18 | 16 | 18 | 16 | 18 | 16 | 18 | 16 | 18 | 16 | 18 |
| D8S1179 | 9 | 11 | 9 | 11 | 9 | 11 | 9 | 11 | 9 | 11 | 9 | 11 |
| TPOX | 10 | 11 | 10 | 11 | 10 | 11 | 10 | 11 | 10 | 11 | 10 | 11 |
| FGA | 22 | 23 | 22 | 23 | 22 | 23 | 22 | 23 | 22 | 23 | 22 | 23 |

Thus, with Examples 13-20 it was shown that iPS cells can be generated from adult HDF and other somatic cells by retroviral transduction of the same four transcription factors, namely Oct3/4, Sox2, Klf4, and c-Myc. The established human iPS cells are indistinguishable from hES cells in many aspects, including morphology, proliferation, feeder dependence, surface markers, gene expression, promoter activities, telomerase activities, in vitro differentiation, and teratoma formation. The four retroviruses are nearly completely silenced in human iPS cells, indicating that these cells are fully reprogrammed and do not depend on continuous expression of the transgenes for self-renewal.

hES cells are different from mouse counterparts in many respects (Rao, M., Dev. Biol. 275:269-286, 2004). hES cell colonies are flatter and do not override each other. hES cells depend on bFGF for self renewal (Amit et al., Dev. Biol. 227:271-78, 2000), whereas mouse ES cells depend on the LIF/Stat3 pathway (Matsuda et al., EMBO J. 18:4261-69, 1999; Niwa et al., Genes Dev. 12:2048-60, 1998). BMP induces differentiation in hES cells (Xu et al., Nat. Methods 2:185-90, 2005) but is involved in self renewal of mouse ES cells (Ying et al., Cell 115:281-92, 2003). Because of these differences, it has been speculated that factors required for reprogramming might differ between humans and mice. On the contrary, our data show that the same four transcription factors induce iPS cells in both humans and mouse. The four factors, however, could not induce human iPS cell colonies when fibroblasts were kept under the culture condition for mouse ES cells after retroviral transduction (See Example 13, above), even though these cells stained positive for alkaline phosphatase. These data suggest that the fundamental transcriptional network governing pluripotency is common in human and mice, but extrinsic factors and signals maintaining pluripotency are unique for each species.

Deciphering of the mechanism by which the four factors induce pluripotency in somatic cells remains elusive. The function of Oct3/4 and Sox2 as core transcription factors to determine pluripotency is well documented (Boyer et al., Cell 122:947-956, 2005; Loh et al., Nat Genet. 38:431-440, 2006; Wang et al., Nature 444:364-368, 2006). They synergistically upregulate "stemness" genes, while suppressing differentiation-associated genes in both mouse and human ES cells. However, they cannot bind their targets genes in differentiated cells, because of other inhibitory mechanisms, including DNA methylation. It may be speculated that c-Myc and Klf4 modifies chromatin structure so that Oct3/4 and Sox2 can bind to their targets (Yamanaka, *Cell Stem Cell* 1:39-49, 2007). Notably, Klf4 interacts with p300 histone acetyltransferase and regulates gene transcription by modulating histone acetylation (Evans et al., *J Biol Chem,* 2007).

The negative role of c-Myc in the self renewal of hES cells has also been reported (Sumi et al., *Oncogene* 26: 5564-5576, 2007). They showed that forced expression of c-Myc induced differentiation and apoptosis of human ES cells. During iPS cell generation, transgenes derived from retroviruses are silenced when the transduced fibroblasts acquire ES-like state. The role of c-Myc in establishing iPS cells may be as a booster of reprogramming, rather than a controller of maintenance of pluripotency.

It has been found that each iPS clone contained 3-6 retroviral integrations for each factor. Thus, each clone had more than 20 retroviral integration sites in total, which may increase the risk of tumorigenesis. In the case of mouse iPS cells, ~20% of chimera mice and their offspring derived from iPS cells developed tumors Okita et al., *Nature* 448:313-17, 2007). This issue must be overcome to use iPS cells in human therapies. Therefore, non-retroviral methods to introduce the four factors, such as adenoviruses or cell-permeable recombinant proteins, are also contemplated as part of the invention. Alternatively, small molecules may replace the four factors for the induction of iPS cells.

Experimental Procedures for Examples 14-20

Cell Culture

HDFs from facial dermis of 36-year-old Caucasian female and HFLS from synovial tissue of 69-year-old Caucasian male were purchased from Cell Applications, Inc. BJ fibroblasts from neonatal foreskin and NTERA-2 clone D1 human embryonic carcinoma cells were obtained from American Type Culture Collection. Human fibroblasts, NTERA-2, PLAT-E, and PLAT-A cells were maintained in Dulbecco's modified eagle medium (DMEM, Nacalai Tesque, Japan) containing 10% fetal bovine serum (FBS, Japan Serum) and 0.5% penicillin and streptomycin (Invitrogen). 293FT cells were maintained in DMEM containing 10% FBS, 2 mM L-glutamine (Invitrogen), $1 \times 10^{-4}$ M nonessential amino acids (Invitrogen), 1 mM sodium pyruvate (Sigma) and 0.5% penicillin and streptomycin. PA6 stroma cells (RIKEN Bioresource Center, Japan) were maintained in α-MEM containing 10% FBS and 0.5% penicillin and streptomycin. iPS cells were generated and maintained in Primate ES medium (ReproCELL, Japan) supplemented with 4 ng/ml recombinant human basic fibroblast growth factor (bFGF, WAKO, Japan).

For passaging, human iPS cells were washed once with PBS and then incubated with DMEM/F12 containing 1 mg/ml collagenase IV (Invitrogen) at 37° C. When colonies at the edge of the dish started dissociating from the bottom, DMEF/F12/collangenase was removed and washed with hES cell medium. Cells were scraped and collected into 15 ml conical tube. An appropriate volume of the medium was added, and the contents were transferred to a new dish on SNL feeder cells. The split ratio was routinely 1:3. For feeder-free culture of iPS cells, the plate was coated with 0.3 mg/ml Matrigel (growth-factor reduced, BD Biosciences) at 4° C. overnight. The plate was warmed to room temperature before use. Unbound Matrigel was aspirated off and washed out with DMEM/F12. iPS cells were seeded on Matrigel-coated plate in MEF-CM or ES medium, both supplemented with 4 ng/ml bFGF. The medium was changed daily. For preparation of MEF-CM, MEFs derived from embryonic day 13.5 embryo pool of ICR mice were plated at $1 \times 10^6$ cells per 100 mm dish and incubated overnight. Next day, the cells were washed once with PBS and cultured in 10 ml of ES medium. Twenty-four h after incubation, the supernatant of MEF culture was collected, filtered through a 0.22 μm pore-size filter, and stored at −20° C. until use.

Plasmid Construction

The open reading frame of human OCT3/4 was amplified by RT-PCR and cloned into pCR2.1-TOPO. An EcoRI fragment of pCR2.1-hOCT3/4 was introduced into the EcoRI site of pMXs retroviral vector. To discriminate each experiment, a 20-bp random sequence, designated $N_{20}$ barcode, was introduced into the NotI/SalI site of Oct3/4 expression vector. A unique barcode sequence was used in each experiment to avoid inter-experimental contamination. The open reading frames of human SOX2, KLF4, and c-MYC were also amplified by RT-PCR and subcloned into pENTR-D-TOPO (Invitrogen). All of the genes subcloned into pENTR-D-TOPO were transferred to pMXs by using the Gateway cloning system (Invitrogen), according to the manufacturer's instructions. Mouse Slc7a1 ORF was also amplified, subcloned into pENTR-D-TOPO, and transferred to pLenti6/UbC/V5-DEST (Invitrogen) by the Gateway system. The regulatory regions of the human OCT3/4 gene and the REX1 gene were amplified by PCR and subcloned into pCRXL-TOPO (Invitrogen). For phOCT4-Luc and phREX1-Luc, the fragments were removed by KpnI/BglII digestion from pCRXL vector and subcloned into the KpnI/BglII site of pGV-BM2. For pPolII-Luc, an AatII (blunted)/NheI fragment of pQBI-polII was inserted into the KpnI (blunted)/NheI site of pGV-BM2. All of the fragments were verified by sequencing. Primer sequences are shown in TABLE 13.

TABLE 13

Primer Sequences

| Primer | SEQ ID NO: | Sequence (5' to 3') | Applications |
| --- | --- | --- | --- |
| hOCT3/4-S944 | 26 | CCC GAG GGC CCC ATT TTG GTA CC | OCT3/4 Tg PCR |
| hSOX2-S691 | 27 | GGC ACC CCT GGC ATG GCT CTT GGC TC | SOX2 Tg PCR |
| hKLF4-S1128 | 28 | ACG ATC GTG GCC CCG GAA AAG GAC C | KLF4 endo and Tg PCR |
| hMYC-S1011 | 29 | CAA CAA CCG AAA ATG CAC CAG CCC CAG | c-MYC Tg PCR |
| pMXs-AS3200 | 30 | TTA TCG TCG ACC ACT GTG CTG CTG | Tg PCR |

TABLE 13-continued

Primer Sequences

| Primer | SEQ ID NO: | Sequence (5' to 3') | Applications |
|---|---|---|---|
| pMXs-L3205 | 31 | CCC TTT TTC TGG AGA CTA AAT AAA | Tg PCR |
| hOCT3/4-S1165 | 32 | GAC AGG GGG AGG GGA GGA GCT AGG | Endo OCT3/4 |
| hOCT3/4-AS1283 | 33 | CTT CCC TCC AAC CAG TTG CCC CAA AC | RT-PCR |
| hSOX2-S1430 | 34 | GGG AAA TGG GAG GGG TGC AAA AGA GG | Endo SOX2 |
| hSOX2-AS1555 | 35 | TTG CGT GAG TGT GGA TGG GAT TGG TG | RT-PCR |
| ECAT4-macaca-968S | 36 | CAG CCC CGA TTC TTC CAC CAG TCC C | NANOG RT-PCR |
| ECAT4-macaca-1334AS | 37 | CGG AAG ATT CCC AGT CGG GTT CAC C | |
| hGDF3-S243 | 38 | CTT ATG CTA CGT AAA GGA GCT GGG | GDF3 RT-PCR |
| hGDF3-AS850 | 39 | GTG CCA ACC CAG GTC CCG AAA GTT | |
| hREXI-RT-U | 40 | CAG ATC CTA AAC AGC TCG CAG AAT | REX1 RT-PCR |
| hREXI-RT-L | 41 | GCG TAC GCA AAT TAA AGT CCA GA | |
| hFGF4-RT-U | 42 | CTA CAA CGC CTA CGA GTC CTA CA | FGF4 RT-PCR |
| hFGF4-RT-L | 43 | GTT GCA CCA GAA AAG TCA GAG TTG | |
| hpH34-S40 | 44 | ATA TCC CGC CGT GGG TGA AAG TTC | ESG1 RT-PCR |
| hpH34-AS259 | 45 | ACT CAG CCA TGG ACT GGA GCA TCC | |
| hECAT15-1-S532 | 46 | GGA GCC GCC TGC CCT GGA AAA TTC | DPPA4 RT-PCR |
| hECAT15-1-AS916 | 47 | TTT TTC CTG ATA TTC TAT TCC CAT | |
| hECAT15-2-S85 | 48 | CCG TCC CCG CAA TCT CCT TCC ATC | DPPA2 RT-PCR |
| hECAT15-2-AS667 | 49 | ATG ATG CCA ACA TGG CTC CCG GTG | |
| hTERT-S3234 | 50 | CCT GCT CAA GCT GAC TCG ACA CCG TG | hTERT RT-PCR |
| hTERT-AS3713 | 51 | GGA AAA GCT GGC CCT GGG GTG GAG C | |
| hKLF4-AS1826 | 52 | TGA TTG TAG TGC TTT CTG GCT GGG CTC C | Endo KLF4 RT-PCR |
| hMYC-S253 | 53 | GCG TCC TGG GAA GGG AGA TCC GGA GC | Endo c-MYC |
| hMYC-AS555 | 54 | TTG AGG GGC ATC GTC GCG GGA GGC TG | RT-PCR |
| hMSX1-S665 | 55 | CGA GAG GAC CCC GTG GAT GCA GAG | MSX1 RT-PCR |
| hMSX1-AS938 | 56 | GGC GGC CAT CTT CAG CTT CTC CAG | |
| hBRACHYURY-S1292 | 57 | GCC CTC TCC CTC CCC TCC ACG CAC AG | BRACHYURY/T RT-PCR |
| hBRACHYURY-AS1540 | 58 | CGG CGC CGT TGC TCA CAG ACC ACA GG | |
| hGFAP-S1040 | 59 | GGC CCG CCA CTT GCA GGA GTA CCA GG | GFAP RT-PCR |
| hGFAP-AS1342 | 60 | CTT CTG CTC GGG CCC CTC ATG AGA CG | |
| hPAX6-S1206 | 61 | ACC CAT TAT CCA GAT GTG TTT GCC CGA G | PAX6 RT-PCR |
| hPAX6-AS1497 | 62 | ATG GTG AAG CTG GGC ATA GGC GGC AG | |
| hFOXA2-S208 | 63 | TGG GAG CGG TGA AGA TGG AAG GGC AC | FOXA2 RT-PCR |
| hFOXA2-AS398 | 64 | TCA TGC CAG CGC CCA CGT ACG AGG AC | |
| hSOX17-S423 | 65 | CGC TTT CAT GGT GTG GGC TAA GGA CG | SOX17 RT-PCR |
| hSOX17-AS583 | 66 | TAG TTG GGG TGG TCC TGC ATG TGC TG | |
| hAADC-S1378 | 67 | CGC CAG GAT CCC CGC TTT GAA ATC TG | AADC RT-PCR |
| hAADC-AS1594 | 68 | TCG GCC GCC AGC TCT TTG ATG TGT TC | |
| hChAT-S1360 | 69 | GGA GGC GTG GAG CTC AGC GAC ACC | ChAT RT-PCR |
| hChAT-AS1592 | 70 | CGG GGA GCT CGC TGA CGG AGT CTG | |
| hMAP2-S5401 | 71 | CAG GTG GCG GAC GTG TGA AAA TTG AGA GTG | MAP2 RT-PCR |
| hMAP2-AS5587 | 72 | CAC GCT GGA TCT GCC TGG GGA CTG TG | |
| hDAT-S1935 | 73 | ACA GAG GGG AGG TGC GCC AGT TCA CG | SLC6A3/DAT |
| hDAT-AS2207 | 74 | ACG GGG TGG ACC TCG CTG CAC AGA TC | RT-PCR |

TABLE 13-continued

Primer Sequences

| Primer | SEQ ID NO: | Sequence (5' to 3') | Applications |
|---|---|---|---|
| hLMX1B-S770 | 75 | GGC ACC AGC AGC AGC AGG AGC AGC AG | LMX1B RT-PCR |
| hLMX1B-AS1020 | 76 | CCA CGT CTG AGG AGC CGA GGA AGC AG | |
| hMYL2A-S258 | 77 | GGG CCC CAT CAA CTT CAC CGT CTT CC | MYL2A RT-PCR |
| hMYL2A-AS468 | 78 | TGT AGT CGA TGT TCC CCG CCA GGT CC | |
| hTnTc-S524 | 79 | ATG AGC GGG AGA AGG AGC GGC AGA AC | TnTc RT-PCR |
| hTnTc-AS730 | 80 | TCA ATG GCC AGC ACC TTC CTC CTC TC | |
| hMEF2C-S1407 | 81 | TTT AAC ACC GCC AGC GCT CTT CAC CTT G | MEF2C RT-PCR |
| hMEF2C-AS1618 | 82 | TCG TGG CGC GTG TGT TGT GGG TAT CTC G | |
| hMYHCB-S5582 | 83 | CTG GAG GCC GAG CAG AAG CGC AAC G | MYHCB RT-PCR |
| hMYHCB-AS5815 | 84 | GTC CGC CCG CTC CTC TGC CTC ATC C | |
| dT$_{20}$ | 85 | TTT TTT TTT TTT TTT TTT TT | Reverse transcription |
| hMYC-S857 | 86 | GCC ACA GCA AAC CTC CTC ACA GCC CAC | Southern blot probe |
| hMYC-AS1246 | 87 | CTC GTC GTT TCC GCA ACA AGT CCT CTT C | |
| hOCT3/4-S | 88 | CAC CAT GGC GGG ACA CCT GGC TTC AG | OCT3/4 cloning |
| hOCT3/4-AS | 89 | ACC TCA GTT TGA ATG CAT GGG AGA GC | |
| hSOX2-S | 90 | CAC CAT GTA CAA CAT GAT GGA GAC GGA GCT G | SOX2 cloning |
| hSOX2-AS | 91 | TCA CAT GTG TGA GAG GGG CAG TGT GC | |
| hKLF4-S | 92 | CAC CAT GGC TGT CAG TGA CGC GCT GCT CCC | KLF4 cloning |
| hKLF4-AS | 93 | TTA AAA ATG TCT CTT CAT GTG TAA GGC GAG | |
| hMYC-S | 94 | CAC CAT GCC CCT CAA CGT TAG CTT CAC CAA | c-MYC cloning |
| hMYC-AS | 95 | TCA CGC ACA AGA GTT CCG TAG CTG TTC AAG | |
| Slc7a1-S | 96 | CAC CAT GGG CTG CAA AAA CCT GCT CGG | Mouse Slc7a1 cloning |
| Slc7a1-AS | 97 | TCA TTT GCA CTG GTC CAA GTT GCT GTC | |
| hREX1-pro5K-S | 98 | ATT GTC GAC GGG GAT TTG GCA GGG TCA CAG GAC | Promoter cloning |
| hREXx1-pro5K-AS | 99 | CCC AGA TCT CCA ATG CCA CCT CCT CCC AAA CG | |
| hOCT3/4-pro5K-S | 100 | CACTCG AGG TGG AGG AGC TGA GGG CAC TGT GG | |
| hOCT3/4-pro5K-AS | 101 | CAC AGA TCT GAA ATG AGG GCT TGC GAA GGG AC | |
| mehREX1-F1-S | 102 | GGT TTA AAA GGG TAA ATG TGA TTA TAT TTA | Bisulfite sequencing |
| mehREX1-F1-AS | 103 | CAA ACT ACA ACC ACC CAT CAA C | |
| mehOCT3/4 F2-S | 104 | GAG GTT GGA GTA GAA GGA TTG TTT TGG TTT | |
| mehOCT3/4 F2-AS | 105 | CCC CCC TAA CCC ATC ACC TCC ACC ACC TAA | |
| mehNANOG-FI-S | 106 | TGG TTA GGT TGG TTT AAA ATT TTT G | |
| mehNANOG-FI-AS | 107 | AAC CCA CCC TTA TAA ATT CTC AAT TA | |

Lentivirus Production and Infection

293FT cells (Invitrogen) were plated at $6 \times 10^6$ cells per 100 mm dish, and incubated overnight. Cells were transfected with 3 µg of pLenti6/UbC-Slc7a1 along with 9 µg of Virapower packaging mix by Lipofectamine 2000 (Invitrogen), according to the manufacturer's instructions. Forty-eight hours after transfection, the supernatant of transfectant was collected and filtered through a 0.45 µm pore-size cellulose acetate filter (Whatman). Human fibroblasts were seeded at $8 \times 10^5$ cells per 100 mm dish 1 day before transduction. The medium was replaced with virus-containing supernatant supplemented with 4 µg/ml polybrene (Nacalai Tesque), and incubated for 24 hours.

Retroviral Infection and iPS Cell Generation

PLAT-E packaging cells were plated at $8 \times 10^6$ cells per 100 mm dish and incubated overnight. Next day, the cells were transfected with pMXs vectors with Fugene 6 transfection reagent (Roche). Twenty-four hours after transfection, the medium was collected as the first virus-containing supernatant and replaced with a new medium, which was collected after 24 hours as the second virus-containing supernatant. Human fibroblasts expressing mouse Slc 7a1 gene were seeded at 8×10⁵ cells per 100 mm dish 1 day before transduction. The virus-containing supernatants were filtered through a 0.45-μm pore-size filter, and supplemented with 4 μg/ml polybrene. Equal amounts of supernatants containing each of the four retroviruses were mixed, transferred to the fibroblast dish, and incubated overnight. Twenty-four hours after transduction, the virus-containing medium was replaced with the second supernatant. Six days after transduction, fibroblasts were harvested by trypsinization and re-plated at 5×10⁴ cells per 100-mm dish on an SNL feeder layer. Next day, the medium was replaced with hES medium supplemented with 4 ng/ml bFGF. The medium was changed every other day. Thirty days after transduction, colonies were picked up and transferred into 0.2 ml of hES cell medium. The colonies were mechanically dissociated to small clumps by pipeting up and down. The cell suspension was transferred on SNL feeder in 24-well plates. This stage was defined as passage 1.

RNA Isolation and Reverse Transcription

Total RNA was purified with Trizol reagent (Invitrogen) and treated with Turbo DNA-free kit (Ambion) to remove genomic DNA contamination. One microgram of total RNA was used for reverse transcription reaction with ReverTraAce-α (Toyobo, Japan) and dT$_{20}$ primer, according to the manufacturer's instructions. PCR was performed with ExTaq (Takara, Japan). Quantitative PCR was performed with Platinum SYBR Green qPCR Supermix UDG (Invitrogen) and analyzed with the 7300 real-time PCR system (Applied Biosystems). Primer sequences are shown in TABLE 13.

Alkaline Phosphatase Staining and Immunocytochemistry

Alkaline phosphatase staining was performed using the Leukocyte Alkaline Phosphatase kit (Sigma). For immunocytochemistry, cells were fixed with PBS containing 4% paraformaldehyde for 10 min at room temperature. After washing with PBS, the cells were treated with PBS containing 5% normal goat or donkey serum (Chemicon), 1% bovine serum albumin (BSA, Nacalai tesque), and 0.1% Triton X-100 for 45 min at room temperature. Primary antibodies included SSEA1 (1:100, Developmental Studies Hybridoma Bank), SSEA3 (1:10, a kind gift from Dr. Peter W. Andrews), SSEA4 (1:100, Developmental Studies Hybridoma Bank), TRA-2-49/6E (1:20, Developmental Studies Hybridoma Bank), TRA-1-60 (1:50, a kind gift from Dr. Peter W. Andrews), TRA-1-81 (1:50, a kind gift from Dr. Peter W. Andrews), Nanog (1:20, AF1997, R&D Systems), βIII-tubulin (1:100, CB412, Chemicon), glial fibrillary acidic protein (1:500, Z0334, DAKO), α-smooth muscle actin (pre-diluted, N1584, DAKO), desmin (1:100, RB-9014, Lab Vision), vimentin (1:100, SC-6260, Santa Cruz), α-fetoprotein (1:100, MAB1368, R&D Systems), tyrosine hydroxylase (1:100, AB 152, Chemicon). Secondary antibodies used were cyanine 3 (Cy3)-conjugated goat anti-rat IgM (1:500, Jackson Immunoresearch), Alexa546-conjugated goat anti-mouse IgM (1:500, Invitrogen), Alexa488-conjugated goat anti-rabbit IgG (1:500, Invitrogen), Alexa488-conjugated donkey anti-goat IgG (1:500, Invitrogen), Cy3-conjugated goat anti-mouse IgG (1:500, Chemicon), and Alexa488-conjugated goat anti-mouse IgG (1:500, Invitrogen). Nuclei were stained with 1 μg/ml Hoechst 33342 (Invitrogen).

In Vitro Differentiation

For EB formation, human iPS cells were harvested by treating with collagenase IV. The clumps of the cells were transferred to poly(2-hydroxyethyl methacrylate)-coated dish in DMEM/F12 containing 20% knockout serum replacement (KSR, Invitrogen), 2 mM L-glutamine, 1×10⁻⁴ M nonessential amino acids, 1×10⁻⁴ M 2-mercaptoethanol (Invitrogen), and 0.5% penicillin and streptomycin. The medium was changed every other day. After 8 days as a floating culture, EBs were transferred to gelatin-coated plate and cultured in the same medium for another 8 days. Co-culture with PA6 was used for differentiation into dopaminergic neurons. PA6 cells were plated on gelatin-coated 6-well plates and incubated for 4 days to reach confluence. Small clumps of iPS cells were plated on PA6-feeder layer in Glasgow minimum essential medium (Invitrogen) containing 10% KSR (Invitrogen), 1×10⁻⁴ M nonessential amino acids, 1×10⁻⁴ M 2-mercaptoethanol (Invitrogen), and 0.5% penicillin and streptomycin. For cardiomyocyte differentiation, iPS cells were maintained on Matrigel-coated plate in MEF-CM supplemented with 4 ng/ml bFGF for 6 days. The medium was then replaced with RPMI1640 (Invitrogen) plus B27 supplement (Invitrogen) medium (RPMI/B27), supplemented with 100 ng/ml human recombinant activin A (R & D Systems) for 24 hours, followed by 10 ng/ml human recombinant bone morphologenic protein 4 (BMP4, R&D Systems) for 4 days. After cytokine stimulation, the cells were maintained in RPMI/B27 without any cytokines. The medium was changed every other day.

Bisulfite Sequencing

Genomic DNA (1 μg) was treated with CpGenome DNA modification kit (Chemicon), according to the manufacturer's recommendations. Treated DNA was purified with QIAquick column (QIAGEN). The promoter regions of the human Oct3/4, Nanog, and Rex1 genes were amplified by PCR. The PCR products were subcloned into pCR2.1-TOPO. Ten clones of each sample were verified by sequencing with the M13 universal primer. Primer sequences used for PCR amplification were provided in TABLE 13.

Luciferase Assay

Each reporter plasmid (1 μg) containing the firefly luciferase gene was introduced into human iPS cells or HDF with 50 ng of pRL-TK (Promega). Forty-eight hours after transfection, the cells were lysed with 1× passive lysis buffer (Promega) and incubated for 15 min at room temperature. Luciferase activities were measured with a Dual-Luciferase reporter assay system (Promega) and Centro LB 960 detection system (BERTHOLD), according to the manufacturer's protocol.

Teratoma Formation

The cells were harvested by collagenase IV treatment, collected into tubes and centrifuged, and the pellets were suspended in DMEM/F12. One quarter of the cells from a confluent 100 mm dish was injected subcutaneously to dorsal flank of a SCID mouse (CREA, Japan). Nine weeks after injection, tumors were dissected, weighted, and fixed with PBS containing 4% paraformaldehyde. Paraffin-embedded tissue was sliced and stained with hematoxylin and eosin.

Western Blotting

The cells at semiconfluent state were lysed with RIPA buffer (50 mM Tris-HCl, pH 8.0, 150 mM NaCl, 1% Nonidet P-40 (NP-40), 1% sodium deoxycholate, and 0.1% SDS), supplemented with protease inhibitor cocktail (Roche). The cell lysate of MEL-1 hES cell line was purchased from Abcam. Cell lysates (20 μg) were separated by electrophoresis on 8% or 12% SDS-polyacrylamide gel and transferred to a polyvinylidine difluoride membrane (Millipore). The blot was blocked with TBST (20 mM Tris-HCl, pH 7.6, 136 mM NaCl, and 0.1% Tween-20) containing 1% skim milk and then incubated with primary antibody solution at 4° C. overnight. After washing with TBST, the membrane was incubated with horseradish peroxidase (HRP)-conjugated secondary antibody for 1 hour at room temperature. Signals were detected with Immobilon Western chemiluminescent HRP substrate (Millipore) and LAS3000 imaging system (FUJIFILM, Japan). Antibodies used for western blotting were anti- Oct3/4 (1:600, SC-5279, Santa Cruz), anti-Sox2 (1:2000, AB5603, Chemicon), anti-Nanog (1:200, R&D Systems), anti-Klf4 (1:200, SC-20691, Santa Cruz), anti-c-Myc (1:200, SC-764, Santa Cruz), anti-E-cadherin (1:1000, 610182, BD Biosciences), anti-Dppa4 (1:500, ab31648, Abcam), anti-FoxD3 (1:200, AB5687, Chemicon), anti-telomerase (1:1000, ab23699, Abcam), anti-Sall4 (1:400, ab29112, Abcam), anti-LIN-28 (1:500, AF3757, R&D systems), anti-β-actin (1:5000, A5441, Sigma), anti-mouse IgG-HRP (1:3000, #7076, Cell Signaling), anti-rabbit IgG-HRP (1:2000, #7074, Cell Signaling), and anti-goat IgG-HRP (1:3000, SC-2056, Santa Cruz).

Southern Blotting

Genomic DNA (5 μg) was digested with BglII, EcoRI, and NcoI overnight. Digested DNA fragments were separated on 0.8% agarose gel and transferred to a nylon membrane (Amersham). The membrane was incubated with digoxigenin (DIG)-labeled DNA probe in DIG Easy Hyb buffer (Roche) at 42° C. overnight with constant agitation. After washing, alkaline phosphatase-conjugated anti-DIG antibody (1:10,000, Roche) was added to a membrane. Signals were raised by CDP-star (Roche) and detected by LAS3000 imaging system.

Short Tandem Repeat Analysis and Karyotyping

The genomic DNA was used for PCR with Powerplex 16 system (Promega) and analyzed by ABI PRISM 3100 Genetic analyzer and Gene Mapper v3.5 (Applied Biosystems). Chromosomal G-band analyses were performed at the Nihon Gene Research Laboratories, Japan.

Detection of Telomerase Activity

Telomerase activity was detected with a TRAPEZE telomerase detection kit (Chemicon), according to the manufacturer's instructions. The samples were separated by TBE-based 10% acrylamide non-denaturing gel electrophoresis. The gel was stained with SYBR Gold (1:10,000, Invitrogen).

Example 21

Generation of Induced Pluripotent Stem Cells without Myc

The direct reprogramming of somatic cells is considered to provide an opportunity to generate patient- or disease-specific pluripotent stem cells. Such pluripotent stem (iPS) cells are induced from mouse fibroblasts by the retroviral transduction of four transcription factors, Oct3/4, Sox2, Klf4, and c-Myc (Takahashi et al., *Cell* 126:663-76, 2006). Mouse iPS cells are indistinguishable from mouse ES cells in many aspects and give rise to germline-competent chimeras (Wernig et al., *Nature* 448:318-24, 2007; Okita et al., *Nature* 448:313-17, 2007; Maherali et al., *Cell Stem Cell* 1:55-70, 2007). It was noted above that each iPS clone contained 3-6 retroviral integrations for each factor. Thus, each clone had more than 20 retroviral integration sites in total, which may increase the risk of tumorigenesis. In the case of mouse iPS cells, ~20% of chimera mice and their offspring derived from iPS cells developed tumors (Okita et al., *Nature* 448:313-17, 2007). In particular, it was found that the reactivation of the c-Myc retrovirus results in an increased incidence of tumor formation in the chimeras and progeny mice generated with mouse iPS cells, thus hindering the clinical application of this technology (Okita et al., *Nature* 448:313-17, 2007). Therefore, a modified protocol for the induction of iPS cells, which does not require the Myc retrovirus was developed. With this new protocol, significantly fewer non-iPS background cells were obtained. Furthermore, the iPS cells generated without Myc were constantly of high quality. These findings are important for the future clinical application of this iPS cell technology.

Substitution of the Four Factors with Other Family Members

This study was initiated to examine whether the family proteins of the four factors could also induce iPS cells. In other words, further investigations were performed to assess which family members of a given gene family could substitute for others as nuclear reprogramming factors. Mouse embryonic fibroblasts (MEF) containing a GFP-IRES-Puro$^r$ transgene driven by the Nanog gene regulatory elements were used (Okita et al., *Nature* 448:313-17, 2007). Nanog is specifically expressed in mouse ES cells and preimplantation embryos (Chambers et al., *Cell* 113: 643-55, 2003; Mitsui et al., *Cell* 113: 631-42, 2003) and can serve as a selection marker during iPS cell induction. By introducing the aforementioned four factors, iPS cells are induced as GFP-expressing colonies. Nanog-selected iPS cells are indistinguishable from ES cells and have been shown to give rise to germline-competent chimeras (Wernig et al., *Nature* 448: 318-24, 2007; Okita et al., *Nature* 448:313-17, 2007; Maherali et al., *Cell Stem Cell* 1:55-70, 2007).

Oct3/4 belongs to the Oct family transcription factors, which contain the POU domain (Ryan et al., *Genes Dev* 11: 1207-25, 1997). The closest homologs of Oct3/4 are Oct1 and Oct6. Oct3/4, Oct1, or Oct6 were introduced together with the remaining three factors, into the Nanog-reporter MEF by retroviruses. With Oct3/4, many GFP-positive colonies were observed (FIG. 43A). In contrast, no GFP-positive colonies were obtained with Oct1 or Oct6, thus indicating the inability of these two homologs to induce iPS cells.

Sox2 belongs to the Sox (SRY-related HMG-box) transcription factors, characterized by the presence of the high mobility group (HMG) domain (Schepers et al., *Dev Cell* 3: 167-70, 2002). Sox1, Sox3, Sox7, Sox15, Sox17, and Sox18 were tested and GFP-positive colonies were obtained with Sox1. In addition, fewer GFP-positive colonies were obtained with Sox3, Sox15, and Sox18 (FIG. 43A). Sox18, however, failed to expand the cells.

Klf4 belongs to Krüppel-like factors (Klfs), zinc-finger proteins that contain amino acid sequences that resemble those of the *Drosophila* embryonic pattern regulator Krüppel (Dang et al., *Int J Biochem Cell Biol* 32: 1103-21, 2000). Klf1, Klf2, and Klf5 were tested and GFP-expressing colonies with Klf2 were thus obtained (FIG. 43A). Klf1 and Klf5 were also capable of inducing iPS cells, but with a lower efficiency.

c-Myc has two related proteins, N-Myc and L-Myc (Adhikary et al., *Nat Rev Mol Cell Biol* 6: 635-45, 2005). GFP-positive colonies emerged with both N-Myc and L-Myc (FIG. 43A). Therefore, some, but not all family proteins of the four factors can induce iPS cells.

The family proteins were also tested for their ability to induce iPS cells from MEFs in which βgeo was knocked into the Fbx15 locus (Tokuzawa et al., *Mol Cell Biol* 23: 2699-708, 2003). Similar results to those with the Nanog-based selection were obtained: Sox2 could be replaced by Sox1 and Sox3, Klf4 by Klf2, and c-Myc by N-Myc and L-Myc. The cells generated by the family proteins were expandable and showed a morphology indistinguishable from that of ES cells (not shown). They gave rise to teratomas in nude mice (FIG. 44). Therefore, some family proteins are capable of inducing iPS cells from both Nanog-reporter MEF and Fbx15-reporter MEF.

As has been stated above, iPS cell generation from somatic cells was evaluated by optimizing retroviral transduction and subsequent culture conditions. Furthermore, optimization would be useful for the application of this iPS cell technology to human cells, especially in clinical situations. Unexpectedly, a few ES cell-like and GFP-positive colonies from Nanog-reporter MEF were obtained without any Myc retroviruses (FIG. 43A). This was in contrast to a previous study in which no GFP-positive colonies could be obtained without c-Myc (Okita et al., Nature 448:313-17, 2007). Consistent with the efforts toward optimization, one difference between the two studies is the timing of the drug selection: In the previous study, puromycin selection was initiated seven days after the transduction, whereas in this experiment the selection was started at 14 days. This suggests that iPS cell induction without Myc is a slower process than that with Myc. Furthermore, as is further discussed herein, the omission of Myc resulted in a less efficient but more specific induction of iPS cells.

Myc Omission Results in More Specific iPS Cell Induction

To test whether iPS cell induction without Myc is a slower process than that with Myc, Nanog-reporter MEFs were transduced with either the four factors or three factors devoid of Myc, and then puromycin selection was started seven, 14, or 21 days after the transduction (FIG. 43B). With the four factors, GFP-positive colonies were observed in all of the conditions. The colony numbers significantly increased when puromycin selection was delayed. Without Myc, no GFP-colonies were observed when selection was initiated seven days after the transduction. In contrast, GFP-positive colonies did emerge even without Myc when selection was started 14 or 21 days after the transduction. The colony numbers were fewer with the three factors than with the four factors in each condition. Nanog-selected iPS cells generated without Myc retroviruses expressed ES cell marker genes at comparable levels to those in ES cells (FIG. 45), and thus gave rise to adult chimeras when transplanted into blastocysts (TABLE 14).

TABLE 14

Summary of blastocysts injections

| iPS clones | origin-genotype* | selection | injected blastocysts | born mice | chimeras |
|---|---|---|---|---|---|
| 142B-6 | MEF-FB/gfp | G418 | 39 | 7 | 3 |
| 142B-12 | | | 46 | 12 | 5 |
| 178B-1 | MEF-Ng | Puro | 156 | 50 | 5 |
| 178B-2 | | | 142 | 43 | 17 |
| 178B-5 | | | 60 | 20 | 5 |
| 178B-6 | | | 28 | 10 | 4 |
| 256H-4 | TTF-ACTB-DsRed | No | 72 | 6 | 5 |
| 256H-13 | | | 96 | 8 | 5 |
| 256H-18 | | | 90 | 17 | 11 |

All iPS clones were induced with three factors devoid of Myc from MEF or TTF.
*FB, Fbx15-βgeo reporter; Ng, Nanog-GFP-IRES-Puro$^r$ reporter; gfp, CAG-EGFP Another difference is that fewer GFP-negative colonies as well as background cells were observed with the three factors devoid of Myc than with the four factors (FIG. 43C). Therefore, the omission of Myc resulted in a less efficient but more specific induction of iPS cells.

It was also possible to generate a few iPS cells without Myc from MEFs, in which βgeo was knocked into the Fbx15 locus (Tokuzawa et al., Mol. Cell. Biol. 23:2699-708, 2003). (FIG. 46A). This is again in contrast to the original report, in which no iPS cells were obtained without c-Myc (Takahashi et al., Cell 126:663-76, 2006). In the two experiments, G418 selection was initiated with the same timing: three days after the transduction. However, the colonies were selected 14-21 days after the transduction in the previous report, whereas ~30 days were required in the current study. Another difference was that the retroviral transfection efficiency was raised by preparing each of the four or three factors separately in an independent Plat-E (Morita et al., Gene Ther. 7:1063-66, 2000) plate in this study. In comparison to the original work in which all the four factors were prepared in a single Plat-E plate, a significant increase in the number of iPS cell colonies was observed (not shown). This is consistent with the notion that iPS cell induction without Myc is a slower and less efficient process than that with Myc.

Fbx15-selected iPS cells, which were generated with the four factors, express lower levels of ES-cell marker genes than ES cells (Takahashi et al., Cell 126:663-76, 2006). They cannot produce adult chimeras when microinjected into blastocysts. In contrast, iPS cells generated without Myc expressed ES-cell marker genes at comparable levels to those in ES cells even with the Fbx15 selection (FIG. 46B). Furthermore, adult chimeras were obtained with high iPS cell contribution from these cells (FIG. 46C, TABLE 14). No increased incidence of tumor formation was observed in these chimeras.

iPS Cell Induction in the Absence of Drug Selection

Next, it was determined whether the omission of Myc would result in efficient isolation of iPS cells without drug selection. The four or three factors were introduced into adult tail tip fibroblasts (TTF) containing the Nanog reporter, but puromycin selection was not applied. DsRed retrovirus was transduced together with the four or three factors to visualize transduced cells. Thirty days after the retroviral transduction, the dishes transduced with the four factors were covered with numerous GFP-negative colonies and background cells (FIG. 47A, TABLE 15).

TABLE 15

Summary of experiments (Nanog-GFP reporter TTF, without selection)

| Experiment Number | Factors | Cell seeded | Total colonies | picked up | established |
|---|---|---|---|---|---|
| 220 | 4 | $5 \times 10^4$ | many (107) | 26 (24) | 25 (22) |
| 256 | 4 | $5 \times 10^4$ | many (4) | | |
| | 3 | $3.5 \times 10^5$ | 7 (4) | 7 (4) | 6 (5) |
| 272 | 4 | $5.4 \times 10^4$ | many (132) | 6 (6) | 5 (4) |
| | 3 | $3.1 \times 10^5$ | 21 (8) | 4 (4) | 2 (2) |
| 309 | 4 | $2.3 \times 10^4$ | many (424) | | |
| | 3 | $9.6 \times 10^5$ | 43 (24) | | |

Numbers in parentheses indicate number of colonies or clones that were positive for GFP. The ratios of the retroviruses, Oct3/4, Sox2, Klf4, (c-Myc), and DsRed, were 1:1:1:(1):4 in experiment 256 and 1:1:1:(1):1 in experiments 272 and 309. In experiment 220, DsRed was not introduced.

Using fluorescent microscopy, small portions of these colonies (4, 132, and 424 colonies in three independent experiments) were found GFP-positive. Of note, the GFP-positive colonies were negative for DsRed, which was consistent with the retroviral silencing observed in Nanog-selected iPS cells (Okita et al., Nature 448:313-17, 2007). In contrast, with the three factors devoid of Myc, a small number (7, 21, and 43 in three independent experiments) of discrete colonies were observed with few background cells. Approximately a half of them expressed GFP in a patchy manner. DsRed was only detected in a small portion of some colonies, indicating that it was largely silenced. No overlap was observed between GFP and DsRed. Most of these colonies were expandable and produced iPS cells, which became positive for GFP and negative for DsRed at passage 2. Therefore, the omission of c-Myc resulted in more specific generation of iPS cells, in which Nanog-GFP is activated whereas the retroviruses are silenced.

Next, generation of iPS cells was attempted from adult TTF that did not have selection markers, but had the DsRed transgene driven by a constitutively active promoter (Vintersten et al. *Genesis* 40:241-46, 2004). The four factors or the three factors devoid of Myc were introduced. In addition, a GFP retrovirus was introduced to monitor silencing. After 30 days without drug selection, ~1000 colonies emerged from 0.5× $10^5$ cells transduced with the four factors. Most of them were positive for GFP, indicating that retroviral silencing did not take place in these cells. In contrast, only 16 colonies (FIG. 47B) emerged from 3.5×$10^5$ cells transduced with the three factors devoid of Myc. Most of these colonies express no GFP, while the remaining expressed GFP in small portions. All of these colonies were expandable and showed iPS- or ES-like morphology at the second passage. They were all negative for GFP, thus indicating retroviral silencing. RT-PCR showed that these cells expressed ES cell marker genes at comparable levels to those in ES cells (FIG. 47C). In addition, RT-PCR confirmed the retroviral silencing of Klf4 and the absence of the Myc transgene in iPS cells generated with the three factors. Furthermore, when transplanted into blastocysts, these cells gave rise to chimeras (FIG. 47D, TABLE 14). Therefore, by omitting Myc, good iPS cells can be efficiently generated from adult TTF without drug selection. These findings should be useful for the application of this iPS cell technology to human cells, especially in clinical situations.

Induction of Human iPS Cells without Myc Retroviruses

FIGS. 48(A)-(C) show induction of human iPS cells without Myc retroviruses. The retroviruses for Oct3/4, Sox2 and Klf4 were introduced into BJ fibroblasts (246G) or HDF (253G). After 30 days, a few hES cell-like colonies emerged. These cells were expandable and showed hES cell-like morphology (FIG. 48(A)). Results were obtained for the expression of ES cell marker genes in human iPS cells derived from HDF without Myc retroviruses (253G) or with Myc (253F) (FIG. 48(B)), as were results for embryoid body-mediated differentiation of human iPS cells generated without Myc retroviruses (FIG. 48(C)).

Experimental Procedures for Example 21

Plasmid construction. The coding regions of family genes were amplified by RT-PCR with primers listed in TABLE 16, subcloned into pDONR201 or pENTR-D-TOPO (Invitrogen), and recombined with pMXs-gw by the LR reaction (Invitrogen).

TABLE 16

Primers used for cloning of the family factors

| Genes | Sequences | SEQ ID NO: |
|---|---|---|
| Sox1 | CAC CAT GTA CAG CAT GAT GAT GGA GAC CGA CCT | 108 |
|  | CTA GAT ATG CGT CAG GGG CAC CGT GC | 109 |
| Sox3 | CAC CAT GTA CAG CCT GCT GGA GAC TGA ACT CAA G | 110 |
|  | TCA GAT GTG GGT CAG CGG CAC CGT TCC ATT | 111 |
| Sox7 | CAC CTC GGC CAT GGC CTC GCT GCT GGG | 112 |
|  | CTC CAT TCC TCC AGC TCT ATG ACA CAC | 113 |
| Sox15 | CAC CAT GGC GCT GAC CAG CTC CTC ACA A | 114 |
|  | TTA AAG GTG GGT TAC TGG CAT GGG | 115 |
| Sox17 | CAC CAG AGC CAT GAG CAG CCC GGA TG | 116 |
|  | CGT CAA ATG TCG GGG TAG TTG CAA TA | 117 |
| Sox18 | CAC CAT GCA GAG ATC GCC GCC CGG CTA CG | 118 |
|  | CTA GCC TGA GAT GCA AGC ACT GTA ATA GAC | 119 |
| Oct1 | CAC CAT GAA TAA TCC ATC AGA AAC CAA T | 120 |
|  | GCT CTG CAC TCA GCT CAC TGT GCC | 121 |
| Oct6 | CAC CAT GGC CAC CAC CGC GCA GTA TCT G | 122 |
|  | GGA ACC CAG TCC GCA GGG TCA CTG | 123 |
| Klf1 | CAC CAT GAG GCA GAA GAG AGA GAG GAG GC | 124 |
|  | TCA GAG GTG ACG CTT CAT GTG CAG AGC TAA | 125 |
| Klf2 | CAC CAT GGC GCT CAG CGA GCC TAT CTT GCC | 126 |
|  | CTA CAT ATG TCG CTT CAT GTG CAA GGC CAG | 127 |
| Klf5 | CAC CAT GCC CAC GCG GGT GCT GAC CAT G | 128 |
|  | TCG CTC AGT TCT GGT GGC GCT TCA | 129 |
| L-MycWT | CAC CAT GGA CTT CGA CTC GTA TCA GCA CTA TTT C | 130 |
|  | TTA GTA GCC ACT GAG GTA CGC GAT TCT CTT | 131 |
| N-MycWT | CAC CAT GCC CAG CTG CAC CGC GTC CAC CAT | 132 |
|  | TTA GCA AGT CCG AGC GTG TTC GAT CT | 133 |

Retroviral transduction. pMXs-based retroviral vectors were transfected into Plat-E cells (Morita et al., *Gene Ther.* 7:1063-66, 2000) using Fugene 6 reagents (Roche) according to manufacturer's instruction. Twenty-four hours after transfection, the medium was replaced. After 24 hours, virus-containing supernatant were used for retroviral infection. In a "mixed" protocol, the mixture of plasmids for the four factors was transfected into a single dish of Plat-E cells. In a "separate" method, each plasmid was transfected into separate dishes of Plat-E cells. Virus-containing supernatant was mixed prior to transduction. Significantly higher transduction efficiency was observed with the separate method.

Induction of iPS cells with drug selection. The induction of iPS cells was performed as previously described (Takahashi et al., *Cell* 126:663-76, 2006; Okita et al., *Nature* 448:313-17, 2007) with some modifications. Briefly, MEFs, which contained either the Nanog-GFP-IRES-Puro$^r$ reporter or the Fbx15-βgeo reporter, or both, were seeded at 1.3 and 8.0×10$^5$ cells/well in 6-well plates and 100 mm dish, respectively, with SNL feeder cells (McMahon et al., *Cell* 62:1073-85, 1990). The transduced cells were cultivated with ES medium containing LIF (Meiner et al., *Proc. Natl. Acad. Sci. U.S.A.* 93:14041-46. (1996). Selection with G418 (300 μg/ml) or puromycin (1.5 μg/ml) was started as indicated. Twenty-five to 30 days after transduction, the number of colonies was recorded. Some colonies were then selected for expansion.

iPS cells induction without drug selection. TTFs were isolated from adult Nanog-reporter mice or adult DsRed-transgenic mice (Vintersten et al., *Genesis* 40:241-46, 2004). Retroviral-containing supernatant was prepared in the separated method. For the four-factor transduction, retrovirus-containing supernatants for Klf4, c-Myc, Oct3/4, Sox2 and DsRed, were mixed with the ratio of 1:1:1:1:4. When the three factors were transduced, retrovirus-containing supernatants for Klf4, Oct3/4, Sox2, Mock, and DsRed were mixed with the ratio of 1:1:1:1:4. With DsRed transgenic mice, the GFP retrovirus was used instead of DsRed. For transfection, TTFs were seeded at 8.0×10$^5$ cells per 100-mm dishes, which did not have feeder cells. TTFs were incubated in the virus/polybrene-containing supernatants for 24 hours. Four days after transduction, TTFs transduced with the three factors were reseeded at 3.5×10$^5$ cells per 100-mm dishes with SNL feeder cells and cultured with ES medium. TTFs transduced with the four factors were re-seeded at 0.5×10$^5$ cells per 100-mm dishes with feeder cells. Thirty to 40 days after transduction, the colonies were selected for expansion.

Characterization of iPS cells. RT-PCR and teratoma formation were performed as previously described. For the chimera experiments, 15-20 iPS cells were injected into BDFI-derived blastocysts, which were then transplanted into the uteri of pseudo-pregnant mice.

Example 22

Establishment of Human iPS Cells from Epithelial Cells with Six Factors

Among the nuclear reprogramming factors disclosed herein is a nuclear reprogramming factor comprising one or more gene products from the following genes: Klf4, c-Myc, Oct3/4, Sox2, Nanog, and Lin28 (NCBI accession number NM_145833 (mouse) and NM_024674 (human)). Establishment of induced pluripotent stem cells was performed with combinations of these gene products. The results are shown in TABLE 17.

TABLE 17

Summary of Experiments with Six Factors

| | Day 23 | | Day 29 | | Day 23 | |
|---|---|---|---|---|---|---|
| | non ES like | ES like | non ES like | ES like | non ES like | ES like |
| 6F | 59 | 39 | 167 | 42 | 16 | 27 |
| -L | 49 | 5 | 53 | 14 | | |
| -N | 220 | 11 | 216 | 47 | | |
| -M | 2 | 0 | 15 | 0 | | |
| -O | 0 | 0 | 0 | 0 | | |
| -S | 491 | 0 | 489 | 0 | | |
| -K | 61 | 0 | 51 | 0 | | |
| -KS | 1206 | 0 | 1305 | 0 | | |
| -KO | 0 | 0 | 0 | 0 | | |
| -KM | 0 | 0 | 0 | 0 | 0 | 0 |
| -KN | 51 | 0 | 57 | 0 | | |
| -KL | 28 | 0 | 41 | 0 | | |
| -SO | 0 | 0 | 0 | 0 | | |
| -SM | 0 | 0 | 0 | 0 | | |
| -SN | 188 | 0 | 171 | 0 | | |
| -SL | 112 | 0 | 136 | 0 | | |
| -OM | 0 | 0 | 0 | 0 | | |
| -ON | 0 | 0 | 0 | 0 | | |
| -OL | 0 | 0 | 0 | 0 | | |
| -MN | 3 | 0 | 8 | 0 | | |
| -ML | 0 | 0 | 0 | 0 | | |
| -NL | 98 | 1 | 119 | 9 | 17 | 6 |
| GFP | 0 | 0 | 0 | 0 | | |
| KO | 0 | 0 | 0 | 0 | | |
| KS | 0 | 0 | 0 | 0 | | |

6×10$^6$ 293FT cells were plated on 10 cm dish and cultured overnight, and then transfected with 3 μg of pLenti6/UbC-Slc7a1 lentiviral vector together with 9 μg of Virapower packaging mix by Lipofectamine 2000 (Invitrogen). After 24 hours, the culture medium was replaced with a fresh medium. After 20 hours, the culture supernatant was collected and filtrated through 0.45-μm pore-size cellulose acetate filter (Whatman). 5×10$^5$ epithelial cells were prepared on the previous day. To the dish which the culture supernatant was removed from, the aforementioned filtrated culture supernatant containing viruses and 4 μg/ml polybrene (Nacalai Tesque) were added. Then, the cells were cultured for 24 hours.

In addition, 1.0×10$^6$ Plat-E cells were plated on 6 cm dish and cultured. On the next day, the cells were transfected with 9.0 μg of pMX-based retrovirus vector incorporating klf4, c-myc, oct3/4, sox2, nanog and/or Lin-28 by using 27 μl of Fugene6 transfection reagent. After 24 hours, the culture medium was replaced with a fresh medium. On the next day, the culture supernatant of Plat-E cells was collected and filtrated through 0.45-μm pore-size cellulose acetate filter (Whatman). Seven days after lentivirus infection, epithelial cells were plated at 3.0×10$^5$ cells per 6 cm dish again, and the aforementioned culture supernatant containing retrovirus and polybrene were added thereto.

The term "6F" in TABLE 17 refers to the six factors (klf4, c-myc, oct3/4, sox2, nanog and Lin-28), the term "L" refers to Lin-28, the term "N" refers to nanog, the term "M" refers to c-Myc, the term "O" refers to Oct3/4, the term "S" refers to Sox2, and the term "K" refers to Klf4, respectively. The symbol "−" refers to colonies obtained by subtracting from the six factors those factors shown by the term subsequent to the symbol "−". For example, the term "−L" shows the colonies obtained with the remaining five factors other than lin-28, and the term "−KS" shows the colonies obtained with the remaining four factors other than Klf4 and Sox2, respectively.

The numbers in TABLE 17 refer to the number of colonies. The term "non-ES like" refers to shows colonies having a non-ES cell like morphology, and the term "ES like" refers to colonies having an ES like cell morphology.

Two experimental results are shown. The first experiment shows the number of colonies from cells introduced with various combinations of factors 23 days or 29 days after gene introduction and the second experiment shows the number of "6F," "−KM," and "−NL." According to these experimental results, the number of colonies from cells not-introduced with lin-28 such as "−L" was larger than that of cell transduced with lin-28, suggesting that Lin-28 plays an important role to improve the efficiency of establishment of iPS cells.

In addition, iPS cell induction experiments were performed with six factors (Klf4, c-Myc, Oct3/4, Sox2, Nanog, and Lin28) and two different combinations of four factors (Klf4, c-Myc, Oct3/4 and Sox2, referred to as Y4F in FIG. 49; and Oct3/4, Sox2, Nanog, and Lin-28, referred to as T4F in FIG. 49). The second combination of four factors, T4F, is the same combination as disclosed in Yu et al., *Science* 318:1917-1920, 2007. In these experiments, use of the six factors and the Y4F combination of four factors generated colonies having a similar morphology as ES-like cell colony, whereas the T4F combination generated no colonies having a similar morphology as ES-like cell colony (FIG. 49).

Example 23

More Efficient iPS Cell Generation with Sall4

Experiments performed with mouse embryonic fibroblasts and adult human dermal fibroblasts showed that iPS cell induction with three factors (Klf4, Oct3/4, and Sox2) is more efficient when Sall4 is added to the combination, that is when Klf4, Oct3/4, Sox2, and Sall4 are used (FIGS. 50(A)-(C) and FIG. 51). More ES like colonies were also observed when Sall4 was added to the four factors (Klf4, Oct3/4, Sox2, and c-Myc) or the three factors (Klf4, Oct3/4, Sox2) under the experimental conditions used. These experiments show that addition of Sall4 to the nuclear reprogramming factor can improve iPS induction efficiency.

Kits of the Present Invention.

One aspect of the present invention includes kits designed for use in the preparation and induction of iPS cells. Another aspect of the invention comprises kits for the prevention or treatment of a medical condition or disease through the use of an NRF, an iPS cell or a cell derived from an iPS cell by induction of differentiation. It is also an object of the present invention to provide compositions and methods useful for in vitro transfection, in vivo transfection, ex vivo transfection, in situ labeling, diagnostic tests, genetic therapy, gene therapy, treatment of medical conditions, and the creation of transgenic animals. One aspect of the present invention comprises kits designed for in vitro transfection, in vivo transfection, ex vivo transfection, in situ labeling, diagnostic tests, genetic therapy, gene therapy, treatment of medical conditions, and the creation of transgenic animals. Accordingly, the present invention includes a composition comprising one or more NRFs, one or more iPS cells, one or more cells derived from an iPS cell or cells, and combinations thereof.

UTILITY AND PRACTICAL APPLICATIONS

By using the nuclear reprogramming factor provided by the present invention, reprogramming of differentiated cell nuclei can be conveniently and highly reproducibly induced without using embryos or ES cells, and induced pluripotent stem cells as undifferentiated cells having differentiation ability, pluripotency and growth ability similar to those of ES cells can be established.

Uses of the induced pluripotent stem cells prepared by the method of the present invention are not particularly limited. The cells can be used for any experiments and research conducted with ES cells, therapeutic treatments utilizing ES cells and the like. For example, desired differentiated cells (e.g., nerve cells, cardiac muscle cells, hemocyte cells and the like) can be derived by treating induced pluripotent stem cells obtained by the method of the present invention with retinoic acid, growth factors such as EGF, glucocorticoid or the like, and stem cell therapy based on cellular auto-transplantation can be achieved by returning the differentiated cells obtained as described above to the patient. However, uses of the induced pluripotent stem cells of the present invention are not limited to the aforementioned specific embodiments.

Thus, the present invention has enabled the generation of iPS cells from adult human dermal fibroblasts and other human somatic cells, which are indistinguishable from human ES cells in their differentiation potential in vitro and in teratomas. Furthermore, the instant invention allows for the generation of patient- and disease-specific pluripotent stem cells. Even with the presence of retroviral integration, human iPS cells are useful for understanding disease mechanisms, drug screening, and toxicology. For example, hepatocytes derived from iPS cells with various genetic and disease backgrounds can be utilized in predicting liver toxicity of drug candidates. Human iPS cells may overcome the ethical issues that hES cells confront.

Reference is made to the following documents: Takahashi, et al. *Cell* 131:861-872, 2007; Nakagawa et al. *Nature Biotechnology* 26(1):101-106, 2008; Takahashi et al., *Cell* 126: 663-676, 2006; Okita et al., *Nature* 448:313-17, 2007; Takahashi, et al. *Nature Protocols* 2(12):3081-89, 2007; and the supplementary figures and data associated with these documents, all of which are incorporated by reference herein in their entireties.

Although the present invention has been described in considerable detail with regard to certain versions thereof, other versions are possible, and alterations, permutations, and equivalents of the versions shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

The attached Sequence Listing includes those sequences disclosed in PCT/JP2006/324881, which is incorporated by reference herein in its entirety.

What is claimed is:

1. A method for preparing an induced pluripotent stem cell by nuclear reprogramming of a somatic cell from a mammalian species, comprising:
   a) introducing into the somatic cell one or more retroviral vectors comprising a gene encoding Oct3/4, a gene encoding Klf4, a gene encoding c-Myc and a gene encoding Sox2 operably linked to a promoter; and b) culturing the transduced somatic cell on a fibroblast feeder layer or extracellular matrix in a cell media that supports growth of ES cells of the mammalian species, wherein one or more pluripotent cells are obtained.

* * * * *

UNITED STATES PATENT AND TRADEMARK OFFICE
CERTIFICATE OF CORRECTION

PATENT NO. : 8,058,065 B2
APPLICATION NO. : 12/457356
DATED : November 15, 2011
INVENTOR(S) : Shinya Yamanaka et al.

Page 1 of 1

It is certified that error appears in the above-identified patent and that said Letters Patent is hereby corrected as shown below:

Page 3, Col. 1, line 11, under Other Publications, change "Pluriportent" to --Pluripotent--.
Page 7, Col. 2, line 33, under Other Publications, change "Pluripotericy." to --Pluripotency.--.
Col. 5, line 37, change "Fbx15$^{62\ geo/\beta geo}$" to --Fbx15$^{\beta geo/\beta geo}$--.
Col. 9, line 20, change "III-tubulin" to --βIII-tubulin--.
Col. 12, line 17, change "Bmil ," to --Bmil,--.
Col. 20, line 1, change "ketatinocytes," to --keratinocytes,--.
Col. 25, line 63, change "drawal" to --withdrawal--.
Col. 30, line 49, change "Fbx15$^{geo/\beta geo}$" to --Fbx15$^{\beta geo/\beta geo}$--.
Col. 36, line 32, change "(hTER7)" to --(hTERT)--.
Col. 46, line 67, change "Slc 7a1" to --Slc7a1--.
Col. 47, line 50, change "AB 152," to --AB152,--.

Signed and Sealed this
Twenty-eighth Day of August, 2012

David J. Kappos
*Director of the United States Patent and Trademark Office*